(12) United States Patent
Allen et al.

(10) Patent No.: US 8,399,436 B2
(45) Date of Patent: Mar. 19, 2013

(54) N-PYRAZOLYL CARBOXAMIDES AS CRAC CHANNEL INHIBITORS

(75) Inventors: David George Allen, Stevenage (GB); Diane Mary Coe, Stevenage (GB); Anthony William James Cooper, Stevenage (GB); Paul Martin Gore, Stevenage (GB); David House, Stevenage (GB); Stefan Senger, Stevenage (GB); Steven Leslie Sollis, Stevenage (GB); Sadie Vile, Harlow (GB); Caroline Wilson, Stevenage (GB)

(73) Assignee: Glaxo Group Limited, Greenford, Middlesex (GB)

(*) Notice: Subject to any disclaimer, the term of this patent is extended or adjusted under 35 U.S.C. 154(b) by 0 days.

(21) Appl. No.: 13/265,037

(22) PCT Filed: Apr. 22, 2010

(86) PCT No.: PCT/EP2010/055319
§ 371 (c)(1),
(2), (4) Date: Oct. 18, 2011

(87) PCT Pub. No.: WO2010/122089
PCT Pub. Date: Oct. 28, 2010

(65) Prior Publication Data
US 2012/0053150 A1    Mar. 1, 2012

Related U.S. Application Data

(60) Provisional application No. 61/172,285, filed on Apr. 24, 2009, provisional application No. 61/295,801, filed on Jan. 18, 2010.

(51) Int. Cl.
*A61K 31/675* (2006.01)
*A61K 31/415* (2006.01)
*A61K 31/4439* (2006.01)
*A61K 31/4245* (2006.01)
*A61K 31/513* (2006.01)
*A61P 11/06* (2006.01)
*C07D 401/12* (2006.01)
*C07D 403/10* (2006.01)
*C07D 413/12* (2006.01)

(52) U.S. Cl. .......... 514/94; 514/269; 514/274; 514/341; 514/378; 514/407; 544/298; 544/316; 546/275.4; 548/112; 548/119; 548/131; 548/255; 548/372

(58) Field of Classification Search .................. None
See application file for complete search history.

(56) References Cited

U.S. PATENT DOCUMENTS
2006/0199845 A1* 9/2006 Sun et al. ...................... 514/332

OTHER PUBLICATIONS

Yonetoku, Y, et al: "Novel potent and selective calcium-release-activated calcium (CRAC) channel inhibitors. Part 2: Synthesis and inhibitory activity of aryl-3-trifluoromethylpyrazoles" BioOrganic & Medicinal Chemicstry, Pergamon, GB LNKD-DOI: 10. 1016 /J.BMC. 2006.03.039, vol. 14, No. 15, Aug. 1, 2006, pp. 5370-5383, XP025133434 ISSN: 0968-0896.
Hall, A. et al.: "Non-acidic pyrazole EP1 receptor antagonists with in vivo analgesic efficacy" BioOrganic & Medicinal Chemistry Letters, Pergamon, Elsevier Science, GB LNKD-DOI:10.1016/j.bmcl. 2008. 04.018, vol. 18, No. 11, Jun. 1, 2008, ISSN: 0960-894X.

* cited by examiner

*Primary Examiner* — Kamal Saeed
(74) *Attorney, Agent, or Firm* — Linda E. Hall; John L. Lemanowicz

(57) ABSTRACT

The present invention relates to amide compounds, processes for their preparation, pharmaceutical compositions containing these compounds and to their use in the treatment of disorders, conditions or disorders such as allergic disorders, inflammatory disorders and disorders of the immune system.

11 Claims, No Drawings

N-PYRAZOLYL CARBOXAMIDES AS CRAC CHANNEL INHIBITORS

This application is a 371 of International Application No. PCT/EP2010/055319, filed 22 Apr. 2010, which claims the benefit of U.S. Provisional Application No. 61/295801, filed 18 Jan. 2010 and U.S. Provisional Application No. 61/172285, filed 24 Apr. 2009, which are incorporated herein in their entirety.

FIELD OF THE INVENTION

The present invention relates to amide compounds, processes for their preparation, intermediates usable in these processes, pharmaceutical compositions containing these compounds and to their use in therapy. More particularly the present invention relates to pyrazole amide derivatives and their use in the treatment of a number of diseases, conditions or disorders such as allergic disorders, inflammatory disorders and disorders of the immune system.

BACKGROUND OF THE INVENTION

Calcium release activated calcium (CRAC) channels are a subset of store operated channels (SOC) which are opened in response to depletion of intracellular calcium stores and represent the critical point of calcium entry into certain cells such as mast cells and T-cells.

Two proteins have been identified as the essential components for CRAC channel function namely STIM1 (stromal interaction molecule 1), a calcium sensor localised in the endoplasmic reticulum, and ORAI1, a pore subunit of the CRAC channel that is gated by STIM1.

Small molecule inhibitors of the CRAC channel current (hereafter ICRAC inhibitors) are known in the art, their identification and therapeutic potential are described by Derler et al (Expert Opin. Drug Discovery; 2008; Vol. 3(7) pp. 787-800). U.S. Pat. No. 6,958,339 discloses a series of pyrazole derivatives that are said to possess calcium release-activated calcium channel inhibitory activity which are believed to be useful in the treatment of allergic, inflammatory or autoimmune diseases.

SUMMARY OF THE INVENTION

A class of compounds has been found that are calcium release activated calcium channel (ICRAC) inhibitors.

In a first aspect of the present invention, there is provided a compound of formula (I) or a prodrug thereof, or a salt thereof

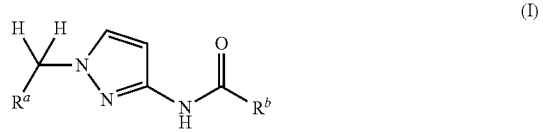

(I)

In a second aspect of the present invention, there is provided a pharmaceutical composition comprising a compound of formula (I) or a prodrug thereof, or a pharmaceutically acceptable salt thereof, and one or more pharmaceutically acceptable carriers, diluents or excipients.

In a third aspect of the present invention, there is provided a compound of formula (I) or a prodrug thereof, or a pharmaceutically acceptable salt thereof, for use in therapy, in particular in the treatment of a disease or condition for which an ICRAC inhibitor is indicated.

In a fourth aspect of the present invention, there is provided a method of treating a disease or condition for which an ICRAC inhibitor is indicated in a subject in need thereof which comprises administering a therapeutically effective amount of compound of formula (I) or a prodrug thereof, or a pharmaceutically acceptable salt thereof.

In a fifth aspect of the present invention, there is provided the use of a compound of formula (I) or a prodrug thereof, or a pharmaceutically acceptable salt thereof, in the manufacture of a medicament for the treatment of a disease or condition for which an ICRAC inhibitor is indicated.

DETAILED DESCRIPTION OF THE INVENTION

In a first aspect of the present invention, there is provided a compound of formula (I) or a prodrug thereof

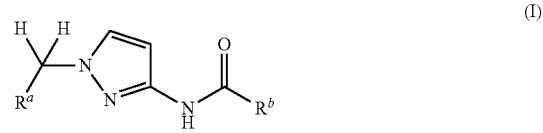

(I)

in which $R^a$ is a group of formula (a1)

(a1)

in which $R^{1a}$ is $C_{1-6}$alkyl, $CF_3$, $OCF_3$, $C_{1-6}$alkoxy or $R^{1a}$ is a group $L^1$-$Z^1$ in which $L^1$ is O, $CH_2$, $OCH_2$ or $CH_2O$ and $Z^1$ is $C_{3-7}$cycloalkyl or aryl;

or $R^a$ is a group of formula (a2)

(a2)

in which $R^{2a}$ is halogen, $C_{1-6}$alkyl, $CF_3$ or $OCH_2Ph$; and $R^{3a}$ is halogen, $C_{1-6}$alkyl, $C_{1-6}$alkoxy, hydroxy, $C_{3-7}$cycloalkyl, $CO_2C_{1-4}$alkyl or $R^{3a}$ is a group $L^2$-$Z^2$ in which $L^2$ is O, $CH_2$ or $O(CH_2)_n$ wherein n is an integer from 1-7; and $Z^2$ is hydroxy, methoxy, $CO_2C_{1-4}$alkyl, $C_{3-7}$cycloalkyl, aryl or heteroaryl;

or $R^a$ is a group of formula (a3)

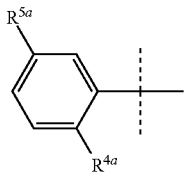

in which
$R^{4a}$ is halogen, $C_{1-6}$alkyl, $C_{1-6}$alkoxy, $CF_3$ or $OCH_2Ph$; and
$R^{5a}$ is halogen, $C_{1-6}$alkyl, hydroxy, $C_{1-6}$alkoxy optionally substituted by methoxy, or $R^{5a}$ is a group $L^3$-$Z^3$ in which $L^3$ is a single bond, O, $CH_2$, $OCH_2$ or $CH_2O$ and $Z^3$ is $C_{3-7}$cycloalkyl, aryl or heteroaryl;
or $R^a$ is a group of formula (a4)

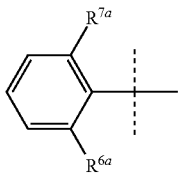

in which
$R^{6a}$ is Cl, Br, $C_{1-6}$alkyl or $CF_3$; and
$R^{7a}$ is halogen, $C_{1-6}$alkyl, $CF_3$, $OCF_3$, $OCHF_2$, $C_{1-6}$alkoxy or $R^{7a}$ is a group $L^4$—$Z^4$ in which $L^4$ is $OCH_2$ and $Z^4$ is $C_{3-7}$cycloalkyl.
$R^b$ is a group of formula (b)

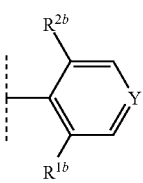

wherein
Y is CH or N,
$R^{1b}$ is halogen, $C_{1-6}$alkyl or $CF_3$;
$R^{2b}$ is H, halogen, $C_{1-6}$alkyl or $C_{1-6}$alkoxy
or a salt thereof.

In one embodiment there is provided a compound of formula (I) as defined above subject to the proviso that it is not a compound selected from
2,6-Difluoro-N-{1-[(2-methylphenyl)methyl]-1H-pyrazol-3-yl}benzamide;
2-Fluoro-N-{1-[(2-methylphenyl)methyl]-1H-pyrazol-3-yl}benzamide;
2,6-Dichloro-N-{1-[(2-methylphenyl)methyl]-1H-pyrazol-3-yl}benzamide;
2-Methyl-N-{1-[(2-methylphenyl]-1H-pyrazol-3-yl}benzamide; and
2-Bromo-N—[1-{(2,5-dichlorophenyl)methyl]-1H-pyrazol-3-yl}benzamide In one embodiment $R^a$ is a group of formula (a1) in which $R^{1a}$ is $C_{2-6}$alkyl, $CF_3$, $OCF_3$, $C_{1-6}$alkoxy or $R^{1a}$ is a group $L^1$-$Z^1$ in which $L^1$ is O, $CH_2$, $OCH_2$ or $CH_2O$ and $Z^1$ is $C_{3-7}$cycloalkyl or aryl;

In a further embodiment $R^a$ is a group of formula (a1) in which $R^{1a}$ is a group $L^1$-$Z^1$ wherein $L^1$ is as defined above and $Z^1$ is phenyl.

In a further embodiment $R^a$ is a group of formula (a1) in which $R^{1a}$ is a group $L^1$-$Z^1$ wherein $L^1$ is $OCH_2$ and $Z^1$ is $C_{3-7}$cycloalkyl (such as cyclopropyl or cyclobutyl).

In one embodiment $R^a$ is a group of formula (a2) in which $R^{1a}$ is methyl, chloro or $CF_3$.

In a further embodiment $R^a$ is a group of formula (a2) in which $R^{1a}$ is halogen (such as chloro or iodo), $C_{1-6}$alkyl (such as methyl or isopropyl), $C_{1-6}$alkoxy (such as methoxy), hydroxy, $C_{3-7}$cycloalkyl (such as cyclopropyl) or $CO_2C_{1-4}$alkyl (such as $CO_2Et$).

In a further embodiment $R^a$ is a group of formula (a2) in which $R^{1a}$ is a group $L^2$-$Z^2$ wherein $L^2$ is O and $Z^2$ is aryl or in which $L^2$ is $O(CH_2)_n$ wherein n is 1 and $Z^2$ is $C_{3-7}$cycloalkyl (such as cyclopropyl), aryl (such as phenyl) or heteroaryl (such as pyridyl, isoxazolyl or oxadiazolyl).

In one embodiment $R^a$ is a group of formula (a3) in which $R^{4a}$ is halogen (particularly chloro), $C_{1-6}$alkoxy (such as methoxy or isopropoxy), $CF_3$ or $OCH_2Ph$ and $R^{5a}$ is halogen, $C_{1-6}$alkyl, hydroxy or $C_{1-6}$alkoxy optionally substituted by methoxy.

In a further embodiment $R^a$ is a group of formula (a3) in which $R^{4a}$ is halogen (such as chloro), $C_{1-6}$alkyl (such as methyl) or $CF_3$ and $R^{5a}$ is a group $L^3$-$Z^3$ wherein $L^3$ is $OCH_2$ and $Z^3$ is $C_{3-7}$cycloalkyl (such as cyclopropyl), aryl (such as phenyl) or heteroaryl (such as pyridyl, isoxazolyl or oxadiazolyl).

In one embodiment $R^a$ is a group of formula (a4) in which $R^{6a}$ is $CF_3$ and $R^{7a}$ is halogen (such as fluoro), $C_{1-6}$alkoxy (such as methoxy) or $R^{7a}$ is a group $L^4$-$Z^4$ wherein $L^4$ is $OCH_2$ and $Z^4$ is $C_{3-7}$cycloalkyl (such as cyclopropyl).

In a further embodiment $R^a$ is a group of formula (a4) in which $R^{6a}$ is $CF_3$ and $R^{7a}$ is fluoro.

In one embodiment $R^b$ is a group of formula (b) wherein
Y is CH or N,
$R^{1b}$ is F, Cl, $C_{1-6}$alkyl or $CF_3$; and
$R^{2b}$ is H, halogen, $C_{1-6}$alkyl or $C_{1-6}$alkoxy In one embodiment $R^b$ is a group of formula (b) in which Y is CH.

In one embodiment $R^b$ is a group of formula (b) in which $R^{1b}$ and $R^{2b}$ are both halogen (such as both fluoro).

In a yet further embodiment $R^b$ is a group of formula (b) in which Y is CH and $R^{1b}$ and $R^{2b}$ are both fluoro.

While the embodiments for each variable have generally been listed above separately for each variable this invention is intended to include all combinations of embodiments described hereinabove including salts thereof.

Particular compounds according to the invention include those described herein.

Specific examples include a compound selected from the group consisting of:
N-[1-({2-Chloro-5-[(cyclopropylmethyl)oxy]phenyl}methyl)-1H-pyrazol-3-yl]-2,6-difluorobenzamide;
N-{1-[(2,4-Dichlorophenyl)methyl]-1H-pyrazol-3-yl}-2,6-difluorobenzamide;
2-Bromo-N-{1-[(2,4-dichlorophenyl)methyl]-1H-pyrazol-3-yl}-6-fluorobenzamide;
2-Chloro-N-{1-[(2,4-dichlorophenyl)methyl]-1H-pyrazol-3-yl}-6-fluorobenzamide;
2,6-Dichloro-N-{1-[(2,4-dichlorophenyl)methyl]-1H-pyrazol-3-yl}benzamide;
N-{1-[(2,4-dichlorophenyl)methyl]-1H-pyrazol-3-yl}-3,5-difluoro-4-pyridinecarboxamide;

N-[1-({5-chloro-2-[(phenylmethyl)oxy]phenyl}methyl)-1H-pyrazol-3-yl]-2,6-difluorobenzamide;
N-{1-[(2,6-dichlorophenyl)methyl]-1H-pyrazol-3-yl}-2,6-difluorobenzamide;
N-[1-({5-chloro-2-[(2-methylpropyl)oxy]phenyl}methyl)-1H-pyrazol-3-yl]-2,6-difluorobenzamide;
N-(1-{[2-bromo-5-(methyloxy)phenyl]methyl}-1H-pyrazol-3-yl)-2,6-difluorobenzamide;
N-(1-{[5-chloro-2-(methyloxy)phenyl]methyl}-1H-pyrazol-3-yl)-2,6-difluorobenzamide;
2,6-Difluoro-N-(1-{[2-(phenyloxy)phenyl]methyl}-1H-pyrazol-3-yl)benzamide;
N-[1-({5-bromo-2-[(phenylmethyl)oxy]phenyl}methyl)-1H-pyrazol-3-yl]-2,6-difluorobenzamide;
2,6-Difluoro-N-[1-({2-[(trifluoromethyl)oxy]phenyl}methyl)-1H-pyrazol-3-yl]benzamide;
2,6-Difluoro-N-(1-{[4-[(phenylmethyl)oxy]-2-(trifluoromethyl)phenyl]methyl}-1H-pyrazol-3-yl)benzamide;
N-{1-[(2-Bromo-6-chlorophenyl)methyl]-1H-pyrazol-3-yl}-2,6-difluorobenzamide;
2,6-Difluoro-N-[1-({2-[(phenylmethyl)oxy]phenyl}methyl)-1H-pyrazol-3-yl]benzamide;
N-[1-({2-chloro-5-[(2-methylpropyl)oxy]phenyl}methyl)-1H-pyrazol-3-yl]-2,6-difluorobenzamide;
N-(1-{[4-[(cyclopropylmethyl)oxy]-2-(trifluoromethyl)phenyl]methyl}-1H-pyrazol-3-yl)-2,6-difluorobenzamide;
2,6-Difluoro-N-(1-{[4-iodo-2-(trifluoromethyl)phenyl]methyl}-1H-pyrazol-3-yl)benzamide;
2,6-Difluoro-N-(1-{[4-methyl-2-(trifluoromethyl)phenyl]methyl}-1H-pyrazol-3-yl)benzamide;
N-(1-{[4-cyclopropyl-2-(trifluoromethyl)phenyl]methyl}-1H-pyrazol-3-yl)-2,6-difluorobenzamide;
2,6-Difluoro-N-{1-[(4-iodo-2-methylphenyl)methyl]-1H-pyrazol-3-yl}benzamide;
N-(1-{[4-chloro-2-(trifluoromethyl)phenyl]methyl}-1H-pyrazol-3-yl)-2,6-difluorobenzamide;
2-Fluoro-N-(1-{[4-iodo-2-(trifluoromethyl)phenyl]methyl}-1H-pyrazol-3-yl)benzamide;
2-Chloro-N-(1-{[4-cyclopropyl-2-(trifluoromethyl)phenyl]methyl}-1H-pyrazol-3-yl)benzamide;
N-(1-{[4-cyclopropyl-2-(trifluoromethyl)phenyl]methyl}-1H-pyrazol-3-yl)-2-fluorobenzamide; and
2,6-Difluoro-N-(1-{[5-iodo-2-(trifluoromethyl)phenyl]methyl}-1H-pyrazol-3-yl)benzamide
or a salt thereof.

Further specific examples of the invention are:
2,6-Difluoro-N-(1-{[2-fluoro-6-(trifluoromethyl)phenyl]methyl}-1H-pyrazol-3-yl)benzamide or a salt thereof; and
2,6-Difluoro-N-(1-{[4-hydroxy-2-(trifluoromethyl)phenyl]methyl}-1H-pyrazol-3-yl)benzamide or a salt thereof Throughout the present specification, unless otherwise stated:
the term "halogen" is used to describe a group selected from fluorine, chlorine, bromine or iodine;
the term "$C_{1-6}$alkyl", whether alone or used as part of another group, is used to describe a group comprising a linear or branched alkyl group containing from 1 to 6 carbon atoms respectively; examples of such groups include methyl, ethyl, propyl, isopropyl, n-butyl, isobutyl, t-butyl, pentyl or hexyl. The term "$C_{2-6}$alkyl" is intended to include all of the above examples with the exception of methyl;
the term "$C_{3-7}$cycloalkyl" is used to describe a non aromatic carbocyclic ring containing at least three and at most seven carbon atoms. Examples of $C_{3-7}$cycloalkyl include, but are not limited to cyclopropyl, cyclobutyl, cyclopentyl or cyclohexyl;
the term "$C_{1-6}$alkoxy" is used to describe a group or a part of the group wherein an oxygen atom is bound to the rest of the molecule and to the above mentioned $C_{1-6}$alkyl group; examples of such groups include methoxy, ethoxy, propoxy, isopropoxy, n-butoxy, isobutoxy, t-butoxy, pentoxy or hexoxy;
The term "aryl" is used to describe an aromatic hydrocarbon ring such as phenyl and naphthyl. Such aryl groups may be optionally substituted by one of more substituents (e.g. two or three, which may be the same or different) selected from the group consisting of halogen, $C_{1-6}$alkyl, or $C_{1-6}$alkoxy;
The term "heteroaryl" is used to describe a 5 or 6 membered aromatic ring containing 1 to 3 heteroatoms selected from oxygen, nitrogen and sulphur. Suitable examples of such aromatic rings include thienyl, furyl, pyrrolyl, triazolyl, imidazolyl, oxazolyl, thiazolyl, oxadiazolyl, isothiazolyl, isoxazolyl, thiadiazolyl, pyrazolyl, pyrimidyl, pyridazinyl, pyrazinyl and pyridyl. The heteroaryl group may be attached to the rest of the molecule by any suitable carbon or nitrogen atom. Such heteroaryl groups may be optionally substituted by one of more substituents (e.g. two or three, which may be the same or different) selected from the group consisting of halogen, $C_{1-6}$alkyl or $C_{1-6}$alkoxy. Certain heteroaryl group e.g. pyridyl may be in the form of an N-oxide.

It will be appreciated that the present invention covers compounds of formula (I) or a prodrug thereof as the free base and as salts thereof. Because of their potential use in medicine, salts of the compounds of formula (I) or a prodrug thereof are desirably pharmaceutically acceptable. Suitable pharmaceutically acceptable salts can include acid or base addition salts. As used herein, the term 'pharmaceutically acceptable salt' means any pharmaceutically acceptable salt of a compound of formula (I) (in stoichiometric or non-stoichiometric form). For a review on suitable salts see Berge et al., J. Pharm. Sci., 66:1-19, (1977). Typically, a pharmaceutically acceptable salt may be readily prepared by using a desired acid or base as appropriate. The resultant salt may precipitate from solution and be collected by filtration or may be recovered by evaporation of the solvent.

Pharmaceutically acceptable acid addition salts include hydrobromide, hydrochloride, sulfate, nitrate, phosphate, succinate, maleate, acetate, propionate, fumarate, citrate, tartrate, lactate, benzoate, salicylate, glutamate, aspartate, p-toluenesulfonate, benzenesulfonate, methanesulfonate, ethanesulfonate, naphthalenesulfonate (e.g. 2-naphthalenesulfonate) or hexanoate salt.

Pharmaceutically acceptable base salts include ammonium salts, alkali metal salts such as those of sodium and potassium, alkaline earth metal salts such as those of calcium and magnesium and salts with organic bases, including salts of primary, secondary and tertiary amines, such as isopropylamine, diethylamine, ethanolamine, trimethylamine, dicyclohexyl amine and N-methyl-D-glucamine.

Other non-pharmaceutically acceptable salts, e.g. formates, oxalates or trifluoroacetates, may be used, for example in the isolation of the compounds of formula (I), and are included within the scope of this invention.

In one embodiment the compound of formula (I) is in the form of a free base.

The invention encompasses all prodrugs, of the compound of formula (I), which upon administration to the recipient is capable of providing (directly or indirectly) the compound of formula (I), or an active metabolite or residue thereof. Such prodrugs are recognizable to those skilled in the art, without undue experimentation. Nevertheless, reference is made to the teaching of Burger's Medicinal Chemistry and Drug Discovery, 5$^{th}$ Edition, Vol 1: Principles and Practice, which is incorporated herein by reference to the extent of such teaching, and to Rautio et al (Nature Reviews; 2008; Vol. 7, p 255-270).

Prodrugs of the compounds of formula (I) can be formed by derivitization of any suitable functional group within the molecule.

In one embodiment there is provided a prodrug of a compound of formula (I) which is a compound of formula (IA) or a pharmaceutically acceptable salt thereof.

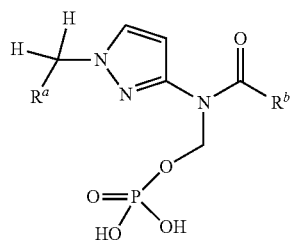

(IA)

wherein R$^a$ and R$^b$ are as defined in formula (I).

In one embodiment there is provided a prodrug of the compound 2,6-difluoro-N-(1-{[2-fluoro-6-(trifluoromethyl)phenyl]methyl}-1H-pyrazol-3-yl)benzamide which is a compound of formula (IB)

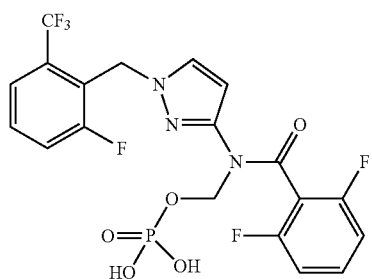

(IB)

in the form of a pharmaceutically acceptable salt.

Suitable pharmaceutically acceptable salts include alkali metal salts (such as sodium or potassium), alkaline earth metals (such as calcium and magnesium) and salts with organic bases.

In a further embodiment there is provided [[(2,6-difluorophenyl)carbonyl](1-{[2-fluoro-6-(trifluoromethyl)phenyl]methyl}-1H-pyrazol-3-yl)amino]methyl dihydrogen phosphate disodium salt.

Further, compounds of formula (I) comprising a hydroxy group (for example compounds of formula (I) in which R$^a$ is a group of formula (a2) wherein R$^{3a}$ is hydroxy or compounds of formula (I) in which R$^a$ is a group of formula (a3) wherein R$^{5a}$ is hydroxy) can be derivatised to form a suitable phosphate prodrug thereof (in which groups such as —PO(OH)$_2$, —CH$_2$PO(OH)$_2$ or —CH$_2$OPO(OH)$_2$ are bonded via the oxygen atom of the R$^{3a}$ or R$^{5a}$ group).

In a further embodiment there is provided a prodrug of the compound 2,6-difluoro-N-(1-{[4-hydroxy-2-(trifluoromethyl)phenyl]methyl}-1H-pyrazol-3-yl)benzamide which is

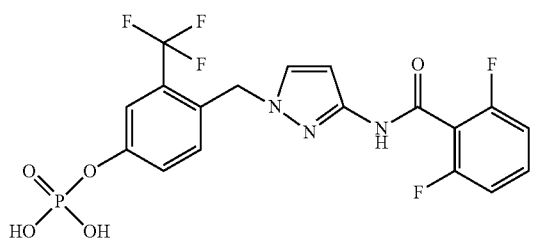 [SMILES: O=C(Nc1ccn(Cc2ccc(OP(=O)(O)O)cc2C(F)(F)F)n1)c1c(F)cccc1F]

or a pharmaceutically acceptable salt thereof.

Suitable pharmaceutically acceptable salts thereof include alkali metal salts (such as sodium or potassium), alkaline earth metals (such as calcium and magnesium) and salts with organic bases.

In a further embodiment there is provided 4-[(3-{[(2,6-difluorophenyl)carbonyl]amino}-1H-pyrazol-1-yl)methyl]-3-(trifluoromethyl)phenyl dihydrogen phosphate disodium salt.

It will be appreciated that many organic compounds can form complexes with solvents in which they are reacted or from which they are precipitated or crystallized. These complexes are known as "solvates". For example, a complex with water is known as a "hydrate". Solvents with high boiling points and/or capable of forming hydrogen bonds such as water, xylene, N-methylpyrrolidinone, methanol and ethanol may be used to form solvates. Methods for identification of solvates include, but are not limited to, NMR and microanalysis. Solvates of the compounds of formula (I) are within the scope of the invention.

The compounds of formula (I) may be in crystalline or amorphous form. Furthermore, some of the crystalline forms of the compounds of formula (I) may exist as polymorphs, which are included within the scope of the present invention. Polymorphic forms of compounds of formula (I) may be characterized and differentiated using a number of conventional analytical techniques, including, but not limited to, X-ray powder diffraction (XRPD) patterns, infrared (1R) spectra, Raman spectra, differential scanning calorimetry (DSC), thermogravimetric analysis (TGA) and solid state nuclear magnetic resonance (SSNMR).

Certain of the compounds described herein may contain one or more chiral atoms so that optical isomers, e.g.—enantiomers or diastereoisomers may be formed. Accordingly, the present invention encompasses isomers of the compounds of formula (I) whether as individual isomers isolated such as to be substantially free of the other isomer (i.e. pure) or as mixtures (i.e. racemates and racemic mixtures). An individual isomer isolated such as to be substantially free of the other isomer (i.e. pure) may be isolated such that less than 10%, particularly less than about 1%, for example less than about 0.1% of the other isomer is present.

Separation of isomers may be achieved by conventional techniques known to those skilled in the art, e.g. by fractional crystallisation, chromatography or HPLC.

Certain compounds of formula (I) may exist in one of several tautomeric forms. It will be understood that the present invention encompasses all tautomers of the compounds of formula (I) whether as individual tautomers or as mixtures thereof.

It will be appreciated from the foregoing that included within the scope of the invention are solvates, isomers and polymorphic forms of the compounds of formula (I) and salts thereof.

The compounds of the invention may be made by a variety of methods, including standard chemistry. Any previously defined variable will continue to have the previously defined meaning unless otherwise indicated. Illustrative general synthetic methods are set out below and then specific compounds of the invention are prepared in the working Examples.

In a further aspect the present invention provides a process for the preparation of a compound of formula (I) which is a process selected from (a), (b), (c), (d), (e) and (f) in which:

(a) comprises the reaction of a compound of formula (II)

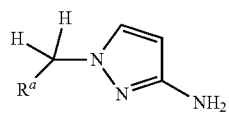

(II)

in which $R^a$ is as defined in formula (I) with a compound of formula (III) or an activated derivative thereof.

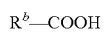

(III)

in which $R^b$ is as defined in formula (I);

(b) comprises the reaction of a compound of formula (IV)

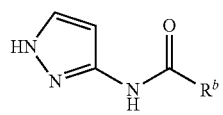

(IV)

in which $R^b$ is as defined in formula (I) with a compound of formula (V)

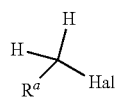

(V)

in which $R^a$ is as defined in formula (I) and Hal is a halogen atom;

(c) comprises alkylation of a compound of formula (VI a1), (VI a2), (VI a3) or (VI a4)

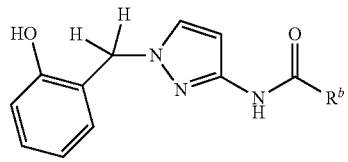

(VI a1)

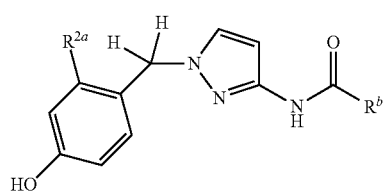

(VI a2)

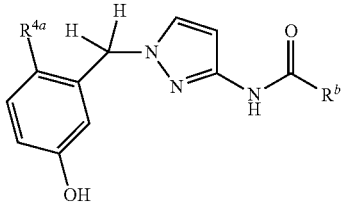

(VI a3)

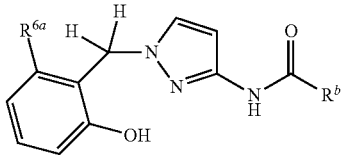

(VI a4)

in which $R^b$, $R^{2a}$, $R^{4a}$ and $R^{6a}$ are as defined in formula (I);

(d) comprises reacting a compound of formula (VII)

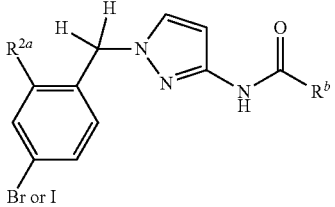

(VII)

in which $R^b$ and $R^{2a}$ as defined in formula (I) with an appropriate organozinc compound or an appropriate boronic acid derivative in the presence of a metal catalyst.

(e) comprises converting a compound of formula (I) into a further compound of formula (I).

(f) comprises converting a compound of formula (I) into a prodrug of a compound of formula (I)

Process (a)

The compounds of formula (II) and carboxylic acid of formula (III) are typically reacted under amide forming conditions that are familiar to those skilled in the art. Such reactions may be carried out in a suitable organic solvent (e.g. DMF or acetonitrile) with an amine (e.g. DIPEA or triethylamine) in the presence of a suitable activating group (e.g. HATU or TBTU).

The reaction may also be carried using an activated derivative of a compound of formula (III) such as an acid chloride. The reaction between an activated compound of formula (III) and a compound of formula (II) is typically carried out in an inert organic solvent such as tetrahydrofuran, chloroform or dichloromethane or a mixed organic/aqueous system at ambient or elevated temperature, optionally in the presence of a suitable base e.g. an organic base (such as triethylamine or diisopropylamine), an alkali metal carbonate (such as potassium carbonate) or a alkali metal hydrogen carbonate (such as sodium hydrogen carbonate).

The compounds of formula (II) and the compounds of formula (III) may be prepared by methods described herein, by analogous methods thereto or are obtainable from commercial sources.

Process (b)

For compounds of formula (V) a suitable Hal group is bromine or chloride. The reaction between the compounds of formula (IV) and (V) may be carried out in an inert organic solvent such as tetrahydrofuran or dimethylformamide at ambient or elevated temperature, optionally in the presence of a suitable base such as potassium or caesium carbonate or a strong base such as sodium t-butoxide or lithium bis(trimethylsilyl)amide (LiHMDS).

The compounds of formula (IV) may be prepared from 3-aminopyrazole (which is commercially available) and an appropriate acid chloride derivative using standard methodology. The compounds of formula (V) are prepared by methods described herein, by analogous methods thereto or are obtainable from commercial sources.

Process (c)

The compounds of formula (VI a1), (VI a2), (VI a3) or (VI a4) may be alkylated by reaction with compounds of general formula R—X in which R is the desired alkylating group and X is a halogen such as bromine or iodine. Such an alkylation reaction is typically carried out in an inert organic solvent such as dimethylformamide or dimethylsulfoxide at ambient or elevated temperature, optionally in the presence of a suitable base such as potassium or caesium carbonate or a strong base such as sodium or potassium t-butoxide.

The compounds of formula (VI a1), (VI a2), (VI a3) or (VI a4) are prepared by methods described herein or by analogous methods thereto.

Process (d)

The reaction between the compounds of formula (VII) and an appropriate boronic acid derivative (e.g. compounds of formula $R^{3a}B(OH)_2$) may be carried out in the presence of a palladium (II) catalyst (e.g. palladium acetate) together with phosphine ligand (e.g. triphenylphosphine) in the presence of a base.

The reaction between the compounds of formula (VII) and an appropriate organo zinc compound (e.g. compounds of formula $R^{3a}ZnBr$) may be carried out in the presence of a palladium (0) catalyst (e.g. palladium tetrakistriphenylphosphine).

The compounds of formula (VII) may be prepared by methods described herein or by analogous methods thereto.

Process (e)

It will be appreciated that certain compounds of formula (I) may be reacted to form further compounds of formula (I). For example, compounds of formula (I) in which $R^a$ is a group of formula (a2) wherein $R^{3a}$ is methoxy can be converted into the corresponding compounds of formula (I) in which $R^3$ is hydroxy by reaction with a demethylating agent (such as boron tribromide) in a suitable organic solvent (such as DCM).

Process (f)

Compounds of formula (I) can be converted to compounds of formula (IA) by reaction with a suitable reagent such and chloromethyl bis(1,1-dimethylethyl) phosphate and subsequent deprotection of the resulting product using procedures described herein or by analogous methods thereto.

Further, prodrugs of the compounds of formula (I) can be prepared by reaction of compounds of formula (VI a2) or formula (VI a3) as defined above with a suitable reagent such as bis(phenylmethyl)hydrogen phosphate and subsequent deprotection of the resulting product using procedures described herein or by analogous methods thereto.

It will be appreciated that in any of the routes (a) to (f) described above, the precise order of the synthetic steps by which the various groups and moieties are introduced into the molecule may be varied. It will be within the skill of the practitioner in the art to ensure that groups or moieties introduced at one stage of the process will not be affected by subsequent transformations and reactions, and to select the order of synthetic steps accordingly. In some instances it may be appropriate to use protecting groups to prevent reactions between one or more groups or moieties. Such procedures are familiar to those skilled in the art (see, for example, "Protective groups in organic synthesis" by T. W. Greene and P. G. M. Wuts (John Wiley & sons 1999) or "Protecting Groups" by P. J. Kocienski (Georg Thieme Verlag 1994).

It will be further appreciated that novel intermediates described herein may also form another aspect of the present invention.

The compounds of formula (I) and salts thereof are believed to be calcium release activated calcium channel inhibitors, and thus be potentially useful in the treatment of diseases or conditions for which such a compound is indicated. Compounds of formula (I) and salts thereof may be used in the form of a prodrug.

The present invention thus provides a compound of formula (I) or a prodrug thereof, or a pharmaceutically acceptable salt thereof, for use in therapy.

In a further embodiment there is provided 2,6-difluoro-N-(1-{[2-fluoro-6-(trifluoromethyl)phenyl]methyl}-1H-pyrazol-3-yl)benzamide for use in therapy.

In a further embodiment there is provided [[(2,6-difluorophenyl)carbonyl](1-{[2-fluoro-6-(trifluoromethyl)phenyl]methyl}-1H-pyrazol-3-yl)amino]methyl dihydrogen phosphate disodium salt for use in therapy.

The present invention thus provides a compound of formula (I), or a prodrug thereof, or a pharmaceutically acceptable salt thereof, for use in the treatment of diseases or conditions for which an ICRAC inhibitor is indicated.

In a further embodiment there is provided 2,6-difluoro-N-(1-{[2-fluoro-6-(trifluoromethyl)phenyl]methyl}-1H-pyrazol-3-yl)benzamide for use in the treatment of diseases or conditions for which an ICRAC inhibitor is indicated.

In a further embodiment there is provided a [[(2,6-difluorophenyl)carbonyl](1-{[2-fluoro-6-(trifluoromethyl)phenyl]methyl}-1H-pyrazol-3-yl)amino]methyl dihydrogen phosphate disodium salt for use in the treatment of diseases or conditions for which an ICRAC inhibitor is indicated.

Also provided is the use of a compound of formula (I) or a prodrug thereof, or a pharmaceutically acceptable salt thereof, in the manufacture of a medicament for the treatment of diseases or conditions for which an ICRAC inhibitor is indicated.

In a further embodiment there is provided the use of 2,6-difluoro-N-(1-{[2-fluoro-6-(trifluoromethyl)phenyl]methyl}-1H-pyrazol-3-yl)benzamide in the manufacture of a medicament for the treatment of diseases or conditions for which an ICRAC inhibitor is indicated.

In a further embodiment there is provided the use of [[(2,6-difluorophenyl)carbonyl](1-{[2-fluoro-6-(trifluoromethyl)phenyl]methyl}-1H-pyrazol-3-yl)amino]methyl dihydrogen phosphate disodium salt in the manufacture of a medicament for the treatment of diseases or conditions for which an ICRAC inhibitor is indicated.

Also provided is a method of treating diseases or conditions for which an ICRAC inhibitor is indicated in a subject in need thereof which comprises administering a therapeutically effective amount of compound of formula (I) or a prodrug thereof, or a pharmaceutically acceptable salt thereof.

In a further embodiment there is provided a method of treating diseases or conditions for which an ICRAC inhibitor is indicated in a subject in need thereof which comprises administering a therapeutically effective amount of the compound 2,6-difluoro-N-(1-{[2-fluoro-6-(trifluoromethyl)phenyl]methyl}-1H-pyrazol-3-yl)benzamide.

In a further embodiment there is provided a method of treating diseases or conditions for which an ICRAC inhibitor is indicated in a subject in need thereof which comprises administering a therapeutically effective amount of the compound [[(2,6-difluorophenyl)carbonyl](1-{[2-fluoro-6-(trifluoromethyl)phenyl]methyl}-1H-pyrazol-3-yl)amino]methyl dihydrogen phosphate disodium salt.

In one embodiment the subject in need thereof is a mammal, such as a human.

As used herein, the term "effective amount" means that amount of a drug or pharmaceutical agent that will elicit the biological or medical response of a tissue, system, mammal or human that is being sought, for instance, by a researcher or clinician. Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function.

Calcium release activated calcium channel inhibitors (i.e. ICRAC inhibitors) are believed to be indicated in the treatment and/or prophylaxis of a variety of diseases, conditions or disorders in mammals such as humans. These include allergic disorders, inflammatory disorders, disorders of the immune system and conditions in which anti-platelet or anti-thrombotic activity is useful.

Examples of allergic disorders include: rhinitis (such as allergic rhinitis), sinusitis, rhinosinusitis, chronic or recurrent otitis media, drug reactions, insect sting reactions, latex allergy, conjunctivitis, urticaria, anaphylaxis and anaphylactoid reactions, atopic dermatitis and food allergies.

Examples of inflammatory disorders include: inflammatory lung disorders (such as asthma, acute respiratory distress syndrome, acute lung injury, chronic obstructive pulmonary disease, bronchiectasis and cystic fibrosis); chronic inflammatory disorders of joints (such as arthritis, rheumatoid arthritis, osteoarthritis and bone diseases associated with increased bone resorption); inflammatory bowel diseases (such as Barrett's oesophagus, ileitis, ulcerative colitis and Crohn's disease); inflammatory disorders of the eye (such as corneal dystrophy, trachoma, uveitis, sympathetic ophthalmitis and endophthalmitis); inflammatory diseases of the kidney (such as glomerulonephritis, nephrosis, nephritic syndrome and IgA nephropathy); inflammatory disorders of the skin (such as psoriasis and eczema); inflammatory diseases of the central nervous system (such as chronic demyelinating diseases of the nervous system, multiple sclerosis, AIDS-related neurodegeneration and Alzheimers disease, infectious meningitis, encephalomyelitis, Parkinson's disease, Huntington's disease, amyotrophic lateral sclerosis and viral or autoimmune encephalitis); inflammatory diseases of the heart (such as myocarditis and cardiomyopathy, ischemic heart disease, myocardial infarction and atherosclerosis); other diseases with significant inflammatory components, including tuberculosis; leprosy; rejection of transplants; pre-eclampsia; endometriosis, chronic liver failure; brain and spinal cord trauma and cancer; and conditions where systemic inflammation of the body may also be present (such as septic shock, hemorrhagic or anaphylactic shock or shock induced by cancer chemotherapy).

Examples of disorders of the immune system include: autoimmune diseases of the central and peripheral nervous system (such as multiple sclerosis, myasthenia gravis, Eaton-Lambert Myasthenic syndrome); autoimmune neuropathies (such as Guillain-Barré); autoimmune diseases of the eye (such as autoimmune uveitis); autoimmune diseases of the blood (such as autoimmune haemolytic anemia, pernicious anemia, and autoimmune thrombocytopenia e.g. Idiopathic Thrombocytopaenic Purpura); autoimmune diseases of the vasculature (such as temporal arteritis, anti-phospholipid syndrome, vasculitides e.g. Wegener's granulomatosis and Behcet's disease); autoimmune diseases of the skin (such as alopecia greata, psoriasis, dermatitis herpetiformis, pemphigus vulgaris, bullous pemphigoid and vitiligo); autoimmune disease of the gastrointestinal tract (such as coeliac disease, Crohn's disease, ulcerative colitis, primary biliary cirrhosis and autoimmune hepatitis); autoimmune disorders of the endocrine glands (such as Type1 diabetes mellitus, autoimmune thyroiditis, Grave's disease, Hashimoto's thyroiditis, autoimmune oophoritis and orchitis); autoimmune disorder of the adrenal gland (such as Addisons disease); and multi system autoimmune diseases including connective tissue and musculoskeletal system diseases (such as rheumatoid arthritis, systemic lupus erythematosus, scleroderma, polymyositis, dermatomyositis), spondyloarthropathies (such as ankylosing spondylitis and psoriatic arthritis).

Examples of conditions where anti-platelet or anti-thrombotic activity is useful for treatment and/or prophylaxis include: ischemic heart disease, myocardial infarction, cerebrovascular accident (stroke) and vascular thrombosis (venous, arterial and intra-cardiac).

Further diseases or conditions which may be treated by the compounds of the invention include conditions where mast cells and basophils contribute to pathology, such as mast cell leukaemia, mastocytosis, endometriosis and basophil leukaemia.

The term "disease or condition for which an ICRAC inhibitor is indicated", is intended to include each of or all of the above disease states.

It is believed that the compounds of formula (I), having ICRAC inhibitory activity, may inhibit mast cell degranulation and/or inhibit T cell activation. Compounds having such activity may be particularly suitable for the treatment of a number of diseases and conditions, for example asthma and rhinitis.

In one embodiment the disease or condition for which an ICRAC inhibitor is indicated is asthma.

In a further embodiment the disease or condition for which an ICRAC inhibitor is indicated is rhinitis While it is possible that for use in therapy, a compound of formula (I) as well as pharmaceutically acceptable salts thereof may be administered as the raw chemical, it is typical to formulate in a suitable composition comprising one or more pharmaceutically acceptable carriers, diluents or excipients. Such compositions may be prepared using standard procedures.

Thus, there is provided a pharmaceutical composition which comprises a compound of formula (I) or a prodrug thereof, or a pharmaceutically acceptable salt thereof, and one or more pharmaceutically acceptable carriers, diluents and/or excipients.

In one embodiment there is provided a pharmaceutical composition which comprises 2,6-difluoro-N-(1-{[2-fluoro-6-(trifluoromethyl)phenyl]methyl}-1H-pyrazol-3-yl)benzamide and one or more pharmaceutically acceptable carriers, diluents or excipients.

In a further embodiment there is provided a pharmaceutical composition which comprises [[(2,6-difluorophenyl)carbonyl](1-{[2-fluoro-6-(trifluoromethyl)phenyl]methyl}-1H-pyrazol-3-yl)amino]methyl dihydrogen phosphate disodium salt and one or more pharmaceutically acceptable carriers, diluents or excipients.

Thus there is provided a pharmaceutical composition for the treatment of diseases or conditions in which an ICRAC inhibitor is indicated comprising a compound of formula (I) or a pharmaceutically acceptable salt thereof.

A pharmaceutical composition comprising a compound of formula (I) or a pharmaceutically acceptable salt thereof, which may be prepared by admixture, suitably at ambient temperature and atmospheric pressure, may be suitable for topical administration (which includes epicutaneous, inhaled, intranasal or ocular administration), enteral administration (which includes oral or rectal administration) or parenteral administration (such as by injection or infusion). Of interest are compositions comprising a compound of formula (I) or a pharmaceutically acceptable salt thereof, suitable for topical administration, particularly suitable for intranasal administration.

Generally, compositions may be in the form of solutions or suspensions (aqueous or non-aqueous), tablets, capsules, oral liquid preparations, powders, granules, lozenges, lotions, creams, ointments, gels, foams, reconstitutable powders or suppositories as required by the route of administration.

Generally, the compositions comprising a compound of formula (I) or a pharmaceutically acceptable salt thereof may contain from about 0.1% to 99% (w/w), such as from about 10 to 60% (w/w) (based on the total weight of the composition), of the compound of formula (I) or the pharmaceutically acceptable salt thereof, depending on the route of administration. The dose of the compound used in the treatment of the aforementioned diseases will vary in the usual way with the seriousness of the diseases, the weight of the sufferer, and other similar factors. However, as a general guide, suitable unit doses may be about 0.05 to 1000 mg, for example about 0.05 to 200 mg, and such unit doses may be administered more than once a day, for example two or three times a day or as desired. Such therapy may extend for a number of weeks or months.

Further provided is a pharmaceutical composition for the treatment of a disease or condition for which an ICRAC inhibitor is indicated comprising a compound of formula (I) or prodrug thereof, or a pharmaceutically acceptable salt thereof. In one embodiment there is provided a pharmaceutical composition for the treatment of an allergic disorder (such as rhinitis) or an inflammatory disorder (such as asthma) comprising a compound of formula (I) or prodrug thereof, or a pharmaceutically acceptable salt thereof.

Thus there is provided a pharmaceutical composition comprising 0.05 to 1000 mg of a compound of formula (I) or a prodrug thereof, or a pharmaceutically acceptable salt thereof, and 0.1 to 2 g of one or more pharmaceutically acceptable carriers, diluents and/or excipients.

The proportion of the compound of formula (I) or a prodrug thereof, or a pharmaceutically acceptable salt thereof, in a topical composition will depend on the precise type of composition to be prepared and the particular route of administration, but will generally be within the range of from about 0.001 to 10% (w/w), based on the total weight of the composition. Generally, however for most types of preparations the proportion used will be within the range of from about 0.005 to 1% (w/w), such as about 0.01 to 1% (w/w), for example about 0.01 to 0.5% (w/w), based on the total weight of the composition. However, in powders for inhalation the proportion used will generally be within the range of from about 0.1 to 5% (w/w), based on the total weight of the composition.

Generally, pharmaceutical compositions suitable for intranasal or inhaled administration may conveniently be formulated as aerosols, solutions, suspensions, drops, gels or dry powders, with one or more pharmaceutically acceptable carriers and/or excipients such as aqueous or non-aqueous vehicles, thickening agents, isotonicity adjusting agents, antioxidants and/or preservatives.

For compositions suitable for intranasal or inhaled administration, the compound of formula (I) or a prodrug thereof, or a pharmaceutically acceptable salt thereof, may typically be in a particle-size-reduced form, which may be prepared by conventional techniques, for example, micronization and milling. Generally, the size-reduced (e.g. micronised) compound of formula (I) or a prodrug thereof, or a pharmaceutically acceptable salt thereof, can be defined by a $D_{50}$ value of about 0.5 to 10 microns, such as of about 2 to 4 microns (for example as measured using laser diffraction).

In one aspect, pharmaceutical compositions comprising a compound of formula (I) or a prodrug thereof, or a pharmaceutically acceptable salt thereof are suitable for intranasal administration. Intranasal compositions comprising a compound of formula (I), or a prodrug thereof, or a pharmaceutically acceptable salt thereof, may permit the compound(s) to be delivered to all areas of the nasal cavities (the target tissue) and further, may permit the compound(s) to remain in contact with the target tissue for longer periods of time. A suitable dosing regime for intranasal compositions would be for the patient to inhale slowly through the nose subsequent to the nasal cavity being cleared. During inhalation the composition would be administered to one nostril while the other is manually compressed. This procedure would then be repeated for the other nostril. Typically, one or two sprays per nostril would be administered by the above procedure up to two or three times each day, ideally once daily. Of particular interest are intranasal compositions suitable for once daily administration.

Intranasal compositions may optionally contain one or more suspending agents, one or more preservatives, one or more wetting agents and/or one or more isotonicity adjusting agents as desired. Compositions suitable for intranasal administration may optionally further contain other excipients, such as antioxidants (for example sodium metabisulphite), taste-masking agents (such as menthol) and sweetening agents (for example dextrose, glycerol, saccharin and/or sorbitol).

The suspending agent, if included, will typically be present in the intranasal composition in an amount of between about 0.1 and 5% (w/w), such as between about 1.5% and 2.4% (w/w), based on the total weight of the composition. Examples of suspending agents include Avicel®, carboxymethylcellulose, veegum, tragacanth, bentonite, methylcellulose and polyethylene glycols, e.g. microcrystalline cellulose or carboxy methylcellulose sodium. Suspending agents may also be included in compositions suitable for inhaled, ocular and oral administration as appropriate.

For stability purposes, intranasal compositions comprising a compound of formula (I) or a pharmaceutically acceptable salt thereof may be protected from microbial or fungal contamination and growth by inclusion of a preservative. Examples of pharmaceutically acceptable anti-microbial agents or preservatives may include quaternary ammonium compounds (e.g. benzalkonium chloride, benzethonium chloride, cetrimide and cetylpyridinium chloride), mercurial agents (e.g. phenylmercuric nitrate, phenylmercuric acetate and thimerosal), alcoholic agents (e.g. chlorobutanol, phenylethyl alcohol and benzyl alcohol), antibacterial esters (e.g. esters of para-hydroxybenzoic acid), chelating agents such as disodium ethylenediaminetetraacetate (EDTA) and other anti-microbial agents such as chlorhexidine, chlorocresol, sorbic acid and its salts (such as potassium sorbate) and polymyxin. Examples of pharmaceutically acceptable antifungal agents or preservatives may include sodium benzoate. The preservative, if included, may be present in an amount of between about 0.001 and 1% (w/w), such as about 0.015% (w/w), based on the total weight of the composition. Preservatives may be included in compositions suitable for other routes of administration as appropriate.

Compositions which contain a suspended medicament may include a pharmaceutically acceptable wetting agent which functions to wet the particles of medicament to facilitate dispersion thereof in the aqueous phase of the composition. Typically, the amount of wetting agent used will not cause foaming of the dispersion during mixing. Examples of wetting agents include fatty alcohols, esters and ethers, such as polyoxyethylene (20) sorbitan monooleate (Polysorbate 80). The wetting agent may be present in intranasal compositions in an amount of between about 0.001 and 0.05% (w/w), for example about 0.025% (w/w), based on the total weight of the composition. Wetting agents may be included in compositions suitable for other routes of administration, e.g. for inhaled and/or ocular administration, as appropriate.

An isotonicity adjusting agent may be included to achieve isotonicity with body fluids e.g. fluids of the nasal cavity, resulting in reduced levels of irritancy. Examples of isotonicity adjusting agents include sodium chloride, dextrose, xylitol and calcium chloride. An isotonicity adjusting agent may be included in intranasal compositions in an amount of between about 0.1 and 10% (w/w), such as about 5.0% (w/w), based on the total weight of the composition. Isotonicity adjusting agents may also be included in compositions suitable for other routes of administration, for example in compositions suitable for inhaled, ocular, oral liquid and parenteral administration, as appropriate.

Further, the intranasal compositions comprising a compound of formula (I), or a prodrug thereof, or a pharmaceutically acceptable salt thereof, may be buffered by the addition of suitable buffering agents such as sodium citrate, citric acid, phosphates such as disodium phosphate (for example the dodecahydrate, heptahydrate, dihydrate and anhydrous forms) or sodium phosphate and mixtures thereof. Buffering agents may also be included in compositions suitable for other routes of administration as appropriate.

Compositions for administration topically to the nose or lung for example, for the treatment of rhinitis, include pressurised aerosol compositions and aqueous compositions delivered to the nasal cavities by pressurised pump. Compositions which are non-pressurised and adapted to be administered topically to the nasal cavity are of particular interest. Suitable compositions contain water as the diluent or carrier for this purpose. Aqueous compositions for administration to the lung or nose may be provided with conventional excipients such as buffering agents, tonicity modifying agents and the like. Aqueous compositions may also be administered to the nose by nebulisation.

A fluid dispenser may typically be used to deliver a fluid composition to the nasal cavities. The fluid composition may be aqueous or non-aqueous, but typically aqueous. Such a fluid dispenser may have a dispensing nozzle or dispensing orifice through which a metered dose of the fluid composition is dispensed upon the application of a user-applied force to a pump mechanism of the fluid dispenser. Such fluid dispensers are generally provided with a reservoir of multiple metered doses of the fluid composition, the doses being dispensable upon sequential pump actuations. The dispensing nozzle or orifice may be configured for insertion into the nostrils of the user for spray dispensing of the fluid composition into the nasal cavity. A fluid dispenser of the aforementioned type is described and illustrated in WO05/044354 the entire content of which is hereby incorporated herein by reference. The dispenser has a housing which houses a fluid discharge device having a compression pump mounted on a container for containing a fluid composition. The housing has at least one finger-operable side lever which is movable inwardly with respect to the housing to cam the container upwardly in the housing to cause the pump to compress and pump a metered dose of the composition out of a pump stem through a nasal nozzle of the housing. In one embodiment, the fluid dispenser is of the general type illustrated in FIGS. 30-40 of WO05/044354.

In one aspect, there is provided an intranasal composition comprising a compound of formula (I) or a prodrug thereof, or a pharmaceutically acceptable salt thereof. In another aspect, such an intranasal composition is benzalkonium chloride-free.

Inhaled administration involves topical administration to the lung, such as by aerosol or dry powder composition.

Aerosol compositions suitable for inhaled administration may comprise a solution or fine suspension of the compound in a pharmaceutically acceptable aqueous or non-aqueous solvent. Aerosol compositions suitable for inhalation can be either a suspension or a solution and generally contain a compound of formula (I) or a prodrug thereof, or a pharmaceutically acceptable salt thereof, and a suitable propellant such as a fluorocarbon or hydrogen-containing chlorofluorocarbon or mixtures thereof, such as hydrofluoroalkanes, e.g. 1,1,1,2-tetrafluoroethane, 1,1,1,2,3,3,3-heptafluoro-n-propane or a mixture thereof. The aerosol composition may optionally contain additional excipients well known in the art such as surfactants or cosolvents. Examples of surfactants include, but are not limited to oleic acid, lecithin, an oligolactic acid or derivative e.g. as described in WO94/21229 and WO98/34596. An example of a cosolvent includes, but is not limited to ethanol. Aerosol compositions may be presented in single or multidose quantities in sterile form in a sealed container, which may take the form of a cartridge or refill for use with an atomizing device or inhaler. Alternatively, the sealed container may be a unitary dispensing device such as a single dose nasal inhaler or an aerosol dispenser fitted with a metering valve (metered dose inhaler), which is intended for disposal once the contents of the container have been exhausted.

Dry powder inhalable compositions may take the form of capsules and cartridges of, for example, gelatine, or blisters of, for example, laminated aluminium foil, for use in an inhaler or insufflator. Such compositions may be formulated comprising a powder mix of a compound of formula (I) or a pharmaceutically acceptable salt thereof and a suitable powder base such as lactose or starch.

Optionally, for dry powder inhalable compositions, a composition suitable for inhaled administration may be incorporated into a plurality of sealed dose containers (e.g. comprising the dry powder composition) mounted longitudinally in a strip or ribbon inside a suitable inhalation device. The container is rupturable or peel-openable on demand and the dose of e.g. the dry powder composition may be administered by inhalation via the device such as the DISKUS™ device, marketed by GlaxoSmithKline. The DISKUS™ inhalation device is for example described in GB 2242134 A, and in such a device, at least one container for the composition in powder form (the container or containers may, for example, be a plurality of sealed dose containers mounted longitudinally in a strip or ribbon) is defined between two members peelably secured to one another; the device comprises: a means of defining an opening station for the said container or containers; a means for peeling the members apart at the opening station to open the container; and an outlet, communicating with the opened container, through which a user can inhale the composition in powder form from the opened container.

Aerosol compositions are typically arranged so that each metered dose or "puff" of aerosol contains about 20 µg-2000 µg, particularly about 20 µg-500 µg of a compound of formula (I) or a pharmaceutically acceptable salt thereof. Administration may be once daily or several times daily, for example 2, 3, 4 or 8 times, giving for example 1, 2 or 3 doses each time. The overall daily dose with an aerosol will be within the range of about 100 µg-10 mg, such as between about 200 µg-2000 µg. The overall daily dose and the metered dose delivered by capsules and cartridges in an inhaler or insufflator will generally be double those with aerosol compositions.

In another aspect, there is provided a pharmaceutical composition comprising a compound of formula (I) or a prodrug thereof, or a pharmaceutically acceptable salt thereof, which is suitable for epicutaneous administration. An epicutaneous composition to be applied to the affected area e.g. the skin, by one or more application per day, may be in the form of, for example, an ointment, a cream, an emulsion, a lotion, a foam, a spray, an aqueous gel, or a microemulsion. Such compositions may optionally contain one or more solubilising agents, skin-penetration-enhancing agents, surfactants, fragrances, preservatives or emulsifying agents.

Ointments, creams and gels, may, for example, be formulated with an aqueous or oily base with the addition of suitable thickening and/or gelling agent and/or solvents. Such bases may thus, for example, include water and/or an oil such as liquid paraffin or a vegetable oil such as arachis oil or castor oil, or a solvent such as polyethylene glycol. Thickening agents and gelling agents which may be used according to the nature of the base include soft paraffin, aluminium stearate, cetostearyl alcohol, polyethylene glycols, woolfat, beeswax, carboxypolymethylene and cellulose derivatives, and/or glyceryl monostearate and/or non-ionic emulsifying agents. Lotions may be formulated with an aqueous or oily base and will in general also contain one or more emulsifying agents, stabilising agents, dispersing agents, suspending agents or thickening agents.

In another aspect, there is provided a pharmaceutical composition comprising a compound of formula (I) or a prodrug thereof, or a pharmaceutically acceptable salt thereof, which is suitable for ocular administration. Such compositions may optionally contain one or more suspending agents, one or more preservatives, one or more wetting/lubricating agents and/or one or more isotonicity adjusting agents. Examples of ophthalmic wetting/lubricating agents may include cellulose derivatives, dextran 70, gelatin, liquid polyols, polyvinyl alcohol and povidone such as cellulose derivatives and polyols.

In another aspect, there is provided a pharmaceutical composition comprising a compound of formula (I) or a prodrug thereof, or a pharmaceutically acceptable salt thereof, which is suitable for oral administration. Tablets and capsules for oral administration may be in unit dose form, and may contain conventional excipients, such as binding agents, fillers, tabletting lubricants, disintegrants and acceptable wetting agents. The tablets may be coated according to methods well known in normal pharmaceutical practice.

Oral liquid preparations may be in the form of, for example, aqueous or oily suspension, solutions, emulsions, syrups or elixirs, or may be in the form of a dry product for reconstitution with water or other suitable vehicle before use. Such liquid preparations may contain conventional additives such as suspending agents, emulsifying agents, non-aqueous vehicles (which may include edible oils), preservatives, and, if desired, conventional flavourings or colorants.

In another aspect, there is provided a pharmaceutical composition comprising a compound of formula (I) or a prodrug thereof, or a pharmaceutically acceptable salt thereof, which is suitable for parenteral administration. Fluid unit dosage forms suitable for parenteral administration may be prepared utilising a compound of formula (I) or pharmaceutically acceptable salt thereof and a sterile vehicle which may be aqueous or oil based. The compound, depending on the vehicle and concentration used, may be either suspended or dissolved in the vehicle. In preparing solutions, the compound may be dissolved for injection and filter sterilised before filling into a suitable vial or ampoule and sealing. Optionally, adjuvants such as a local anaesthetic, preservatives and buffering agents may be dissolved in the vehicle. To enhance the stability, the composition may be frozen after filling into the vial and the water removed under vacuum. The lyophilised parenteral composition may be reconstituted with a suitable solvent just prior to administration. Parenteral suspensions may be prepared in substantially the same manner, except that the compound is suspended in the vehicle instead of being dissolved, and sterilisation cannot be accomplished by filtration. The compound may be sterilised by exposure to ethylene oxide before suspension in a sterile vehicle. A surfactant or wetting agent may be included in the composition to facilitate uniform distribution of the compound.

The compounds and pharmaceutical compositions according to the invention may be used in combination with or include one or more other therapeutic agents, for example selected from anti-inflammatory agents, anticholinergic agents (particularly an $M_1/M_2/M_3$ receptor antagonist), $\beta_2$-adrenoreceptor agonists, antiinfective agents such as antibiotics or antivirals, or antihistamines. The invention thus provides, in a further aspect, a combination comprising a compound of formula (I) or a prodrug thereof, or a pharmaceutically acceptable salt thereof, together with one or more other therapeutically active agents, for example selected from an anti-inflammatory agent such as a corticosteroid or an NSAID, an anticholinergic agent, a $\beta_2$-adrenoreceptor agonist, an antiinfective agent such as an antibiotic or an antiviral, or an antihistamine. One embodiment of the invention encompasses combinations comprising a compound of formula (I) or a prodrug thereof, or a pharmaceutically acceptable salt thereof together with a $\beta_2$-adrenoreceptor agonist, and/or an anticholinergic, and/or a PDE-4 inhibitor, and/or an antihistamine.

One embodiment of the invention encompasses combinations comprising one or two other therapeutic agents.

It will be clear to a person skilled in the art that, where appropriate, the other therapeutic ingredient(s) may be used in the form of salts, for example as alkali metal or amine salts or as acid addition salts, or prodrugs, or as esters, for example lower alkyl esters, or as solvates, for example hydrates to optimise the activity and/or stability and/or physical characteristics, such as solubility, of the therapeutic ingredient. It will be clear also that, where appropriate, the therapeutic ingredients may be used in optically pure form.

The invention provides, in another aspect, a combination comprising a compound of formula (I) or a prodrug thereof, or a pharmaceutically acceptable salt thereof. together with a $\beta_2$-adrenoreceptor agonist.

Examples of $\beta_2$-adrenoreceptor agonists include salmeterol (which may be a racemate or a single enantiomer such as the R-enantiomer), salbutamol (which may be a racemate or a single enantiomer such as the R-enantiomer), formoterol (which may be a racemate or a single diastereomer such as the R,R-diastereomer), salmefamol, fenoterol, carmoterol, etanterol, naminterol, clenbuterol, pirbuterol, flerbuterol, reproterol, bambuterol, indacaterol, terbutaline and salts thereof, for example the xinafoate (1-hydroxy-2-naphthalenecarboxylate) salt of salmeterol, the sulphate salt or free base of salbutamol or the fumarate salt of formoterol. In one embodiment the $\beta_2$-adrenoreceptor agonists are long-acting $\beta_2$-adrenoreceptor agonists, for example, compounds which provide effective bronchodilation for about 12 hours or longer. A further example of a $\beta_2$-adrenoreceptor agonist is the compound 4-{(1R)-2-[(6-{2-[(2,6-dichlorophenyl)methoxy]ethoxy}hexyl)amino]-1-hydroxyethyl}-2-(hydroxyethyl)phenol triphenylacetete (Vilanterol Trifenacetate).

Other $\beta_2$-adrenoreceptor agonists include those disclosed in WO02/066422, WO02/070490, WO02/076933, WO03/024439, WO03/072539, WO03/091204, WO04/016578, WO04/022547, WO04/037807, WO04/037773, WO04/037768, WO04/039762, WO04/039766, WO01/42193 and WO03/042160.

Examples of $\beta_2$-adrenoreceptor agonists include:
3-(4-{[6-({(2R)-2-hydroxy-2-[4-hydroxy-3-(hydroxymethyl)phenyl]ethyl}amino)hexyl]oxy}butyl)benzenesulfonamide;
3-(3-{[7-({(2R)-2-hydroxy-2-[4-hydroxy-3-hydroxymethyl)phenyl]ethyl}-amino)heptyl]oxy}propyl)benzenesulfonamide;
4-{(1R)-2-[(6-{2-[(2,6-dichlorobenzyl)oxy]ethoxy}hexyl) amino]-1-hydroxyethyl}-2-(hydroxymethyl)phenol;
4-{(1R)-2-[(6-{4-[3-(cyclopentylsulfonyl)phenyl] butoxy}hexyl)amino]-1-hydroxyethyl}-2-(hydroxymethyl)phenol;
N-[2-hydroxyl-5-[(1R)-1-hydroxy-2-[[2-4-[[(2R)-2-hydroxy-2-phenylethyl]amino]phenyl]ethyl]amino]ethyl] phenyl]formamide;
N-2{2-[4-(3-phenyl-4-methoxyphenyl)aminophenyl]ethyl}-2-hydroxy-2-(8-hydroxy-2(1H)-quinolinon-5-yl)ethylamine; and
5-[(R)-2-(2-{4-[4-(2-amino-2-methyl-propoxy)-phenylamino]-phenyl}-ethylamino)-1-hydroxy-ethyl]-8-hydroxy-1H-quinolin-2-one.

The $\beta_2$-adrenoreceptor agonist may be in the form of a salt formed with a pharmaceutically acceptable acid selected from sulphuric, hydrochloric, fumaric, hydroxynaphthoic (for example 1- or 3-hydroxy-2-naphthoic), cinnamic, substituted cinnamic, triphenylacetic, sulphamic, sulphanilic, naphthaleneacrylic, benzoic, 4-methoxybenzoic, 2- or 4-hydroxybenzoic, 4-chlorobenzoic and 4-phenylbenzoic acid.

The invention provides, in another aspect, a combination comprising a compound of formula (I) or a prodrug thereof, or a pharmaceutically acceptable salt thereof, together with a corticosteroid.

Suitable anti-inflammatory agents include corticosteroids. Examples of corticosteroids are those oral and inhaled corticosteroids and their pro-drugs which have anti-inflammatory activity. Examples include methyl prednisolone, prednisolone, dexamethasone, fluticasone propionate, 6α,9α-difluoro-11β-hydroxy-16α-methyl-17α-[(4-methyl-1,3-thiazole-5-carbonyl)oxy]-3-oxo-androsta-1,4-diene-17β-carbothioic acid S-fluoromethyl ester, 6α,9α-difluoro-17α-[(2-furanylcarbonyl)oxy]-11β-hydroxy-16α-methyl-3-oxo-androsta-1,4-diene-17β-carbothioic acid S-fluoromethyl ester (fluticasone furoate), 6α,9α-difluoro-11β-hydroxy-16α-methyl-3-oxo-17α-propionyloxy-androsta-1,4-diene-17β-carbothioic acid S-(2-oxo-tetrahydro-furan-3S-yl) ester, 6α,9α-difluoro-11β-hydroxy-16α-methyl-3-oxo-17α-(2,2,3,3-tetramethycyclopropylcarbonyl)oxy-androsta-1,4-diene-17β-carbothioic acid S-cyanomethyl ester and 6α,9α-difluoro-1,6-hydroxy-16α-methyl-17α-(1-methycyclopropylcarbonyl)oxy-3-oxo-androsta-1,4-diene-17β-carbothioic acid S-fluoromethyl ester, beclomethasone esters (for example the 17-propionate ester or the 17,21-dipropionate ester), budesonide, flunisolide, mometasone esters (for example mometasone furoate), triamcinolone acetonide, rofleponide, ciclesonide (16α,17-[[(R)-cyclohexylmethylene]bis(oxy)]-11β,21-dihydroxy-pregna-1,4-diene-3,20-dione), butixocort propionate, RPR-106541, and ST-126. In one embodiment corticosteroids include fluticasone propionate, 6α,9α-difluoro-11β-hydroxy-16α-methyl-17α-[(4-methyl-1,3-thiazole-5-carbonyl)oxy]-3-oxo-androsta-1,4-diene-17β-carbothioic acid S-fluoromethyl ester, 6α,9α-difluoro-17α-[(2-furanylcarbonyl)oxy]-11β-hydroxy-16α-methyl-3-oxo-androsta-1,4-diene-17β-carbothioic acid S-fluoromethyl ester, 6α,9α-difluoro-11β-hydroxy-16α-methyl-3-oxo-17α-(2,2,3,3-tetramethycyclopropylcarbonyl)oxy-androsta-1,4-diene-17β-carbothioic acid S-cyanomethyl ester and 6α,9α-difluoro-11β-hydroxy-16α-methyl-17α-(1-methycyclopropylcarbonyl)oxy-3-oxo-androsta-1,4-diene-17β-carbothioic acid S-fluoromethyl ester. In one embodiment the corticosteroid is 6α,9α-difluoro-17α-[(2-furanylcarbonyl)oxy]-11β-hydroxy-16α-methyl-3-oxo-androsta-1,4-diene-17β-carbothioic acid S-fluoromethyl ester.

Further examples of corticosteroids may include those disclosed in WO02/088167, WO02/100879, WO02/12265, WO02/12266, WO05/005451, WO05/005452, WO06/072599 and WO06/072600.

Non-steroidal compounds having glucocorticoid agonism that may possess selectivity for transrepression over transactivation and that may be useful in combination therapy include those disclosed in the following published patent applications and patents: WO03/082827, WO98/54159, WO04/005229, WO04/009017, WO04/018429, WO03/104195, WO03/082787, WO03/082280, WO03/059899, WO03/101932, WO02/02565, WO01/16128, WO00/66590, WO03/086294, WO04/026248, WO03/061651, WO03/08277, WO06/000401, WO06/000398, WO06/015870, WO06/108699, WO07/000,334 and WO07/054,294.

Examples of anti-inflammatory agents include non-steroidal anti-inflammatory drugs (NSAID's).

Examples of NSAID's include sodium cromoglycate, nedocromil sodium, phosphodiesterase (PDE) inhibitors (for example, theophylline, PDE4 inhibitors or mixed PDE3/PDE4 inhibitors), leukotriene antagonists, inhibitors of leukotriene synthesis (for example montelukast), iNOS inhibitors, tryptase and elastase inhibitors, beta-2 integrin antagonists and adenosine receptor agonists or antagonists (e.g. adenosine 2a agonists), cytokine antagonists (for example chemokine antagonists, such as a CCR3 antagonist) or inhibitors of cytokine synthesis, or 5-lipoxygenase inhibitors. An iNOS (inducible nitric oxide synthase inhibitor) is preferably for oral administration. Examples of iNOS inhibitors include those disclosed in WO93/13055, WO98/30537, WO02/50021, WO95/34534 and WO99/62875. Examples of CCR3 inhibitors include those disclosed in WO02/26722.

The invention thus provides, in another aspect, a combination comprising a compound of formula (I) or a prodrug thereof, or a pharmaceutically acceptable salt thereof, together with a PDE4 inhibitor.

In one embodiment the invention provides the use of the compounds of formula (I) or a pharmaceutically acceptable salt thereof in combination with a phosphodiesterase 4 (PDE4) inhibitor, especially in the case of a formulation adapted for inhalation. The PDE4-specific inhibitor useful in this aspect of the invention may be any compound that is known to inhibit the PDE4 enzyme or which is discovered to act as a PDE4 inhibitor, and which are only PDE4 inhibitors, not compounds which inhibit other members of the PDE family, such as PDE3 and PDE5, as well as PDE4.

Compounds include cis-4-cyano-4-(3-cyclopentyloxy-4-methoxyphenyl)cyclohexan-1-carboxylic acid, 2-carbomethoxy-4-cyano-4-(3-cyclopropylmethoxy-4-difluoromethoxyphenyl)cyclohexan-1-one and cis-[4-cyano-4-(3-cyclopropylmethoxy-4-difluoromethoxyphenyl)cyclohexan-1-ol]. Also, cis-4-cyano-4-[3-(cyclopentyloxy)-4-methoxyphenyl]cyclohexane-1-carboxylic acid (also known as cilomilast) and its salts, esters, pro-drugs or physical forms, which is described in U.S. Pat. No. 5,552,438 issued 3 Sep., 1996; this patent and the compounds it discloses are incorporated herein in full by reference.

Other compounds include AWD-12-281 from Elbion (Hofgen, N. et al. 15th EFMC Int Symp Med Chem (Sep. 6-10, Edinburgh) 1998, Abst P.98; CAS reference No. 247584020-9); a 9-benzyladenine derivative nominated NCS-613 (INSERM); D-4418 from Chiroscience and Schering-Plough; a benzodiazepine PDE4 inhibitor identified as CI-1018 (PD-168787) and attributed to Pfizer; a benzodioxole derivative disclosed by Kyowa Hakko in WO99/16766; K-34 from Kyowa Hakko; V-11294A from Napp (Landells, L. J. et al. Eur Resp J [Annu Cong Eur Resp Soc (Sep. 19-23, Geneva) 1998] 1998, 12 (Suppl. 28): Abst P2393); roflumilast (CAS reference No 162401-32-3) and a phthalazinone (WO99/47505, the disclosure of which is hereby incorporated by reference) from Byk-Gulden; Pumafentrine, (−)-p-[(4aR*,10bS*)-9-ethoxy-1,2,3,4,4a,10b-hexahydro-8-methoxy-2-methylbenzo[c][1,6]naphthyridin-6-yl]-N,N-diisopropyl-benzamide which is a mixed PDE3/PDE4 inhibitor which has been prepared and published on by Byk-Gulden, now Altana; arofylline under development by Almirall-Prodesfarma; VM554/UM565 from Vernalis; or T-440 (Tanabe Seiyaku; Fuji, K. et al. J Pharmacol Exp Ther, 1998, 284(1): 162), and T2585.

Further compounds are disclosed in the published international patent application WO04/024728 (Glaxo Group Ltd), WO04/056823 (Glaxo Group Ltd) and WO04/103998 (Glaxo Group Ltd).

The invention provides, in another aspect, a combination comprising a compound of formula (I) or a prodrug thereof or a pharmaceutically acceptable salt thereof together with an anticholinergic.

Examples of anticholinergic agents are those compounds that act as antagonists at the muscarinic receptors, in particular those compounds which are antagonists of the $M_1$ or $M_3$ receptors, dual antagonists of the $M_1/M_3$ or $M_2/M_3$, receptors or pan-antagonists of the $M_1/M_2/M_3$ receptors. Exemplary compounds for administration via inhalation include ipratropium (for example, as the bromide, CAS 22254-24-6, sold under the name Atrovent), oxitropium (for example, as the bromide, CAS 30286-75-0) and tiotropium (for example, as the bromide, CAS 136310-93-5, sold under the name Spiriva). Also of interest are revatropate (for example, as the hydrobromide, CAS 262586-79-8) and LAS-34273 which is disclosed in WO01/04118. Exemplary compounds for oral administration include pirenzepine (CAS 28797-61-7), darifenacin (CAS 133099-04-4, or CAS 133099-07-7 for the hydrobromide sold under the name Enablex), oxybutynin (CAS 5633-20-5, sold under the name Ditropan), terodiline (CAS 15793-40-5), tolterodine (CAS 124937-51-5, or CAS 124937-52-6 for the tartrate, sold under the name Detrol), otilonium (for example, as the bromide, CAS 26095-59-0, sold under the name Spasmomen), trospium chloride (CAS 10405-02-4) and solifenacin (CAS 242478-37-1, or CAS 242478-38-2 for the succinate also known as YM-905 and sold under the name Vesicare).

Other anticholinergic agents include compounds which are disclosed in U.S. patent application 60/487,981 including, for example:
(3-endo)-3-(2,2-di-2-thienylethenyl)-8,8-dimethyl-8-azoniabicyclo[3.2.1]octane bromide;
(3-endo)-3-(2,2-diphenylethenyl)-8,8-dimethyl-8-azoniabicyclo[3.2.1]octane bromide;
(3-endo)-3-(2,2-diphenylethenyl)-8,8-dimethyl-8-azoniabicyclo[3.2.1]octane 4-methylbenzenesulfonate;
(3-endo)-8,8-dimethyl-3-[2-phenyl-2-(2-thienyl)ethenyl]-8-azoniabicyclo[3.2.1]octane bromide; and/or
(3-endo)-8,8-dimethyl-3-[2-phenyl-2-(2-pyridinyl)ethenyl]-8-azoniabicyclo[3.2.1]octane bromide.

Further anticholinergic agents include compounds which are disclosed in U.S. patent application 60/511,009 including, for example:
(endo)-3-(2-methoxy-2,2-di-thiophen-2-yl-ethyl)-8,8-dimethyl-8-azonia-bicyclo[3.2.1]octane iodide;
3-((endo)-8-methyl-8-aza-bicyclo[3.2.1]oct-3-yl)-2,2-diphenyl-propionitrile;
(endo)-8-methyl-3-(2,2,2-triphenyl-ethyl)-8-aza-bicyclo[3.2.1]octane;
3-((endo)-8-methyl-8-aza-bicyclo[3.2.1]oct-3-yl)-2,2-diphenyl-propionamide;
3-((endo)-8-methyl-8-aza-bicyclo[3.2.1]oct-3-yl)-2,2-diphenyl-propionic acid;
(endo)-3-(2-cyano-2,2-diphenyl-ethyl)-8,8-dimethyl-8-azonia-bicyclo[3.2.1]octane iodide;
(endo)-3-(2-cyano-2,2-diphenyl-ethyl)-8,8-dimethyl-8-azonia-bicyclo[3.2.1]octane bromide;
3-((endo)-8-methyl-8-aza-bicyclo[3.2.1]oct-3-yl)-2,2-diphenyl-propan-1-ol;
N-benzyl-3-((endo)-8-methyl-8-aza-bicyclo[3.2.1]oct-3-yl)-2,2-diphenyl-propionamide;
(endo)-3-(2-carbamoyl-2,2-diphenyl-ethyl)-8,8-dimethyl-8-azonia-bicyclo[3.2.1]octane iodide;
1-benzyl-3-[3-((endo)-8-methyl-8-aza-bicyclo[3.2.1]oct-3-yl)-2,2-diphenyl-propyl]-urea;
1-ethyl-3-[3-((endo)-8-methyl-8-aza-bicyclo[3.2.1]oct-3-yl)-2,2-diphenyl-propyl]-urea;
N-[3-((endo)-8-methyl-8-aza-bicyclo[3.2.1]oct-3-yl)-2,2-diphenyl-propyl]-acetamide;
N-[3-((endo)-8-methyl-8-aza-bicyclo[3.2.1]oct-3-yl)-2,2-diphenyl-propyl]-benzamide;
3-((endo)-8-methyl-8-aza-bicyclo[3.2.1]oct-3-yl)-2,2-di-thiophen-2-yl-propionitrile;
(endo)-3-(2-cyano-2,2-di-thiophen-2-yl-ethyl)-8,8-dimethyl-8-azonia-bicyclo[3.2.1]octane iodide;
N-[3-((endo)-8-methyl-8-aza-bicyclo[3.2.1]oct-3-yl)-2,2-diphenyl-propyl]-benzenesulfonamide;
[3-((endo)-8-methyl-8-aza-bicyclo[3.2.1]oct-3-yl)-2,2-diphenyl-propyl]-urea;
N-[3-((endo)-8-methyl-8-aza-bicyclo[3.2.1]oct-3-yl)-2,2-diphenyl-propyl]-methanesulfonamide; and/or
(endo)-3-{2,2-diphenyl-3-[(1-phenyl-methanoyl)-amino]-propyl}-8,8-dimethyl-8-azonia-bicyclo[3.2.1]octane bromide.

Further compounds include:
(endo)-3-(2-methoxy-2,2-di-thiophen-2-yl-ethyl)-8,8-dimethyl-8-azonia-bicyclo[3.2.1]octane iodide;
(endo)-3-(2-cyano-2,2-diphenyl-ethyl)-8,8-dimethyl-8-azonia-bicyclo[3.2.1]octane iodide;
(endo)-3-(2-cyano-2,2-diphenyl-ethyl)-8,8-dimethyl-8-azonia-bicyclo[3.2.1]octane bromide;
(endo)-3-(2-carbamoyl-2,2-diphenyl-ethyl)-8,8-dimethyl-8-azonia-bicyclo[3.2.1]octane iodide;

(endo)-3-(2-cyano-2,2-di-thiophen-2-yl-ethyl)-8,8-dimethyl-8-azonia-bicyclo[3.2.1]octane iodide; and/or
(endo)-3-{2,2-diphenyl-3-[(1-phenyl-methanoyl)-amino]-propyl}-8,8-dimethyl-8-azonia-bicyclo[3.2.1]octane bromide.

The invention thus provides, in another aspect, a combination comprising a compound of formula (I) or a prodrug thereof, or a pharmaceutically acceptable salt thereof, together with an antihistamine.

In one embodiment the invention provides a combination comprising a compound of formula (I), or a pharmaceutically acceptable salt thereof, together with an H1 antagonist. Examples of H1 antagonists include, without limitation, amelexanox, astemizole, azatadine, azelastine, acrivastine, brompheniramine, cetirizine, levocetirizine, efletirizine, chlorpheniramine, clemastine, cyclizine, carebastine, cyproheptadine, carbinoxamine, descarboethoxyloratadine, doxylamine, dimethindene, ebastine, epinastine, efletirizine, fexofenadine, hydroxyzine, ketotifen, loratadine, levocabastine, mizolastine, mequitazine, mianserin, noberastine, meclizine, norastemizole, olopatadine, picumast, pyrilamine, promethazine, terfenadine, tripelennamine, temelastine, trimeprazine and triprolidine, particularly cetirizine, levocetirizine, efletirizine and fexofenadine. In a further embodiment the invention provides a combination comprising a compound of formula (I), or a pharmaceutically acceptable salt thereof, together with an H3 antagonist (and/or inverse agonist). Examples of H3 antagonists include, for example, those compounds disclosed in WO2004/035556 and in WO2006/045416. Other histamine receptor antagonists which may be used in combination with the compounds of formula (I), or a pharmaceutically acceptable salt thereof, include antagonists (and/or inverse agonists) of the H4 receptor, for example, the compounds disclosed in Jablonowski et al., *J. Med. Chem.* 46:3957-3960 (2003).

The invention thus provides, in another aspect, a combination comprising a compound of formula (I) or a pharmaceutically acceptable salt thereof together with another calcium release activated calcium channel inhibitor.

The individual compounds of such combinations may be administered either sequentially or simultaneously in separate or combined pharmaceutical formulations.

In one embodiment, the individual compounds will be administered simultaneously in a combined pharmaceutical composition. Appropriate doses of known therapeutic agents will be readily appreciated by those skilled in the art.

The combinations referred to above may conveniently be presented for use in the form of a pharmaceutical composition and thus pharmaceutical compositions comprising a combination as defined above together with one or more pharmaceutically acceptable carrier, diluents and/or excipient represent a further aspect of the invention.

The individual compounds of such combinations may be administered either sequentially in separate pharmaceutical compositions as well as simultaneously in combined pharmaceutical compositions. Additional therapeutically active ingredients may be suspended in the composition together with a compound of formula (I). Appropriate doses of known therapeutic agents will be readily appreciated by those skilled in the art.

The compounds of the invention may be prepared by the methods described below or by similar methods. Thus the following Intermediates and Examples serve to illustrate the preparation of the compounds of the invention, and are not to be considered as limiting the scope of the invention in any way.

EXAMPLES

General

Mass directed autopreparative HPLC was undertaken under the conditions given below. The UV detection was an averaged signal from wavelength of 210 nm to 350 nm and mass spectra were recorded on a mass spectrometer using alternate-scan positive and negative mode electrospray ionization.

Method A:
Method A was conducted on a Supelcosil ABZ+Plus column (typically 150 mm×30 mm i.d. 5 μm packing diameter) at ambient temperature. The solvents employed were:
A=0.1% v/v solution of formic acid in water
B=MeCN:Water 95:5+0.05% formic acid Method B:
Method B was conducted on a Sunfire $C_{18}$ column (typically 150 mm×30 mm i.d. 5 μm packing diameter) at ambient temperature. The solvents employed were:
A=0.1% v/v solution of Formic acid in water
B=0.1% v/v solution of Formic acid in acetonitrile.

Method C:
Method C was conducted on a Sunfire $C_{18}$ column (typically 150 mm×30 mm i.d. 5 μm packing diameter) at ambient temperature. The solvents employed were:
A=0.1% v/v solution of trifluoroacetic acid in water
B=0.1% v/v solution of trifluoroacetic acid in acetonitrile.

Method D:
Method D was conducted on a Sunfire $C_{18}$ column (typically 100 mm×19 mm i.d. 5 μm packing diameter) at ambient temperature. The solvents employed were:
A=0.1% v/v solution of trifluoroacetic acid in water
B=0.1% v/v solution of trifluoroacetic acid in acetonitrile.

Method E:
Method E was conducted on an XBridge $C_{18}$ column (typically 150 mm×19 mm i.d. 5 μm packing diameter) at ambient temperature. The solvents employed were:
A=10 mM aqueous ammonium bicarbonate adjusted to pH 10 with ammonia solution.
B=acetonitrile.

Experimental Details

Experimental details of LC-MS systems 1-8 as referred to herein are as follows:
System 1
Column: 3.3 cm×4.6 mm ID, 3 μm ABZ+PLUS from Supelco®
Flow Rate: 3 mL/min.
Temp.: RT
UV detection range: 215 to 330 nm
Mass spectrum: Recorded on a mass spectrometer using alternative-scan positive and negative mode electrospray ionisation.
Solvents: A: 0.1% formic acid+10 mM ammonium acetate
B: 95% acetonitrile+0.05% formic acid

|  | Time (min.) | A % | B % |
|---|---|---|---|
| Gradient: | 0 | 100 | 0 |
|  | 0.7 | 100 | 0 |
|  | 4.2 | 0 | 100 |
|  | 4.6 | 0 | 100 |
|  | 4.8 | 100 | 0 |

System 2
Column: 50 mm×2.1 mm ID, 1.7 μm Acquity HPLC BEH $C_{18}$
Flow Rate: 1 mL/min.
Temp.: 40° C.
UV Detection Range: 220 to 330 nm
Mass spectrum: Recorded on a mass spectrometer using alternative-scan positive and negative mode electrospray ionisation.
Solvents: A: 0.1% formic acid+10 mM ammonium acetate
B: 95% acetonitrile+0.05% formic acid

|  | Time (min.) | A % | B % |
|---|---|---|---|
| Gradient: | 0 | 97 | 3 |
|  | 0.1 | 97 | 3 |
|  | 1.4 | 0 | 100 |
|  | 1.9 | 0 | 100 |
|  | 2 | 97 | 3 |

System 3
Column: 50 mm×2.1 mm ID, 1.7 μm Acquity HPLC BEH $C_{18}$
Flow Rate: 1 mL/min.
Temp.: 40° C.
UV Detection Range: 210 to 350 nm
Mass spectrum: Recorded on a mass spectrometer using alternative-scan positive and negative mode electrospray ionisation.
Solvents: A: 0.1% v/v formic acid in water
B: 0.1% v/v formic acid in acetonitrile

|  | Time (min.) | A % | B % |
|---|---|---|---|
| Gradient: | 0 | 97 | 3 |
|  | 1.5 | 0 | 100 |
|  | 1.9 | 0 | 100 |
|  | 2.0 | 97 | 3 |

System 4
Column: 30 mm×4.6 mm ID, 3.5 μm Sunfire $C_{18}$ column
Flow Rate: 3 mL/min.
Temp.: 30° C.
UV Detection Range: 210 to 350 nm
Mass spectrum: Recorded on a mass spectrometer using alternative-scan positive and negative mode electrospray ionisation.
Solvents: A: 0.1% v/v solution of formic acid in water
B: 0.1% v/v solution of formic acid in acetonitrile

|  | Time (min.) | A % | B % |
|---|---|---|---|
| Gradient: | 0 | 97 | 3 |
|  | 0.1 | 97 | 3 |
|  | 4.2 | 0 | 100 |
|  | 4.8 | 0 | 100 |
|  | 4.9 | 97 | 3 |
|  | 5.0 | 97 | 3 |

System 5
Column: 50 mm×2.1 mm ID, 1.7 μm Acquity HPLC BEH $C_{18}$
Flow Rate: 1 mL/min.
Temp.: 40° C.
UV Detection Range: 220 to 330 nm
Mass spectrum: Recorded on a mass spectrometer using alternative-scan positive and negative mode electrospray ionisation.
Solvents: A: 0.1% v/v solution of trifluoroacetic acid in water
B: 0.1% v/v solution of trifluoroacetic acid in acetonitrile

|  | Time (min.) | A % | B % |
|---|---|---|---|
| Gradient: | 0 | 97 | 3 |
|  | 1.5 | 0 | 100 |
|  | 1.9 | 0 | 100 |
|  | 2.0 | 97 | 3 |

System 6
Column: 30 mm×4.6 mm ID, 3.5 μm Sunfire $C_{18}$ column
Flow Rate: 3 mL/min.
Temp.: 30° C.
UV Detection Range: 210 to 350 nm
Mass spectrum: Recorded on a mass spectrometer using alternative-scan positive and negative mode electrospray ionisation.
Solvents: A: 0.1% v/v solution of trifluoroacetic acid in water
B: 0.1% v/v solution of trifluoroacetic acid in acetonitrile

|  | Time (min.) | A % | B % |
|---|---|---|---|
| Gradient: | 0 | 97 | 3 |
|  | 0.1 | 97 | 3 |
|  | 4.2 | 0 | 100 |
|  | 4.8 | 0 | 100 |
|  | 4.9 | 97 | 3 |
|  | 5.0 | 97 | 3 |

System 7
Column: 50 mm×2.1 mm ID, 1.7 μm Acquity HPLC BEH $C_{18}$
Flow Rate: 1 mL/min.
Temp.: 40° C.
UV Detection Range: 220 to 350 nm
Mass spectrum: Recorded on a mass spectrometer using alternative-scan positive and negative mode electrospray ionisation.
Solvents: A: 10 mM ammonium bicarbonate in water adjusted to pH10 with ammonia solution
B: Acetonitrile

|  | Time (min.) | A % | B % |
|---|---|---|---|
| Gradient: | 0 | 99 | 1 |
|  | 1.5 | 3 | 97 |
|  | 1.9 | 3 | 97 |
|  | 2.0 | 0 | 100 |

System 8
Column: 50 mm×4.6 mm ID, 3.5 μm XBridge $C_{18}$ column
Flow Rate: 3 mL/min.
Temp.: 30° C.
UV Detection Range: 210 to 350 nm
Mass spectrum: Recorded on a mass spectrometer using alternative-scan positive and negative mode electrospray ionisation.

Solvents: A: 10 mM ammonium bicarbonate in water adjusted to pH10 with ammonia solution
B: Acetonitrile

|  | Time (min.) | A % | B % |
|---|---|---|---|
| Gradient: | 0 | 99 | 1 |
|  | 0.1 | 99 | 1 |
|  | 4.0 | 3 | 97 |
|  | 5.0 | 3 | 97 |

Abbreviations:
The following list provides definitions of certain abbreviations as used herein. It will be appreciated that the list is not exhaustive, but the meaning of those abbreviations not herein below defined will be readily apparent to those skilled in the art.
Ac (acetyl);
Bu (butyl);
nBu (n-butyl);
tert-Bu (t-butyl);
DCM (dichloromethane);
DIPEA (N,N-Diisopropylethylamine);
DMF (N,N-dimethylformamide);
DMSO (dimethylsulfoxide);
Et (ethyl);
EtOAc (ethyl acetate);
g (grams);
h (hours)
HATU (2-(7-aza-1H-benzotriazole-1-yl)-1,1,3,3-tetramethyluronium hexafluorophosphate)
HCl (Hydrochloric acid)
Hz (Hertz);
L (liters);
LCMS (liquid chromatography-mass spectrometry)
LDA (lithium diisopropylamide);
M (molar);
MDAP (mass directed autopreparative HPLC);
Me (methyl);
MeOH (methanol);
mg (milligrams);
MHz (megahertz);
min (minutes);
ml (milliliters);
µl (microliters);
mM (millimolar);
mmol (millimoles);
mol (moles);
NBS (N-Bromosuccinimide)
PFA (perfluoroalkoxy)
Ph (phenyl);
$^i$Pr (isopropyl);
Rf (retention factor)
Si (Silica)
SPE (solid phase extraction);
TBTU (O-(benzotriazol-1-yl)-N,N,N',N'-tetramethyluronium tetrafluoroborate);
TEA (triethylamine);
TFA (trifluoroacetic acid);
THF (tetrahydrofuran);
TLC (thin layer chromatography);
TMS (trimethylsilyl);
All references to ether are to diethyl ether and brine refers to a saturated aqueous solution of NaCl.

The names of the described Examples have been obtained using the compound naming programme "ACD Name Pro 6.02".

Intermediate 1

[2-(Butyloxy)phenyl]methanol

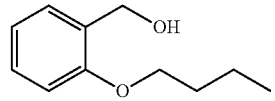

A solution of 2-(hydroxymethyl)phenol (1.24 g, 10 mmol, Aldrich) and 1-bromobutane (1.18 ml, 11 mmol, Acros) in ethanol (5 ml) (total volume approximately 7 ml) was mixed in a flow reactor (Vapourtec R4, 30 ml PFA tubing, 110° C.) with a solution of aqueous NaOH (2N, 5 ml, 10 mmol) in water (2 ml). The reagents were each pumped at 0.5 ml/min, giving a reaction time of 30 minutes. After the 30 ml reactor, the solution passed through a second "cooling" reactor (5 ml) at 50° C. At the reactor output, a 250 psi back pressure regulator was used. After all starting solutions had been consumed, the system was purged with an additional 70 ml solvents (1:1, ethanol:water). The collected material was concentrated in vacuo. The residue was partitioned between water and EtOAc, and treated with saturated aqueous sodium bicarbonate solution. The aqueous phase was further extracted with EtOAc, and the combined organic extracts were dried (hydrophobic frit) and concentrated in vacuo. The residue was purified on silica (100 g) using 0-100% ethyl acetate-cyclohexane. The appropriate fractions were combined and concentrated in vacuo to give the title compound (1.4 g); LCMS: (System 4) $t_{RET}$=2.51 min, no MH$^+$ detected.

Intermediate 2

1-(Bromomethyl)-2-(butyloxy)benzene

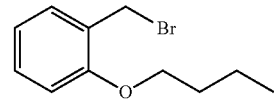

A solution of 2-(butyloxy)phenyl]methanol (for a preparation see Intermediate 1)(6 g, 33.3 mmol) in DCM (30 ml) (total solution volume 34 ml) was mixed in a flow reactor (Vapourtec R4, 35 ml PFA tubing reactor, maintained at 25° C.) with a solution of phosphorus tribromide in DCM (1 molar, 33.6 ml, 33.6 mmol, Aldrich). The solutions were each pumped at 0.583 ml/min, giving a reaction time of 30 min. The output was collected into a stirred flask of water, which was subsequently treated with aqueous sodium bicarbonate (100 ml). The aqueous layer was extracted with DCM (×2), and the combined organic extracts were dried (hydrophobic frit) and concentrated in vacuo to give the title compound as an opaque yellow oil (6.8 g, 84%);

$^1$H NMR (DMSO-d6) 7.38 (1H, dd, J 7.5, 2 Hz), 7.29 (1H, ddd, J 9, 7.5, 2 Hz), 7.00 (1H, d, J=9 Hz), 6.90 (1H, td, J 7.5, 1 Hz), 4.63 (2H, s), 4.03 (2H, t, J=6.5 Hz), 1.78-1.66 (2H, m), 1.56-1.44 (2H, m), 0.94 (3H, t, J=7.5 Hz).

Intermediate 3

1-(Bromomethyl)-2-(phenylmethyl)benzene

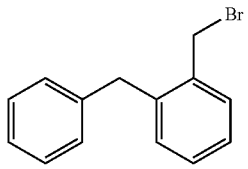 [SMILES: BrCc1ccccc1Cc1ccccc1]

2-(Phenylmethyl)phenyl]methanol (393 mg, 1.98 mmol, Acros) was dissolved in DCM (5 ml) and cooled to −10° C. (external acetone/CO$_2$ bath) under nitrogen. A solution of phosphorous tribromide (190 µl, 2.02 mmol, Aldrich) in DCM (5 ml) was added dropwise to the stirred solution under nitrogen. The reaction mixture was stirred under nitrogen and allowed to warm slowly to ambient temperature overnight. The reaction mixture was re-cooled in an ice-water bath and quenched by the addition of saturated aqueous sodium hydrogen carbonate solution (5 ml) with stirring. The layers were separated and the aqueous layer was washed with DCM (2×10 ml). The combined DCM extracts were dried (MgSO$_4$) and concentrated to give the title compound as an oil, which became a pale pink crystalline solid on standing (466 mg); LCMS: (System 4) $t_{RET}$=3.22 min, no MH$^+$ detected.

Intermediate 4

2-Chloro-6-{[(methyloxy)methyl]oxy}benzoic acid

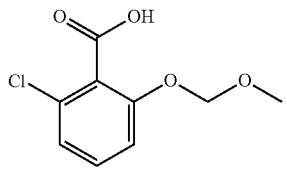

To a solution of 3-chlorophenol (8 ml, 77 mmol, ABCR) in DCM (120 ml) was added dimethoxymethane (32 ml, 362 mmol, Aldrich) and then p-toluenesulphonic acid (0.164 g, 0.952 mmol, Alfa Aesar). The solution was heated to reflux under nitrogen using a Soxhlet apparatus containing 3A activated molecular sieves (approximately 20 g)* for 24 h. *The 3A molecular sieves were replaced after 6 h. Approximately a quarter of the reaction mixture was applied to a 70 g aminopropyl cartridge (prewashed with methanol). The cartridge was eluted with methanol (1-2 column volumes) and several fractions collected. Appropriate fractions were combined (TLC 50:50 DCM in cyclohexane) and the solvent removed in vacuo to give 1-chloro-3-{[(methyloxy)methyl]oxy}benzene as a colourless mobile oil (1.66 g). The remaining reaction mixture was applied evenly to 3×70 g aminopropyl cartridges (pre-washed with methanol). The cartridges were eluted with methanol (1-2 column volumes) and several fractions collected. Appropriate fractions were combined (TLC 50:50 DCM in cyclohexane) and the solvent removed in vacuo to leave a colourless mobile oil (first batch). The mixed fractions were combined and the solvent removed in vacuo to leave a colourless mobile oil. The residue from the mixed fractions was applied to a 70 g aminopropyl cartridge (pre-washed with methanol) and eluted with methanol. Appropriate fractions were combined (TLC 50:50 DCM in cyclohexane) and added to the first batch. The solvent was removed in vacuo to give another batch of 1-chloro-3-{[(methyloxy)methyl]oxy}benzene as a colourless mobile oil (5.27 g). To THF (20 ml) under nitrogen at 0° C. was added 1.6 M n-butyllithium in hexanes (18.1 ml, 29.0 mmol, Aldrich). To the solution at −60° C. was added a solution of 2,2,6,6-tetramethylpiperidine (4.90 ml, 29.0 mmol, Alfa Aesar) in THF (5 ml) and then a solution of 1-chloro-3-{[(methyloxy)methyl]oxy}benzene (5.01 g, 29.0 mmol) in THF (10 ml). The temperature was maintained below −50° C. during the addition. The solution was stirred at −60° C. to −70° C. for 1 h. To the solution was added a large excess of freshly ground solid carbon dioxide and the mixture allowed to warm to ambient temperature. The reaction mixture was diluted with water (100 ml) and diethyl ether (130 ml). The phases were separated and aqueous phase carefully acidified to pH1 using concentrated HCl. The suspension was extracted with dichloromethane (3×40 ml). The solvent was removed in vacuo to give the title compound as a white solid (4.36 g);
LCMS: (System 1) (M-H)$^-$=215, $t_{RET}$=1.98 min.

Intermediate 5

2-Chloro-6-hydroxybenzoic acid

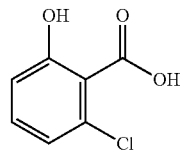 [SMILES: O=C(O)c1c(O)cccc1Cl]

To a solution of 2-chloro-6-{[(methyloxy)methyl]oxy}benzoic acid (for a preparation see Intermediate 4)(2 g, 9.23 mmol) in THF (20 ml) was added 6 M aqueous HCl (20 ml, 120 mmol). The solution was stirred at ambient temperature for 3 h. The solution was partitioned between ethyl acetate (150 ml) and water (30 ml). The phases were separated and the organic extract washed with water (25 ml). The organic extract was dried (MgSO$_4$), filtered and the solvent removed in vacuo to give the title compound as a white solid (1.54 g); LCMS: (System 1) (M-H)$^-$=171, $t_{RET}$=3.26 min.

Intermediate 6

3-Chloro-2-(hydroxymethyl)phenol

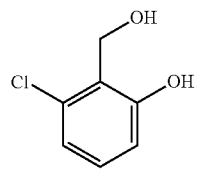

To a solution of 2-chloro-6-hydroxybenzoic acid (for a preparation see Intermediate 5)(1.45 g, 8.39 mmol) in THF (20 ml) at ambient temperature under nitrogen was added 1 M borane-tetrahydrofuran complex (16 ml, 16.0 mmol, Aldrich). The solution was stirred at ambient temperature for 10-15 min and then heated to 80° C. for 1 h. The resulting suspension was allowed to cool to ambient temperature and quenched with methanol (10 ml). The resulting solution was heated to 80° C. for 30 min and at ambient temperature overnight. The solvent was removed in vacuo and the oil dried under high vacuum to give the title compound as a solid (1.36 g); LCMS: (System 1) (M-H)$^-$=157, $t_{RET}$=2.22 min.

Intermediate 7

{2-Chloro-6-[(phenylmethyl)oxy]phenyl}methanol

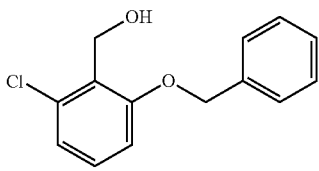

To a solution of 3-chloro-2-(hydroxymethyl)phenol (for a preparation see Intermediate 6)(1.37 g, 8.62 mmol) in absolute ethanol (30 ml) was added 2 M sodium hydroxide (4.74 ml, 9.49 mmol) and then benzyl bromide (1.03 ml, 8.62 mmol, Aldrich). The solution was stirred at ambient temperature for 3 days under nitrogen. The solvent was removed under reduced pressure to leave an aqueous suspension. The aqueous residue was partitioned between 2 M aqueous sodium hydroxide (40 ml) and ethyl acetate (60 ml). The phases were separated and the aqueous phase extracted with ethyl acetate (40 ml). The combined organic extracts were dried (MgSO$_4$), filtered and the solvent removed under reduced pressure to give the title compound as a very pale brown oil (1.87 g); LCMS: (System 1) (M-H)$^-$=247, $t_{RET}$=3.20 min.

Intermediate 8

2-(Bromomethyl)-1-chloro-3-[(phenylmethyl)oxy]benzene

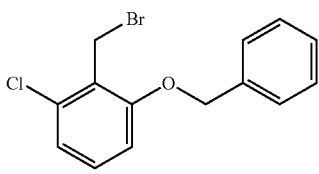 [SMILES: Clc1cccc(OCc2ccccc2)c1CBr]

To a solution of {2-chloro-6-[(phenylmethyl)oxy]phenyl}methanol (for a preparation see Intermediate 7) (1.1 g, 4.42 mmol) in DCM (12 ml) at 0-5° C. under nitrogen was added dropwise a solution of phosphorus tribromide (0.417 ml, 4.42 mmol, Aldrich) in DCM (3 ml). The solution was allowed to warm to ambient temperature and stirred for 3 h. The solution in an ice-water bath was diluted with dichloromethane (40 ml) and then treated with saturated aqueous sodium hydrogen carbonate (20 ml). The phases were separated and the organic extract dried (MgSO$_4$), filtered and the solvent removed in vacuo to give the title compound as a yellow oil (0.829 g); LCMS: (System 1) (M-H)$^-$=311, $t_{RET}$=3.84 min.

Intermediate 9

2,6-Difluoro-N-(1H-pyrazol-3-yl)benzamide

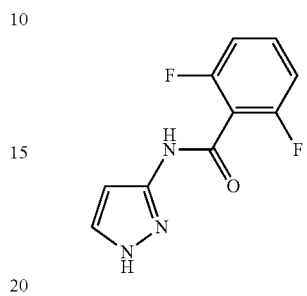

To a stirred solution of 3-aminopyrazole (60 g, 0.722 mol, ABCR) in acetonitrile (500 ml) at 0° C. (ice/brine bath) was added, dropwise, triethylamine (201 ml, 1.44 mol) at such a rate to keep the temperature below 5° C. The reaction mixture was stirred at 0° C. for 0.5 h then a solution of 2,6-difluorobenzoyl chloride (127.5 g, 0.722 mol, Aldrich) in acetonitrile (200 ml) was added over approximately 1 h, keeping the temperature between 0-7° C. The reaction was allowed to warm to room temperature and stirred overnight. The reaction mixture was concentrated under reduced pressure and the residue partitioned between water (250 ml) and EtOAc (500 ml). Some solid formed at the interface, this was filtered off and turned out to be product—combined with isolated product at the end for drying. The aqueous layer was separated and extracted with EtOAc (2×500 ml). The combined organics were washed with water (500 ml), dried (MgSO$_4$), charcoaled, filtered and concentrated under reduced pressure to give a yellow solid. The combined residues were triturated with DCM (500 ml) then water (100 ml) and the solid collected by filtration and dried on the sinter, then under high vacuum overnight to give the title compound as a white solid (108.5 g);

$^1$H NMR (DMSO-d6) 12.5 (1H, s), 11.22 (1H, s), 7.66 (1H, s), 7.61-7.47 (1H, m), 7.26-7.16 (2H, m), 6.61 (1H, s).

mp 201-204° C.

Intermediate 10

N-[1-({2-Chloro-6-[(phenylmethyl)oxy]phenyl}methyl)-1H-pyrazol-3-yl]-2,6-difluorobenzamide

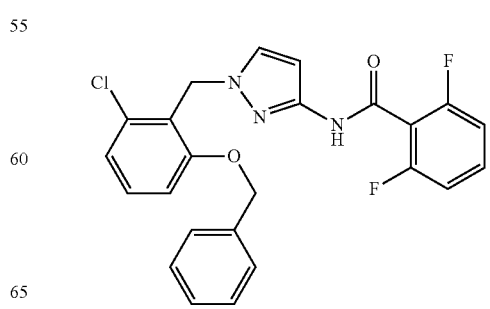

To a mixture of 2,6-difluoro-N-(1H-pyrazol-3-yl)benzamide (for a preparation see Intermediate 9) (0.360 g, 1.61 mmol) and potassium carbonate (0.308 g, 2.23 mmol) was added a solution 2-(bromomethyl)-1-chloro-3-[(phenylmethyl)oxy]benzene (for a preparation see Intermediate 8)(0.50 g, 1.61 mmol) in DMF (5 ml). The suspension was stirred overnight at ambient temperature. The suspension was partitioned between ethyl acetate (30 ml) and water (30 ml). The phases were separated and the organic phase washed with ethyl acetate (30 ml). The combined organic extracts were washed with brine (30 ml) and the solvent removed in vacuo. The residue was loaded in dichloromethane and purified on silica 50 g using 0-50% ethyl acetate-cyclohexane. The appropriate fractions were combined and evaporated in vacuo to give the title compound as a white solid (0.212 g); LCMS: (System 1) MH$^+$=455, $t_{RET}$=3.59 min.

Intermediate 11

N-{1-[(2-Chloro-6-hydroxyphenyl)methyl]-1H-pyrazol-3-yl}-2,6-difluorobenzamide

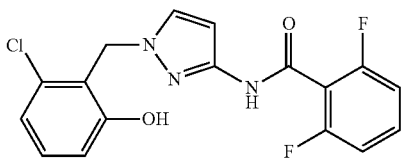 [SMILES: O=C(Nc1ccn(Cc2c(O)cccc2Cl)n1)c1c(F)cccc1F]

A solution of N-[1-({2-chloro-6-[(phenylmethyl)oxy]phenyl}methyl)-1H-pyrazol-3-yl]-2,6-difluorobenzamide (for a preparation see Intermediate 10)(0.148 g, 0.326 mmol) in ethyl acetate (20 ml) was hydrogenated using an H-cube (settings: 20° C., 1 bar, 1 ml/min flow rate) and 5% Pd/C CatCart 30 as the catalyst. The solution was hydrogenated again using an H-cube (settings: 20° C., 1 bar, 1 ml/min flow rate) and 10% Pd/C CatCart 30 as the catalyst. The solvent was removed in vacuo to give the title compound as a colourless gum (70 mg); LCMS: (System 1) MH$^+$=364, $t_{RET}$=3.14 min.

Intermediate 12

4-Chloro-3-(hydroxymethyl)phenol

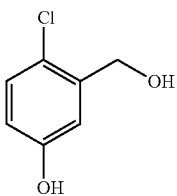

To a solution of 2-chloro-5-hydroxybenzoic acid (2.96 g, 17.2 mmol, Apin) in THF (60 ml) under nitrogen was slowly added 1 M borane in THF (30 ml, 30.0 mmol). The suspension was stirred for 20 minutes at ambient temperature. The mixture was refluxed at 80° C., under nitrogen for 3 h. The reaction mixture was allowed to cool to ambient temperature then carefully quenched using methanol (20 ml). The mixture was then refluxed for a further 1 h at 80° C. under nitrogen. The solvent was removed in vacuo and left under high pressure vacuum overnight to give the title compound as a cloudy gum (3.38 g); LCMS: (System 4) (M-H)-=157, $t_{RET}$=1.50 min.

Intermediate 13

N-{1-[(2-Chloro-5-hydroxyphenyl)methyl]-1H-pyrazol-3-yl}-2,6-difluorobenzamide

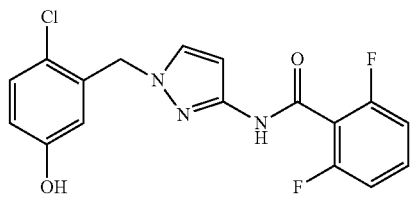 [SMILES: O=C(Nc1ccn(Cc2cc(O)ccc2Cl)n1)c1c(F)cccc1F]

A solution of N-[1-({2-chloro-5-[(phenylmethyl)oxy]phenyl}methyl)-1H-pyrazol-3-yl]-2,6-difluorobenzamide (for a preparation see Example 5)(2.44 g, 5.38 mmol) in ethyl acetate (50 ml) was added to 10% palladium on carbon (wet) (0.585 g, 0.275 mmol) under vacuum. The mixture was hydrogenated at ambient temperature for 2 h. A further amount of 10% palladium on carbon wet (0.79 g) was added and the reaction was stirred for a further 2 h. The reaction mixture was filtered using a 10 g celite cartridge. The filtrate was concentrated in vacuo to leave a brown solid (2.01 g). The residue was preabsorbed on florosil and purified on silica (100 g×2) using 0-100% ethyl acetate-cyclohexane. The appropriate fractions were combined and evaporated in vacuo to give the title compound as a white foam (1.24 g); LCMS: (System 4) MH$^+$=364, $t_{RET}$=2.42 min.

Intermediate 14

5-Chloro-2-(hydroxymethyl)phenol

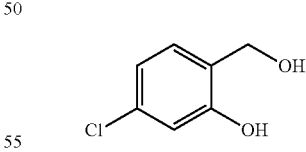

To a solution of 4-chloro-2-hydroxybenzoic acid (2.0 g, 11.6 mmol, Aldrich) in THF (50 ml) was added dropwise 1 M borane in THF (20.9 ml, 20.9 mmol). The suspension was allowed to stir for 30 min at ambient temperature. The mixture was refluxed at 80° C. for 2.5 h. The solvent was removed in vacuo. The residue was loaded in dichloromethane and purified on silica 100 g using 0-100% ethyl acetate/cyclohexane. The appropriate fractions were combined and evaporated in vacuo to give the title compound as a white solid (1.51 g);

LCMS: (System 1) (M-H)-=157, $t_{RET}$=2.44 min.

Intermediate 15

{4-Chloro-2-[(phenylmethyl)oxy]phenyl}methanol

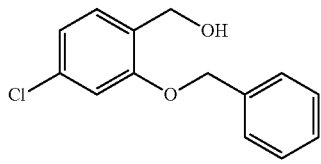 [SMILES: OCc1ccc(Cl)cc1OCc1ccccc1]

To a solution of 5-Chloro-2-(hydroxymethyl)phenol (for a preparation see Intermediate 14)(1.51 g, 9.54 mmol) in ethanol (20 ml), was added sodium hydroxide (5.25 ml, 10.5 mmol). To the mixture was added a solution of benzyl bromide (1.14 ml, 9.54 mmol, Aldrich) in ethanol (30 ml) dropwise. The reaction was stirred under nitrogen overnight at ambient temperature. The solvent was removed in vacuo to leave an aqueous suspension. The suspension was diluted with water (50 ml) and dichloromethane (40 ml). The phases were separated and the aqueous phase extracted with dichloromethane (30 ml). The combined organic extracts were washed with saturated aqueous sodium hydrogen carbonate (20 ml) and the solvent removed in vacuo to leave a white solid (1.52 g). The residue was loaded in dichloromethane and purified on silica 100 g using 0-50% ethyl acetate-cyclohexane. The appropriate fractions were combined and evaporated in vacuo to give the title compound as a white solid (1.32 g);

LCMS: (System 2) (M-H)$^-$=247, $t_{RET}$=1.17 min.

Intermediate 16

3-Chloro-4-(hydroxymethyl)phenol

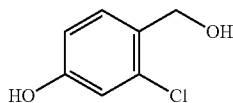

To a solution of 2-chloro-4-hydroxybenzoic acid hydrate (5.0 g, 26.2 mmol, Acros) in THF (80 ml) was added dropwise 1 M borane-tetrahydrofuran complex (50 ml, 50 mmol, Aldrich) at ambient temperature under nitrogen. The resulting suspension was stirred at ambient temperature for 20 min and then heated to 80° C. for 1.5 h. To the reaction at ambient temperature was added a further amount of 1 M borane-tetrahydrofuran (20 ml, 20 mmol) and the suspension heated to 80° C. for 1 h. The solution was allowed to cool to ambient temperature and then carefully quenched by dropwise addition of methanol (40 ml). The solution was heated to 80° C. for 40 min. The solvent was removed in vacuo and the residue applied to a 50 g aminopropyl cartridge (pre-washed with methanol). The cartridge was eluted with methanol and the combined methanol fractions concentrated in vacuo to leave a white solid (4.58 g). A portion of the semi-crude material (1.5 g) was pre-absorbed on florosil and purified on silica (100 g) using 0-100% ethyl acetate-cyclohexane. The appropriate fractions were combined and evaporated in vacuo to give the title compound as a white solid (0.92 g); LCMS: (System 4) (M-H)$^-$=157, $t_{RET}$=1.29 min.

Intermediate 17

4-(1-Hydroxymethyl)-3-(trifluoromethyl)phenol

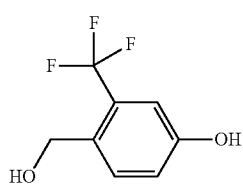 [SMILES: OCc1ccc(O)cc1C(F)(F)F]

To a solution of 4-hydroxy-2-(trifluoromethyl)benzoic acid (4.62 g, 22.4 mmol, Fluorochem) in THF (60 ml) at ambient temperature under nitrogen was added dropwise 1.0 M borane-tetrahydrofuran complex (48 ml, 48.0 mmol). The solution was heated to 80° C. for 2 h. To the solution at ambient temperature was added methanol dropwise (40 ml). The solution was heated to 80° C. for 30 min. The solvent was removed in vacuo and the residue dissolved in methanol (100 ml). The solvent was removed in vacuo to leave the title compound as a white solid (4.39 g);

LCMS: (System 8) (M-H)$^-$=191, $t_{RET}$=1.41 min.

Intermediate 18

[4-[(Phenylmethyl)oxy]-2-(trifluoromethyl)phenyl]methanol

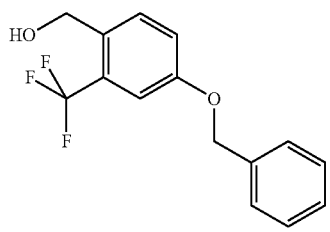 [SMILES: OCc1ccc(OCc2ccccc2)cc1C(F)(F)F]

To a solution of 4-(hydroxymethyl)-3-(trifluoromethyl)phenol (for a preparation see Intermediate 17)(3.86 g, 20.1 mmol) in ethanol (80 mL) was added benzyl bromide (2.4 ml, 20.2 mmol, Aldrich) and then 2 M sodium hydroxide (11 ml, 22 mmol). The mixture was stirred at ambient temperature overnight under nitrogen. The solvent was removed in vacuo to leave an aqueous suspension. The residue was partitioned between dichloromethane (100 ml) and water (100 ml). The phases were separated and the aqueous phase extracted with dichloromethane (50 ml). The combined organic extracts were dried (MgSO$_4$), filtered and the solvent removed in vacuo to leave an oil. The residue was loaded in dichloromethane and purified on silica 100 g using 0-100% ethyl acetate-cyclohexane. The appropriate fractions were combined and evaporated in vacuo to give the title compound as a white solid (4.68 g);

LCMS: (System 8) (M-H)$^-$=281, $t_{RET}$=3.07 min.

Intermediate 19

Ethyl 4-methyl-3-(trifluoromethyl)benzoate

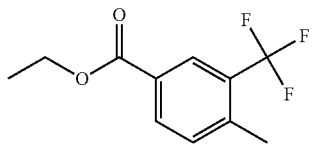 [SMILES: CCOC(=O)c1ccc(C)c(C(F)(F)F)c1]

To a slight suspension of 4-methyl-3-(trifluoromethyl)benzoic acid (2.18 g, 10.7 mmol, ABCR) in ethanol (30 ml) was added concentrated sulphuric acid specific gravity 1.84 (0.5 ml, 9.38 mmol). The resulting solution was heated to reflux overnight under nitrogen. The solution was diluted with DCM (100 ml) and then water (100 ml). The phases were separated and the organic extract washed with saturated aqueous sodium hydrogen carbonate (50 ml), dried (MgSO$_4$), filtered and the solvent removed in vacuo to give the title compound as a mobile pale yellow oil (2.27 g); LCMS: (System 4) MH$^+$=233, t$_{RET}$=3.29 min.

Intermediate 20

Ethyl 4-(bromomethyl)-3-(trifluoromethyl)benzoate

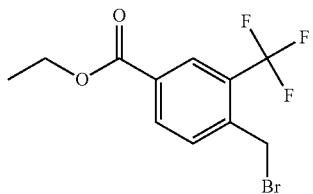 [SMILES: CCOC(=O)c1ccc(CBr)c(C(F)(F)F)c1]

To a solution of ethyl 4-methyl-3-(trifluoromethyl)benzoate (for a preparation see Intermediate 19)(2.25 g, 9.69 mmol) in carbon tetrachloride (25 ml) was added NBS (1.90 g, 10.7 mmol, Aldrich) and then benzyl peroxide (0.030 g, 0.124 mmol, Acros). The suspension was heated overnight at 90° C. under nitrogen. The suspension was filtered through a hydrophobic frit and the residue washed with carbon tetrachloride (10 ml). The filtrate was concentrated in vacuo to leave a mobile colourless oil (3.1 g). The residue was loaded in dichloromethane and purified on silica (100 g×2) using 0-100% dichloromethane-cyclohexane. The appropriate fractions were combined and evaporated in vacuo to give the title compound as a white crystalline solid (1.6 g). LCMS: (System 4) MH$^+$=312, t$_{RET}$=3.32 min

Intermediate 21

4-[(3-{[(2,6-Difluorophenyl)carbonyl]amino}-1H-pyrazol-1-yl)methyl]-3-(trifluoromethyl)benzoic acid

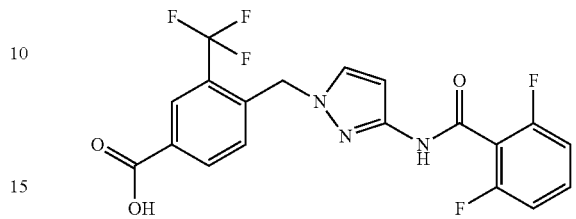

To a solution of ethyl 4-[(3-{[(2,6-difluorophenyl)carbonyl]amino}-1H-pyrazol-1-yl)methyl]-3-(trifluoromethyl) benzoate (for a preparation see Example 43)(0.773 g, 1.71 mmol) in methanol (20 ml) was added 2 M aqueous sodium hydroxide (5 ml, 10 mmol). The solution was heated to 60° C. under air for 45 min. The solvent was removed at reduced pressure and the residue dissolved in water (50 ml). The solution was acidified using 2M HCl aqueous (10 ml). The suspension was diluted with ethyl acetate (50 ml) and the phases separated. The aqueous phase was extracted with ethyl acetate (25 ml). The combined organic extracts were dried (MgSO$_4$), filtered and the solvent removed in vacuo to give the title compound as a white solid (0.666 g); LCMS: (System 4) MH$^+$=426, t$_{RET}$=2.48 min.

Intermediate 22

N-(1-{[4-(Bromomethyl)-2-(trifluoromethyl)phenyl]methyl}-1H-pyrazol-3-yl)-2,6-difluorobenzamide

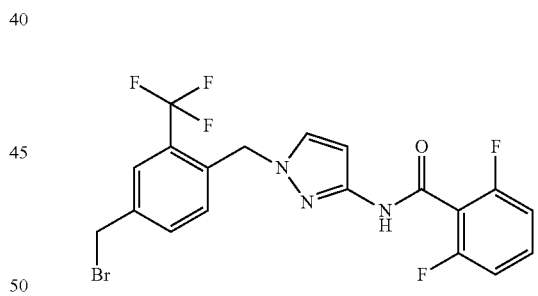

To a stirred solution of 2,6-difluoro-N-(1-{[4-(hydroxymethyl)-2-(trifluoromethyl)phenyl]methyl}-1H-pyrazol-3-yl) benzamide (for a preparation see Example 44) (0.119 g, 0.289 mmol) in DCM (6.5 ml) in an ice-water bath under nitrogen was added phosphorus tribromide (0.027 ml, 0.289 mmol, Aldrich). The cloudy mixture was allowed to warm to ambient temperature and stirred for 1 h. The reaction mixture was diluted with saturated sodium hydrogen carbonate aqueous (15 ml) and ice (15 ml). The biphasic mixture was diluted with DCM (25 ml). The phases were separated and the aqueous phase washed with DCM (20 ml). The combined organic extracts were dried (MgSO$_4$), filtered and the solvent removed in vacuo to give the title compound a colourless gum (98 mg). LCMS: (System 4) MH$^+$=475.9, t$_{RET}$=3.06 min.

Intermediate 23

Methyl 4-chloro-3-[(3-{[(2,6-difluorophenyl)carbonyl]amino}-1H-pyrazol-1-yl)methyl]benzoate

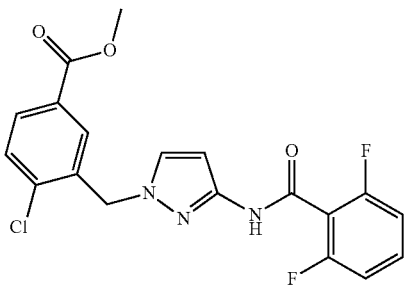 [SMILES: COC(=O)c1ccc(Cl)c(Cn2ccc(NC(=O)c3c(F)cccc3F)n2)c1]

1.0 M LiHMDS (5.00 ml, 5.00 mmol) in THF/ethylbenzene was added slowly to a solution of 2,6-difluoro-N-(1H-pyrazol-3-yl)benzamide (for a preparation see Intermediate 9)(1.12 g, 5 mmol) in THF (50 ml) under nitrogen at ambient temperature. The solution was stirred for 20 min and a solution of methyl 3-(bromomethyl)-4-chlorobenzoate (1.32 g, 5.0 mmol, synthesised according to WO2006079857) in THF (4 ml) was added in one portion. The solution was stirred for 2 h and left overnight. The solution was treated with aqueous ammonium chloride (50 ml) and extracted with ethyl acetate (2×50 ml). The combined organic extracts were dried ($Na_2SO_4$), filtered and solvent evaporated in vacuo. The residue was purified on a silica cartridge (50 g) eluted with 0-100% cyclohexane/EtOAc to give the title compound (1.95 g) as a white solid after evaporation from diethyl ether; LCMS: (System 4) $MH^+$=406/408, $t_{RET}$=2.69 min.

Intermediate 50

4-Chloro-3-[(3-{[(2,6-difluorophenyl)carbonyl]amino}-1H-pyrazol-1-yl)methyl]benzoic acid

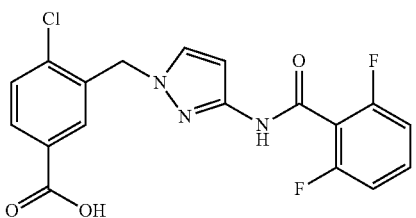 [SMILES: O=C(O)c1ccc(Cl)c(Cn2ccc(NC(=O)c3c(F)cccc3F)n2)c1]

To a solution of methyl 4-chloro-3-[(3-{[(2,6-difluorophenyl)carbonyl]amino}-1H-pyrazol-1-yl)methyl]benzoate (for a preparation see Intermediate 23)(0.95 g, 2.34 mmol) in methanol (20 ml) was added sodium hydroxide (2.4 ml, 4.80 mmol). The reaction was stirred for 4 h, under nitrogen, at ambient temperature. The solvent was evaporated in vacuo, and the residue partitioned between diethyl ether (60 ml) and 2N aqueous HCl (50 ml). The residue was insoluble and the diethyl ether was removed in vacuo. The aqueous suspension was filtered through a hydrophobic frit, and the residue washed with ether and dried under vacuum to give the title compound as a white solid (0.651 g);
LCMS: (System 4) $MH^+$=392/394, $t_{RET}$=2.46 min.

Intermediate 51

N-[1-({5-[(2-acetylhydrazino)carbonyl]-2-chlorophenyl}methyl)-1H-pyrazol-3-yl]-2,6-difluorobenzamide

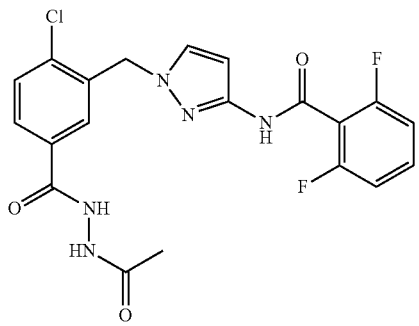 [SMILES: CC(=O)NNC(=O)c1ccc(Cl)c(Cn2ccc(NC(=O)c3c(F)cccc3F)n2)c1]

To a solution of 4-chloro-3-[(3-{[(2,6-difluorophenyl)carbonyl]amino}-1H-pyrazol-1-yl)methyl]benzoic acid (for a preparation see Intermediate 50)(206 mg, 0.526 mmol) in DMF (2 ml) was added acetohydrazide (60 mg, 0.810 mmol, Acros). To the reaction mixture was added HATU (320 mg, 0.842 mmol) and DIPEA (0.211 mL, 1.21 mmol). The reaction was stirred overnight, under nitrogen and at ambient temperature. The solution was partitioned between dichloromethane (5 ml) and water (5 ml). The phases were separated and the aqueous layer washed with dichloromethane (5 ml). The combined organic extracts were concentrated in vacuo to leave a green oil. The residue was loaded in dichloromethane and purified on silica (50 g) using 0-100% ethyl acetate-cyclohexane and then 0-15% methanol(+1% $Et_3N$)-dichloromethane. The appropriate fractions were combined and evaporated in vacuo to give the title compound as a white solid (135 mg);
LCMS: (System 4) $MH^+$=448/450, $t_{RET}$=2.04 min.

Intermediate 24

[2-Chloro-6-(methyloxy)phenyl]methanol

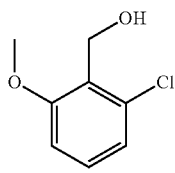

To a stirred solution of 2-chloro-6-(methyloxy)benzoic acid (0.252 g, 1.35 mmol, Arkpharminc) in dry THF (15 ml) at ambient temperature under nitrogen was added 1 M borane tetrahydrofuran complex (4.1 ml of solution in THF, 4.1 mmol, Aldrich) dropwise. The solution was then heated at reflux for 24 h and allowed to cool. The reaction mixture was quenched by the dropwise addition of methanol (4 ml), then heated at reflux for 30 min and allowed to cool. The solvent was removed in vacuo and the residue was partitioned between dilute aqueous ~1M aqueous HCl and chloroform, the aqueous phase being extracted with more chloroform and the chloroform solutions being filtered through a phase separator. The combined chloroform solutions were evaporated in vacuo to give the title compound as a pale yellow solid (0.225 g); LCMS: (System 4) MH$^+$=173, $t_{RET}$=1.86 min.

Intermediate 25

2-(Bromomethyl)-3-chlorophenyl methyl ether

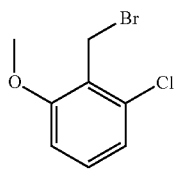

[2-Chloro-6-(methyloxy)phenyl]methanol (0.224 g, 1.30 mmol) in dry dichloromethane (4.5 ml) under nitrogen was stirred and cooled to −10° C. A solution of phosphorus tribromide (0.357 g, 1.32 mmol, Aldrich) in dry dichloromethane (4.5 ml) was added dropwise over about 40 min. The reaction temperature was slowly allowed to warm to 5° C. over about six hours then cooled to 0° C. and saturated aqueous sodium bicarbonate (5 ml) was added. The layers were separated and the aqueous phase further extracted with chloroform. The combined organic extract was dried with magnesium sulphate, filtered and solvent evaporated in vacuo to give the title compound as a slightly yellow solid (0.232 g); LCMS: (System 4) $t_{RET}$=3.07 min (no MH$^+$ detected).

Intermediate 26

{2-[(Cyclobutylmethyl)oxy]phenyl}methanol

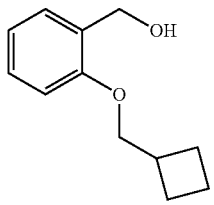 [SMILES: OCc1ccccc1OCC1CCC1]

A mixture of 2-(hydroxymethyl)phenol (1 g, 8.06 mmol, Aldrich), (bromomethyl)cyclobutane (2.401 g, 16.11 mmol, Aldrich), potassium carbonate (2.227 g, 16.11 mmol) in anhydrous DMF (10 ml) was stirred at room temperature over the weekend then at 80° C. overnight. The reaction mixture was filtered and evaporated in vacuo. The residue was partitioned between water (20 ml) and ethylacetate (20 ml). The aqueous phase was extracted with further ethyl acetate (20 ml), the combined ethyl acetate extracts were evaporated in vacuo. The sample was loaded in dichloromethane and purified by SPE on silica (70 g) using 0-50% ethyl acetate/cyclohexane. The appropriate fractions were combined and evaporated in vacuo to give the title compound as a colourless oil (1.54 g);

LCMS: (System 3) $t_{RET}$=1.21 min, no strong MH$^+$ or (M-H)$^-$ detected

TLC: Rf=0.64 (cyclohexane:EtOAc 2:1)

Intermediate 27

1-(Bromomethyl)-2-[(cyclobutylmethyl)oxy]benzene

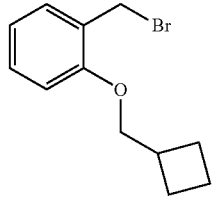 [SMILES: BrCc1ccccc1OCC1CCC1]

A solution of {2-[(cyclobutylmethyl)oxy] phenyl}methanol (for a preparation see Intermediate 26) (0.5 g, 2.60 mmol) in anhydrous DCM (5 ml) was cooled to 5° C. under nitrogen. A solution of phosphorus tribromide (0.248 ml, 2.63 mmol) in anhydrous DCM (2 ml) was added dropwise. The reaction mixture was stirred allowing to warm up to ambient temperature for 1.5 h. The reaction mixture was then poured onto a mixture of ice/water (40 ml) and saturated sodium bicarbonate (15 ml). DCM (30 ml) was added and the layers were separated. The aqueous phase was extracted with DCM (20 ml). The combined DCM extracts were dried (Na$_2$SO$_4$) and evaporated in vacuo to give the title compound as a pale yellow oil (0.50 g); LCMS: (System 4) $t_{RET}$=3.61 min, no strong MH$^+$ or (M-H)$^-$ detected.

TLC: Rf=0.91 in cyclohexane:EtOAc 4:1

Intermediate 28

2-(1H-pyrazol-3-yl)-1H-isoindole-1,3(2H)-dione

A mixture of 1H-pyrazol-3-amine (12 g, 144 mmol, Fluka Chemie AG) and phthalic anhydride (21.39 g, 144 mmol, Fluka Chemie AG) in 1,4-dioxane (200 ml) was heated at reflux for five days and allowed to cool to room temperature. The solid was filtered and washed with ether to give the title compound as an off white solid (22.44 g); LCMS: (System 3) MH$^+$=214, $t_{RET}$=0.67 min.

Intermediate 29

1-({2-[(Phenylmethyl)oxy]phenyl}methyl)-1H-pyrazol-3-amine

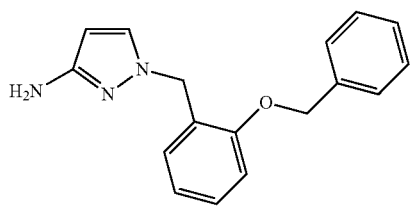 [SMILES: Nc1ccn(Cc2ccccc2OCc2ccccc2)n1]

To a stirred solution of 1-(bromomethyl)-2-[(phenylmethyl)oxy]benzene (for a preparation see Intermediate 3)(9.74 g, 35.1 mmol, Sinochem) in DMF (100 ml) was added 2-(1H-pyrazol-3-yl)-1H-isoindole-1,3(2H)-dione (for a preparation see Intermediate 28) (7.49 g, 35.1 mmol) followed by potassium carbonate (6.8 g, 49.2 mmol). The mixture was stirred for four days at ambient temperature then partitioned between ethyl acetate and water and the layers separated. The organic layer was washed with 10% lithium chloride solution in water, then with brine, then dried over magnesium sulphate and filtered. Evaporation in vacuo gave an orange oil (12 g), this was applied to 330 g silica and purified using 0-80% ethyl acetate-cyclohexane to give two batches of impure 2-[1-({2-[(Phenylmethyl)oxy]phenyl}methyl)-1H-pyrazol-3-yl]-1H-isoindole-1,3(2H)-dione as yellow oils (1.6 g, 3.23 g).

To a solution of 2-[1-({2-[(phenylmethyl)oxy]phenyl}methyl)-1H-pyrazol-3-yl]-1H-isoindole-1,3(2H)-dione (4.83 g, approx 11.8 mmol) in THF (50 ml) was added hydrazine hydrate (2.86 ml, 59 mmol) and the solution was stirred overnight at ambient temperature. A white solid was filtered off and the filtrate dried over magnesium sulphate, filtered and evaporated to give an oil. The oil was applied to 100 g silica and purified using 0-100% ethyl acetate-cyclohexane to give the title compound as a pale yellow oil (1.66 g); LCMS: (System 3) MH$^+$=280, $t_{RET}$=0.96 min.

Intermediate 30

2,6-Difluoro-N-{1-[(2-hydroxyphenyl)methyl]-1H-pyrazol-3-yl}benzamide

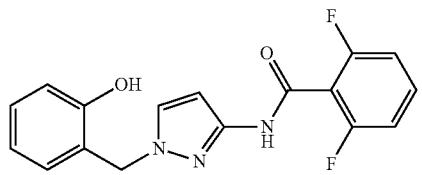 [SMILES: O=C(Nc1ccn(Cc2ccccc2O)n1)c1c(F)cccc1F]

A solution of 2,6-difluoro-N-[1-({2-[(phenylmethyl)oxy]phenyl}methyl)-1H-pyrazol-3-yl]benzamide (for a preparation see Example 59)(2.34 g, 5.58 mmol) in ethyl acetate (20 ml) was stirred overnight with 10% palladium on carbon (wet) (0.594 g, 0.279 mmol) under an atmosphere of hydrogen. The reaction mixture was filtered and the filtrate evaporated in vacuo to give a colourless oil. The oil was dissolved in ether and the solution evaporated in vacuo to give the title compound as a white foam (1.82 g); LCMS: (System 3) MH$^+$=330, $t_{RET}$=0.92 min.

Intermediate 31

4-Iodo-2-(trifluoromethyl)benzoic acid

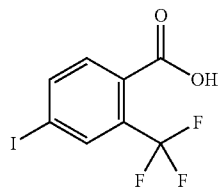 [SMILES: O=C(O)c1ccc(I)cc1C(F)(F)F]

To a suspension of 4-amino-2-(trifluoromethyl)benzoic acid (10 g, 48.7 mmol, Apollo) in water (43 ml) in an ice-water bath (internal temperature at 5° C.) was added concentrated sulphuric acid specific gravity 1.84 (7 mL, 131 mmol). To the slight suspension was added a solution of sodium nitrite, super free flowing (3.76 g, 54.5 mmol, Aldrich) in ice cold water (20 ml) dropwise. The suspension was stirred in an ice-water bath for 20 min. To the mixture was added a solution of potassium iodide, extra pure briquettes (12.14 g, 73.1 mmol, Acros) in ice cold 1 M sulphuric acid (30 ml). The mixture was allowed to warm to ambient temperature and then heated to 80° C. for 45 min under nitrogen. The mixture was allowed to cool to ambient temperature. The mixture was partitioned between ethyl acetate (300 ml) and water (300 ml). The phases were separated and the organic phase washed with brine (50 ml×2), dried (MgSO$_4$), filtered and the solvent removed in vacuo to give the title compound as a dark brown solid (16.7 g); LCMS: (System 4) (M-H)$^-$=315, $t_{RET}$=2.64 min.

Intermediate 32

2,6-Difluoro-N-{1-[(2-methyl-4-nitrophenyl)methyl]-1H-pyrazol-3-yl}benzamide

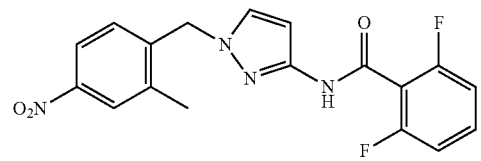

To a solution of 2-methyl-4-nitrobenzoic acid (5 g, 27.6 mmol, Aldrich) in THF) (95 ml) was added dropwise 1.0 M borane-tetrahydrofuran complex (55 ml, 55.0 mmol, Aldrich) at ambient temperature under nitrogen. The resulting red solution was heated to 80° C. for 2 h. To the solution at ambient temperature was added methanol (30 ml) and then heated to 80° C. for 30 min. The solvent was evaporated in vacuo to leave a yellow oil. The residue was dissolved in methanol (80 ml) and the solvent evaporated in vacuo to leave (2-methyl-4-nitrophenyl)methanol as a yellow solid (4.73 g).

To a solution of (2-methyl-4-nitrophenyl)methanol (2 g, 12 mmol) in DCM (25 ml) in an ice-water bath under nitrogen was added a solution of phosphorous tribromide (1.13 ml, 12 mmol, Aldrich) in DCM (20 ml). The resulting solution was allowed to warm to ambient temperature and stirred for 2 h. The reaction mixture was poured onto ice-water (70 ml) and saturated sodium hydrogen carbonate (30 ml). The mixture was diluted with DCM (50 ml) and the phases separated. The aqueous extract was washed with DCM (20 ml). The combined organic extracts were washed with water (50 ml), dried (MgSO$_4$), filtered and the solvent removed in vacuo to leave 1-(bromomethyl)-2-methyl-4-nitrobenzene as a yellow solid (1.5 g).

To a solution of 2,6-difluoro-N-(1H-pyrazol-3-yl)benzamide (for a preparation see Intermediate 9)(1.5 g, 6.72 mmol) in THF (30 ml) at ambient temperature under nitrogen was added 1.0 M lithium bis(trimethylsilyl)amide in THF (6.5 ml, 6.50 mmol, Aldrich). The solution was stirred for 30 min. To the solution was added a solution of 1-(bromomethyl)-2-methyl-4-nitrobenzene (1.5 g, 6.52 mmol) in THF (20 ml). The resulting pale orange solution was stirred at ambient temperature under nitrogen over the weekend. The solvent was evaporated in vacuo and the residue partitioned between ethyl acetate (150 ml) and saturated aqueous sodium hydrogen carbonate (50 ml). The phases were separated and the aqueous layer washed with ethyl acetate (25 ml). The combined organic phases were dried (MgSO$_4$), filtered and the solvent removed in vacuo to leave a yellow oil (2.87 g). The sample was loaded in dichloromethane and purified on silica 100 g using 0-100% ethyl acetate-cyclohexane. The appropriate fractions were combined and evaporated in vacuo to give the title compound as a white foam (1.6 g); LCMS: (System 4) MH+=373, $t_{RET}$=2.65 min.

Intermediate 33

N-{1-[(4-amino-2-methylphenyl)methyl]-1H-pyrazol-3-yl}-2,6-difluorobenzamide

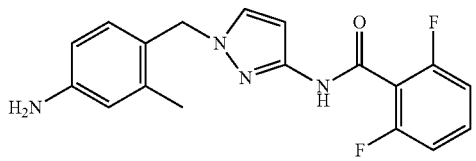 [SMILES: Cc1cc([N+](=O)[O-])ccc1Cn1ccc(NC(=O)c2c(F)cccc2F)n1]

To 10% palladium on activated carbon (wet, degussa type E101 NE/W) (350 mg, 3.29 mmol, Aldrich) was added a solution of 2,6-difluoro-N-{1-[(2-methyl-4-nitrophenyl)methyl]-1H-pyrazol-3-yl}benzamide (for a preparation see Intermediate 32)(1.6 g, 4.30 mmol) in ethanol (80 ml). The solution was hydrogenated for 1.5 h at ambient temperature. The suspension was filtered through a celite cartridge (10 g) and the catalyst residue washed with methanol (50 ml). The solvent was removed in vacuo to give the title compound as a white foam (1.43 g). LCMS: (System 4) MH+=343, $t_{RET}$=1.50 min.

Intermediate 34

Methyl 4-(phenyloxy)-2-(trifluoromethyl)benzoate

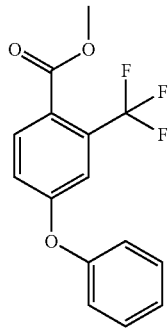 [SMILES: COC(=O)c1ccc(Oc2ccccc2)cc1C(F)(F)F]

To a solution of 4-fluoro-2-(trifluoromethyl)benzoic acid (2.02 g, 9.71 mmol, Aldrich) in methanol and chloroform (1:1, 32 ml) was added a 2 M TMS-diazomethane in ether (~7 ml) in portions, over about 2 h, allowing the solution to cool down between additions. The solution was evaporated in vacuo and the residue dissolved in chloroform (~20 ml). The solution was evaporated in vacuo to give methyl 4-fluoro-2-(trifluoromethyl)benzoate as a slightly yellow-brown liquid (2.07 g).

To a stirred mixture of phenol (332 mg, 3.53 mmol, Aldrich) and DMSO (3 ml) under nitrogen was added potassium t-butoxide (396 mg, 3.53 mmol, Aldrich). The mixture was warmed to 66° C. and methyl 4-fluoro-2-(trifluoromethyl) benzoate (470 mg, 2.12 mmol) was added at this temperature.

As a separate reaction, a stirred mixture of phenol (94 mg, 1.0 mmol, Aldrich) and DMSO (3 ml) under nitrogen was added potassium t-butoxide (112 mg, 1.0 mmol, Aldrich). To the mixture at ambient temperature was added methyl 4-fluoro-2-(trifluoromethyl)benzoate (470 mg, 2.12 mmol) and stirred over the weekend.

Both reactions were combined and added to dilute aqueous sodium bicarbonate. The mixture was extracted with ether a few times. The combined organic extracts were dried (Na$_2$SO$_4$), filtered and the solvent removed in vacuo to leave a yellow oil (0.835 g). The residue was purified on silica 50 g using 0-100% DCM-cyclohexane. The appropriate fractions were combined and evaporated in vacuo to give the title compound as a colourless oil (0.516 g); LCMS: (System 4) MH+=297, $t_{RET}$=3.36 min.

Intermediate 35

4-(Phenyloxy)-2-(trifluoromethyl)benzoic acid

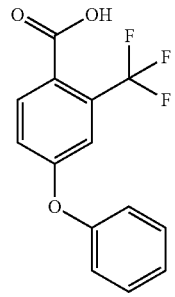 [SMILES: O=C(O)c1ccc(Oc2ccccc2)cc1C(F)(F)F]

To a solution of methyl 4-(phenyloxy)-2-(trifluoromethyl) benzoate (for a preparation see Intermediate 34) (0.516 g, 1.74 mmol) in ethanol (17.5 ml), was added a 2 M aqueous sodium hydroxide (1.5 ml). The solution was stirred and left to stand over 3 days. The solvent was removed in vacuo and then water added. The solution was made acidic with dilute aqueous HCl and the resulting white precipitate extracted into chloroform. The phases were separated using a hydrophobic frit. The solvent was removed in vacuo to give the title compound as a white solid (0.508 g); LCMS: (System 4) (M-H)−= 281, $t_{RET}$=2.85 min.

Intermediate 36

5-(Phenyloxy)-2-(trifluoromethyl)benzoic acid

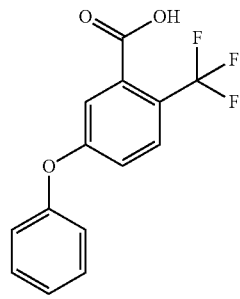 [SMILES: O=C(O)c1cc(Oc2ccccc2)ccc1C(F)(F)F]

To a solution of 5-fluoro-2-(trifluoromethyl)benzoic acid (2.0 g, 9.62 mmol, Aldrich) in a mixture of chloroform and methanol (1:1, 40 ml) was added a 2 M solution of TMS-diazomethane in ether (approximately 8 ml) dropwise, in portions over about 1 h, allowing the solution to cool down between additions. The solution was evaporated in vacuo. To the residue was added chloroform (approximately 40 ml) and the solvent removed in vacuo to give methyl 5-fluoro-2-(trifluoromethyl)benzoate as a colourless slightly cloudy oil (2.09 g). To a stirred solution of phenol (1.06 g, 11.3 mmol, Aldrich) in DMSO (8 ml) under nitrogen was added potassium t-butoxide (1.27 g, 11.3 mmol) and the mixture stirred to dissolve. To the mixture was added methyl 5-fluoro-2-(trifluoromethyl)benzoate (2.09 g, 9.41 mmol) in DMSO (2 ml) and the mixture allowed to stand for one week. To the dark coloured mixture was added dilute aqueous sodium bicarbonate and the mixture extracted with ether four times. The combined organic extracts were dried (Na$_2$SO$_4$), filtered and the solvent removed in vacuo to leave a yellow oil (approximately 2 g). The residue was purified on silica 50 g using 0-100% DCM-cyclohexane. The appropriate fractions were combined and evaporated in vacuo to give methyl 5-(phenyloxy)-2-(trifluoromethyl)benzoate as a colourless oil (0.516 g).

To a solution of methyl 5-(phenyloxy)-2-(trifluoromethyl)benzoate (0.504 g, 1.70 mmol) in ethanol (20 ml), was added 2 M aqueous sodium hydroxide (2.0 ml, 4 mmol). The solution was stirred and left to stand overnight. The solvent was evaporated in vacuo. The residue was dissolved in water and diluted with aqueous 2 M HCl. The mixture extracted with chloroform and the phases separated using a hydrophobic frit. The solvent was removed in vacuo to give a colourless oil (0.540 g). The residue was dissolved in chloroform and dried (Na$_2$SO$_4$), filtered and the solvent removed in vacuo to give the title compound as a colourless oil (0.519 g); LCMS: (System 4) (M-H)$^-$=281, t$_{RET}$=2.84 min.

Intermediate 37

1-{[4-Chloro-2-(trifluoromethyl)phenyl]methyl}-1H-pyrazol-3-amine

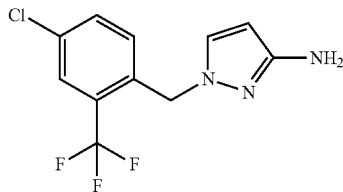 [SMILES: Nc1ccn(Cc2ccc(Cl)cc2C(F)(F)F)n1]

A mixture of 2-(1H-pyrazol-3-yl)-1H-isoindole-1,3(2H)-dione (for a preparation see Intermediate 28) (3 g, 14.1 mmol) and potassium carbonate (2.92 g, 21.1 mmol) in DMF (30 ml) was stirred under nitrogen at ambient temperature for 5 min. To the pale yellow suspension was added 1-(bromomethyl)-4-chloro-2-(trifluoromethyl)benzene (3.85 g, 14.07 mmol, Alfa Aesar). The mixture turned to a colourless suspension. The reaction mixture was stirred at ambient temperature under nitrogen overnight. The reaction mixture was diluted with DCM (50 ml) and water (50 ml). To the emulsion was added brine (30 ml). The resulting phases were separated and the aqueous layer further extracted with DCM (50 ml). The combined organic extracts were filtered through a hydrophobic frit and the solvent removed in vacuo to give 2-(1-{[4-chloro-2-(trifluoromethyl)phenyl]methyl}-1H-pyrazol-3-yl)-1H-isoindole-1,3(2H)-dione (6.14 g) as an off-white gum.

To a solution of crude 2-(1-{[4-chloro-2-(trifluoromethyl)phenyl]methyl}-1H-pyrazol-3-yl)-1H-isoindole-1,3(2H)-dione (6.14 g, 15.1 mmol) in THF (50 ml) was added hydrazine hydrate (3.67 ml, 76 mmol, Aldrich). The resulting colourless solution was stirred at 50° C. for 1 h. A white solid precipitated. The reaction was cooled down to ambient temperature and filtered through a sinter funnel. The filtrate was then passed through a hydrophobic frit and concentrated under reduced pressure. The sample was pre-absorbed on florosil (15 ml of DCM:MeOH=1:1) and purified on silica 100 g using 0-50% ethyl acetate-dichloromethane. The appropriate fractions were combined and evaporated in vacuo to give the title compound as a white solid (1.57 g); LCMS: (System 3) MH$^+$=276, t$_{RET}$=0.90 min.

Intermediate 38

1-{[2-(Phenyloxy)phenyl]methyl}-1H-pyrazol-3-amine

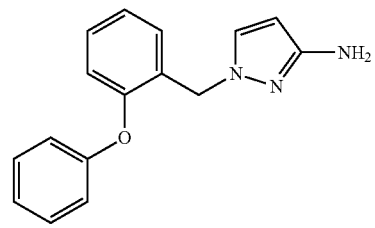 [SMILES: Nc1ccn(Cc2ccccc2Oc2ccccc2)n1]

A solution of 2-(1H-pyrazol-3-yl)-1H-isoindole-1,3(2H)-dione (for a preparation see Intermediate 28)(3.08 g, 14.4 mmol) in THF (30 ml) under nitrogen, was treated with 1.0 M lithium bis(trimethylsilyl)amide in THF (15.9 ml, 15.9 mmol, Aldrich) and stirred at room temperature for 15 min. 1-(Bromomethyl)-2-(phenyloxy)benzene (3.8 g, 14.4 mmol, Maybridge) in THF (10 ml) was added and the mixture stirred overnight. The mixture was diluted with DCM (50 ml) and water (50 ml). To the emulsion was added brine (30 ml) and diluted aqueous HCl (15 ml). The resulting phases were separated and the aqueous layer was further extracted with DCM (50 ml). The combined organic extracts were filtered through a hydrophobic frit and the filtrate concentrated under reduced pressure. The residue was loaded in dichloromethane and purified on silica 330 g using 0-50% ethyl acetate-dichloromethane. The appropriate fractions were combined and evaporated in vacuo to give 2-(1-{[2-(phenyloxy)phenyl]methyl}-1H-pyrazol-3-yl)-1H-isoindole-1,3(2H)-dione as an off-white gum (2.35 g).

To a solution of crude 2-(1-{[2-(phenyloxy)phenyl]methyl}-1H-pyrazol-3-yl)-1H-isoindole-1,3(2H)-dione (2.35 g, 5.94 mmol) in THF (30 ml) was added hydrazine hydrate (1.44 ml, 29.7 mmol, Aldrich). The resulting colourless solution was stirred at 50° C. for 2 h. A white solid precipitated. The suspension was cooled to ambient temperature and filtered through a sinter funnel. The filtrate was then filtered through a hydrophobic frit and concentrated under reduced pressure to give the title compound as a white solid (1.58 g); LCMS: (System 3) MH$^+$=266, t$_{RET}$=0.86 min.

Intermediate 39

1-{[4-Iodo-2-(trifluoromethyl)phenyl]methyl}-1H-pyrazol-3-amine

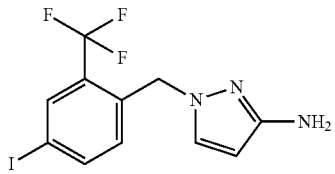 [SMILES: Nc1ccn(Cc2ccc(I)cc2C(F)(F)F)n1]

To a solution of 2-(1H-pyrazol-3-yl)-1H-isoindole-1,3 (2H)-dione (for a preparation see Intermediate 28)(0.72 g, 3.38 mmol) in THF (20 ml) was added 1.0 M lithium bis (trimethylsilyl)amide in THF (3.5 ml, 3.50 mmol, Aldrich). The slight suspension was stirred for 30 min. To the yellow solution was added a solution of 1-(bromomethyl)-4-iodo-2-(trifluoromethyl)benzene (for a preparation see within Example 73)(1.24 g, 3.40 mmol) in THF (10 ml). The resulting yellow solution was stirred at ambient temperature under nitrogen overnight. The solvent was removed in vacuo and the residue partitioned between DCM (100 ml) and water (100 ml). To aid the separation, brine (50 ml) and dilute hydrochloric acid (25 ml) were added. The phases were separated and the aqueous phase washed with dichloromethane (50 ml). The organic phases were combined, dried (MgSO$_4$), filtered and the solvent removed in vacuo to leave 2-(1-{[4-iodo-2-(trifluoromethyl)phenyl]methyl}-1H-pyrazol-3-yl)-1H-isoindole-1,3(2H)-dione as an orange solid (1.7 g).

To a solution of crude 2-(1-{[4-iodo-2-(trifluoromethyl) phenyl]methyl}-1H-pyrazol-3-yl)-1H-isoindole-1,3(2H)-dione (1.7 g, 3.42 mmol) in THF (30 ml) was added hydrazine monohydrate (0.83 ml, 17.1 mmol, Aldrich). The resulting yellow solution was stirred at ambient temperature under nitrogen for 5 h. The resulting suspension was filtered using a hydrophobic frit and the residue washed with ether (approximately 25 ml). The filterate was concentrated in vacuo and the residue loaded in dichloromethane and purified on silica 100 g using 0-100% ethyl acetate-dichloromethane+0-20% methanol (+1% Et$_3$N). The appropriate fractions were combined and evaporated in vacuo to give the title compound as a pale yellow solid (0.624 g); LCMS: (System 4) MH$^+$=368, t$_{RET}$=2.54 min.

Similarly prepared was:

Intermediate 52

1-{[4-(Methyloxy)-2-(trifluoromethyl)phenyl]methyl}-1H-pyrazol-3-amine

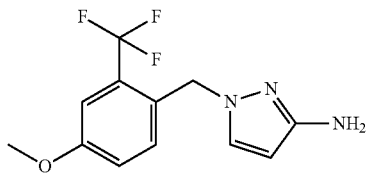 [SMILES: COc1ccc(Cn2ccc(N)n2)c(C(F)(F)F)c1]

Using 1-(bromomethyl)-4-(methyloxy)-2-(trifluoromethyl)benzene (Fluorochem) instead of 1-(bromomethyl)-4-iodo-2-(trifluoromethyl)benzene;
LCMS: (System 4) MH$^+$=272, t$_{RET}$=1.90 min.

Intermediate 40

2,6-Difluoro-N-(1-{[5-nitro-2-(trifluoromethyl)phenyl]methyl}-1H-pyrazol-3-yl)benzamide

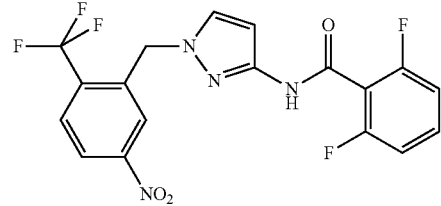 [SMILES: O=C(Nc1ccn(Cc2cc([N+](=O)[O-])ccc2C(F)(F)F)n1)c1c(F)cccc1F]

To a solution of 2-methyl-4-nitrobenzotrifluoride (5.05 g, 24.6 mmol, synthesised according to Journal of medicinal chemistry (1996), 39(23), 4608-4621) in carbon tetrachloride (50 ml) was added NBS (4.77 g, 26.8 mmol, Aldrich) and then benzoyl peroxide (0.110 g, 0.454 mmol, Acros). The mixture was heated to 90° C. overnight, cooled to ambient temperature and the allowed to stand for 4 days. The suspension was filtered and the residue washed with carbon tetrachloride (10 ml). The solvent was removed in vacuo to give 2-(bromomethyl)-4-nitro-1-(trifluoromethyl)benzene as a mobile orange oil (7.33 g).

To a solution of 2,6-difluoro-N-(1H-pyrazol-3-yl)benzamide (for a preparation see Intermediate 9)(3.9 g, 17.5 mmol) in THF (35 ml) at ambient temperature was added 1.0 M lithium bis(trimethylsilyl)amide in THF (17.5 ml, 17.50 mmol, Aldrich) dropwise. The solution was stirred for 20 min. To the solution was added a solution of 2-(bromomethyl)-4-nitro-1-(trifluoromethyl)benzene (7.3 g, 25.7 mmol) in THF (10 ml). The resulting dark brown solution was stirred at ambient temperature for 4.5 h. The solvent was removed in vacuo and the residue partitioned between ethyl acetate (125 ml) and saturated aqueous sodium hydrogen carbonate (75 ml). The phases were separated and the organic phase washed with saturated aqueous sodium hydrogen carbonate (25 ml), dried (MgSO$_4$), filtered and the solvent removed in vacuo to leave a brown oil (~11 g). The residue was loaded in dichloromethane and purified on silica 100 g×2 using 0-100% ethyl acetate-cyclohexane. The appropriate fractions were combined and evaporated in vacuo to give the title compound as a yellow solid (4.31 g); LCMS: (System 4) MH$^+$=427, t$_{RET}$=2.80 min.

Intermediate 41

N-(1-{[5-amino-2-(trifluoromethyl)phenyl]methyl}-1H-pyrazol-3-yl)-2,6-difluorobenzamide

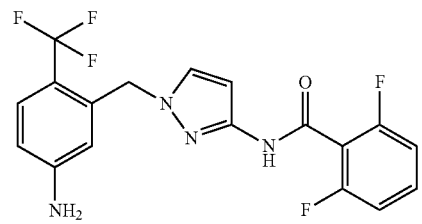 [SMILES: Nc1ccc(C(F)(F)F)c(Cn2ccc(NC(=O)c3c(F)cccc3F)n2)c1]

To 10% palladium on activated carbon degussa type E101 NE/W (wet) (440 mg, 4.14 mmol, Aldrich) was added a slight suspension of the 2,6-difluoro-N-(1-{[5-nitro-2-(trifluoromethyl)phenyl]methyl}-1H-pyrazol-3-yl)benzamide (for a preparation see Intermediate 40) (2.0 g, 4.69 mmol) in a solution of ethanol (80 ml) under vacuum. A further amount of 10% palladium on activated carbon degussa type E101 NE/W (wet) (0.2 g) was added after 2 h. The suspension was hydrogenated for a total of 4 h at ambient temperature. The suspension was filtered and the residue washed with ethanol (50 ml). The solvent was removed in vacuo to leave a pale yellow foam (1.79 g); LCMS: (System 4) MH$^+$=397, $t_{RET}$=2.65 min.

Intermediate 42

2,6-Difluoro-N-(1-{[5-hydroxy-2-(trifluoromethyl)phenyl]methyl}-1H-pyrazol-3-yl)benzamide

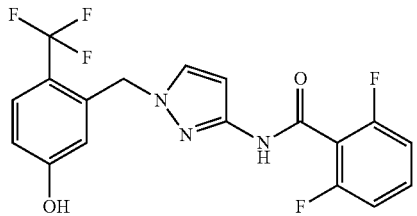 [SMILES: O=C(Nc1ccn(Cc2cc(O)ccc2C(F)(F)F)n1)c1c(F)cccc1F]

To a suspension of N-(1-{[5-amino-2-(trifluoromethyl)phenyl]methyl}-1H-pyrazol-3-yl)-2,6-difluorobenzamide (for a preparation see Intermediate 41) (1.0 g, 2.52 mmol) in water (15 ml) in an ice-water bath was added a solution of sodium nitrite (0.346 g, 5.01 mmol, Aldrich) in water (3 ml). The solution was maintained at 0-10° C. for 20 min. To the solution was added urea (0.94 g, 15.65 mmol, Aldrich) and then copper (II) sulphate (0.139 g, 0.868 mmol, Fluka). The mixture was heated to 90° C. for 30 min. The mixture was partitioned between water (150 ml) and ethyl acetate (130 ml). The phases were separated and the aqueous phase washed with ethyl acetate (50 ml). The combined organic extracts were dried (MgSO$_4$), filtered and the solvent removed in vacuo to leave an oil. The residue was loaded in dichloromethane and purified on silica 100 g using a 0-100% ethyl acetate-cyclohexane. The appropriate fractions were combined and evaporated in vacuo to give the title compound as an orange solid (0.462 g); LCMS: (System 4) MH$^+$=398, $t_{RET}$=2.36 min.

Intermediate 43

2-Fluoro-N-1H-pyrazol-3-ylbenzamide

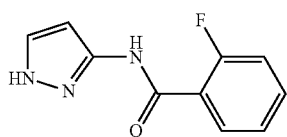 [SMILES: O=C(Nc1cc[nH]n1)c1ccccc1F]

To a solution of 1H-pyrazol-3-amine (249 mg, 3 mmol, Aldrich) in acetonitrile (10 ml) was added triethylamine (0.836 ml, 6.0 mmol, Aldrich) and the stirred solution cooled in an ice-water bath. A solution of 2-fluorobenzoyl chloride (0.358 ml, 3.0 mmol, Alfa Aesar) in acetonitrile (10 ml) was added dropwise. The mixture was stirred under nitrogen and allowed to warm slowly to ambient temperature overnight. The solvent was concentrated in vacuo. The residue was partitioned between ethyl acetate (~50 ml) and water approximately 50 ml). The phases were separated and the aqueous phase washed with further ethyl acetate (2×approximately 30 ml). The combined organic layers were filtered through a hydrophobic frit and the filtrate concentrated in vacuo to give the crude material (0.64 g). The sample was loaded in dichloromethane and purified on silica 70 g using 0-100% ethyl acetate-cyclohexane. The appropriate fractions were combined and concentrated in vacuo to give the title compound as a colourless solid (342 mg); LCMS: (System 4) MH$^+$=206, $t_{RET}$=1.50 min.

Intermediate 44

2,6-Dichloro-N-1H-pyrazol-3-ylbenzamide

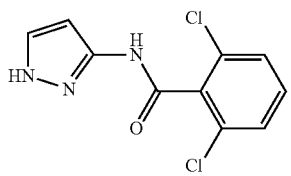 [SMILES: O=C(Nc1cc[nH]n1)c1c(Cl)cccc1Cl]

To a solution of 1H-pyrazol-3-amine (160 mg, 1.93 mmol, Fluka) in acetonitrile (10 ml) was added triethylamine (0.537 ml, 3.85 mmol, Aldrich) and the stirred solution cooled in an ice-water bath. A solution of 2,6-dichlorobenzoyl chloride (0.276 ml, 1.926 mmol, Aldrich) in acetonitrile (5 ml) was added dropwise. The mixture was stirred under nitrogen and allowed to warm slowly to ambient temperature overnight. The mixture was concentrated in vacuo. The residue was partitioned between DCM (20 ml) and water (20 ml). Insoluble material precipitated. The layers were separated and the aqueous phase then extracted with ethyl acetate (approximately 50 ml). The combined organic layers were filtered through a hydrophobic frit and concentrated in vacuo to give the crude material as an off-white foam. The residue was dissolved in methanol and adsorbed onto fluorosil. The sample was purified on silica 50 g using 0-100% ethyl acetate-cyclohexane. The appropriate fractions were combined and concentrated in vacuo to give the title compound as a colourless solid (0.303 g).

LCMS: (System 4) MH$^+$=256, $t_{RET}$=1.71 min.

Intermediate 45

2-chloro-N-1H-pyrazol-3-ylbenzamide

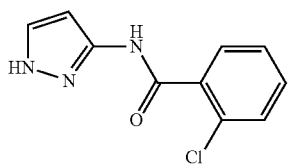 [SMILES: O=C(Nc1cc[nH]n1)c1ccccc1Cl]

To a solution of 1H-pyrazol-3-amine (166 mg, 2 mmol, Aldrich) in acetonitrile (8 ml) was added triethylamine (0.558 ml, 4.0 mmol, Aldrich) and the stirred solution was cooled in an ice-water bath. To the mixture was added a solution of 2-chlorobenzoyl chloride (0.253 ml, 2.0 mmol, Aldrich) in acetonitrile (7 ml). The mixture was stirred under nitrogen and allowed to warm slowly to ambient temperature overnight. The mixture was concentrated in vacuo. The residue was partitioned between ethyl acetate (approximately 30 ml) and water (approximately 30 ml). The layers were separated and the aqueous phase was washed with further ethyl acetate (2×20 ml). The combined organic layers were filtered through a hydrophobic frit and the filtrate concentrated in vacuo to give the crude material (0.47 g). The sample was loaded in dichloromethane and purified on silica 50 g using 0-100% ethyl acetate-cyclohexane. The appropriate fractions were combined and concentrated in vacuo to give the title compound as a colourless solid (0.198 g); LCMS: (System 4) MH$^+$=222, $t_{RET}$=1.54 min.

Intermediate 46

2-Methyl-N-1H-pyrazol-3-ylbenzamide

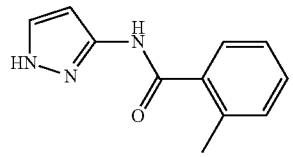

To a stirred solution of 1H-pyrazol-3-amine (246 mg, 2.96 mmol, Aldrich) in acetonitrile (10 ml) was added triethylamine (1.24 ml, 8.88 mmol) and the solution then cooled in an ice-water bath. A solution of 2-methylbenzoyl chloride (0.850 ml, 6.52 mmol, Aldrich) in acetonitrile (5 ml) was added dropwise. The mixture was stirred under nitrogen and allowed to warm slowly to room temperature over 3 h, then stirred at room temp for 30 min. The resulting heavy cream suspension was left to stand overnight. The mixture was partitioned between ethyl acetate (approximately 100 ml) and water (approximately 100 ml). The layers were separated and the aqueous phase was washed with further ethyl acetate (2×50 ml). The combined organic layers were dried (MgSO$_4$) and concentrated in vacuo to give a yellow oil (1.19 g). The residue was dissolved in THF (30 ml) and stirred with polystyrene-supported-trisamine (3.2 mmol/g, 6.4 g, 20.5 mmol, Novabiochem) at ambient temperature over 3 days. The mixture was filtered to remove the resin, washing with further THF (20 ml) then ethyl acetate (total of 250 ml in portions). The combined filtrate and washings were concentrated in vacuo to give the crude product (0.79 g) as a yellow gum. The residue was adsorbed on fluorosil, and purified on silica 70 g using 0-100% ethyl acetate-dichloromethane+0-20% methanol. The appropriate fractions were combined and concentrated in vacuo to give the title compound as a cream solid (503 mg); LCMS: (System 4) MH$^+$=202, $t_{RET}$=1.54 min.

Intermediate 47

2,6-Difluoro-N-{1-[(2-methyl-5-nitrophenyl)methyl]-1H-pyrazol-3-yl}benzamide

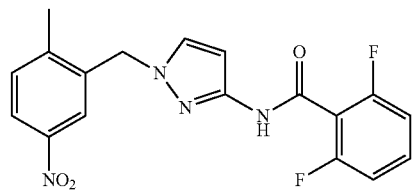

To a solution of 2-methyl-5-nitrobenzoic acid (3.0 g, 16.6 mmol, Acros) in THF (60 ml) at ambient temperature under nitrogen was added dropwise 1.0 M borane-tetrahydrofuran complex (33.1 ml, 33.1 mmol, Aldrich). The solution was heated to 80° C. for 1.5 h. To the solution at ambient temperature was slowly added methanol (20 ml) and then heated to 80° C. for 30 min. The solvent was removed in vacuo to leave an oil. The residue was dissolved in methanol (approximately 30 ml) and the solvent removed in vacuo to give (2-methyl-5-nitrophenyl)methanol as a yellow solid (3.18 g).

To a slight suspension of (2-methyl-5-nitrophenyl)methanol (2.0 g, 12 mmol) in DCM (20 ml) in an ice-water bath under nitrogen was a added a solution of phosphorus tribromide (1.13 mL, 12 mmol, Aldrich) in DCM (20 ml). The resulting solution was allowed to warm to ambient temperature and stirred for 45 min. The solution was poured onto a mixture of ice-water (50 ml) and saturated sodium hydrogen carbonate (50 ml). The biphasic mixture was diluted with dichloromethane (50 ml) and the phases separated. The aqueous phase was extracted with dichloromethane (20 ml). The combined organic extracts were dried (MgSO$_4$), filtered and the solvent removed in vacuo to give 2-(bromomethyl)-1-methyl-4-nitrobenzene as a pale yellow solid (1.81 g).

To a solution of 2,6-difluoro-N-1H-pyrazol-3-ylbenzamide (for a preparation see Intermediate 9) (1.80 g, 8.07 mmol) in THF (30 ml) at ambient temperature under nitrogen was added 1.0 M lithium bis(trimethylsilyl)amide in THF (8 mL, 8.00 mmol) and stirred for 20 min. To the solution was added a solution of 2-(bromomethyl)-1-methyl-4-nitrobenzene (1.81 g, 7.87 mmol) in THF (20 ml) and stirred overnight. The solvent was removed in vacuo and the residue partitioned between ethyl acetate (150 ml) and saturated aqueous sodium hydrogen carbonate (50 ml). The phases were separated and the aqueous phase washed with ethyl acetate (25 ml). The combined organic extracts were dried (MgSO$_4$), and the solvent removed in vacuo to leave a yellow oil (3.5 g). The residue was loaded in dichloromethane and purified on silica 100 g using 0-100% ethyl acetate-cyclohexane. The appropriate fractions were combined and evaporated in vacuo to give the title compound as a white foam (2.1 g); LCMS (System 4) MH$^+$=373, $t_{RET}$=2.60 min.

Intermediate 48

N-{1-[(5-amino-2-methylphenyl)methyl]-1H-pyrazol-3-yl}-2,6-difluorobenzamide

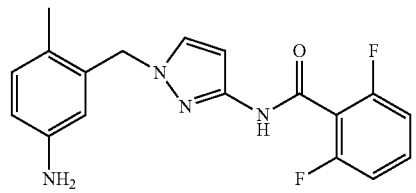 [SMILES: Cc1ccc(N)cc1Cn1ccc(NC(=O)c2c(F)cccc2F)n1]

To 10% palladium on activated carbon degussa type E101 NE/W (wet) (280 mg) was added a slight suspension of 2,6-difluoro-N-{1-[(2-methyl-5-nitrophenyl)methyl]-1H-pyrazol-3-yl}benzamide (for a preparation see Intermediate 47) (1.27 g, 3.41 mmol) in a mixture of ethyl acetate (20 ml) and ethanol (50 ml) under vacuum. The suspension was hydrogenated for 1.5 h at ambient temperature. The suspension was filtered and the residue washed with methanol (30 ml). The solvent was removed in vacuo to leave a white solid (1.09 g); LCMS (System 4) MH$^+$=343, $t_{RET}$=1.43 min.

Intermediate 49

2,6-Difluoro-N-{1-[(5-hydroxy-2-methylphenyl)methyl]-1H-pyrazol-3-yl}benzamide

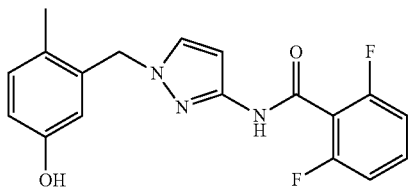 [SMILES: Cc1ccc(O)cc1Cn1ccc(NC(=O)c2c(F)cccc2F)n1]

To N-{1-[(5-amino-2-methylphenyl)methyl]-1H-pyrazol-3-yl}-2,6-difluorobenzamide (for a preparation see Intermediate 48) (0.312 g, 0.911 mmol) in an ice-water bath was added sulphuric acid specific gravity 1.84 (3 ml, 56.3 mmol). To the stirred suspension was slowly added water (5 ml). To the slight suspension was added a solution of sodium nitrite (0.132 g, 1.91 mmol, Aldrich) in water (1 ml). The solution was maintained at 0-5° C. for 20 min. To the solution was added urea (0.350 g, 5.83 mmol, Aldrich) and then copper (II) sulphate (50 mg, 0.313 mmol, Fluka). The mixture was heated to 90° C. for 30 min. The mixture was allowed to stand at ambient temperature overnight. The mixture was diluted with water (100 ml) and then ethyl acetate (50 ml). The phases were separated and the aqueous phase extracted with ethyl acetate (25 ml). The combined organic extracts were concentrated in vacuo to leave a brown gum (0.3 g). The residue was loaded in dichloromethane and purified on silica 50 g using 0-100% ethyl acetate-cyclohexane. The appropriate fractions were combined and evaporated in vacuo to give the title compound as a yellow foam (206 mg); LCMS (System 4) MH$^+$=344, $t_{RET}$=2.36 min.

Intermediate 53

1-(Bromomethyl)-2-(ethyloxy)benzene

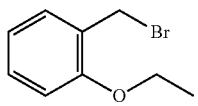

To a solution of [2-(ethyloxy)phenyl]methanol (315 mg, 2.07 mmol, Acros) in DCM (8 ml) cooled in an ice/water bath was added dropwise a solution of phosphorous tribromide (196 μl, 2.08 mmol, Aldrich) in dichloromethane (2 ml) under nitrogen. The reaction mixture was stirred under nitrogen, allowed to warm up slowly and stirred at ambient temperature overnight. The reaction mixture was re-cooled in an ice-water bath and quenched by the addition of saturated aqueous sodium hydrogen carbonate (10 ml) with stirring. The phases were separated and the aqueous phase washed with DCM (×2). The DCM extracts were dried (hydrophobic frit) and concentrated to give the product as an oily-solid mixture (445 mg). The material was suspended in DCM and purified on silica (10 g) eluting with cyclohexane (100 ml) then EtOAc/cyclohexane, 10% (100 ml), 25% (100 ml). The appropriate fractions were concentrated in vacuo to give the title compound (393 mg) as a colourless oil;
LCMS (System 4) No MH$^+$, $t_{RET}$=3.08 min.

Intermediate 54

1-({5-Chloro-2-[(phenylmethyl)oxy]phenyl}methyl)-3-nitro-1H-pyrazole

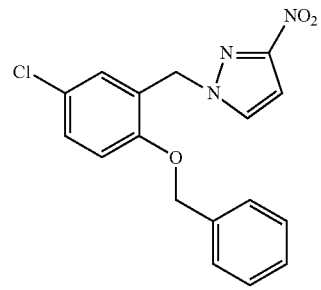 [SMILES: O=[N+]([O-])c1ccn(Cc2cc(Cl)ccc2OCc2ccccc2)n1]

3-Nitro-1H-pyrazole (Fluorochem) (0.505 g, 4.47 mmol) was dissolved in DMF (10 ml). Potassium carbonate (0.973 g, 7.04 mmol) and sodium iodide (75 mg, 0.50 mmol) were added. 2-(Bromomethyl)-4-chloro-1-[(phenylmethyl)oxy]benzene (WO2006066968) (1.33 g, 4.25 mmol) was added and washed in with further DMF (10 ml). The reaction was stirred at room temperature for 30 min, then concentrated in vacuo. The crude material was treated with water (150 ml). The aqueous mixture was extracted with EtOAc (3×150 ml). The combined organic extracts were dried (MgSO$_4$) and concentrated in vacuo. The residue was purified on silica (70 g) using 0-100% EtOAc-cyclohexane. Appropriate fractions were concentrated in vacuo to give the title compound as a yellow solid (952 mg);
LCMS: (System 1) (M+NH$_4$)$^+$=361/363, $t_{RET}$=3.65 min.

Intermediate 55

1-({5-Chloro-2-[(phenylmethyl)oxy]phenyl}methyl)-1H-pyrazol-3-amine

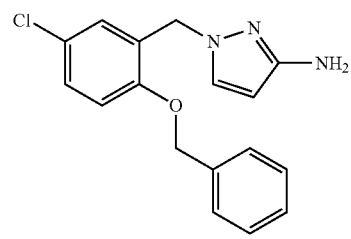 [SMILES: Nc1ccn(Cc2cc(Cl)ccc2OCc2ccccc2)n1]

1-({5-Chloro-2-[(phenylmethyl)oxy]phenyl}methyl)-3-nitro-1H-pyrazole (for a preparation see Intermediate 54) (159 mg, 0.46 mmol) was dissolved in ethanol (10 ml). Stannous chloride (hydrated) (522 mg, 2.31 mmol) was added and the reaction was stirred and heated to 85° C. overnight under nitrogen. The reaction mixture was treated with saturated aqueous sodium bicarbonate solution. The mixture was partitioned between water and ethyl acetate. The mixture was filtered to remove the solid tin residues. The ethyl acetate layer was separated, and the aqueous layer was extracted with further ethyl acetate (2×50 ml). The combined organic fractions were concentrated in vacuo to give the title compound as an off-white solid (156 mg);

LCMS: (System 1) MH$^+$=314/316, $t_{RET}$=3.22 min.

Intermediate 56

[2-Methyl-6-(methyloxy)phenyl]methanol

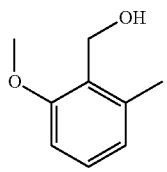

To a solution of 1.0 M lithium aluminium hydride in anhydrous THF (3.6 ml, 3.6 mmol), under nitrogen, was added anhydrous THF (12 ml). Ethyl 2-methyl-6-(methyloxy)benzoate (1 g, 5.2 mmol, ABCR) in anhydrous THF (2 ml) was then added over 5 min with stirring. The solution was stirred for 15 min and then heated at gentle reflux for 100 min. The solution was allowed to cool. A 5% solution of water in ethanol was added dropwise. The solvent was removed in vacuo and acidified using 1 to 2M aqueous HCl. The mixture was extracted with chloroform and the organic solvent removed in vacuo to give the title compound as yellow solid (0.775 g); LCMS: (System 4) MH$^+$=152, $t_{RET}$=1.78 min.

Intermediate 57

2-(bromomethyl)-1-methyl-3-(methyloxy)benzene

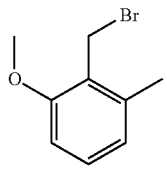

[2-Methyl-6-(methyloxy)phenyl]methanol (for a preparation see Intermediate 56)(300 mg, 1.971 mmol) in dichloromethane (4.5 ml) under nitrogen was stirred and cooled to −10° C. A solution of phosphorus tribromide (186 μl, 1.97 mmol) in DCM (4 ml) was then added dropwise over about 15 min and the solution stirred for a further 30 min at this temperature. The solution was allowed to warm up to ambient temperature. After a few hours, saturated aqueous sodium bicarbonate (approximately 5 ml) was added and the mixture stirred vigorously. The suspension was stored in freezer overnight. The phases were separated and the aqueous phase extracted further with chloroform. The combined organic extracts were dried (MgSO$_4$), filtered and evaporated in vacuo to give the title compound as yellow solid (424 mg); LCMS: (System 4) No MH$^+$, $t_{RET}$=3.01 min.

Intermediate 58

4-[(3-{[(2,6-Difluorophenyl)carbonyl]amino}-1H-pyrazol-1-yl)methyl]-3-(trifluoromethyl)phenyl bis(phenylmethyl) phosphate

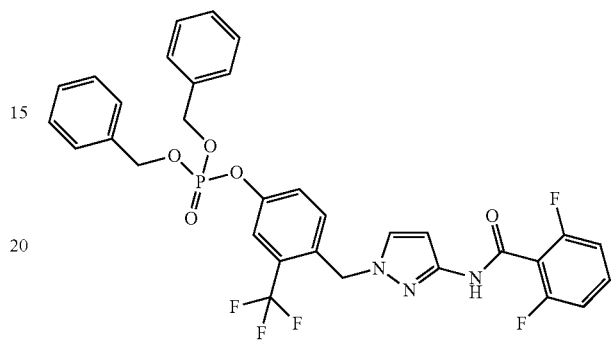

A stirred solution of bis(phenylmethyl)hydrogen phosphate (15 g, 54 mmol) and DMF (0.150 ml, 1.94 mmol) in anhydrous dichloromethane (160 ml), was cooled to 0° C. To the solution was added oxalyl chloride (9.44 mL, 108 mmol) dropwise. The reaction mixture stirred at ambient temperature for 1.5 h. The solvents were evaporated in vacuo. The residue was diluted with toluene (100 ml) and evaporated in vacuo to give bis(phenylmethyl) chloridophosphate (17.12 g) as a pale orange liquid. To a stirred solution of 2,6-difluoro-N-(1-{[4-hydroxy-2-(trifluoromethyl)phenyl]methyl}-1H-pyrazol-3-yl)benzamide (for a preparation see Example 36) (14.1 g, 35.5 mmol) in DMF (150 ml) was added sodium hydride (2.13 g, 53.2 mmol) portionwise. The resulting suspension was stirred at 0-5° C. for 2 h. Dibenzylphosphoryl chloride (17.12 g, 57.7 mmol) dissolved in toluene (100 ml) was then added dropwise and the reaction mixture was stirred at room temperature for 1.5 h. The reaction mixture was partitioned between ethyl acetate (200 ml) and water (200 ml). The organic layer was washed with water (100 ml), 10% aqueous lithium chloride solution (100 ml), brine, dried over magnesium sulphate and evaporated in vacuo. The residue was dissolved in DCM and loaded onto a 750 g silica column. The column was eluted with 0-25% methanol in DCM over 8 column volumes. The appropriate fractions were combined and evaporated in vacuo to give the title compound as a colourless gum (17.61 g); LCMS (System 3) MH$^+$=658, $t_{RET}$=1.28 min.

Intermediate 59

Bis(1,1-dimethylethyl)hydrogen phosphate potassium salt

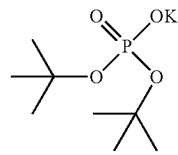

A solution of bis(1,1-dimethylethyl)hydrogen phosphite (100 g, 515 mmol, Alfa Aesar) and potassium bicarbonate (30.9 g, 309 mmol) in water (800 ml) was cooled to 5° C. in an ice bath. To this mixture, potassium permanganate (57.0 g, 360 mmol) was added portionwise over 1 h maintaining the temperature below 20° C. The reaction mixture was stirred at ambient temperature for 18 h. The reaction was heated to 60° C. and then filtered slowly through a pad of celite. The filtrate was evaporated in vacuo to give the title compound as a white solid (109.7 g);

$^1$H NMR (d6-DMSO) δ 1.26 (18 H, s).

Intermediate 60

Chloromethyl bis(1,1-diethylethyl) phosphate

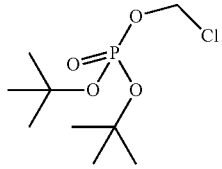

To a solution of bis(1,1-dimethylethyl)hydrogen phosphate potassium salt (for a preparation see Intermediate 59) (109.7 g, 442 mmol) in water (500 ml) was added sodium bicarbonate (148 g, 1767 mmol) and tetrabutylammonium hydrogen sulfate (15.00 g, 22.09 mmol). To this mixture was added dichloromethane (500 ml) and the reaction mixture was cooled to 5° C. A solution of chloromethyl chloridosulfate (91 g, 552 mmol, Apollo Scientific) in dichloromethane (500 ml) was then added dropwise over 50 min. The reaction mixture was allowed to warm to ambient temperature and stirred for 18 h. The two phases were separated and the aqueous phase was extracted using DCM (250 ml). The combined organics were washed with brine (4×200 ml) and dried over sodium sulphate. The solvent was removed in vacuo to give a liquid. This was redissolved in DCM (250 ml) and washed with water (2×150 ml). The organic phase was dried and evaporated in vacuo to give the title compound as a colourless gum (17.61 g); LCMS (System 3) MH$^+$=658, $t_{RET}$=1.28 min.

Intermediate 59

Bis(1,1-dimethylethyl)hydrogen phosphate potassium salt

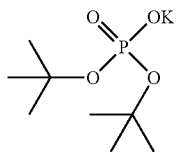

over sodium sulphate and evaporated in vacuo to give the title compound as a liquid (68.2 g); $^1$H NMR (CDCl$_3$) δ 5.64 (2 H, d, J=15 Hz), 1.52 (18 H, s).

Intermediate 61

[[(2,6-Difluorophenyl)carbonyl](1-{[2-fluoro-6-(trifluoromethyl)phenyl]methyl}-1H-pyrazol-3-yl)amino]methyl bis(1,1-dimethylethyl) phosphate

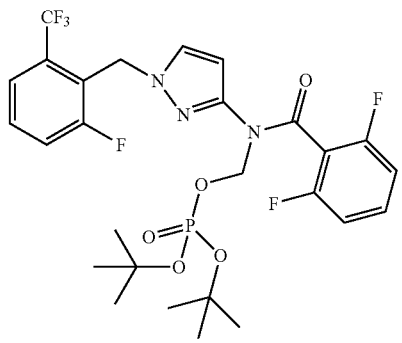 [SMILES: CC(C)(C)OP(=O)(OCN(C(=O)c1c(F)cccc1F)c1ccn(Cc2c(F)cccc2C(F)(F)F)n1)OC(C)(C)C]

A solution of 2,6-difluoro-N-(1-{[2-fluoro-6-(trifluoromethyl)phenyl]methyl}-1H-pyrazol-3-yl)benzamide (for a preparation see Example 29)(61.25 g, 153 mmol), chloromethyl bis(1,1-dimethylethyl) phosphate (for a preparation see Intermediate 60)(47.6 g, 184 mmol) and potassium hydroxide (14.18 g, 215 mmol) in N,N-dimethylformamide (500 ml) was stirred at ambient temperature for 7 days. The reaction mixture was partitioned between ethyl acetate (350 ml) and water/brine (250 ml, 1:1 volume/volume). The organic phase was washed with brine (250 ml) and dried over magnesium sulphate. The solvent was removed in vacuo. The sample was loaded in dichloromethane and purified on a silica Redisep cartridge 1500 g using a gradient of 0-75% ethyl acetate-cyclohexane over 8 column volumes. The appropriate fractions were combined and evaporated in vacuo to give the title compound as a colourless gum (which started to crystallise to a white solid (72.44 g); LCMS: (System 8) MH$^+$=622, $t_{RET}$=3.40 min.

Example 1

N-(1-{[2-(butyloxy)phenyl]methyl}-1H-pyrazol-3-yl)-2,6-difluorobenzamide

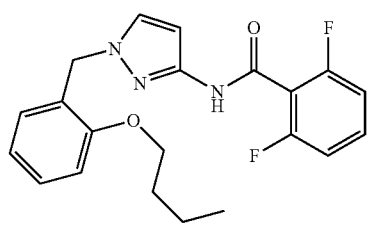 [SMILES: CCCCOc1ccccc1Cn1ccc(NC(=O)c2c(F)cccc2F)n1]

2,6-Difluoro-N-1H-pyrazol-3-ylbenzamide (for a preparation see Intermediate 9)(89 mg, 0.40 mmol), potassium carbonate (83 mg, 0.60 mmol) and 1-(bromomethyl)-2-(butyloxy)benzene (for a preparation see Intermediate 2)(114 mg, 0.47 mmol) were weighed into a vial with a stirrer. N,N- dimethylformamide (1 ml) was added, the vial was capped and the mixture was stirred at room temperature for 28 h. The reaction mixture was filtered (hydrophobic frit), washing with MeOH to give a total volume of 2 ml. This solution was purified by MDAP (Sunfire column, formic acid buffer) (Method B). The solvent was removed to give the title compound as a colourless solid (9.4 mg); LCMS: (System 4) MH$^+$=386, $t_{RET}$=3.17 min.

Example 2

2,6-Difluoro-N-(1-{[2-(phenylmethyl)phenyl]methyl}-1H-pyrazol-3-yl)benzamide

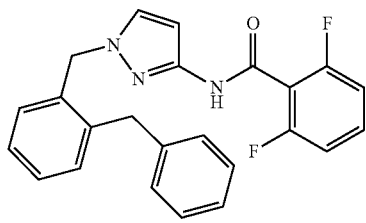 [SMILES: O=C(Nc1ccn(Cc2ccccc2Cc2ccccc2)n1)c1c(F)cccc1F]

2,6-Difluoro-N-1H-pyrazol-3-ylbenzamide (for a preparation see Intermediate 9)(45 mg, 0.202 mmol), potassium carbonate (42 mg, 0.304 mmol) and 1-(bromomethyl)-2-(phenylmethyl)benzene (for a preparation see Intermediate 3)(64 mg, 0.245 mmol) were weighed into a vial with a stirrer. DMF (1 ml) was added, the vial was capped and the mixture was stirred at room temperature for 17 h. The reaction mixture was filtered, washing with MeOH to give a total volume of 2 ml. This solution was purified by MDAP (Sunfire column, formic acid buffer) (Method B). The solvent was removed to give the title compound as a colourless solid (10 mg); LCMS: (System 4) MH$^+$=404, $t_{RET}$=3.23 min.

Example 3

2,6-Difluoro-N-[1-({2-[(phenyloxy)methyl]phenyl}methyl)-1H-pyrazol-3-yl]benzamide

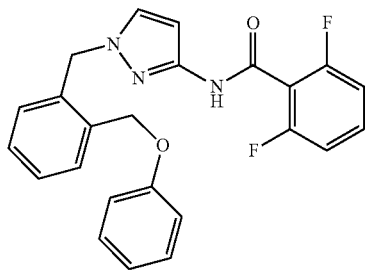 [SMILES: O=C(Nc1ccn(Cc2ccccc2COc2ccccc2)n1)c1c(F)cccc1F]

2,6-Difluoro-N-1H-pyrazol-3-ylbenzamide (for a preparation see Intermediate 9)(45 mg, 0.202 mmol), potassium carbonate (42 mg, 0.304 mmol) and 1-(bromomethyl)-2-[phenyloxy)methyl]benzene (Maybridge) (68 mg, 0.245 mmol) were weighed into a vial with a stirrer. DMF (1 ml) was added, the vial was capped and the mixture was stirred at ambient temperature for 17 h. The reaction mixture was filtered, washing with MeOH to give a total volume of 2 ml. This solution was purified by MDAP (Sunfire column, formic acid buffer) (Method B). The solvent was removed to give the title compound as a colourless gum (19 mg); LCMS: (System 4) MH$^+$=420, $t_{RET}$=3.17 min.

Example 4

N-[1-({2-Chloro-6-[(2-methylpropyl)oxy]phenyl}methyl)-1H-pyrazol-3-yl]-2,6-difluorobenzamide

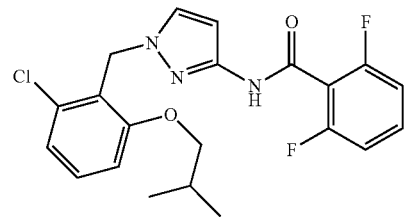 [SMILES: CC(C)COc1cccc(Cl)c1Cn1ccc(NC(=O)c2c(F)cccc2F)n1]

To a solution of N-{1-[(2-chloro-6-hydroxyphenyl)methyl]-1H-pyrazol-3-yl}-2,6-difluorobenzamide (for as preparation see Intermediate 11)(37 mg, 0.102 mmol) in DMF (1 ml) was added potassium carbonate (18 mg, 0.13 mmol) and then 1-bromo-2-methylpropane (0.014 ml, 0.132 mmol, Aldrich). The suspension was stirred at ambient temperature overnight. A further amount of potassium carbonate (7 mg, 0.05 mmol) and then 1-bromo-2-methylpropane (0.014 ml, 0.132 mmol, Aldrich) was added to the suspension. The suspension was stirred at ambient temperature for a further 4 h. The suspension was diluted with methanol (0.5 ml) and then filtered through a cotton wool plug. The filtrate was purified by MDAP (supelcosil ABZ+Plus column) eluting with solvents A/B (A: Water+0.1% Formic acid, B: MeCN:Water 95:5+0.05% Formic acid) (Method A). The solvent was evaporated in vacuo to give the title compound as a colourless gum (4 mg); LCMS: (System 1) MH$^+$=420, $t_{RET}$=3.63 min.

Example 5

N-[1-({2-Chloro-5-[(phenylmethyl)oxy]phenyl}methyl)-1H-pyrazol-3-yl]-2,6-difluorobenzamide

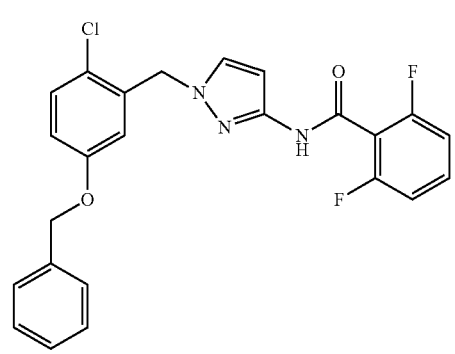 [SMILES: O=C(Nc1ccn(Cc2cc(OCc3ccccc3)ccc2Cl)n1)c1c(F)cccc1F]

To a solution of 4-chloro-3-(hydroxymethyl)phenol (for as preparation see Intermediate 12) (3.3 g, 20.8 mmol) in ethanol (30 ml) was added 2 M sodium hydroxide (10 ml, 20 mmol). To the mixture was added dropwise a solution of benzyl bromide (2.48 ml, 20.8 mmol, Aldrich) in ethanol (30 ml). The reaction was stirred under nitrogen overnight at ambient temperature. The ethanol was removed in vacuo to leave a cream solid and the residue partitioned between water (80 ml) and dichloromethane (60 ml). The phases were separated and the aqueous phase extracted with dichloromethane (40 ml). The combined organic extracts were washed with saturated aqueous sodium hydrogen carbonate (40 ml) and the solvent removed in vacuo to leave a white solid (4.6 g). The sample was loaded in dichloromethane and purified on silica (2×100 g) using 0-100% ethyl acetate-cyclohexane. The appropriate fractions were combined and evaporated in vacuo to give {2-chloro-5-[(phenylmethyl)oxy]phenyl}methanol as a clear oil (4.12 g). To a solution of {2-chloro-5-[(phenylmethyl)oxy]phenyl}methanol (1.22 g, 4.91 mmol) in DCM (25 ml) at −10 to −15° C., under nitrogen, was added a solution of phosphorus tribromide (0.463 ml, 4.91 mmol, Aldrich) in DCM (10 ml) dropwise. The solution was allowed to warm to ambient temperature and stirred for 3 h under nitrogen. To the reaction mixture in an ice-bath was added dropwise saturated aqueous sodium hydrogen carbonate (15 ml). The mixture was diluted with water (80 ml) and DCM (100 ml). The phases were separated and the aqueous phase washed with DCM (60 ml). The combined organic extracts were washed with water (50 ml). The organic extract was dried (MgSO$_4$), filtered and the solvent removed in vacuo to give 3-(bromomethyl)-4-chlorophenyl phenylmethyl ether as a colourless gum (1.11 g).

To a solution of 2,6-difluoro-N-1H-pyrazol-3-ylbenzamide (for as preparation see Intermediate 9) (0.790 g, 3.54 mmol) in THF (30 ml) was added 1.0 M lithium bis(trimethylsilyl)amide in THF (3.54 ml, 3.54 mmol). The reaction mixture was stirred for 30 min. To the reaction mixture was added 3-(bromomethyl)-4-chlorophenyl phenylmethyl ether (1.11 g, 3.56 mmol) in THF (10 ml). The reaction was stirred overnight, under nitrogen at ambient temperature. The solvent was evaporated in vacuo. The residue was partitioned between ethyl acetate (100 ml) and water (70 ml). The phases were separated and the organic phase washed with brine (70 ml). The phases were separated and the organic phase was evaporated in vacuo. The sample was loaded in dichloromethane and purified on silica (2×100 g) using 0-100% ethyl acetate-cyclohexane. The appropriate fractions were combined and evaporated in vacuo to give the title compound as an off-white gum (1.03 g);

LCMS: (System 4) MH$^+$=454, $t_{RET}$=3.33 min.

Example 6

N-(1-{[5-(Butyloxy)-2-chlorophenyl]methyl}-1H-pyrazol-3-yl)-2,6-difluorobenzamide

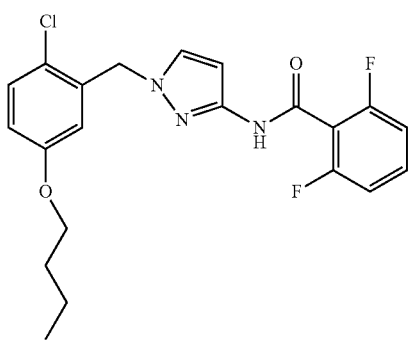 [SMILES: CCCCOc1ccc(Cl)c(Cn2ccc(NC(=O)c3c(F)cccc3F)n2)c1]

To a solution of N-{1-[(2-chloro-5-hydroxyphenyl)methyl]-1H-pyrazol-3-yl}-2,6-difluorobenzamide(for as preparation see Intermediate 13) (35 mg, 0.096 mmol) in DMSO (0.5 ml) was added potassium t-butoxide (10.80 mg, 0.096 mmol). The reaction was stirred for 5 min before adding 1-bromobutane (0.012 ml, 0.115 mmol, Acros). The reaction mixture was stirred under nitrogen for 72 h at ambient temperature. The reaction mixture was filtered through a hydrophobic frit and the filtrate diluted with methanol (0.5 ml) and the sample purified by MDAP on Sunfire C18 column using Acetonitrile-Water with a Formic acid modifier (Method B). The solvent was evaporated in vacuo to give the title compound as a brown gum (11.2 mg); LCMS: (System 4) MH$^+$=420, $t_{RET}$=3.41 min.

Example 7

N-[1-({2-Chloro-5-[(cyclopropylmethyl)oxy]phenyl}methyl)-1H-pyrazol-3-yl]-2,6-difluorobenzamide

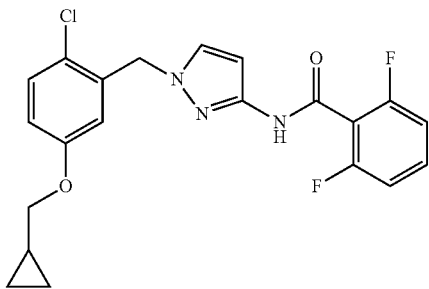 [SMILES: O=C(Nc1ccn(Cc2cc(OCC3CC3)ccc2Cl)n1)c1c(F)cccc1F]

To a solution of N-{1-[(2-chloro-5-hydroxyphenyl)methyl]-1H-pyrazol-3-yl}-2,6-difluorobenzamide (for as preparation see Intermediate 13) (46 mg, 0.126 mmol) in DMSO (0.5 ml) was added potassium t-butoxide (15 mg, 0.134 mmol). The reaction was stirred for 10 min. To the reaction mixture was added (bromomethyl)cyclopropane (0.012 ml, 0.126 mmol, Lancaster). The reaction was heated to 60° C. and stirred overnight under nitrogen. The reaction mixture was filtered through a hydrophobic frit and the filtrate diluted with methanol (0.5 ml) and the sample purified by MDAP on Sunfire C18 column using Acetonitrile-Water with a Formic acid modifier (Method B). The solvent was evaporated in vacuo to give the title compound as a white solid (15.6 mg); LCMS: (System 4) MH$^+$=418, $t_{RET}$=3.20 min.

Example 8

N-(1-{[2-chloro-5-(methyloxy)phenyl]methyl}-1H-pyrazol-3-yl)-2,6-difluorobenzamide

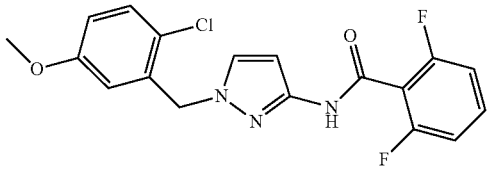 [SMILES: COc1ccc(Cl)c(Cn2ccc(NC(=O)c3c(F)cccc3F)n2)c1]

To a solution of N-{1-[(2-chloro-5-hydroxyphenyl)methyl]-1H-pyrazol-3-yl}-2,6-difluorobenzamide (for as preparation see Intermediate 13) (73 mg, 0.20 mmol) in DMSO (0.5 ml) was added potassium t-butoxide (21 mg, 0.187 mmol). The reaction was stirred for 5 min before adding methyl iodide (0.012 mL, 0.201 mmol, Aldrich). The reaction was stirred at ambient temperature, overnight and under nitrogen. The reaction mixture was filtered through a hydrophobic frit and the filtrate diluted with methanol (0.5 ml) and the sample purified by MDAP on Sunfire C18 column using Acetonitrile-Water with a Formic acid modifier (Method B). The solvent was evaporated in vacuo to give the title compound (10.5 mg); LCMS: (System 4) MH$^+$=378, $t_{RET}$=2.86 min.

Example 9

N-[1-({4-Chloro-2-[(phenylmethyl)oxy]phenyl]methyl)-1H-pyrazol-3-yl}-2,6-difluorobenzamide

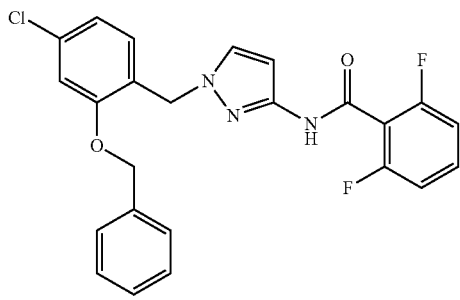 [SMILES: O=C(Nc1ccn(Cc2ccc(Cl)cc2OCc2ccccc2)n1)c1c(F)cccc1F]

To a solution of {4-chloro-2-[(phenylmethyl)oxy]phenyl}methanol (for as preparation see Intermediate 15) (0.501 g, 2.02 mmol) in DCM (10 ml) at −10 to −15° C., under nitrogen, was added a solution of phosphorus tribromide (0.190 ml, 2.02 mmol, Aldrich) in DCM (5 ml) dropwise. The solution was allowed to warm to ambient temperature and stirred for 4.5 h. To the reaction mixture in an ice-water bath was added dropwise saturated aqueous sodium hydrogen carbonate (5 ml). The mixture was diluted with water (45 ml) and dichloromethane (55 ml). The phases were separated and the aqueous phase washed with DCM (30 ml). The combined organic extracts were washed with water (10 ml). The organic extract was dried (MgSO$_4$), filtered and the solvent removed in vacuo to give 1-(bromomethyl)-4-chloro-2-[(phenylmethyl)oxy]benzene as a colourless gum (0.505 g).

To a mixture of 2,6-difluoro-N-1H-pyrazol-3-ylbenzamide (for as preparation see Intermediate 9) (76 mg, 0.340 mmol) and potassium carbonate (96 mg, 0.692 mmol) was added a solution of 1-(bromomethyl)-4-chloro-2-[(phenylmethyl)oxy]benzene (0.106 g, 0.340 mmol) in DMF (1 ml). The reaction was stirred overnight, at ambient temperature and under nitrogen. The suspension was filtered using a hydrophobic frit and the residue washed with methanol (1 ml). The filtrate was purified by MDAP (supelcosil ABZ+Plus column) eluting with solvents A/B (A: Water+0.1% Formic acid, B: MeCN:Water 95:5+0.05% Formic acid) (Method A). The solvent was evaporated in vacuo to give the title compound as a white solid (27 mg); LCMS: (System 1) MH$^+$=454, $t_{RET}$=3.68 min.

Example 10

N-{1-[(2,4-Dichlorophenyl)methyl]-1H-pyrazol-3-yl}-2,6-difluorobenzamide

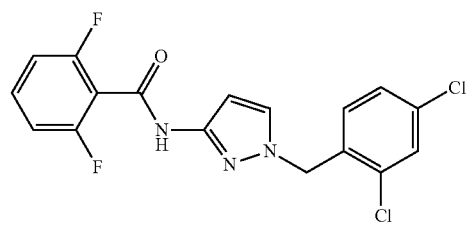 [SMILES: O=C(Nc1ccn(Cc2ccc(Cl)cc2Cl)n1)c1c(F)cccc1F]

1-[(2,4-Dichlorophenyl)methyl]-1H-pyrazol-3-amine (40 µl, 0.23 mmol, Art-Chem GmbH) was dissolved in dichloromethane (2 ml). Triethylamine (64 µl, 0.46 mmol) and then 2,6-difluorobenzoyl chloride (49 mg, 0.28 mmol, Aldrich) were added and the reaction was stirred at room temperature for 2 h. The reaction was quenched by addition of water (5 ml). The organic phase was separated (by hydrophobic frit) and concentrated under a flow of nitrogen. The residue was purified by MDAP (supelcosil ABZ+Plus column) eluting with solvents A/B (A: Water+0.1% Formic acid, B: MeCN:Water 95:5+0.05% Formic acid) (Method A). The appropriate fractions were concentrated in vacuo then under nitrogen flow. The sample was dissolved in methanol and applied to a 5 g aminopropyl ion exchange cartridge (prewashed with MeOH) and eluted with MeOH. The relevant fractions were combined and concentrated to give the title compound as a colourless solid (36 mg); LCMS: (System 1) MH$^+$=382/384, $t_{RET}$=3.47 min.

Example 11

2-Bromo-6-chloro-N-{1-[(2,4-dichlorophenyl)methyl]-1H-pyrazol-3-yl}benzamide

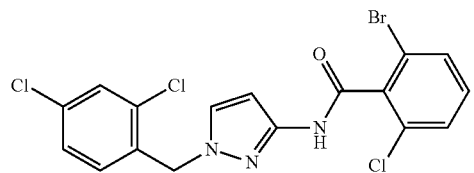 [SMILES: O=C(Nc1ccn(Cc2ccc(Cl)cc2Cl)n1)c1c(Cl)cccc1Br]

A solution of HATU (28 mg, 0.075 mmol) in N,N-Dimethylformamide (200 µl) was added to 2-bromo-6-chlorobenzoic acid (13.2 mg, 0.075 mmol, Fluorochem) followed by N,N-diisopropylamine (0.026 ml, 0.15 mmol) and left to stand for 5 minutes at room temperature.

A solution of 1-[(2,4-dichlorophenyl)methyl]-1H-pyrazol-3-amine (14 mg, 0.059 mmol, ChemCollect GmbH) in N,N-dimethylformamide (200 µl) was then added and the solution left to stand for 18 h at ambient temperature. The sample was purified by MDAP (Method D) and the solvent removed in vacuo using Genevac to give the title compound (13 mg); LCMS: (System 1) MH$^+$=460, $t_{RET}$=3.52 min.

Similarly prepared were:

| Example | Structure | Name | LCMS $t_{RET}$/min | MH+ |
|---|---|---|---|---|
| 12 | 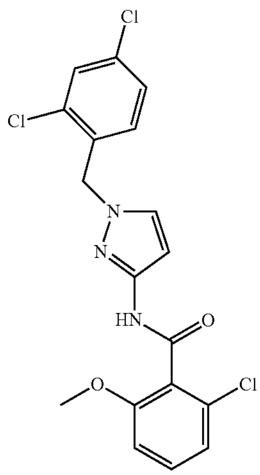 [SMILES: COc1cccc(Cl)c1C(=O)Nc1ccn(Cc2ccc(Cl)cc2Cl)n1] | 2-Chloro-N-{1-[(2,4-dichlorophenyl)methyl]-1H-pyrazol-3-yl}-6-(methyloxy)benzamide | 3.40 (System 1) | 410 |
| 13 | 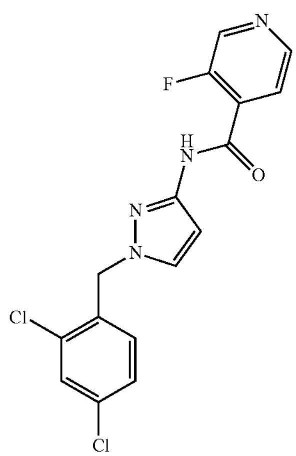 [SMILES: O=C(Nc1ccn(Cc2ccc(Cl)cc2Cl)n1)c1ccncc1F] | N-{1-[(2,4-dichlorophenyl)methyl]-1H-pyrazol-3-yl}-3-fluoro-4-pyridinecarboxamide | 1.06 (System 3) | 365 |
| 14 | 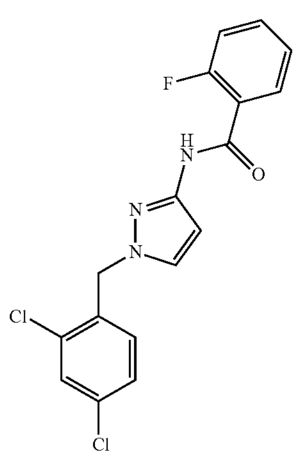 [SMILES: O=C(Nc1ccn(Cc2ccc(Cl)cc2Cl)n1)c1ccccc1F] | N-{1-[(2,4-dichlorophenyl)methyl]-1H-pyrazol-3-yl}-2-fluorobenzamide | 1.21 (System 3) | 364 |

-continued

| Example | Structure | Name | LCMS t$_{RET}$/min | MH⁺ |
|---|---|---|---|---|
| 15 | 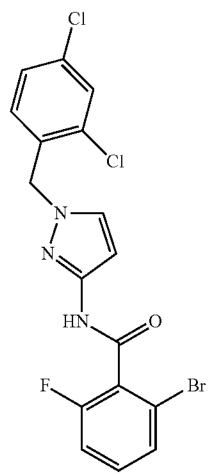 [SMILES: O=C(Nc1ccn(Cc2ccc(Cl)cc2Cl)n1)c1c(F)cccc1Br] | 2-Bromo-N-{1-[(2,4-dichlorophenyl)methyl]-1H-pyrazol-3-yl}-6-fluorobenzamide | 3.46 (System 1) | 42 |
| 16 | 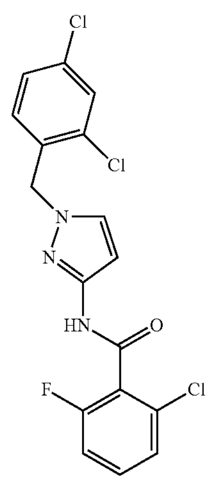 [SMILES: O=C(Nc1ccn(Cc2ccc(Cl)cc2Cl)n1)c1c(F)cccc1Cl] | 2-Chloro-N-{1-[(2,4-dichlorophenyl)methyl]-1H-pyrazol-3-yl}-6-fluorobenzamide | 1.19 (System 3) | 398 |
| 17 | 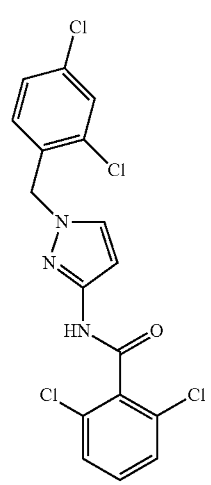 [SMILES: O=C(Nc1ccn(Cc2ccc(Cl)cc2Cl)n1)c1c(Cl)cccc1Cl] | 2,6-Dichloro-N-{1-[(2,4-dichlorophenyl)methyl]-1H-pyrazol-3-yl}benzamide | 1.22 (System 3) | 414 |

| Example | Structure | Name | LCMS $t_{RET}$/min | MH+ |
|---|---|---|---|---|
| 137 | 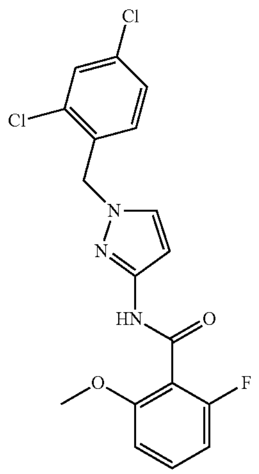 [SMILES: COc1cccc(F)c1C(=O)Nc1ccn(Cc2ccc(Cl)cc2Cl)n1] | N-{1-[(2,4-Dichlorophenyl)methyl]-1H-pyrazol-3-yl}-2-fluoro-6-(methyloxy)benzamide | 3.34 (System 1) | 394/396 |

Example 18

N-{1-[(2,4-dichlorophenyl)methyl]-1H-pyrazol-3-yl}-3,5-difluoro-4-pyridinecarboxamide

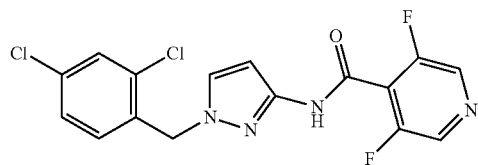 [SMILES: O=C(Nc1ccn(Cc2ccc(Cl)cc2Cl)n1)c1c(F)cncc1F]

To a solution of 3,5-difluoro-4-pyridinecarboxylic acid (15.9 mg, 0.1 mmol, Frontier Scientific) in dimethylformamide (0.1 ml) was added HATU (38 mg, 0.1 mmol) in dimethylformamide (0.2 mL), followed by N,N-diisopropylethylamine (0.050 ml, 0.286 mmol) and the resulting solution left for 5 min. Finally, a solution of 1-[(2,4-dichlorophenyl)methyl]-1H-pyrazol-3-amine (24.2 mg, 0.01 mmol, ChemCollect GmbH) in N,N-dimethylformamide (0.1 ml) was added and the resulting solution shaken for 10 min. The solution was then left to stand for 16 h at ambient temperature after which the solvent was removed. A 1:1 mixture of dimethylsulphoxide:methanol (0.6 ml) was added and the solution purified by MDAP on SUNFIRE C18 column (Method D). The appropriate fraction was concentrated in vacuo then under nitrogen flow to give the title compound (4.4 mg);

LCMS: (System 3) MH+=383/385, $t_{RET}$=1.12 min.

Example 19

N-[1-({5-chloro-2-[(phenylmethyl)oxy]phenyl}methyl)-1H-pyrazol-3-yl]-2,6-difluorobenzamide

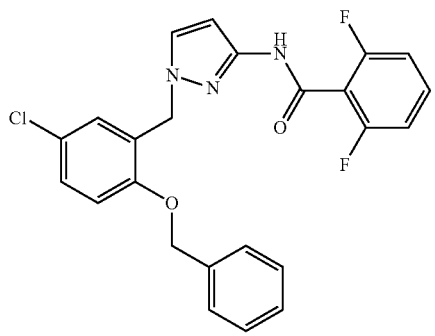 [SMILES: O=C(Nc1ccn(Cc2cc(Cl)ccc2OCc2ccccc2)n1)c1c(F)cccc1F]

2,6-Difluoro-N-(1H-pyrazol-3-yl)benzamide (for a preparation see Intermediate 9)(174 mg, 0.78 mmol) was dissolved in DMF (2.5 ml). Sodium iodide (33 mg, 0.22 mmol) and potassium carbonate (164 mg, 1.19 mmol) were added followed by 2-(bromomethyl)-4-chloro-1-[(phenylmethyl)oxy]benzene (synthesised according to WO2006066968) (233 mg, 0.75 mmol) washed in with further DMF (2.5 ml). The reaction mixture was stirred at ambient temperature overnight. The reaction mixture was then stirred and heated to 80° C. for 3 h under a nitrogen atmosphere and allowed to cool. Further 2-(bromomethyl)-4-chloro-1-[(phenylmethyl)oxy]benzene (51 mg) was added, and the reaction was stirred and heated to 80° C. under a nitrogen atmosphere for 3 h. The reaction mixture was concentrated in vacuo. The crude material was treated with water (50 ml) and extracted with EtOAc (3×50 ml). The extracts were combined, dried (MgSO4) and concentrated in vacuo. The residue was purified on silica (50 g) using 0-100% EtOAc-cyclohexane. Appropriate fractions were concentrated in vacuo to give the title compound as a colourless gum (20 mg);

LCMS: (System 1) MH+=454/456, $t_{RET}$=3.66 min.

Example 20

2,6-Difluoro-N-(1-{[2-(trifluoromethyl)phenyl]methyl}-1H-pyrazol-3-yl)benzamide

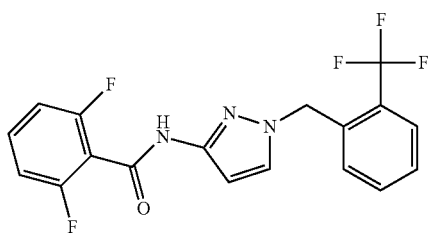 [SMILES: O=C(Nc1ccn(Cc2ccccc2C(F)(F)F)n1)c1c(F)cccc1F]

A solution of 2,6-difluoro-N-1H-pyrazol-3-ylbenzamide ((for a preparation see Intermediate 9)(31.9 mg, 0.1 mmol) in dimethylformamide (0.4 ml) was treated with potassium t-butoxide (11.3 mg, 0.1 mmol) and allowed to stand at room temperature for 10 min. A solution of 2-(trifluoromethyl) benzyl bromide (22.3 mg, 0.1 mmol, Aldrich) in acetonitrile (0.2 ml) was finally added and the solution left to stand for 16 h at room temperature. The solvent was removed using a Genevac and the crude mixture dissolved in a 1:1 mixture of dimethylsulphoxide:methanol (0.6 ml) and the solution purified by MDAP on SUNFIRE C18 (Method D). The appropriate fraction was concentrated in vacuo using a Genevac to give the title compound (2.3 mg);

LCMS: (System 3) MH$^+$=381, $t_{RET}$=1.19 min.

Similarly prepared were:

| Example | Structure | Name | LCMS $t_{RET}$/min | MH$^+$ |
|---|---|---|---|---|
| 21 | 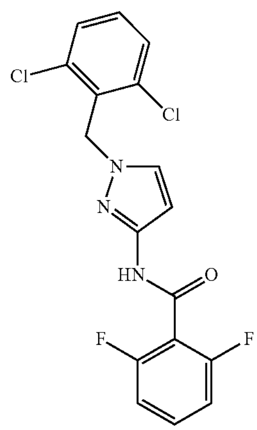 [SMILES: O=C(Nc1ccn(Cc2c(Cl)cccc2Cl)n1)c1c(F)cccc1F] | N-{1-[(2,6-dichlorophenyl)methyl]-1H-pyrazol-3-yl}-2,6-difluorobenzamide | 3.38 (System 1) | 382/384 |
| 22 | 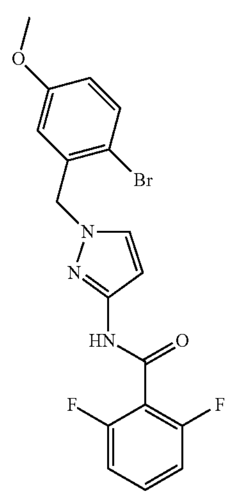 [SMILES: COc1ccc(Br)c(Cn2ccc(NC(=O)c3c(F)cccc3F)n2)c1] | N-(1-{[2-bromo-5-(methyloxy)phenyl]methyl}-1H-pyrazol-3-yl)-2,6-difluorobenzamide | 3.37 (System 1) | 422/424 |

-continued

| Example | Structure | Name | LCMS t_RET/min | MH+ |
|---|---|---|---|---|
| 23 | 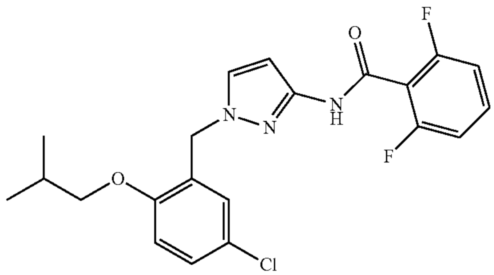 [SMILES: CC(C)COc1ccc(Cl)cc1Cn1ccc(NC(=O)c2c(F)cccc2F)n1] | N-[1-({5-chloro-2-[(2-methylpropyl)oxy]phenyl}methyl)-1H-pyrazol-3-yl]-2,6-difluorobenzamide | 3.75 (System 1) | 420/422 |
| 24 | 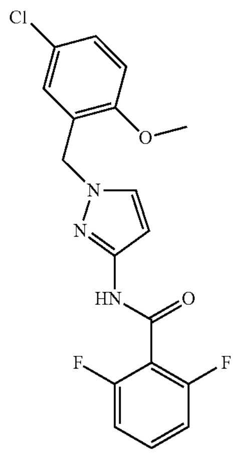 [SMILES: COc1ccc(Cl)cc1Cn1ccc(NC(=O)c2c(F)cccc2F)n1] | N-(1-{[5-chloro-2-(methyloxy)phenyl]methyl}-1H-pyrazol-3-yl)-2,6-difluorobenzamide | 3.36 (System 1) | 378/380 |
| 25 | 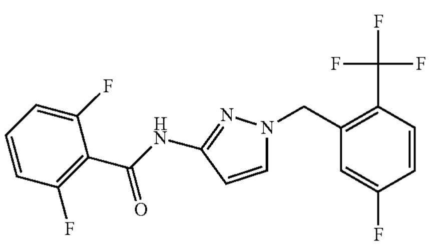 [SMILES: O=C(Nc1ccn(Cc2cc(F)ccc2C(F)(F)F)n1)c1c(F)cccc1F] | 2,6-Difluoro-N-(1-{[5-fluoro-2-(trifluoromethyl)phenyl]methyl}-1H-pyrazol-3-yl)benzamide | 3.40 (System 1) | 400 |
| 26 | 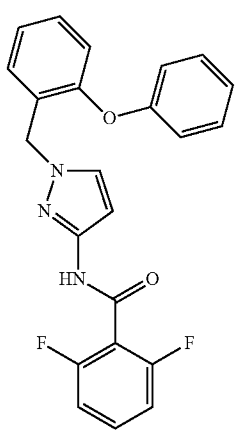 [SMILES: O=C(Nc1ccn(Cc2ccccc2Oc2ccccc2)n1)c1c(F)cccc1F] | 2,6-Difluoro-N-(1-{[2-(phenyloxy)phenyl]methyl}-1H-pyrazol-3-yl)benzamide | 3.55 (System 1) | 406 |

| Example | Structure | Name | LCMS $t_{RET}$/min | MH+ |
|---|---|---|---|---|
| 27 | 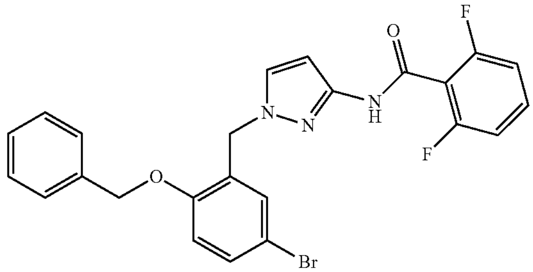 | N-[1-({5-bromo-2-[(phenylmethyl)oxy]phenyl}methyl)-1H-pyrazol-3-yl]-2,6-difluorobenzamide | 3.74 (System 1) | 498/500 |
| 28 | 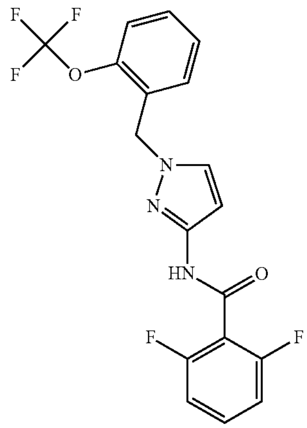 [SMILES: O=C(Nc1ccn(Cc2ccccc2OC(F)(F)F)n1)c1c(F)cccc1F] | 2,6-Difluoro-N-[1-({2-[(trifluoromethyl)oxy]phenyl}methyl)-1H-pyrazol-3-yl]benzamide | 1.14 (System 3) | 398 |
| 138 | 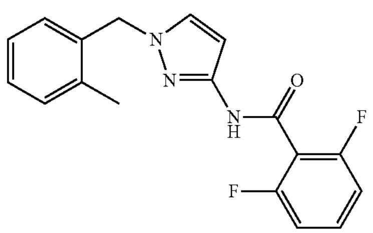 [SMILES: Cc1ccccc1Cn1ccc(NC(=O)c2c(F)cccc2F)n1] | 2,6-Difluoro-N-{1-[(2-methylphenyl)methyl]-1H-pyrazol-3-yl}benzamide | 1.02 (System 3) | 328 |

Example 29

2,6-Difluoro-N-(1-{[2-fluoro-6-(trifluoromethyl)phenyl]methyl}-1H-pyrazol-3-yl)benzamide

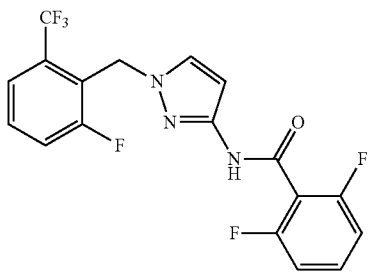 [SMILES: O=C(Nc1ccn(Cc2c(F)cccc2C(F)(F)F)n1)c1c(F)cccc1F]

A solution of 2,6-difluoro-N-1H-pyrazol-3-ylbenzamide (for a preparation see Intermediate 9) (4.59 g, 20.6 mmol) in THF (45 ml) was cooled to 5° C. under nitrogen. A solution of 1.0 M lithium bis(trimethylsilyl)amide in THF (20.6 ml, 20.6 mmol) was added dropwise maintaining the temperature below 10° C. After 10 minutes a solution of 2-(bromomethyl)-1-fluoro-3-(trifluoromethyl)benzene (5.29 g, 20.6 mmol, JRD fluorochemicals Ltd) in THF (9 ml) was added and the reaction mixture was stirred at room temperature overnight. The reaction was quenched using 1 M hydrochloric acid (50 ml). The reaction mixture was extracted with ethyl acetate (2×50 ml). The combined organic extracts were washed with brine (50 ml), dried with magnesium sulphate, filtered and solvent removed in vacuo. The crude material was dissolved in DCM and applied to a 330 g silica cartridge. The cartridge was eluted with 0-100% ethyl acetate in cyclohexane over 45 min. The required fractions were combined and evaporated in vacuo, to give the title compound as a white solid (6.75 g). The white solid (6.75 g) was dissolved in ethyl acetate (70 ml) and heated to 50° C. Cyclohexane (280 ml) was then added dropwise over 20 min.

The solution was left to cool to room temperature overnight. White crystals formed which were filtered, washed with the same solvent mixture (50 ml) and dried in an oven at 40° C. to give the title compound as a white solid (5.07 g). LCMS: (System 3) MH+=400, $t_{RET}$=1.10 min. $^1$H NMR (400 MHz, Chloroform-d) δ=8.17 (1 H, br, s), 7.59-7.46 (2 H, m), 7.44-7.31 (2 H, m), 7.28 (1 H, d, J=2.5 Hz), 6.98 (2 H, t, J=8.0 Hz), 6.84 (1 H, d, J=2.5 Hz), 5.40 (2 H, s).

Example 30

{N-[1-({2-Chloro-4-[(phenylmethyl)oxy]phenyl}methyl)-1H-pyrazol-3-yl]-2,6-difluorobenzamide

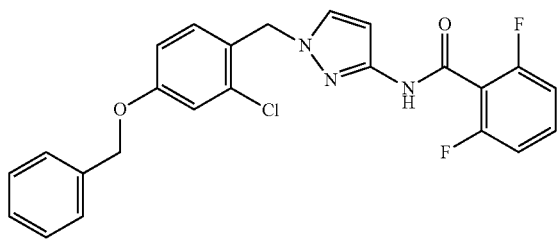 [SMILES: O=C(Nc1ccn(Cc2ccc(OCc3ccccc3)cc2Cl)n1)c1c(F)cccc1F]

To a solution of 3-chloro-4-(hydroxymethyl)phenol (for a preparation see Intermediate 16)(3 g, 18.9 mmol) in ethanol (80 ml) was added benzyl bromide (2.25 ml, 18.9 mmol, Aldrich) and then 2 M aqueous sodium hydroxide (10.4 ml, 20.8 mmol). The mixture was stirred at ambient temperature overnight under nitrogen. The solvent was removed in vacuo to leave an aqueous suspension. The residue was partitioned between dichloromethane (100 ml) and water (100 ml). The phases were separated and the aqueous phase extracted with dichloromethane (50 ml). The combined organic extracts were dried (MgSO$_4$), filtered and the solvent removed in vacuo to leave an oil. The residue was loaded in dichloromethane and purified on silica (100 g×2) using 0-100% ethyl acetate-cyclohexane. The appropriate fractions were combined and evaporated in vacuo to give {2-chloro-4-[(phenylmethyl)oxy]phenyl}methanol as a white solid (2.18 g).

To a solution of {2-chloro-4-[(phenylmethyl)oxy]phenyl}methanol (2.08 g, 8.36 mmol) in DCM (20 ml) under nitrogen in an ice-water bath was added a solution of phosphorus tribromide (0.83 ml, 8.80 mmol, Aldrich) in DCM (10 ml). The solution was allowed to warm to ambient temperature and stirred for 1.5 h. The reaction mixture was poured onto ice-water (70 ml) and saturated aqueous sodium hydrogen carbonate (30 ml). The mixture was diluted with DCM (50 ml), and the phases separated. The aqueous extract was washed with dichloromethane (20 ml). The combined organic extracts were washed with water (50 ml), dried (MgSO$_4$), filtered and the solvent removed in vacuo to give 1-(bromomethyl)-2-chloro-4-[(phenylmethyl)oxy]benzene as white solid (2.48 g).

To a solution of 2,6-difluoro-N-(1H-pyrazol-3-yl)benzamide (for a preparation see Intermediate 9)(0.961 g, 4.31 mmol) and 1-(bromomethyl)-2-chloro-4-[(phenylmethyl)oxy]benzene (1.21 g, 3.88 mmol) in anhydrous NMP (15 ml) was added 2,6-lutidine (0.5 ml, 4.29 mmol, Aldrich). The reaction vessel (20 ml) was sealed and heated in Biotage Initiator microwave to 160° C. for 30 min. After cooling the reaction mixture was partitioned between saturated aqueous sodium hydrogen carbonate (120 ml) and ethyl acetate (100 ml). The phases were separated and the aqueous phase extracted with ethyl acetate (50 ml). The combined organic extracts were washed with saturated aqueous sodium hydrogen carbonate (50 ml), dried (MgSO$_4$), filtered and the solvent removed in vacuo to leave a red oil (2.84 g). The residue was loaded in dichloromethane and purified on silica (100 g×2) using 0-100% ethyl acetate-cyclohexane. The appropriate fractions were combined and evaporated in vacuo to give the title compound as a white solid (0.778 g); LCMS: (System 4) MH$^+$=454, t$_{RET}$=3.35 min.

Example 31

N-{1-[(2-Chloro-4-hydroxyphenyl)methyl]-1H-pyrazol-3-yl}-2,6-difluorobenzamide

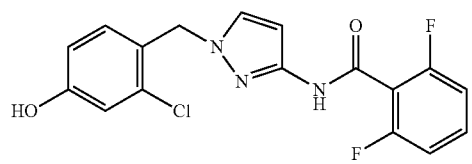 [SMILES: O=C(Nc1ccn(Cc2ccc(O)cc2Cl)n1)c1c(F)cccc1F]

A solution of {N-[1-({2-chloro-4-[(phenylmethyl)oxy]phenyl}methyl)-1H-pyrazol-3-yl]-2,6-difluorobenzamide (for a preparation see Example 30)(0.731 g, 1.61 mmol) in methanol (35 ml) was hydrogenated using the H-cube (settings: ambient, 1 bar, 1 ml/min flow rate) and 10% Pd/C CatCart 30 as the catalyst. The solvent was removed in vacuo to leave an oil. The residue was loaded in dichloromethane and purified on silica (100 g) using 0-100% ethyl acetate-cyclohexane. The appropriate fractions were combined and evaporated in vacuo to give the title compound as a colourless oil (0.331 g); LCMS: (System 4) MH$^+$=364, t$_{RET}$=2.36 min.

Example 32

N-[1-({2-Chloro-4-[(7-hydroxyheptyl)oxy]phenyl}methyl)-1H-pyrazol-3-yl]-2,6-difluorobenzamide

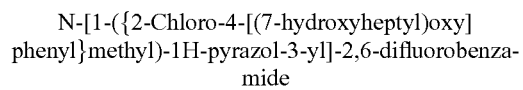

To a solution of N-{1-[(2-chloro-4-hydroxyphenyl)methyl]-1H-pyrazol-3-yl}-2,6-difluorobenzamide (for a preparation see Example 31)(30 mg, 0.082 mmol) in acetonitrile (0.5 ml) was added potassium t-butoxide (9.4 mg, 0.084 mmol) and then 7-bromo-1-heptanol (0.015 ml, 0.099 mmol, Aldrich). The reaction vessel was sealed and heated in a Biotage Initiator microwave to 100° C. for 15 min. After cooling the reaction was diluted with DMSO (0.5 ml) and purified by MDAP on Sunfire C18 column using Acetonitrile-Water with a Formic acid modifier (Method B). The solvent was evaporated in vacuo to give the title compound as a colourless gum (6.7 mg);

LCMS: (System 4) MH$^+$=478, t$_{RET}$=3.02 min.

Example 33

N-(1-{[2-Chloro-4-(methyloxy)phenyl]methyl}-1H-pyrazol-3-yl)-2,6-difluorobenzamide

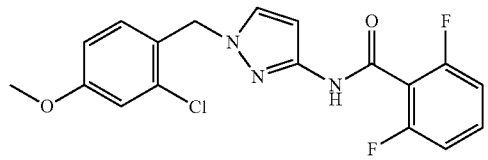 [SMILES: COc1ccc(Cn2ccc(NC(=O)c3c(F)cccc3F)n2)c(Cl)c1]

To a solution of N-{1-[(2-chloro-4-hydroxyphenyl)methyl]-1H-pyrazol-3-yl}-2,6-difluorobenzamide (for a preparation see Example 31)(30 mg, 0.082 mmol) in DMSO (0.5 ml) was added potassium t-butoxide (9.6 mg, 0.086 mmol) and then methyl iodide (6 µl, 0.096 mmol, Aldrich). The solution was stirred at ambient temperature overnight. The solution was diluted with methanol (0.5 ml) and purified by MDAP on Sunfire C18 column using Acetonitrile-Water with a Formic acid modifier (Method B). The solvent was evaporated in vacuo to give the title compound as a colourless gum (7.3 mg); LCMS: (System 4) MH$^+$=378, $t_{RET}$=2.85 min.

Example 34

N-(1-{[4-(Butyloxy)-2-chlorophenyl]methyl}-1H-pyrazol-3-yl)-2,6-difluorobenzamide

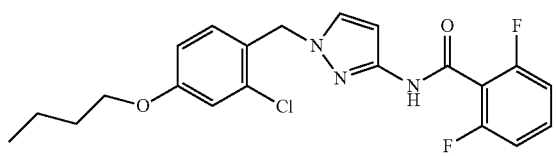 [SMILES: CCCCOc1ccc(Cn2ccc(NC(=O)c3c(F)cccc3F)n2)c(Cl)c1]

Potassium t-butoxide (9.7 mg, 0.086 mmol, Aldrich) was added to a solution of N-{1-[(2-chloro-4-hydroxyphenyl)methyl]-1H-pyrazol-3-yl}-2,6-difluorobenzamide (for a preparation see Example 31)(29.4 mg, 0.081 mmol) in DMSO (0.5 ml). The reaction was stirred for 5 min before adding 1-bromobutane (10.42 µL, 0.097 mmo, Acros). The reaction was stirred for 56 h at ambient temperature. The reaction mixture was diluted with methanol (0.5 ml) and the sample purified by MDAP on Sunfire C18 column using Acetonitrile-Water with a Formic acid modifier. (Method B). The solvent was evaporated in vacuo to give the title compound as a yellow gum (14.5 mg); LCMS: (System 4) MH$^+$=420, $t_{RET}$=3.45 min.

Example 35

2,6-Difluoro-N-(1-{[4-[(phenylmethyl)oxy]-2-(trifluoromethyl)phenyl]methyl}-1H-pyrazol-3-yl)benzamide

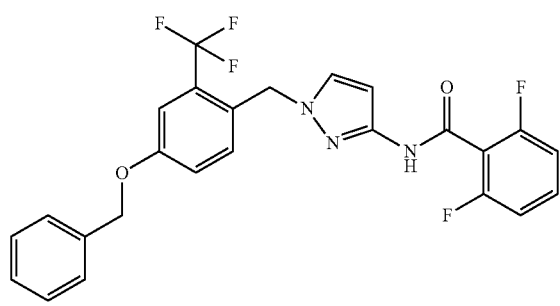 [SMILES: O=C(Nc1ccn(Cc2ccc(OCc3ccccc3)cc2C(F)(F)F)n1)c1c(F)cccc1F]

To a solution of [4-[(phenylmethyl)oxy]-2-(trifluoromethyl)phenyl]methanol (for a preparation see Intermediate 18)(3.11 g, 11.02 mmol) in DCM (40 ml) under nitrogen in an ice-water bath was added a solution of phosphorus tribromide (1.09 ml, 11.6 mmol, Aldrich) in DCM (20 ml). The solution was allowed to warm to ambient temperature and stirred for 1.5 h. The reaction mixture was poured onto ice-water (150 ml) and saturated aqueous sodium hydrogen carbonate (75 ml). The mixture was diluted with dichloromethane (100 ml), and the phases separated. The aqueous extract was washed with dichloromethane (50 ml). The combined organic extracts were washed with water (50 ml), dried (MgSO$_4$), filtered and the solvent removed in vacuo to give 4-(bromomethyl)-3-(trifluoromethyl)phenyl phenylmethyl ether as a white solid (2.96 g).

To a solution of 2,6-difluoro-N-(1H-pyrazol-3-yl)benzamide (for a preparation see Intermediate 9)(1.05 g, 4.70 mmol) in anhydrous THF (30 ml) was added 1.0 M lithium bis(trimethylsilyl)amide in THF (4.7 ml, 4.70 mmol) at ambient temperature under nitrogen. The solution was stirred at ambient temperature for 20 min. To the solution was added a solution of 4-(bromomethyl)-3-(trifluoromethyl)phenyl phenylmethyl ether (1.47 g, 4.26 mmol) in THF (15 ml). The mixture was stirred overnight. The solvent was removed in vacuo and the residue partitioned between ethyl acetate (120 ml) and saturated aqueous sodium hydrogen carbonate (100 ml). The phases were separated and the aqueous phase washed with ethyl acetate (30 ml). The combined organic extracts were dried (MgSO$_4$), filtered and the solvent removed in vacuo to leave a pale yellow oil (~2.5 g). The residue was loaded in dichloromethane and purified on silica (100 g) using 0-100% ethyl acetate-cyclohexane. The appropriate fractions were combined and evaporated in vacuo to give the title compound as a white foam (1.61 g); LCMS: (System 4) MH$^+$=488, $t_{RET}$=3.37 min.

Example 36

2,6-Difluoro-N-(1-{[4-hydroxy-2-(trifluoromethyl)phenyl]methyl}-1H-pyrazol-3-yl)benzamide

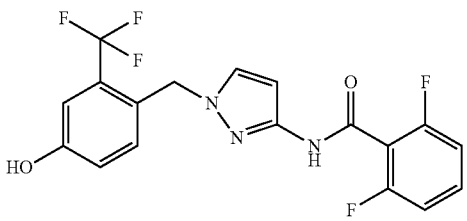 [SMILES: O=C(Nc1ccn(Cc2ccc(O)cc2C(F)(F)F)n1)c1c(F)cccc1F]

A solution of 2,6-difluoro-N-1H-pyrazol-3-ylbenzamide (for a preparation see Intermediate 9)(4 g, 17.9 mmol) in THF (100 ml) under nitrogen, was treated with 1.0 M lithium bis(trimethylsilyl)amide in THF (19.7 ml, 19.7 mmol, Aldrich) and stirred at ambient temperature for 15 min. 1-(bromomethyl)-4-methoxy-2-(trifluoromethyl)benzene (4.82 g, 17.9 mmol, JRD fluorochemicals Ltd) in THF (5 ml) was added and the mixture stirred for 60 h. The mixture was concentrated in vacuo and the residue partitioned between chloroform and saturated aqueous sodium hydrogen carbonate solution. The organic layer was separated and the aqueous extracted once more with chloroform. The combined extracts were concentrated, giving an off white solid (7.72 g). DCM (100 ml) was added, then treated with 1.0 M boron tribromide in DCM (35.8 ml, 35.8 mmol, Aldrich) at ambient temperature and stirred under nitrogen for 18 h. The mixture was treated with water and partitioned with chloroform. The organic layer was separated and the aqueous extracted once more with chloroform. The combined extracts were concentrated, giving an off white solid. The residue was purified by silica column chromatography using ethyl acetate-cyclohexane as eluents. The appropriate fractions were combined and concentrated in vacuo to give the title compound as a white solid (4.35 g). The white solid (4.2 g) was boiled in cyclohexane (approximately 50 ml) and then treated with 2-propanol (approximately 20 ml) until the solid dissolved. The solution was allowed to cool to ambient temperature and left to form crystals for 5 days, which were collected by filtration and then dried for 18 h under vacuum, yielding a white crystalline solid (3.4 g); LCMS: (System 3) MH$^+$=398, $t_{RET}$=0.97 min; m.p. 138° C.

Example 139

2,6-Difluoro-N-(1-{[4-hydroxy-2-(trifluoromethyl)phenyl]methyl}-1H-pyrazol-3-yl)benzamide sodium salt

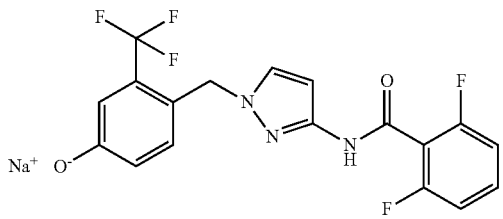 [SMILES: [Na+] ; O=C(Nc1ccn(Cc2ccc([O-])cc2C(F)(F)F)n1)c1c(F)cccc1F]

To a suspension of 2,6-difluoro-N-(1-{[4-hydroxy-2-(trifluoromethyl)phenyl]methyl}-1H-pyrazol-3-yl)benzamide (for a preparation see Example 36)(49.2 mg, 0.124 mmol) in water (15 ml) was added sodium hydroxide (0.062 mL, 0.124 mmol). The resulting suspension was stirred at 60° C. for 5 h. Almost all the compound went into solution. The solvent was removed using a stream of nitrogen to give the title compound as a white solid (52 mg); LCMS: (System 3) MH$^+$=398, $t_{RET}$=0.96 min.

Example 37

2,6-Difluoro-N-(1-{[4-[(4-pyridinylmethyl)oxy]-2-(trifluoromethyl)phenyl]methyl}-1H-pyrazol-3-yl)benzamide trifluoroacetate

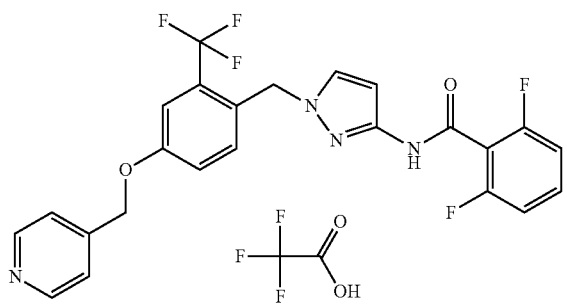 [SMILES: O=C(Nc1ccn(Cc2ccc(OCc3ccncc3)cc2C(F)(F)F)n1)c1c(F)cccc1F ; O=C(O)C(F)(F)F]

To a solution of 2,6-difluoro-N-(1-{[4-hydroxy-2-(trifluoromethyl)phenyl]methyl}-1H-pyrazol-3-yl)benzamide (for a preparation see Example 36)(100 mg, 0.252 mmol) in DMSO (1 ml) was added cesium carbonate (165 mg, 0.506 mmol) and then 4-(bromomethyl)pyridine hydrobromide (90 mg, 0.356 mmol, Aldrich) under nitrogen at ambient temperature. The resulting dark green suspension was then stirred for 7 h. A further amount of cesium carbonate (161 mg, 0.494 mmol) and then 4-(bromomethyl)pyridine hydrobromide (90 mg, 0.356 mmol, Aldrich) was added to the reaction mixture and stirred overnight. The mixture was filtered using a hydrophobic frit and the filtrate diluted with methanol (1 ml). The filtrate was purified by MDAP on Sunfire C18 column using Acetonitrile-Water with a TFA modifier (Method C). The solvent was evaporated in vacuo to give the title compound as a brown gum (44 mg);
LCMS: (System 4) MH$^+$=489, $t_{RET}$=2.05 min.

Example 38

2,6-Difluoro-N-(1-{[4-[(3-pyridinylmethoxy)oxy]-2-(trifluoromethyl)phenyl]methyl}-1H-pyrazol-3-yl)benzamide trifluoroacetate

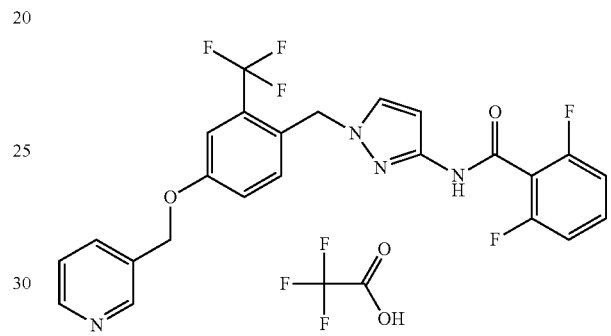

To a solution of 2,6-difluoro-N-(1-{[4-hydroxy-2-(trifluoromethyl)phenyl]methyl}-1H-pyrazol-3-yl)benzamide (for a preparation see Example 36)(100 mg, 0.252 mmol) in DMSO (1 ml) was added cesium carbonate (166 mg, 0.509 mmol) and then 3-(bromomethyl)pyridine hydrobromide (89 mg, 0.352 mmol, Aldrich) at ambient temperature under nitrogen. The resulting yellow suspension was stirred for 3 h. The mixture was filtered using a hydrophobic frit and the filtrate diluted with methanol (1 ml). The filtrate was purified by MDAP on Sunfire C18 column using Acetonitrile-Water with a TFA modifier (Method C). The solvent was evaporated in vacuo to give the title compound (65 mg) as a yellow solid; LCMS: (System 4) MH$^+$=489, $t_{RET}$=2.25 min.

Example 39

2,6-Difluoro-N-(1-{[4-(methyloxy)-2-(trifluoromethyl)phenyl]methyl}-1H-pyrazol-3-yl)benzamide

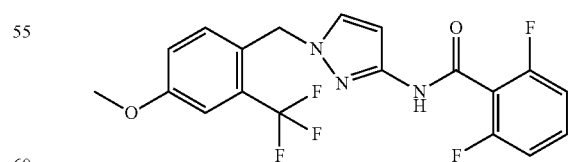

To a solution of 2,6-difluoro-N-(1-{[4-hydroxy-2-(trifluoromethyl)phenyl]methyl}-1H-pyrazol-3-yl)benzamide (for a preparation see Example 36)(72 mg, 0.181 mmol) in DMSO (0.5 ml) was added potassium t-butoxide (20 mg, 0.178 mmol). The reaction mixture was stirred for 5 min before adding methyl iodide (0.011 ml, 0.181 mmol, Aldrich). The reaction was stirred at ambient temperature, overnight and under nitrogen. The reaction mixture was filtered through a hydrophobic frit and the filtrate diluted with methanol (0.5 ml) and the sample purified by MDAP on Sunfire C18 column using Acetonitrile-Water with a Formic acid modifier (Method B). The solvent was evaporated in vacuo to give the title compound as a white solid (20.3 mg);
LCMS: (System 4) MH$^+$=412, $t_{RET}$=3.01 min.

Example 40

Ethyl 4-{[4-[(3-{[(2,6-difluorophenyl)carbonyl]amino}-1H-pyrazol-1-yl)methyl]-3-(trifluoromethyl)phenyl]oxy}butanoate

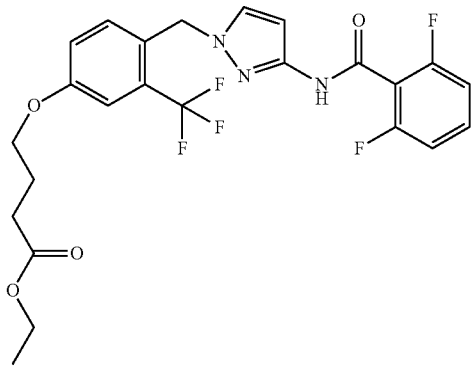 [SMILES: CCOC(=O)CCCOc1ccc(Cn2ccc(NC(=O)c3c(F)cccc3F)n2)c(C(F)(F)F)c1]

To a solution of 2,6-difluoro-N-(1-{[4-hydroxy-2-(trifluoromethyl)phenyl]methyl}-1H-pyrazol-3-yl)benzamide (for a preparation see Example 36)(77 mg, 0.194 mmol) in DMSO (0.5 ml) was added potassium t-butoxide (22 mg, 0.196 mmol). The reaction was stirred for 15 min. To the reaction was added ethyl 4-bromobutanoate (0.028 ml, 0.195 mmol, Aldrich). The reaction was stirred overnight, under nitrogen and at 60° C. The reaction mixture was filtered through a hydrophobic frit, the filtrate was diluted with methanol (0.5 ml) and the sample purified by MDAP on Sunfire C18 column using Acetonitrile-Water with a Formic acid modifier (Method B). The solvent was evaporated in vacuo to give the title compound as a brown gum (39.8 mg);
LCMS: (System 4) MH$^+$=512, $t_{RET}$=3.27 min.

Example 41

Methyl {[4-[(3-{[(2,6-difluorophenyl)carbonyl]amino}-1H-pyrazol-1-yl)methyl]-3-(trifluoromethyl)phenyl]oxy}acetate

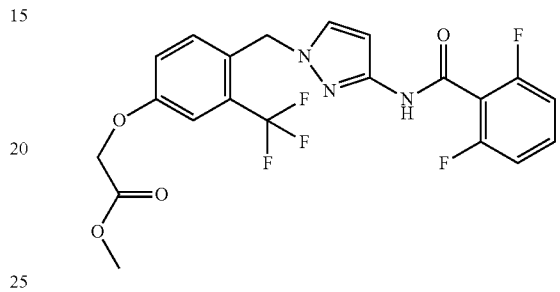

To a solution of 2,6-difluoro-N-(1-{[4-hydroxy-2-(trifluoromethyl)phenyl]methyl}-1H-pyrazol-3-yl)benzamide (for a preparation see Example 36)(81 mg, 0.204 mmol) in DMSO (0.5 ml) was added potassium t-butoxide (23 mg, 0.205 mmol). The reaction was stirred for 15 min before adding methyl bromoacetate (0.020 ml, 0.211 mmol, Aldrich). The reaction was heated to 60° C. and stirred overnight, under nitrogen. The reaction mixture was filtered through a hydrophobic frit and the filtrate diluted with methanol (0.5 ml) and the sample purified by MDAP on Sunfire C18 column using Acetonitrile-Water with a Formic acid modifier (Method B). The solvent was evaporated in vacuo to give the title compound as a brown gum (38.5 mg); LCMS: (System 4) MH$^+$=470, $t_{RET}$=2.90 min.
Similarly prepared was:

| Example | Structure | Name | LCMS $t_{RET}$/min | MH$^+$ |
|---|---|---|---|---|
| 140 | 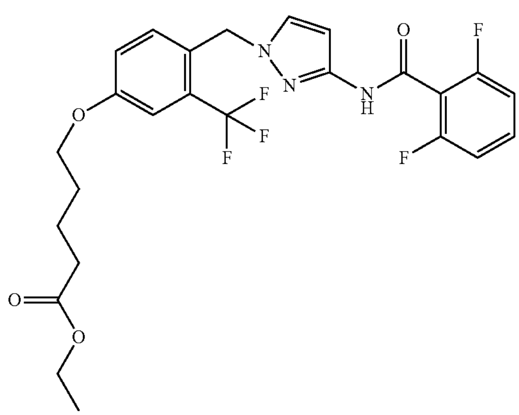 [SMILES: CCOC(=O)CCCCOc1ccc(Cn2ccc(NC(=O)c3c(F)cccc3F)n2)c(C(F)(F)F)c1] | Ethyl 5-{[4-[(3-{[(2,6-difluorophenyl)carbonyl]amino}-1H-pyrazol-1-yl)methyl]-3-(trifluoromethyl)phenyl]oxy}pentanoate | 3.38 (System 4) | 526 |

Example 42

2,6-Difluoro-N-(1-{[4-{[2-(methyloxy)ethyl]oxy}-2-(trifluoromethyl)phenyl]methyl}-1H-pyrazol-3-yl)benzamide

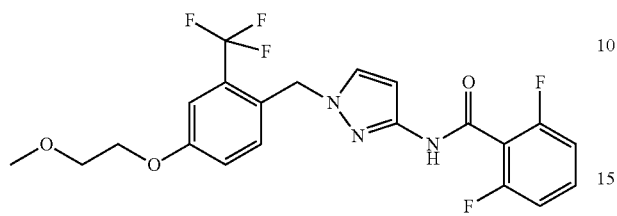

To a solution of 2,6-difluoro-N-(1-{[4-hydroxy-2-(trifluoromethyl)phenyl]methyl}-1H-pyrazol-3-yl)benzamide ((for a preparation see Example 36)101 mg, 0.254 mmol) in DMSO (1 ml) was added cesium carbonate (166 mg, 0.508 mmol) and then 1-bromo-2-(methyloxy)ethane (0.035 ml, 0.372 mmol, Aldrich) under nitrogen at ambient temperature. The solution was stirred for 6 h. The mixture was filtered using a hydrophobic frit and the filtrate diluted with methanol (1 ml). The filtrate was purified by MDAP on Sunfire C18 column using Acetonitrile-Water with a Formic acid modifier (Method B). The solvent was evaporated in vacuo to give the title compound as a pale yellow gum (35 mg); LCMS: (System 4) MH$^+$=456, $t_{RET}$=2.84 min.

Example 43

Ethyl 4-[(3-{[(2,6-difluorophenyl)carbonyl]amino}-1H-pyrazol-1-yl)methyl]-3-(trifluoromethyl)benzoate

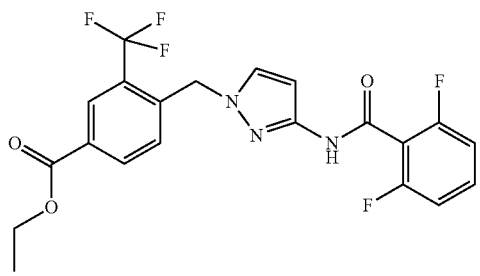 [SMILES: CCOC(=O)c1ccc(Cn2ccc(NC(=O)c3c(F)cccc3F)n2)c(C(F)(F)F)c1]

To a solution of 2,6-difluoro-N-(1H-pyrazol-3-yl)benzamide (for a preparation see Intermediate 9)(1.29 g, 5.78 mmol) in THF (30 ml) was added 1.0M lithium bis(trimethylsilyl)amide in THF (5.66 ml, 5.66 mmol) at ambient temperature under nitrogen. The solution was stirred at ambient temperature for 30 min. To the solution was added a solution of ethyl 4-(bromomethyl)-3-(trifluoromethyl)benzoate (for a preparation see Intermediate 20)(1.6 g, 5.14 mmol) in THF (20 ml). The mixture was stirred for 3.5 h at ambient temperature under nitrogen. The solvent was removed in vacuo and the residue partitioned between ethyl acetate (100 ml) and saturated aqueous sodium hydrogen carbonate (75 ml). The phases were separated and the aqueous phase washed with ethyl acetate (25 ml). The combined organic extracts were dried (MgSO$_4$), filtered and the solvent removed in vacuo to leave a pale yellow oil (2.8 g). The residue was loaded in dichloromethane and purified on silica (100 g) using 0-100% ethyl acetate-cyclohexane. The appropriate fractions were combined and evaporated in vacuo to give the title compound as a white foam (1.68 g); LCMS: (System 4) MH$^+$=454, $t_{RET}$=3.15 min.

Example 44

2,6-Difluoro-N-(1-{[4-(hydroxymethyl)-2-(trifluoromethyl)phenyl]methyl}-1H-pyrazol-3-yl)benzamide

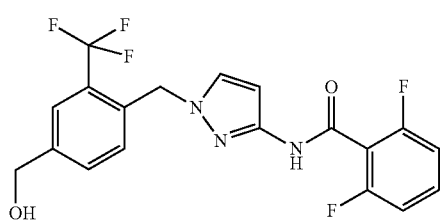 [SMILES: O=C(Nc1ccn(Cc2ccc(CO)cc2C(F)(F)F)n1)c1c(F)cccc1F]

To a solution of 4-[(3-{[(2,6-difluorophenyl)carbonyl]amino}-1H-pyrazol-1-yl)methyl]-3-(trifluoromethyl)benzoic acid (for a preparation see Intermediate 21)(0.340 g, 0.80 mmol) in THF (5 ml) at ambient temperature under nitrogen was added 1.0 M borane-tetrahydrofuran complex (1.3 ml, 1.30 mmol). The solution was stirred at ambient temperature under nitrogen for 1 h. To the suspension was added a further amount of 1.0 M borane-tetrahydrofuran complex (1.3 ml, 1.30 mmol). The solution was stirred for a further 2 h. The solvent was removed in vacuo to leave a colourless gum. The residue was re-dissolved in THF (5 ml). To the solution was added 1.0M boran-tetrahydrofuran complex (2 ml, 2 mmol) and stirred for 6 h. The solution was quenched with methanol (10 ml), stirred for 5 min and then the solvent removed in vacuo. The residue was loaded in dichloromethane and purified on silica (20 g) using 0-100% ethyl acetate-cyclohexane+ 0-20% methanol. The appropriate fractions were combined and evaporated in vacuo to give the title compound as a colourless gum (0.20 g);

LCMS: (System 4) MH$^+$=412, $t_{RET}$=2.42 min.

Example 45

2,6-difluoro-N-(1-{[4-(2H-1,2,3-triazol-2-ylmethyl)-2-(trifluoromethyl)phenyl]methyl}-1H-pyrazol-3-yl)benzamide

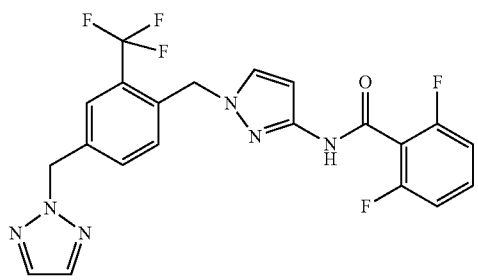 [SMILES: O=C(Nc1ccn(Cc2ccc(Cn3nccn3)cc2C(F)(F)F)n1)c1c(F)cccc1F]

To a stirred solution of 1H-1,2,3-triazole (34 mg, 0.492 mmol, Alfa Aesar) in THF (2 ml) at ambient temperature under nitrogen was added 1.0 M lithium bis(trimethylsilyl)

amide in THF (0.5 ml, 0.500 mmol). The resulting yellow cloudy mixture was stirred at ambient temperature for 10 min. To a solution of N-(1-{[4-(bromomethyl)-2-(trifluoromethyl)phenyl]methyl}-1H-pyrazol-3-yl)-2,6-difluorobenzamide (for a preparation see Intermediate 22)(49 mg, 0.103 mmol) in THF (2 ml) at ambient temperature was added a solution of the 1H-1,2,3-triazole anion (0.5 ml, 0.167 mmol). After 1.5 h, a further amount of 1H-1,2,3-triazole anion (0.5 ml, 0.167 mmol) was added to the mixture and stirred overnight. The solvent was removed in vacuo and the residue was dissolved in 1:1 MeOH:DMSO (1 ml) and purified by MDAP on Sunfire C18 column using Acetonitrile-Water with a Formic acid modifier (Method B). The solvent was evaporated in vacuo to give the title compound as a colourless gum (1.8 mg); LCMS: (System 4) MH$^+$=463.1, $t_{RET}$=2.85 min.

Similarly prepared was:

lar sieves (418 mg) (pre-dried in the oven overnight) and then 21% sodium ethoxide in ethanol (0.2 ml, 0.536 mmol, Alfa Aesar). To the reaction mixture was added methyl 4-chloro-3-[(3-{[(2,6-difluorophenyl)carbonyl]amino}-1H-pyrazol-1-yl)methyl]benzoate (for a preparation see Intermediate 23) (105 mg, 0.259 mmol). The reaction was heated to reflux (100° C.) and stirred for 3 h under nitrogen. The reaction mixture was evaporated in vacuo and the residue dissolved in methanol (0.5 ml) and filtered through a hydrophobic frit. The residue was dissolved with DMSO (0.5 ml) and the sample was purified by MDAP on Sunfire C18 column using Acetonitrile-Water with a Formic acid modifier (Method B). The solvent was evaporated in vacuo to give the title compound as a white gum (6.1 mg);

LCMS: (System 4) MH$^+$=430, $t_{RET}$=2.83 min.

| Example | Structure | Name | LCMS $t_{RET}$/min | MH$^+$ |
|---|---|---|---|---|
| 141 | 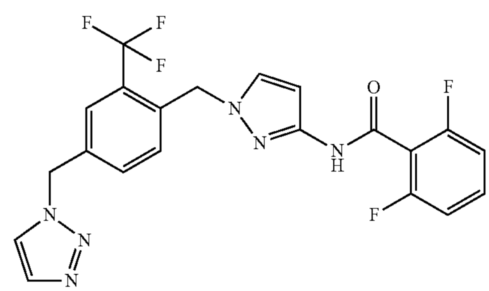 [SMILES: O=C(Nc1ccn(Cc2ccc(Cn3ccnn3)cc2C(F)(F)F)n1)c1c(F)cccc1F] | 2,6-Difluoro-N-(1-{[4-(1H-1,2,3-triazol-1-ylmethyl)-2-(trifluoromethyl)phenyl]methyl}-1H-pyrazol-3-yl)benzamide | 2.55 (System 4) | 463 |

Example 46

N-(1-{[2-Chloro-5-(3-methyl-1,2,4-oxadiazol-5-yl)phenyl]methyl}-1H-pyrazol-3-yl)-2,6-difluorobenzamie

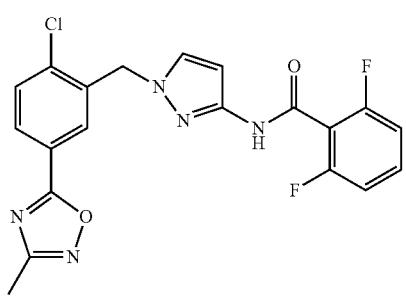 [SMILES: Cc1noc(-c2ccc(Cl)c(Cn3ccc(NC(=O)c4c(F)cccc4F)n3)c2)n1]

Example 47

2,6-Difluoro-N-[1-({2-methyl-4-[(phenylmethyl)oxy]phenyl}methyl)-1H-pyrazol-3-yl]benzamide

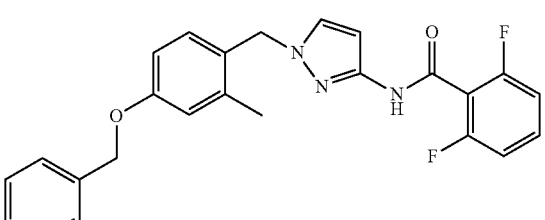

To a solution of acetamide oxime (89 mg, 1.20 mmol, GFS chemicals) in ethanol (2 ml) was added 4A activated molecu- To a solution of 4-hydroxy-2-methyl benzoic acid (5 g, 32.9 mmol, Aldrich) in THF (60 ml) at ambient temperature under nitrogen was added dropwise 1.0M borane-tetrahydrofuran complex (70 ml, 70.0 mmol). The suspension was heated at 80° C. for 2 h. To the solution at ambient temperature was added methanol (40 ml) dropwise. The solution was heated to 80° C. for 30 min. The solvent was removed in vacuo and the residue dissolved in methanol (100 ml). The solvent was removed in vacuo to leave a white solid (4.63 g). The residue was further purified by SPE on aminopropyl (NH2) 70 g (prewashed with methanol) and eluted with methanol (three column volumes). The solvent was removed in vacuo to give impure 4-(hydroxymethyl)-3-methylphenol as an orange solid (4.25 g).

To a solution of 4-(hydroxymethyl)-3-methylphenol (4.25 g, 30.8 mmol) in ethanol (90 ml) was added 2M aqueous sodium hydroxide (17 ml, 34 mmol) and then benzyl bromide (3.65 ml, 30.8 mmol, Aldrich). The pale yellow mixture was stirred at ambient temperature under nitrogen overnight. The solvent was removed in vacuo to leave an aqueous suspension. The residue was partitioned between dichloromethane (100 ml) and water (100 ml). The phases were separated and the aqueous phase extracted with dichloromethane (50 ml). The combined organic extracts were dried (MgSO$_4$), filtered and the solvent removed in vacuo to leave an orange oil. The residue was loaded in dichloromethane and purified on silica (100 g×3) using 0-100% ethyl acetate-cyclohexane. The appropriate fractions were combined and the solvent evaporated in vacuo to give {2-methyl-4-[(phenylmethyl)oxy]phenyl}methanol (2.59 g).

To a solution of {2-methyl-4-[(phenylmethyl)oxy]phenyl}methanol (1.49 g, 6.53 mmol) in DCM (20 ml) under nitrogen in an ice-water bath was added a solution of phosphorus tribromide (0.62 ml, 6.57 mmol, Aldrich) in DCM (10 ml). The solution was allowed to warm to ambient temperature and stirred for 3 h. The reaction mixture was poured onto ice-water (70 ml) and saturated aqueous sodium hydrogen carbonate (30 ml). The mixture was diluted with DCM (50 ml) and the phases separated. The aqueous extract was washed with dichloromethane DCM (20 ml). The combined organic extracts were washed with water (50 ml), dried (MgSO$_4$), filtered and the solvent removed in vacuo to leave 4-(bromomethyl)-3-methylphenyl phenylmethyl ether as a yellow oil (1.72 g).

To a solution of 2,6-difluoro-N-1H-pyrazol-3-ylbenzamide (for a preparation see Intermediate 9)(1.31 g, 5.87 mmol) in anhydrous THF (30 ml) was added 1.0 M lithium bis(trimethylsilyl)amide in THF (6 ml, 6 mmol) at ambient temperature under nitrogen. The yellow solution was stirred for 20 min. To the solution was added a solution of 4-(bromomethyl)-3-methylphenyl phenylmethyl ether (1.72 g, 5.91 mmol) in THF (13 ml). The mixture was stirred overnight. The solvent was removed in vacuo and the residue partitioned between ethyl acetate (120 ml) and saturated aqueous sodium hydrogen carbonate (100 ml). The phases were separated and the aqueous phase washed with ethyl acetate (30 ml). The combined organic extracts were dried (MgSO$_4$), filtered and the solvent removed in vacuo to leave a yellow oil (3.10 g). The residue was loaded in DCM and purified on silica (100 g) using 0-100% ethyl acetate-cyclohexane. The appropriate fractions were combined and the solvent evaporated in vacuo to give the title compound as a yellow gum (1.9 g); LCMS: (System 4) MH$^+$=434, t$_{RET}$=3.14 min.

Example 48

2,6-Difluoro-N-{1-[(4-hydroxy-2-methylphenyl)methyl]-1H-pyrazol-3-yl}benzamide

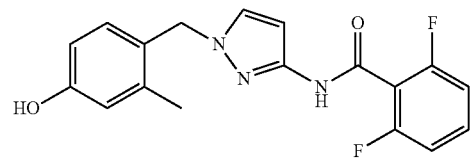 [SMILES: Cc1cc(O)ccc1Cn1ccc(NC(=O)c2c(F)cccc2F)n1]

To 10% palladium on carbon 50% wt water, degussa type E101 NE/W (406 mg, 3.82 mmol) was added under vacuum a solution of 2,6-difluoro-N-[1-({2-methyl-4-[(phenylmethyl)oxy]phenyl}methyl)-1H-pyrazol-3-yl]benzamide (for a preparation see Example 47)(1.79 g, 4.13 mmol) in ethyl acetate (30 ml). The suspension was hydrogenated at ambient temperature for 1.5 h. The suspension was filtered through a celite cartridge (10 g) and the cartridge washed with methanol (100 ml). The solvent was removed in vacuo to give the title compound as a grey foam (1.34 g);

LCMS: (System 4) MH$^+$=344, t$_{RET}$=2.19 min.

Example 49

2,6-difluoro-N-[1-({2-methyl-4-[(2-pyridinylmethyl)oxy]phenyl}methyl]-1H-pyrazol-3-yl]benzamide

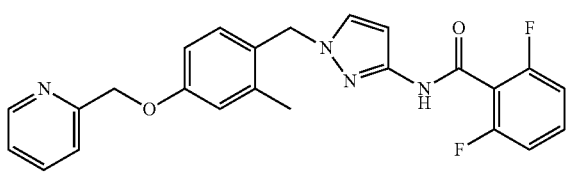 [SMILES: Cc1cc(OCc2ccccn2)ccc1Cn1ccc(NC(=O)c2c(F)cccc2F)n1]

To a solution of 2,6-difluoro-N-{1-[(4-hydroxy-2-methylphenyl)methyl]-1H-pyrazol-3-yl}benzamide (for a preparation see Example 48)(103 mg, 0.30 mmol) in dimethyl sulfoxide (1 ml) was added cesium carbonate (195 mg, 0.60 mmol) and then 2-(bromomethyl)pyridine hydrobromide (107 mg, 0.423 mmol, Aldrich). The resulting red solution was stirred at ambient temperature under nitrogen overnight. The mixture was filtered using a hydrophobic frit and the filtrate diluted with methanol (1 ml). The filtrate was purified by MDAP on Sunfire C18 column using Acetonitrile-Water with a Formic acid modifier (Method B). The solvent was evaporated in vacuo to give the title compound as an orange gum (28.3 mg); LCMS: (System 4) MH$^+$=435, t$_{RET}$=2.27 min.

Similarly prepared were:

| Example | Structure | Name | LCMS $t_{RET}$/min | MH+ |
|---|---|---|---|---|
| 50 | 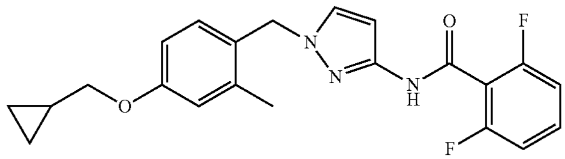 [SMILES: Cc1cc(OCC2CC2)ccc1Cn1ccc(NC(=O)c2c(F)cccc2F)n1] | N-[1-({4-[(cyclopropylmethyl)oxy]-2-methylphenyl}methyl)-1H-pyrazol-3-yl]-2,6-difluorobenzamide | 3.06 (System 4) | 398 |
| 142 | 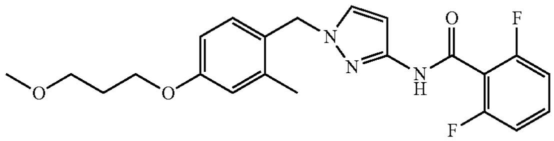 [SMILES: COCCCOc1ccc(Cn2ccc(NC(=O)c3c(F)cccc3F)n2)c(C)c1] | 2,6-Difluoro-N-{1-[(2-methyl-4-{[3-(methyloxy)propyl]oxy}phenyl)methyl]-1H-pyrazol-3-yl}benzamide | 2.77 (System 4) | 416 |
| 143 | 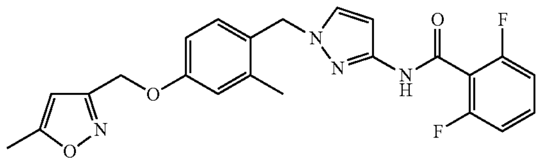 [SMILES: Cc1cc(COc2ccc(Cn3ccc(NC(=O)c4c(F)cccc4F)n3)c(C)c2)no1] | 2,6-Difluoro-N-{1-[(2-methyl-4-{[(5-methyl-3-isoxazolyl)methyl]oxy}phenyl)methyl]-1H-pyrazol-3-yl}benzamide | 2.86 (System 4) | 439 |

Example 51

N-(1-{[2-chloro-6-(methyloxy)phenyl]methyl}-1H-pyrazol-3-yl)-2,6-difluorobenzamide

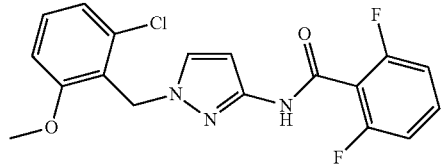 [SMILES: COc1cccc(Cl)c1Cn1ccc(NC(=O)c2c(F)cccc2F)n1]

To a stirred solution of 2,6-difluoro-N-1H-pyrazol-3-yl-benzamide (for a preparation see Intermediate 9)(0.05 g, 0.224 mmol) in dry THF (1.5 ml) under nitrogen was added a 1 M solution of lithium bis(trimethylsilyl)amide in THF (0.224 ml, 0.224 mmol, Aldrich) dropwise, fairly quickly. The solution was stirred for 30 min then a solution of 2-(bromomethyl)-3-chlorophenyl methyl ether (for a preparation see Intermediate 25)(0.053 g, 0.224 mmol) in dry THF (1.5 ml) was added and stirring continued for 90 min then the solution was left to stand overnight. The solvent was removed in vacuo and the residue was partitioned between chloroform and half saturated sodium bicarbonate and the aqueous phase further extracted with chloroform, the chloroform fractions being filtered through a phase separator. The chloroform was removed in vacuo and the residue purified on MDAP (Method B) to give the title compound as a white solid (0.07 g); LCMS: (System 4) MH+=378, $t_{RET}$=2.77 min.

Example 52

2,6-Difluoro-N-(1-{[2-fluoro-6-(methyloxy)phenyl]methyl}-1H-pyrazol-3-yl)benzamide

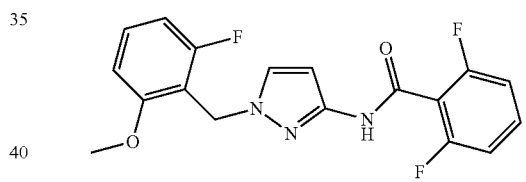

The title compound was made in a similar fashion to the preparation of Example 51 replacing 2-(bromomethyl)-3-chlorophenyl methyl ether with 2-(bromomethyl)-1-fluoro-3-(methyloxy)benzene (Apollo); LCMS: (System 4) MH+=362, $t_{RET}$=2.74 min Example 53

N-(1-{[2-chloro-6-(trifluoromethyl)phenyl]methyl}-1H-pyrazol-3-yl)-2,6-difluorobenzamide

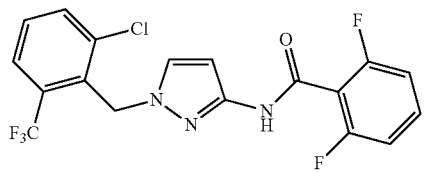 [SMILES: O=C(Nc1ccn(Cc2c(Cl)cccc2C(F)(F)F)n1)c1c(F)cccc1F]

The title compound was made in a similar fashion to the preparation of Example 51 replacing 2-(bromomethyl)-3- chlorophenyl methyl ether with 2-(bromomethyl)-1-chloro-3-(trifluoromethyl)benzene (JRD Fluorochemicals); LCMS: (System 4) MH$^+$=416, $t_{RET}$=2.99 min.

Example 54

N-{1-[(2,6-Dimethylphenyl)methyl]-1H-pyrazol-3-yl}-2,6-difluorobenzamide

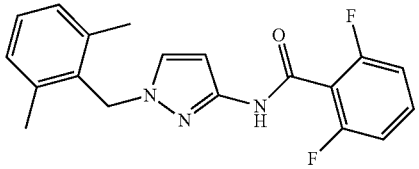 [SMILES: Cc1cccc(C)c1Cn1ccc(NC(=O)c2c(F)cccc2F)n1]

The title compound was made in a similar fashion to the preparation of Example 51 replacing 2-(bromomethyl)-3-chlorophenyl methyl ether with 2-(chloromethyl)-1,3-dimethylbenzene (ABCR); LCMS: (System 4) MH$^+$=342, $t_{RET}$=2.86 min.

Example 55

N-{1-[(2-Bromo-6-chlorophenyl)methyl]-1H-pyrazol-3-yl}-2,6-difluorobenzamide

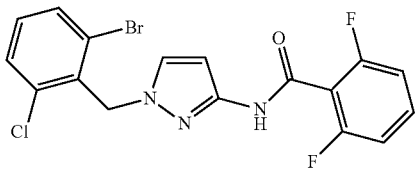 [SMILES: O=C(Nc1ccn(Cc2c(Cl)cccc2Br)n1)c1c(F)cccc1F]

The title compound was made in a similar fashion to the preparation of Example 51 replacing 2-(bromomethyl)-3-chlorophenyl methyl ether with 1-bromo-2-(bromomethyl)-3-chlorobenzene (Fluorochem); LCMS: (System 4) MH$^+$=426 and 428, $t_{RET}$=2.86 min.

Example 56

N-[1-({2-[(Cyclobutylmethyl)oxy]phenyl}methyl)-1H-pyrazol-3-yl]-2,6-difluorobenzamide

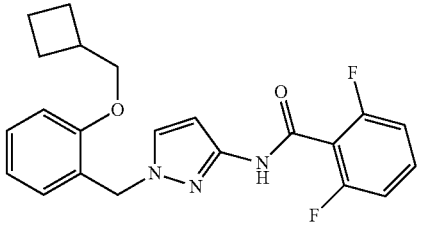 [SMILES: O=C(Nc1ccn(Cc2ccccc2OCC2CCC2)n1)c1c(F)cccc1F]

The title compound was made in a similar fashion to the preparation of Example 51 replacing 2-(bromomethyl)-3-chlorophenyl methyl ether with 1-(bromomethyl)-2-[(cyclobutylmethyl)oxy]benzene; LCMS: (System 4) MH$^+$=398, $t_{RET}$=3.23 min.

Example 57

N-[1-({2-Chloro-6-[(cyclobutylmethyl)oxy]phenyl}methyl)-1H-pyrazol-3-yl]-2,6-difluorobenzamide To a stirred solution of N-{1-[(2-chloro-6-hydroxyphenyl)methyl]-1H-pyrazol-3-yl}-2,6-difluorobenzamide (for a preparation see Intermediate 11)(0.047 g, 0.13 mmol) in dry DMSO (0.6 ml) in a reactivial was added potassium t-butoxide (0.0145 g, 0.13 mmol). The mixture was stirred for 20 min and then (bromomethyl)cyclobutane (0.023 g, 0.15 mmol, Aldrich) added. The mixture was stirred and heated at 60° C. for 24 h. The cooled reaction mixture was added to chloroform (about 20 ml) and this solution filtered through a hydrophobic frit and evaporated in vacuo. The residue was purified on MDAP (Method B) to give the title compound as a white solid (0.038 g); LCMS: (System 4) MH$^+$=432, $t_{RET}$=3.36 min.

Example 58

N-[1-({2-chloro-6-[(cyclopropylmethyl)oxy]phenyl}methyl)-1H-pyrazol-3-yl]-2,6-difluorobenzamide

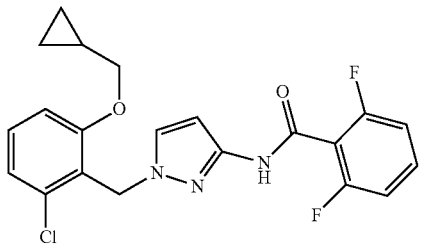 [SMILES: O=C(Nc1ccn(Cc2c(Cl)cccc2OCC2CC2)n1)c1c(F)cccc1F]

The title compound was made in a similar fashion to the preparation of Example 57 replacing (bromomethyl)cyclobutane with (bromomethyl)cyclopropane (Aldrich); LCMS: (System 4) MH$^+$=418, t$_{RET}$=3.14 min.

Example 59

2,6-Difluoro-N-[1-({2-[(phenylmethyl)oxy]phenyl}methyl)-1H-pyrazol-3-yl]benzamide

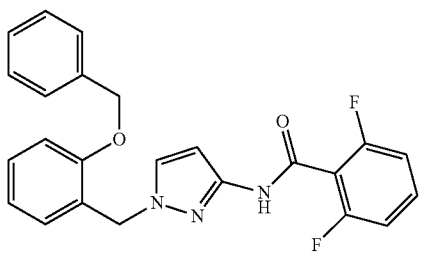 [SMILES: O=C(Nc1ccn(Cc2ccccc2OCc2ccccc2)n1)c1c(F)cccc1F]

To a stirred solution of 1-({2-[(phenylmethyl)oxy]phenyl}methyl)-1H-pyrazol-3-amine
(for a preparation see Intermediate 29) (1.66 g, 5.94 mmol) in acetonitrile (20 ml) was added triethylamine (1.66 ml, 11.9 mmol) followed by 2,6-difluorobenzoyl chloride (0.747 ml, 5.94 mmol, Aldrich). After stirring for 4 h the solvent was removed in vacuo and the solid residue partitioned between ethyl acetate and water. The aqueous layer was further extracted with ethyl acetate and the combined organic extracts were washed with brine, dried over magnesium sulphate, filtered and evaporated in vacuo to give the title compound as an off white foam (2.34 g); LCMS: (System 3) MH$^+$=420, t$_{RET}$=1.22 min.

Example 60

N-[1-({2-[(Cyclopropylmethyl)oxy]phenyl}methyl)-1H-pyrazol-3-yl]-2,6-difluorobenzamide

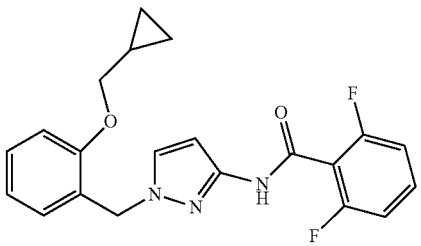 [SMILES: O=C(Nc1ccn(Cc2ccccc2OCC2CC2)n1)c1c(F)cccc1F]

The title compound was made in a similar fashion to the preparation of Example 57, replacing intermediate N-{1-[(2-Chloro-6-hydroxyphenyl)methyl]-1H-pyrazol-3-yl}-2,6-difluorobenzamide with intermediate 2,6-Difluoro-N-{1-[(2-hydroxyphenyl)methyl]-1H-pyrazol-3-yl}benzamide (for a preparation see Intermediate 30) and replacing (bromomethyl)cyclobutane with (bromomethyl)cyclopropane (Aldrich); LCMS: (System 4) MH$^+$=384, t$_{RET}$=2.97 min

Example 61

N-[1-({2-chloro-5-[(1,2,4-oxadiazol-3-ylmethyl)oxy]phenyl}methyl)-1H-pyrazol-3-yl]-2,6-difluorobenzamide

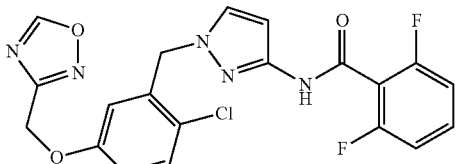

To a solution of N-{1-[(2-chloro-5-hydroxyphenyl)methyl]-1H-pyrazol-3-yl}-2,6-difluorobenzamide (for a preparation see Intermediate 13)(36 mg, 0.1 mmol) in dimethylsulphoxide (0.18 ml) was added a solution of potassium t-butoxide (11 mg, 0.1 mmol) in dimethylsulphoxide (0.1 ml). The reaction mixture was stirred for 30 min at ambient temperature before addition of 3-(chloromethyl)-1,2,4-oxadiazole (14 mg, 0.12 mmol, Acros) in dimethylsulphoxide (0.12 ml). The reaction mixture was stirred at 50° C. for 24 h. N,N-diisopropylethylamine (40 μl, 0.23 mmol) was added and reaction mixture reheated to 60° C. for a further 24 h.

Additional 3-(chloromethyl)-1,2,4-oxadiazole was added (0.08 mmol, 80 uL from a 1 mmol stock solution in DMSO) and heating continued at 60° C. for 18 h. Additional dimethylsulphoxide added (200 μl) and the reaction was purified by MDAP (Method D) on a Sunfire C18 column using Acetonitrile-Water with a TFA modifier. Solvent was evaporated in vacuo using a Genevac to give the title compound (3.4 mg); LCMS: (System 4) MH$^+$=446, t$_{RET}$=2.75 min.

Similarly prepared were:

| Example | Name | t_RET/min (System 4) | MH+ |
|---|---|---|---|
| 62 | N-{1-[(2-chloro-5-{[(5-methyl-3-isoxazolyl)methyl]oxy}phenyl)methyl]-1H-pyrazol-3-yl}-2,6-difluorobenzamide | 2.96 | 459 |
| 63 | N-[1-({2-chloro-5-[(2-methylpropyl)oxy]phenyl}methyl)-1H-pyrazol-3-yl]-2,6-difluorobenzamide | 3.40 | 420 |
| 64 | N-[1-({2-chloro-5-[(2-pyridinylmethyl)oxy]phenyl}methyl)-1H-pyrazol-3-yl]-2,6-difluorobenzamide trifluoroacetate | 2.52 | 455 |

| Example | Name | t_{RET}/min (System 4) | MH+ |
|---|---|---|---|
| 65 | N-{1-[(2-chloro-5-{[3-(methyloxy)propyl]oxy}phenyl)methyl]-1H-pyrazol-3-yl}-2,6-difluorobenzamide | 2.97 | 436 |
| 66 | 2,6-Difluoro-N-(1-{[4-[(1,2,4-oxadiazol-3-ylmethyl)oxy]-2-(trifluoromethyl)phenyl]methyl}-1H-pyrazol-3-yl)benzamide | 2.87 | 480 |
| 67 | 2,6-Difluoro-N-(1-{[4-{[(5-methyl-3-isoxazolyl)methyl]oxy}-2-(trifluoromethyl)phenyl]methyl}-1H-pyrazol-3-yl)benzamide | 3.08 | 493 |
| 68 | N-(1-{[4-[(cyclopropylmethyl)oxy]-2-(trifluoromethyl)phenyl]methyl}-1H-pyrazol-3-yl)-2,6-difluorobenzamide | 3.33 | 452 |

| Example | | Name | t_RET/min (System 4) | MH+ |
|---|---|---|---|---|
| 69 | 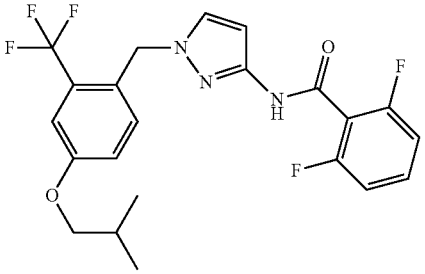 [SMILES: CC(C)COc1ccc(Cn2ccc(NC(=O)c3c(F)cccc3F)n2)c(C(F)(F)F)c1] | 2,6-Difluoro-N-(1-{[4-[(2-methylpropyl)oxy]-2-(trifluoromethyl)phenyl]methyl}-1H-pyrazol-3-yl)benzamide | 3.56 | 454 |
| 70 | 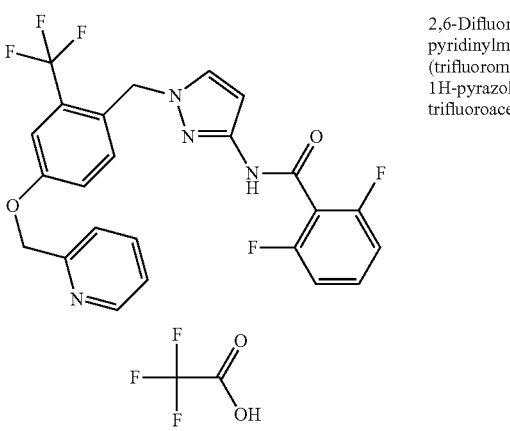 | 2,6-Difluoro-N-(1-{[4-[(2-pyridinylmethyl)oxy]-2-(trifluoromethyl)phenyl]methyl}-1H-pyrazol-3-yl)benzamide trifluoroacetate | 2.73 | 489 |
| 71 | 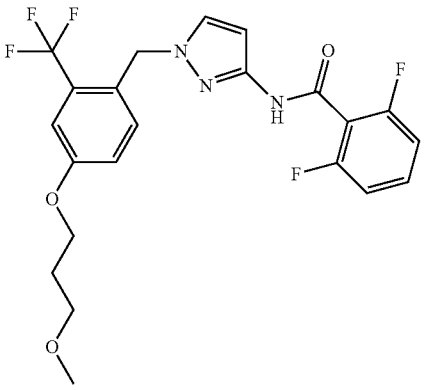 [SMILES: COCCCOc1ccc(Cn2ccc(NC(=O)c3c(F)cccc3F)n2)c(C(F)(F)F)c1] | 2,6-Difluoro-N-(1-{[4-{[3-(methyloxy)propyl]oxy}-2-(trifluoromethyl)phenyl]methyl}-1H-pyrazol-3-yl)benzamide | 3.11 | 470 |

Example 72

2,6-Difluoro-N-(1-{[4-[(3-hydroxypropyl)oxy]-2-(trifluoromethyl)phenyl]methyl}-1H-pyrazol-3-yl)benzamide

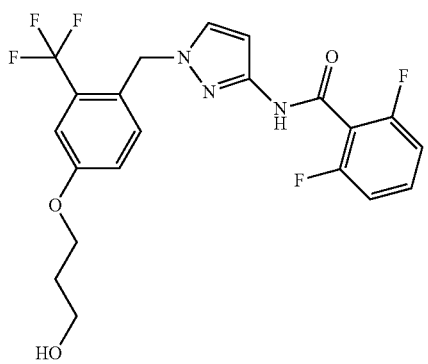 [SMILES: O=C(Nc1ccn(Cc2ccc(OCCCO)cc2C(F)(F)F)n1)c1c(F)cccc1F]

To a solution of 2,6-difluoro-N-(1-{[4-hydroxy-2-(trifluoromethyl)phenyl]methyl}-1H-pyrazol-3-yl)benzamide (for a preparation see Example 36)(36.3 mg, 0.1 mmol) in dimethylsulphoxide (0.18 ml) was added a solution of potassium t-butoxide (11 mg, 0.1 mmol) in dimethylsulphoxide (0.1 ml). The reaction mixture was stirred for 30 min at ambient temperature before addition of 3-bromo-1-propanol (17 mg, 0.12 mmol, Aldrich) in dimethylsulphoxide (0.12 ml). The reaction mixture was stirred at 50° C. for 24 h. N,N-diisopropylethylamine (40 µl, 0.23 mmol) was added and reaction mixture reheated to 60° C. for a further 24 h.

Additional 3-bromo-1-propanol was added (0.08 mmol, 80 µl from a 1 mmol stock solution in DMSO) and heating continued at 60° C. for 18 h. Additional dimethylsulphoxide was added (200 µl) and purified by MDAP (Method D) on a Sunfire C18 column using Acetonitrile-Water with a TFA modifier. Solvent was evaporated in vacuo using a Genevac. The sample was re-dissolved in DMSO (400 µl) and purified by MDAP on Xbridge column (Method E) using Acetonitrile-Water with an ammonium carbonate modifier. The solvent was evaporated in vacuo using the Genevac to give the title compound (5.2 mg); LCMS: (System 4) MH$^+$=456, $t_{RET}$=2.58 min.

Example 73

2,6-Difluoro-N-(1-{[4-iodo-2-(trifluoromethyl)phenyl]methyl}-1H-pyrazol-3-yl)benzamide

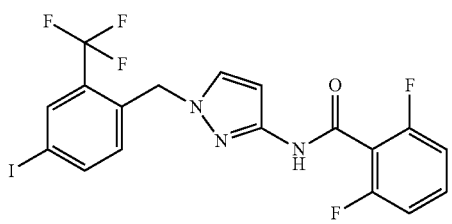 [SMILES: O=C(Nc1ccn(Cc2ccc(I)cc2C(F)(F)F)n1)c1c(F)cccc1F]

To a solution of 4-iodo-2-(trifluoromethyl)benzoic acid (for a preparation see Intermediate 31)(16.7 g, 52.8 mmol) in THF (150 ml) at ambient temperature under nitrogen was added 1.0 M borane-tetrahydrofuran complex (100 ml, 100 mmol, Aldrich) dropwise. The solution was heated to 80° C. for 1.5 h. To the solution at ambient temperature was added methanol (75 ml) and then heated to 80° C. for 1 h. The solvent was removed in vacuo to leave a mobile oil. The residue was partitioned between ethyl acetate (200 ml) and 2 N aqueous HCl (100 ml). The phases were separated and the organic phase washed with 2 N aqueous sodium hydroxide (100 ml), brine (50 ml), then dried (MgSO$_4$), filtered and the solvent removed in vacuo to give [4-iodo-2-(trifluoromethyl)phenyl]methanol as a pale brown solid (14.8 g).

To a solution of [4-iodo-2-(trifluoromethyl)phenyl]methanol (2.1 g, 6.95 mmol) in DCM (15 ml) in an ice-water bath was added dropwise a solution of phosphorous tribromide (0.66 ml, 7.00 mmol, Aldrich) in DCM (15 ml). The resulting solution was allowed to warm to ambient temperature and stirred under nitrogen for 2 h. The reaction mixture was poured onto a mixture of ice-water (50 ml) and saturated sodium hydrogen carbonate (50 ml). The biphasic mixture was diluted with DCM (50 ml). The phases were separated and the aqueous phase washed with DCM (50 ml). The combined organic phases were washed with water (50 ml), dried (MgSO$_4$), filtered and the solvent removed in vacuo to leave 1-(bromomethyl)-4-iodo-2-(trifluoromethyl)benzene as a brown oil (1.24 g).

To a solution of 2,6-difluoro-N-1H-pyrazol-3-ylbenzamide (for a preparation see Intermediate 9)(2.65 g, 11.9 mmol) in THF (20 ml) was added 1.0 lithium bis(trimethylsilyl)amide in THF (7.3 ml, 7.30 mmol, Aldrich) and stirred for 15 min. To the solution was added a solution of 1-(bromomethyl)-4-iodo-2-(trifluoromethyl)benzene (1.62 g, 4.44 mmol) in THF (10 ml). The resulting orange solution was stirred at ambient temperature under nitrogen overnight. The solvent was removed in vacuo and the residue partitioned between ethyl acetate (200 ml) and saturated aqueous sodium hydrogen carbonate (150 ml). The phases were separated and the aqueous phase washed with ethyl acetate (50 ml). The combined organic phases were dried (MgSO$_4$), filtered and the solvent removed in vacuo. The residue was loaded in dichloromethane and purified on silica 100 g×2 using 0-50% ethyl acetate-cyclohexane. The appropriate fractions were combined and evaporated in vacuo to give the title compound as a white foam (1.3 g). LCMS: (System 4) MH$^+$=508, $t_{RET}$=3.22 min.

Example 74

2,6-Difluoro-N-(1-{[4-(2-methylpropyl)-2-(trifluoromethyl)phenyl]methyl}-1H-pyrazol-3-yl)benzamide

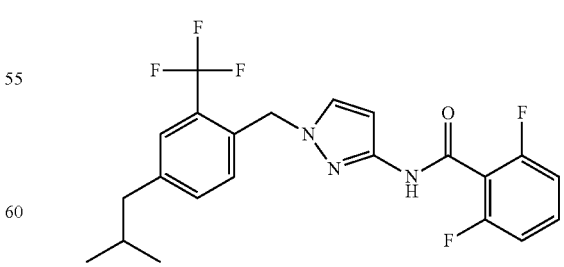

To a solution of 2,6-difluoro-N-(1-{[4-iodo-2-(trifluoromethyl)phenyl]methyl}-1H-pyrazol-3-yl)benzamide (for a preparation see Example 73)(75 mg, 0.148 mmol) in THF (1 ml) was added tetrakis(triphenyl-phosphine)palladium (0)

(17.1 mg, 0.015 mmol, Aldrich). To the solution was added 0.5 M t-butylzinc bromide in THF (0.6 ml, 0.30 mmol, Aldrich) and the mixture stirred at 80° C. under nitrogen for 3 h. A further amount of tetrakis (triphenylphosphine) palladium (0) (30 mg) and then 0.5 M t-butylzinc bromide in THF (1 ml, 0.5 mmol) was added to the mixture at ambient temperature. The mixture was heated to 80° C. for a further 3 h. The solvent was removed in vacuo and the residue dissolved in 1:1 MeOH:DMSO ml×2 and purified by MDAP on Sunfire C18 column (Method B) using Acetonitrile-Water with a Formic acid modifier. The solvent was evaporated in vacuo to give the title compound as a brown gum (12 mg); LCMS: (System 4) MH$^+$=438, $t_{RET}$=3.47 min.

Example 75

2,6-Difluoro-N-{[4-methyl-2-(trifluoromethyl)phenyl]methyl}-1H-pyrazol-3-yl)benzamide

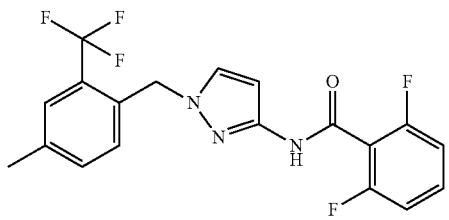 [SMILES: Cc1ccc(Cn2ccc(NC(=O)c3c(F)cccc3F)n2)c(C(F)(F)F)c1]

To a solution of 2,6-difluoro-N-(1-{[4-iodo-2-(trifluoromethyl)phenyl]methyl}-1H-pyrazol-3-yl)benzamide (for a preparation see Example 73) (106 mg, 0.209 mmol) in THF (1 ml) was added tetrakis(triphenyl-phosphine)palladium (0) (25 mg, 0.022 mmol, Aldrich). To the solution was added 2.0 M methylzinc chloride in THF (0.5 mL, 1.0 mmol, Aldrich) and the mixture stirred at 80° C. under nitrogen for 4 h. The solvent was removed in vacuo and the residue diluted with methanol:DMSO (1:1, 2 ml). The suspension was filtered and the filterate purified by MDAP on Sunfire C18 column (Method B) using Acetonitrile-Water with a Formic acid modifier. The solvent was evaporated in vacuo to give the title compound as a white solid (43.3 mg);

LCMS: (System 4) MH$^+$=396, $t_{RET}$=3.0 min.

Example 76

N-(1-{[4-cyclopropyl-2-(trifluoromethyl)phenyl]methyl}-1H-pyrazol-3-yl)-2,6-difluorobenzamide

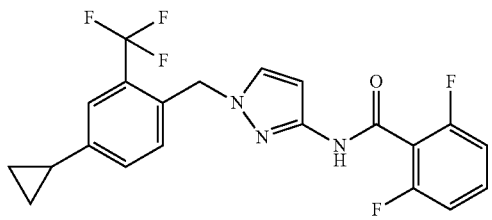 [SMILES: O=C(Nc1ccn(Cc2ccc(C3CC3)cc2C(F)(F)F)n1)c1c(F)cccc1F]

To a mixture of 2,6-difluoro-N-(1-{[4-iodo-2-(trifluoromethyl)phenyl]methyl}-1H-pyrazol-3-yl)benzamide (for a preparation see Example 73)(250 mg, 0.493 mmol), potassium phosphate tribasic (330 mg, 1.56 mmol, Aldrich), tricyclohexyl phosphine (14 mg, 0.05 mmol, Aldrich) and cyclopropyl boronic acid (127 mg, 1.48 mmol, Fluorochem) in toluene (4 ml) was added water (0.2 mL) and then palladium (II) acetate (11 mg, 0.049 mmol, ABCR). The mixture was heated to 100° C. under nitrogen overnight. The mixture was partitioned between DCM (10 ml) and water (10 ml). The phases were separated using a hydrophobic frit and the aqueous phase washed with DCM (10 ml). The combined organic extracts were concentrated in vacuo to leave a yellow gum (175 mg). A portion of the residue (150 mg) was dissolved in 1:1 MeOH:DMSO ml×3 and purified by MDAP on Sunfire C18 column (Method B) using Acetonitrile-Water with a Formic acid modifier. The solvent was evaporated in vacuo to give the title compound as a colourless gum (117 mg);

LCMS: (System 4) MH$^+$=422, $t_{RET}$=3.25 min.

Example 77

2,6-Difluoro-N-{1-[(4-iodo-2-methylphenyl)methyl]-1H-pyrazol-3-yl}benzamide

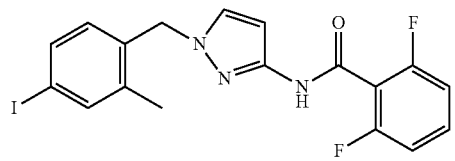 [SMILES: Cc1cc(I)ccc1Cn1ccc(NC(=O)c2c(F)cccc2F)n1]

To a suspension of N-{1-[(4-amino-2-methylphenyl)methyl]-1H-pyrazol-3-yl}-2,6-difluorobenzamide (for a preparation see Intermediate 33)(400 mg, 1.17 mmol) in water (1.7 ml) in an ice-water bath (internal temperature 5° C.) was added concentrated sulphuric acid specific gravity 1.84 (165 µl, 3.10 mmol) and then a solution of sodium nitrite, super free flowing (90 mg, 1.305 mmol, Aldrich) in ice-cold water (0.5 ml) dropwise. The resulting yellow solution was stirred in an ice-water bath for 30 min. To the mixture was added a solution of potassium iodide, extra pure briquettes (291 mg, 1.75 mmol, Acros) in ice cold ~1 M sulphuric acid (3 ml). The mixture was allowed to warm to ambient temperature and then heated to 80° C. for 1 h. The mixture was allowed to cool to room temperature for 1 h and was then partitioned between ethyl acetate (50 ml) and water (50 ml). The phases were separated and the organic phase washed with water (20 ml), brine (20 ml), dried (MgSO$_4$), filtered and the solvent removed in vacuo to leave a dark red/brown oil (515 mg). The sample was loaded in dichloromethane and purified on silica 50 g using 0-50% ethyl acetate-cyclohexane. The appropriate fractions were combined and evaporated in vacuo to give the title compound as a yellow oil (223 mg); LCMS: (System 4) MH$^+$=454, $t_{RET}$=3.14 min.

Example 78

2,6-Difluoro-N-(1-{[4-(phenyloxy)-2-(trifluoromethyl)phenyl]methyl}-1H-pyrazol-3-yl)benzamide

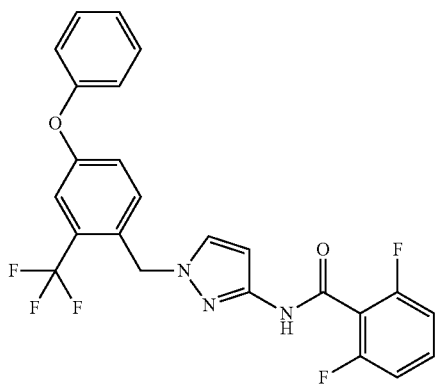 [SMILES: O=C(Nc1ccn(Cc2ccc(Oc3ccccc3)cc2C(F)(F)F)n1)c1c(F)cccc1F]

To a stirred solution of 4-(phenyloxy)-2-(trifluoromethyl)benzoic acid (for a preparation see Intermediate 35)(0.507 g, 1.80 mmol), in THF (40 ml), under nitrogen, was added borane-tetrahydrofuran complex (0.463 g, 5.39 mmol, Aldrich) carefully over about 2 min. The solution was stirred for 40 min at ambient temperature and then heated at gentle reflux for 20 h. To the mixture at ambient temperature was added methanol (10 ml) dropwise and then the solution was heated to reflux for 30 min. The solvent was evaporated in vacuo and the residue acidified with dilute aqueous HCl. The mixture was extracted with chloroform and the phases separated using a hydrophobic frit. The solvent was evaporated in vacuo to leave [4-(phenyloxy)-2-(trifluoromethyl)phenyl]methanol as a colourless oil (0.491 g). [4-(phenyloxy)-2-(trifluoromethyl)phenyl]methanol (0.491 g, 1.83 mmol) in dichloromethane (10 ml) under nitrogen was stirred and cooled to −5° C. A solution of phosphorus tribromide (0.173 ml, 1.831 mmol) in DCM (3.5 ml) was then added dropwise over about 10 min. The solution was then allowed to warm to room temperature and stirred for 4 h. A saturated solution of aqueous sodium bicarbonate (10 ml) was then added and the mixture stirred vigorously. The emulsion was further diluted with water and chloroform. The phases were separated using a hydrophobic frit. The aqueous phase was further extracted with chloroform. The combined organic extracts were dried ($Na_2SO_4$) and filtered. The filtrate was re-dried with ($MgSO_4$), filtered and the solvent removed in vacuo to give 4-(bromomethyl)-3-(trifluoromethyl)phenyl ether as a colourless oil (0.518 g).

To 2,6-difluoro-N-1H-pyrazol-3-ylbenzamide (for a preparation see Intermediate 9)(45 mg, 0.20 mmol) in dry THF (3.0 ml) under nitrogen at room temperature was added 1.0 M lithium bis(trimethylsilyl)amide in THF (0.20 ml, 0.20 mmol) dropwise. The solution was stirred for approximately 30 min and then 4-(bromomethyl)-3-(trifluoromethyl)phenyl ether (67 mg, 0.20 mmol) in THF (2 ml) was added. The solution was stirred for 3 h and then left to stand overnight. The solvent was removed under a stream of nitrogen. To the residue was added aqueous sodium bicarbonate and then the residue extracted with chloroform three times. The combined chloroform extracts were filtered through a hydrophobic frit. The filtrate was concentrated in vacuo. The residue was purified on MDAP (Method B). The appropriate fractions were combined and the residue dried under high vacuum to give the title compound as a thick white gum (72.3 mg); LCMS: (System 4) $MH^+$=474, $t_{RET}$=3.35 min.

Example 79

2,6-Difluoro-N-(1-{[5-(Phenyloxy)-2-(trifluoromethyl)phenyl]methyl}-1H-pyrazol-3-yl)benzamide

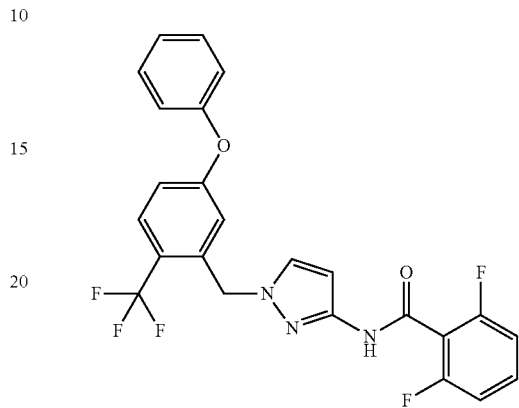

To a stirred solution of crude 5-(phenyloxy)-2-(trifluoromethyl)benzoic acid (for a preparation see Intermediate 36) (0.519 g, 1.84 mmol) in dry THF (40 ml) under nitrogen was added 1.0 M borane-tetrahydrofuran complex (6 ml, 6.0 mmol, Aldrich) dropwise. The solution was stirred for 30 min then heated at gentle reflux for 21 h. To the solution at ambient temperature was added methanol (10 ml) dropwise and then heated at reflux for 30 min. The solvent was removed in vacuo and then water added to the residue. The mixture was diluted with 2 M hydrochloric acid and the mixture was extracted with chloroform. The organic extract was concentrated in vacuo to give [5-(phenyloxy)-2-(trifluoromethyl)phenyl]methanol as a colourless oil (0.494 g).

[5-(phenyloxy)-2-(trifluoromethyl)phenyl]methanol (0.493 g, 1.84 mmol) in dichloromethane (12 ml) under nitrogen was stirred and cooled to −5° C. A solution of phosphorus tribromide (173 μl, 1.84 mmol) in DCM (3.5 ml) was added dropwise over about 2 min. The solution was then allowed to warm to room temperature and left to stand overnight. The solution was cooled to 4° C. and stirred well as saturated aqueous sodium bicarbonate (11 ml) was added in portions over 2 min. The biphasic mixture was stirred for a further 20 min. The mixture was diluted with water and DCM. The phases were separated using a hydrophobic frit and the aqueous phase washed with DCM. The combined organic extracts were stored in a freezer over the weekend and the DCM solution decanted off from crystals of ice. The organic phase was further dried ($MgSO_4$), filtered and the solvent removed in vacuo to leave crude 2-(bromomethyl)-4-(phenyloxy)-1-(trifluoromethyl)benzene as a colourless oil (0.425 g).

To a stirred solution of 2,6-difluoro-N-1H-pyrazol-3-ylbenzamide (for a preparation see Intermediate 9)(100 mg, 0.448 mmol) in dry THF (6.0 ml) under nitrogen at ambient temperature was added 1.0 M lithium bis(trimethylsilyl)amide (0.45 ml, 0.45 mmol) dropwise and then the solution stirred for approximately 30 min. To the solution was added a solution of crude 2-(bromomethyl)-4-(phenyloxy)-1-(trifluoromethyl)benzene (0.135 g) in dry THF (2.5 ml) and stirred for 7 h. The solvent was removed using a stream of nitrogen. To the residue was added saturated aqueous sodium bicarbonate (approximately 7 ml) and then the residue extracted three times with chloroform. The combined organic extracts were filtered through a hydrophobic frit. The solvent was removed in vacuo and the residue purified on MDAP (Method B). The appropriate fractions were combined and solvent evaporated in vacuo. The residue was dried under high vacuum at 45° C. to give the title compound as a white solid (85 mg); LCMS: (System 4) MH$^+$=474, $t_{RET}$=3.30 min.

Example 80

N-(1-{[4-chloro-2-(trifluoromethyl)phenyl]methyl}-1H-pyrazol-3-yl)-2,6-difluorobenzamide

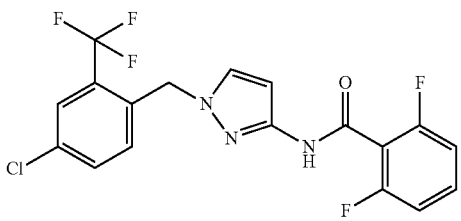 [SMILES: O=C(Nc1ccn(Cc2ccc(Cl)cc2C(F)(F)F)n1)c1c(F)cccc1F]

To a solution of 2,6-difluoro-N-1H-pyrazol-3-ylbenzamide (for a preparation see Intermediate 9)(3 g, 13.4 mmol) in THF (30 ml) was added 1.0 M lithium bis(trimethylsilyl) amide in THF (13.5 ml, 13.5 mmol, Aldrich). The resulting orange solution was stirred at ambient temperature under nitrogen for 30 min. To the reaction was added a solution of 1-(bromomethyl)-4-chloro-2-(trifluoromethyl)benzene (3.7 g, 13.5 mmol, Fluorochem) in THF (5 ml). The resulting orange solution was stirred at ambient temperature under nitrogen overnight. The solvent was removed in vacuo and the residue partitioned between ethyl acetate (125 ml) and aqueous sodium bicarbonate (75 ml). The phases were separated and the organic phase washed with aqueous sodium bicarbonate (50 ml). The combined aqueous phases were washed with ethyl acetate (75 ml). The organic phases were combined, dried, filtered and the solvent removed in vacuo. The residue was loaded in dichloromethane and purified on silica 100 g×2 using a 0-50% ethyl acetate-cyclohexane. The appropriate fractions were combined and evaporated in vacuo to give the title compound as a yellow solid (2.83 g); LCMS: (System 4) MH$^+$=416, $t_{RET}$=3.14 min.

Example 81

2,6-Difluoro-N-(1-{[4-(1-methylethyl)-2-(trifluoromethyl)phenyl]methyl}-1H-pyrazol-3-yl)benzamide

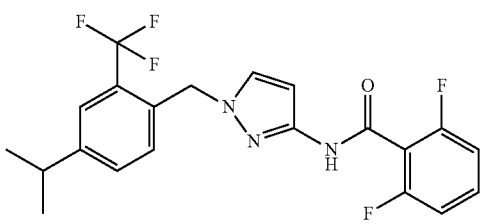 [SMILES: CC(C)c1ccc(Cn2ccc(NC(=O)c3c(F)cccc3F)n2)c(C(F)(F)F)c1]

To a solution of N-(1-{[4-chloro-2-(trifluoromethyl)phenyl]methyl}-1H-pyrazol-3-yl)-2,6-difluorobenzamide (for a preparation see Example 80)(100 mg, 0.241 mmol) in a mixture of THF (0.9 ml) and N-methyl-2-pyrrolidone (0.1 ml) was added iron(III) acetylacetonate (17 mg, 0.048 mmol, Aldrich). The resulting red solution was stirred for 10 min and then treated with a solution of 15% isopropylmagnesium bromide in THF (1.2 ml, 0.60 mmol, Fluorochem) at ambient temperature. The solution was stirred at room temperature under nitrogen overnight. The reaction mixture was quenched with methanol (1 ml) and the solvent removed in vacuo. The residue was dissolved in 1:1 MeOH:DMSO (2 ml) and purified by MDAP (Method B) on Sunfire C18 column using Acetonitrile-Water with a Formic acid modifier. The solvent was evaporated in vacuo to give the title compound as a yellow solid (26 mg); LCMS: (System 4) MH$^+$=424, $t_{RET}$=3.41 min.

Example 82

N-(1-{[4-Chloro-2-(trifluoromethyl)phenyl]methyl}-1H-pyrazol-3-yl)-3-fluoro-4-pyridinecarboxamide

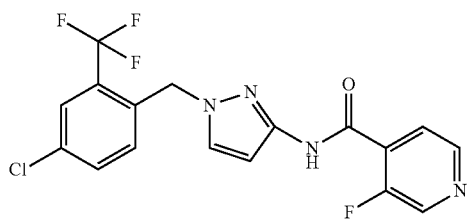

To 3-fluoro-4-pyridinecarboxylic acid (27 mg, 0.191 mmol, Aldrich) was added a solution of HATU (24 mg, 0.189 mmol, Advanced asymmetrics) in DMF (0.5 ml), DIPEA (0.076 ml, 0.435 mmol) and then a solution of 1-{[4-chloro-2-(trifluoromethyl)phenyl]methyl}-1H-pyrazol-3-amine (for a preparation see Intermediate 37)(40 mg, 0.145 mmol) in DMF (0.5 ml). The resulting yellow solution was stirred at ambient temperature overnight. Further amounts of HATU (72 mg, 0.189 mmol), 3-fluoro-4-pyridinecarboxylic acid (27 mg, 0.191 mmol) and DIPEA (0.076 ml, 0.435 mmol) were added. The reaction mixture was stirred at ambient temperature for a further 2 h. The reaction mixture was diluted with methanol and purified by MDAP on Sunfire C18 column (Method B) using Acetonitrile-Water with a Formic acid modifier. The solvent was evaporated in vacuo to give the title compound as a white solid (49 mg); LCMS: (System 4) MH$^+$=399 $t_{RET}$=2.82 min.

Similarly prepared were:

| Example | Structure | Name | LCMS $t_{RET}$/min | MH+ |
|---|---|---|---|---|
| 83 | 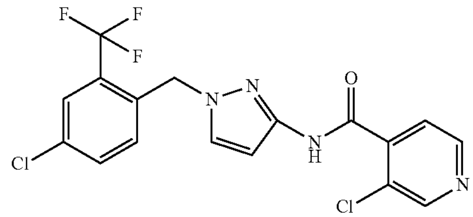 [SMILES: O=C(Nc1ccn(Cc2ccc(Cl)cc2C(F)(F)F)n1)c1ccncc1Cl] | 3-Chloro-N-(1-{[4-chloro-2-(trifluoromethyl)phenyl]methyl}-1H-pyrazol-3-yl)-4-pyridinecarboxamide | 2.89 (System 4) | 415 |
| 84 | 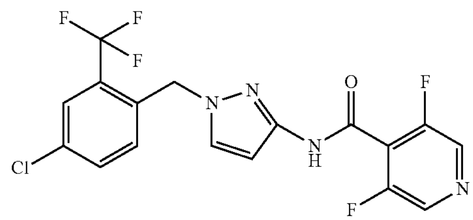 [SMILES: O=C(Nc1ccn(Cc2ccc(Cl)cc2C(F)(F)F)n1)c1c(F)cncc1F] | N-(1-{[4-chloro-2-(trifluoromethyl)phenyl]methyl}-1H-pyrazol-3-yl)-3,5-difluoro-4-pyridinecarboxamide | 2.94 (System 4) | 417 |
| 85 | 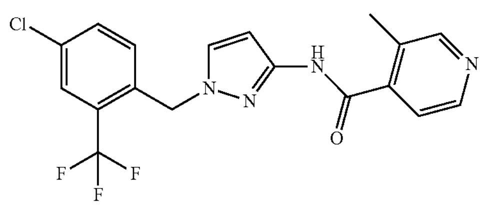 [SMILES: Cc1cnccc1C(=O)Nc1ccn(Cc2ccc(Cl)cc2C(F)(F)F)n1] | N-(1-{[4-chloro-2-(trifluoromethyl)phenyl]methyl}-1H-pyrazol-3-yl)-3-methyl-4-pyridinecarboxamide | 0.97 (System 3) | 395 |

Example 144

N-(1-{[4-chloro-2-(trifluoromethyl)phenyl]methyl}-1H-pyrazol-3-yl)-3-methyl-4-pyridinecarboxamide HCl salt

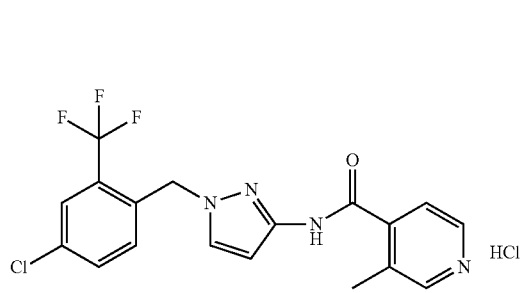 [SMILES: Cc1cnccc1C(=O)Nc1ccn(Cc2ccc(Cl)cc2C(F)(F)F)n1 ; Cl]

To a solution of N-(1-{[4-chloro-2-(trifluoromethyl)phenyl]methyl}-1H-pyrazol-3-yl)-3-methyl-4-pyridinecarboxamide (for a preparation see Example 85)(30 mg, 0.076 mmol) in methanol (1 ml) was added 4.0 M hydrochloride in 1,4-dioxane (0.15 ml, 0.60 mmol). The solvent was removed under a stream of nitrogen and dried in a vacuum oven at 40° C. for 30 min to give the title compound (32 mg); LCMS: (System 4) MH+=395, $t_{RET}$=2.34 min.

Example 86

3-Methyl-N-(1-{[2-(phenyloxy)phenyl]methyl}-1H-pyrazol-3-yl)-4-pyridinecarboxamide

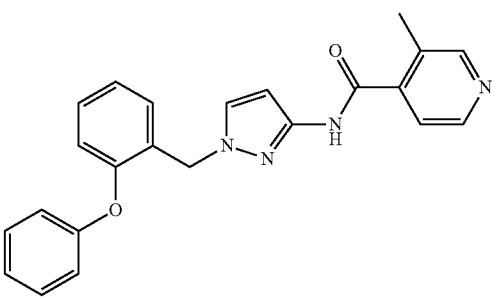 [SMILES: Cc1cnccc1C(=O)Nc1ccn(Cc2ccccc2Oc2ccccc2)n1]

A solution of HATU (38 mg, 0.1 mmol) in N,N-dimethylformamide (0.3 ml) was added to 3-methyl-isonicotinic acid (14 mg, 0.1 mmol, AstaTech Inc) followed by N,N-diisopropylamine (0.050 ml, 0.286 mmol) and left to stand for 10 minutes at ambient temperature. A solution of 1-{[2-(phenyloxy)phenyl]methyl}-1H-pyrazol-3-amine (for a preparation see Intermediate 38)(27 mg, 0.101 mmol) in N,N-dimethylformamide (0.1 ml) was then added and the solution left to stand at room temperature overnight. Purification by MDAP (Method D) gave the title compound (20.2 mg); LCMS: (System 1) MH+=385, $t_{RET}$=0.93 min.

Similarly prepared were:

| Example | Structure | Name | LCMS $t_{RET}$/min | MH+ |
|---|---|---|---|---|
| 87 | 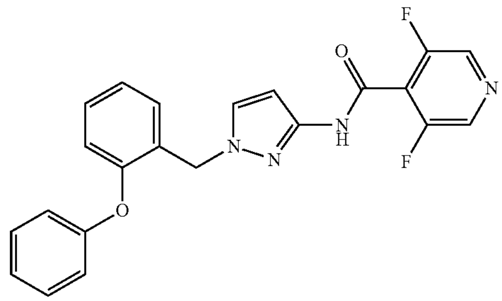 [SMILES: O=C(Nc1ccn(Cc2ccccc2Oc2ccccc2)n1)c1c(F)cncc1F] | 3,5-Difluoro-N-(1-{[2-(phenyloxy)phenyl]methyl}-1H-pyrazol-3-yl)-4-pyridinecarboxamide | 1.11 min (System 3) | 407 |
| 145 | 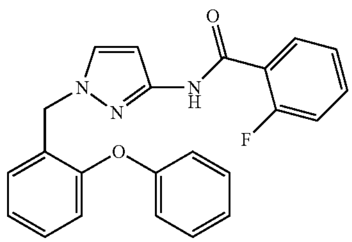 [SMILES: O=C(Nc1ccn(Cc2ccccc2Oc2ccccc2)n1)c1ccccc1F] | 2-Fluoro-N-(1-{[2-(phenyloxy)phenyl]methyl}-1H-pyrazol-3-yl)bnezamide | 1.20 (System 3) | 388 |
| 146 | 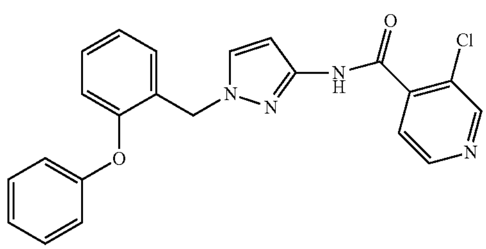 [SMILES: O=C(Nc1ccn(Cc2ccccc2Oc2ccccc2)n1)c1ccncc1Cl] | 3-Chloro-N-(1-{[2-(phenyloxy)phenyl]methyl}-1H-pyrazol-3-yl)-4-pyridinecarboxamide | 1.09 (System 3) | 405 |

Example 88

3-Fluoro-N-(1-{[4-iodo-2-(trifluoromethyl)phenyl]methyl}-1H-pyrazol-3-yl)-4-pyridinecarboxamide

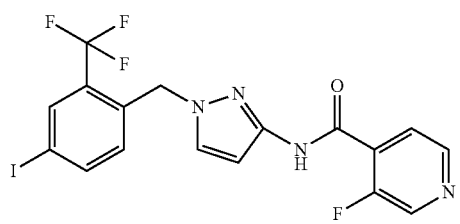

To 3-fluoro-4-pyridinecarboxylic acid (38 mg, 0.269 mmol, Aldrich) was added a solution of HATU (100 mg, 0.263 mmol, Advanced asymmetrics) in DMF (0.5 ml), DIPEA (0.11 ml, 0.630 mmol) and then a solution of 1-{[4-iodo-2-(trifluoromethyl)phenyl]methyl}-1H-pyrazol-3-amine (for a preparation see Intermediate 39)(75 mg, 0.204 mmol) in DMF (0.5 ml). The resulting orange solution was stirred at ambient temperature overnight. The reaction mixture was diluted with methanol (1 ml) and purified by MDAP on Sunfire C18 column (Method B) using Acetonitrile-Water with a Formic acid modifier. The solvent was evaporated in vacuo to give the title compound as a white solid (86 mg); LCMS: (System 4) MH+=491, $t_{RET}$=3.0 min.

Similarly prepared were:

| Example | Structure | Name | LCMS $t_{RET}$/min | MH+ |
|---|---|---|---|---|
| 89 | 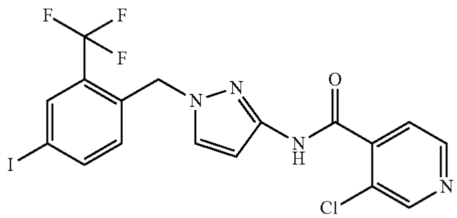 [SMILES: O=C(Nc1ccn(Cc2ccc(I)cc2C(F)(F)F)n1)c1ccncc1F] | 3-Chloro-N-(1-{[4-iodo-2-(trifluoromethyl)phenyl]methyl}-1H-pyrazol-3-yl)-4-pyridinecarboxamide | 2.98 (System 4) | 507 |
| 90 | 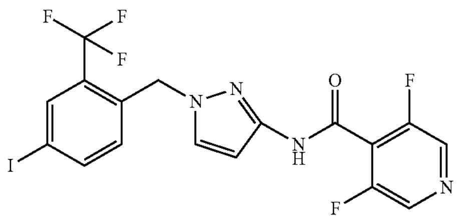 [SMILES: O=C(Nc1ccn(Cc2ccc(I)cc2C(F)(F)F)n1)c1c(F)cncc1F] | 3,5-Difluoro-N-(1-{[4-iodo-2-(trifluoromethyl)phenyl]methyl}-1H-pyrazol-3-yl)-4-pyridinecarboxamide | 3.06 (System 4) | 509 |
| 147 | 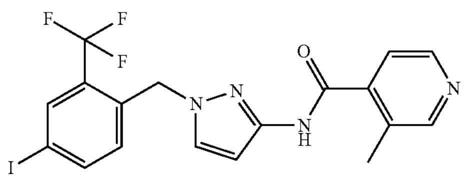 [SMILES: Cc1cnccc1C(=O)Nc1ccn(Cc2ccc(I)cc2C(F)(F)F)n1] | N-(1-{[4-iodo-2-(trifluoromethyl)phenyl]methyl}-1H-pyrazol-3-yl)-3-methyl-4-pyridinecarboxamide | 2.51 (System 4) | 487 |

Example 148

N-(1-{[4-iodo-2-(trifluoromethyl)phenyl]methyl}-1H-pyrazol-3-yl)-3-methyl-4-pyridecarboxamide HCl salt

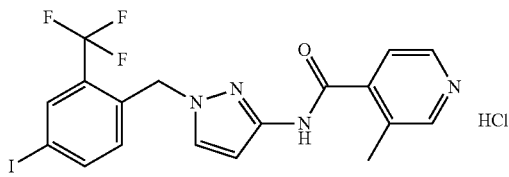 [SMILES: Cc1cnccc1C(=O)Nc1ccn(Cc2ccc(I)cc2C(F)(F)F)n1 ; Cl]

To N-(1-{[4-iodo-2-(trifluoromethyl)phenyl]methyl}-1H-pyrazol-3-yl)-3-methyl-4-pyridinecarboxamide (for a preparation see Intermediate 39)(20 mg) dissolved in methanol (1 ml) was added 4.0 M hydrochloride in 1,4-dioxane (0.85 ml, 3.40 mmol). The solvent was removed under a stream of nitrogen and dried in a vacuum oven at 40° C. for 1 h to give the title compound as a white solid (19 mg); LCMS: (System 4) MH+=487, $t_{RET}$=2.51 min.

Example 91

N-(1-{[4-cyclopropyl-2-(trifluoromethyl)phenyl]methyl}-1H-pyrazol-3-yl)-3-fluoro-4-pyridinecarboxamide

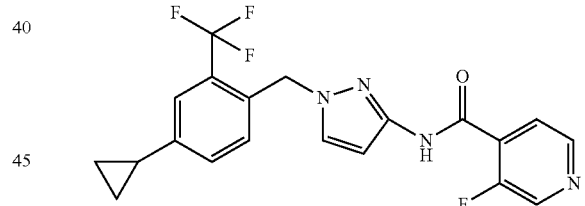

To a solution of 3-fluoro-N-(1-{[4-iodo-2-(trifluoromethyl)phenyl]methyl}-1H-pyrazol-3-yl)-4-pyridinecarboxamide (for a preparation see Example 88)(40 mg, 0.082 mmol) in toluene (2 ml) was added potassium phosphate tribasic (52 mg, 0.245 mmol, Aldrich), tricyclohexyl phosphine (7 mg, 0.025 mmol, Aldrich), cyclopropyl boronic acid (21 mg, 0.244 mmol, Fluorochem), water (0.1 ml) and then palladium (II) acetate (6 mg, 0.027 mmol. ABCR). The resulting slight suspension was heated to 100° C. and stirred under nitrogen overnight. The reaction mixture was partitioned between DCM (10 ml) and water (10 ml). The phases were separated using a hydrophobic frit and the aqueous phase washed with DCM (10 ml). The organic phases were combined and the solvent removed in vacuo. The residue was dissolved in 1:1 MeOH:DMSO (1 ml) and purified by MDAP on Sunfire C18 column (Method B) using Acetonitrile-Water with a Formic acid modifier. The solvent was evaporated in vacuo to give the title compound as a white solid (16 mg); LCMS: (System 4) MH+=405, $t_{RET}$=2.98 min.

Similarly prepared were:

| Example | Structure | Name | LCMS $t_{RET}$/min | MH+ |
|---|---|---|---|---|
| 92 | 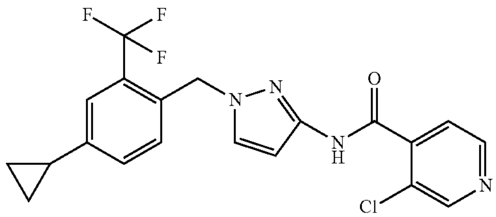 [SMILES: O=C(Nc1ccn(Cc2ccc(C3CC3)cc2C(F)(F)F)n1)c1ccncc1Cl] | 3-Chloro-N-(1-{[4-cyclopropyl-2-(trifluoromethyl)phenyl]methyl}-1H-pyrazol-3-yl)-4-pyridinecarboxamide | 2.98 (System 4) | 421 |
| 93 | 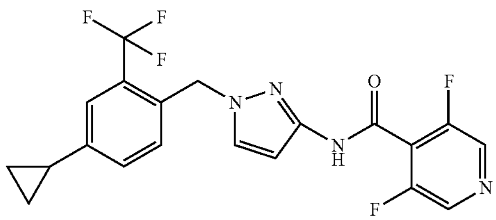 [SMILES: O=C(Nc1ccn(Cc2ccc(C3CC3)cc2C(F)(F)F)n1)c1c(F)cncc1F] | N-(1-{[4-cyclopropyl-2-(trifluoromethyl)phenyl]methyl}-1H-pyrazol-3-yl)-3,5-difluoro-4-pyridinecarboxamide | 3.09 (System 4) | 423 |
| 149 | 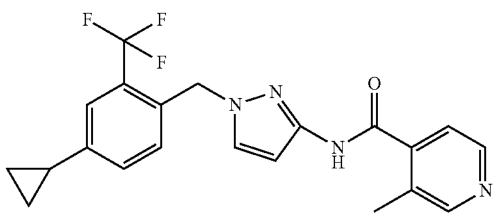 [SMILES: Cc1cnccc1C(=O)Nc1ccn(Cc2ccc(C3CC3)cc2C(F)(F)F)n1] | N-(1-{[4-cyclopropyl-2-(trifluoromethyl)phenyl]methyl}-1H-pyrazol-3-yl)-3-methyl-4-pyridinecarboxamide | 2.50 (System 4) | 401 |

Example 150

N-(1-{[4-cyclopropyl-2-(trifluoromethyl)phenyl]methyl}-1H-pyrazol-3-yl)-3-methyl-4-pyridinecarboxamide HCl salt

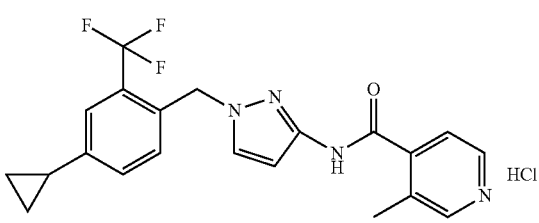 [SMILES: Cc1cnccc1C(=O)Nc1ccn(Cc2ccc(C3CC3)cc2C(F)(F)F)n1 ; Cl]

To N-(1-{[4-cyclopropyl-2-(trifluoromethyl)phenyl]methyl}-1H-pyrazol-3-yl)-3-methyl-4-pyridinecarboxamide (for a preparation see Example 149)(20 mg) dissolved in methanol (1 ml) was added 4.0 M hydrochloride in 1,4-dioxane (0.4 ml, 1.60 mmol). The solvent was removed under a stream of nitrogen to give the title compound as an orange gum (38 mg); LCMS: (System 4) MH+=401, $t_{RET}$=2.50 min.

Example 94

2-Fluoro-N-(1-{[4-iodo-2-(trifluoromethyl)phenyl]methyl}-1H-pyrazol-3-yl)benzamide

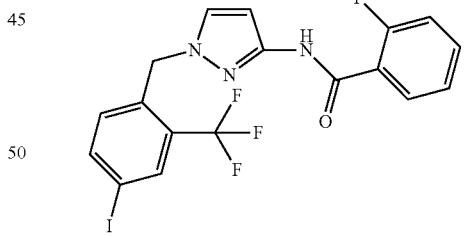

To 2-fluorobenzoic acid (22 mg, 0.157 mmol, Aldrich) was added a solution of HATU (58 mg, 0.153 mmol, Advanced asymmetrics) in DMF (0.5 ml), DIPEA (0.062 ml, 0.355 mmol) and then a solution of 1-{[4-iodo-2-(trifluoromethyl)phenyl]methyl}-1H-pyrazol-3-amine (for a preparation see Intermediate 39)(43 mg, 0.117 mmol) in DMF (0.5 ml). The resulting yellow solution was stirred at ambient temperature overnight. The reaction mixture was diluted with methanol (1 ml) and purified by MDAP on Sunfire C18 column (Method B) using Acetonitrile-Water with a Formic acid modifier. The solvent was evaporated in vacuo to give the title compound as a white solid (40 mg); LCMS: (System 4) MH+=490, $t_{RET}$=3.38 min.

Similarly prepared were:

| Example | Structure | Name | LCMS $t_{RET}$/min | MH+ |
|---|---|---|---|---|
| 95 | 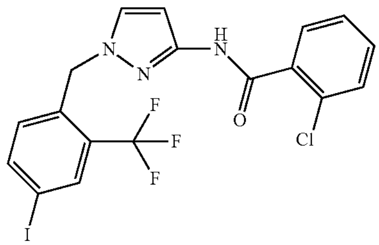 [SMILES: O=C(Nc1ccn(Cc2ccc(I)cc2C(F)(F)F)n1)c1ccccc1Cl] | 2-Chloro-N-(1-{[4-iodo-2-(trifluoromethyl)phenyl]methyl}-1H-pyrazol-3-yl)benzamide | 3.30 (System 4) | 506 |
| 96 | 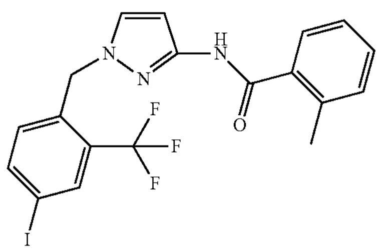 [SMILES: Cc1ccccc1C(=O)Nc1ccn(Cc2ccc(I)cc2C(F)(F)F)n1] | N-(1-{[4-iodo-2-(trifluoromethyl)phenyl]methyl}-1H-pyrazol-3-yl)-2-methylbenzamide | 3.30 (System 4) | 486 |

Example 97

2-Chloro-N-(1-{[4-cyclopropyl-2-(trifluoromethyl)phenyl]methyl}-1H-pyrazol-3-yl)benzamide

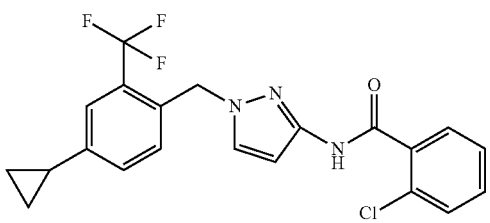 [SMILES: O=C(Nc1ccn(Cc2ccc(C3CC3)cc2C(F)(F)F)n1)c1ccccc1Cl]

To a mixture of N-(1-{[4-iodo-2-(trifluoromethyl)phenyl]methyl}-1H-pyrazol-3-yl)-2-chlorobenzamide (for a preparation see Example 95)(30 mg, 0.059 mmol) was added potassium phosphate tribasic (38 mg, 0.179 mmol, Aldrich), tricyclohexyl phosphine (5 mg, 0.018 mmol, Aldrich), cyclopropyl boronic acid (16 mg, 0.186 mmol, Fluorochem) in toluene (2 ml). Water (0.1 ml) was added followed by palladium (II) acetate (4 mg, 0.018 mmol, ABCR). The resulting yellow suspension was heated to 100° C. and stirred under nitrogen overnight. The reaction mixture was partitioned between DCM (10 ml) and water (10 ml). The phases were separated using a hydrophobic frit and the aqueous layer was washed with DCM (10 ml). The organic layers were combined and the solvent removed in vacuo. The residue was dissolved in 1:1 MeOH:DMSO (1 ml) and purified by MDAP on Sunfire C18 column (Method B) using Acetonitrile-Water with a Formic acid modifier. The solvent was evaporated in vacuo to give the title compound as a yellow gum (6 mg); LCMS: (System 4) MH+=420, $t_{RET}$=3.22 min.

Similarly prepared were:

| Example | Structure | Name | LCMS $t_{RET}$/min | MH+ |
|---|---|---|---|---|
| 98 | 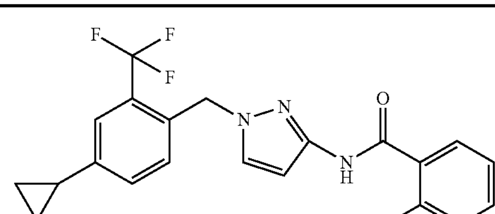 | N-(1-{[4-cyclopropyl-2-(trifluoromethyl)phenyl]methyl}-1H-pyrazol-3-yl)-2-fluorobenzamide | 3.30 (System 4) | 404 |

-continued

| Example | Structure | Name | LCMS $t_{RET}$/min | MH+ |
|---|---|---|---|---|
| 99 | 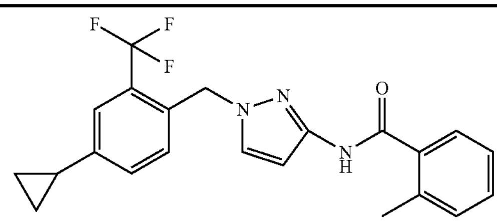 | N-(1-{[4-cyclopropyl-2-(trifluoromethyl)phenyl]methyl}-1H-pyrazol-3-yl)-2-methylbenzamide | 3.30 (System 4) | 400 |

Example 100

N-(1-{5-[(cyclopropylmethyl)oxy]-2-(trifluoromethyl)phenyl]methyl}-1H-pyrazol-3-yl)-2,6-difluorobenzamide

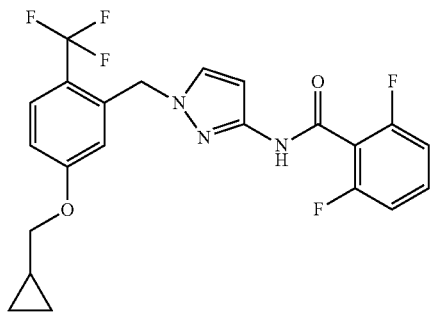 [SMILES: O=C(Nc1ccn(Cc2cc(OCC3CC3)ccc2C(F)(F)F)n1)c1c(F)cccc1F]

To a solution of 2,6-difluoro-N-(1-{[5-hydroxy-2-(trifluoromethyl)phenyl]methyl}-1H-pyrazol-3-yl)benzamide (for a preparation see Intermediate 42)(75 mg, 0.189 mmol) in DMSO (1 ml) was added potassium t-butoxide (23 mg, 0.205 mmol, Aldrich). The solution was stirred at ambient temperature for 5 min. To the solution was added (bromomethyl)cyclopropane (0.023 ml, 0.245 mmol, Alfa Aesar) and the mixture stirred overnight at ambient temperature under nitrogen. The solution was diluted with methanol (1 ml) and purified by MDAP on Sunfire C18 column (Method B) using Acetonitrile-Water with a Formic acid modifier. The solvent was evaporated in vacuo to give the title compound as a white solid (36 mg); LCMS: (System 4) MH+=452, $t_{RET}$=3.18 min.

Similarly prepared was:

| Example | Structure | Name | LCMS $t_{RET}$/min | MH+ |
|---|---|---|---|---|
| 101 | 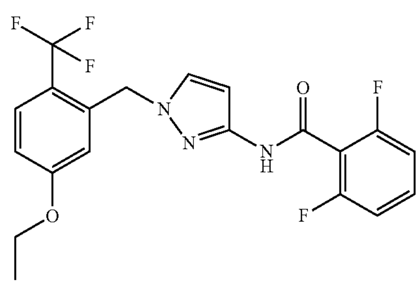 [SMILES: CCOc1ccc(C(F)(F)F)c(Cn2ccc(NC(=O)c3c(F)cccc3F)n2)c1] | N-(1-{[5-(ethyloxy)-2-(trifluoromethyl)phenyl]methyl}-1H-pyrazol-3-yl)-2,6-difluorobenzamide | 3.05 (System 4) | 426 |
| 151 | 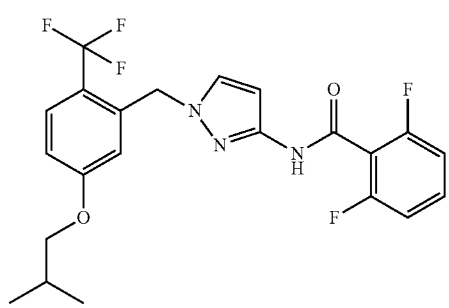 [SMILES: CC(C)COc1ccc(C(F)(F)F)c(Cn2ccc(NC(=O)c3c(F)cccc3F)n2)c1] | 2,6-Difluoro-N-(1-{[5-[(2-methylpropyl)oxy]-2-(trifluoromethyl)phenyl]methyl}-1H-pyrazol-3-yl)benzamide | 3.38 (System 4) | 454 |

Example 102

2,6-Difluoro-N-(1-{[5-iodo-2-(trifluoromethyl)phenyl]methyl}-1H-pyrazol-3-yl)benzamide

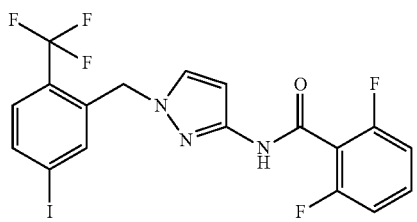 [SMILES: O=C(Nc1ccn(Cc2cc(I)ccc2C(F)(F)F)n1)c1c(F)cccc1F]

To a suspension of N-(1-{[5-amino-2-(trifluoromethyl)phenyl]methyl}-1H-pyrazol-3-yl)-2,6-difluorobenzamide (for a preparation see Intermediate 41)(0.6 g, 1.51 mmol) in water (6 ml) in an ice-water bath (internal temperature at 5° C.) was added concentrated sulphuric acid specific gravity 1.84 (1 ml, 18.8 mmol). To the slight suspension was added a solution of sodium nitrite, super free flowing (0.125 g, 1.82 mmol, Aldrich) in water (3 ml) dropwise. The suspension was stirred in an ice-water bath for 20 min. To the mixture was added a solution of potassium iodide, extra pure briquettes (0.377 g, 2.27 mmol, Acros) in ice-cold approximately 1 M sulphuric acid (5.5 ml). The mixture was allowed to warm to ambient temperature and then heated to 80° C. for 30 min under nitrogen. The tarry suspension was partitioned between ethyl acetate (130 ml) and water (50 ml). The phases were separated and the organic phase washed with saturated aqueous sodium hydrogen carbonate (2×50 ml), dried (MgSO$_4$), filtered and the solvent removed at reduced pressure to leave a dark red foam (0.77 g). The sample was loaded in dichloromethane and purified on silica 100 g using 0-100% ethyl acetate-cyclohexane. The appropriate fractions were combined and evaporated in vacuo to give the title compound as a white foam (0.412 g); LCMS: (System 4) MH$^+$=508 t$_{RET}$=3.10 min.

Example 103

N-(1-{[5-cyclopropyl-2-(trifluoromethyl)phenyl]methyl}-1H-pyrazol-3-yl)-2,6-difluorobenzamide

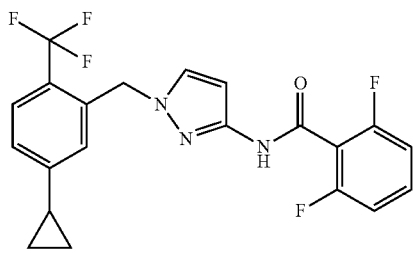 [SMILES: O=C(Nc1ccn(Cc2cc(C3CC3)ccc2C(F)(F)F)n1)c1c(F)cccc1F]

To a solution of 2,6-difluoro-N-(1-{[5-iodo-2-(trifluoromethyl)phenyl]methyl}-1H-pyrazol-3-yl)benzamide (for a preparation see Example 102)(75 mg, 0.148 mmol) in THF (1 ml) was added tetrakis(triphenyl-phosphine)palladium(0) (20 mg, 0.017 mmol, Aldrich). To the solution was added 0.5 M cyclopropylzinc bromide in THF (0.6 ml, 0.30 mmol, Reike metals) and the mixture stirred at 80° C. under nitrogen overnight.

A further amount of tetrakis(triphenylphosphine) palladium(0) (20 mg, Aldrich) and then 0.5 M cyclopropylzinc bromide in THF (0.6 ml, 0.3 mmol, Reike metals) was added to the mixture at ambient temperature. The mixture was heated to 80° C. for a further 3 h. The solvent was removed in vacuo and the residue dissolved in 1:1 MeOH:DMSO ml×2 and purified by MDAP on Sunfire C18 column (Method B) using Acetonitrile-Water with a Formic acid modifier. The solvent was evaporated in vacuo to give the title compound as a white solid (37 mg); LCMS: (System 4) MH$^+$=422, t$_{RET}$=3.14 min.

Example 104

2,6-Difluoro-N-(1-{[5-methyl-2-(trifluoromethyl)phenyl]methyl}-1H-pyrazol-3-yl)benzamide

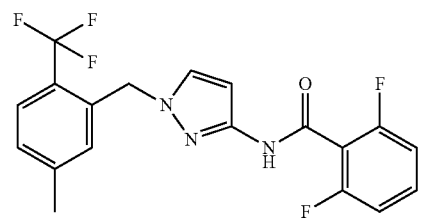 [SMILES: Cc1ccc(C(F)(F)F)c(Cn2ccc(NC(=O)c3c(F)cccc3F)n2)c1]

To a solution of 2,6-difluoro-N-(1-{[5-iodo-2-(trifluoromethyl)phenyl]methyl}-1H-pyrazol-3-yl)benzamide (for a preparation see Example 102)(80 mg, 0.158 mmol) in THF (1 ml) was added tetrakis(triphenyl-phosphine)palladium(0) (25 mg, 0.022 mmol, Aldrich). To the solution was added 2.0 M methylzinc chloride in THF (0.5 mL, 1.0 mmol, Aldrich) and the mixture stirred at 80° C. under nitrogen for 4 h. The solvent was removed in vacuo and the residue diluted with methanol:DMSO (1:1, 2 ml). The suspension was filtered and purified by MDAP on Sunfire C18 column (Method B) using Acetonitrile-Water with a Formic acid modifier. The solvent was evaporated in vacuo to give the title compound as a white solid (26.3 mg); LCMS: (System 4) MH$^+$=396, t$_{RET}$=3.00 min.

Example 105

N-(1-{[5-chloro-2-(trifluoromethyl)phenyl]methyl}-1H-pyrazol-3-yl)-2,6-difluorobenzamide

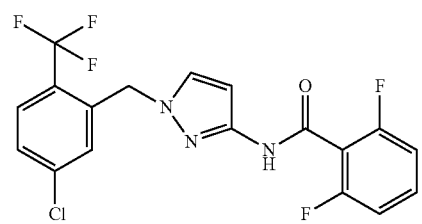 [SMILES: O=C(Nc1ccn(Cc2cc(Cl)ccc2C(F)(F)F)n1)c1c(F)cccc1F]

To a solution of 2,6-difluoro-N-(1-{[5-iodo-2-(trifluoromethyl)phenyl]methyl}-1H-pyrazol-3-yl)benzamide (for a preparation see Example 102)(100 mg, 0.197 mmol) in DMF (0.3 mL) was added nickel (II) chloride (130 mg, 1.0 mmol, Alfa Aesar). The reaction vessel was sealed and heated in Biotage Initiator using initial very high to 170° C. The microwave cut out due to high pressure after 1-2 min of reaching temperature. The mixture was diluted with methanol (1 ml) and DMSO (1 ml). The filtrate was dissolved in 1:1 MeOH:DMSO (1 ml) and purified by MDAP on Sunfire C18 column (Method B) using Acetonitrile-Water with a Formic acid modifier. The solvent was evaporated in vacuo to give the title compound (2 mg) as a white gum;

LCMS: (System 8) MH$^+$=416, $t_{RET}$=3.11 min.

Example 106

N-[1-({2-bromo-6-[(trifluoromethyl)oxy]phenyl}methyl)-1H-pyrazol-3-yl]-2,6-difluorobenzamide

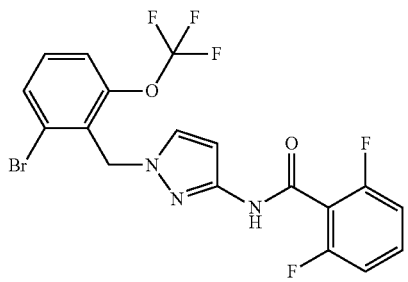 [SMILES: O=C(Nc1ccn(Cc2c(Br)cccc2OC(F)(F)F)n1)c1c(F)cccc1F]

To a stirred solution of 2-bromo-6-[(trifluoromethyl)oxy]benzoic acid (1.116 g, 3.92 mmol, Parkway Scientific), in THF (45 ml), under nitrogen, was added 1.0 M borane-tetrahydrofuran complex (12 ml, 12 mmol) carefully over about 2 minutes. The solution was then heated at gentle reflux for 24 h and allowed to cool. Methanol (20 ml) was added dropwise. The solution was heated at reflux for 30 min and allowed to cool. The solvent was evaporated in vacuo and acidified with dilute aqueous HCl. The mixture was extracted with chloroform and then filtered through a hydrophobic frit. The chloroform was evaporated in vacuo to give {2-bromo-6-[(trifluoromethyl)oxy]phenyl}methanol as a colourless oil (1.07 g). {2-bromo-6-[(trifluoromethyl)oxy]phenyl}methanol (1.06 g, 3.91 mmol) in dichloromethane (14 ml) under nitrogen was stirred and cooled to −10° C. A solution of phosphorus tribromide (0.37 ml, 3.91 mmol) in DCM (3.5 ml) was then added dropwise over about 12 min. The temperature was allowed to rise to ambient temperature over about 3 h then stirred for a further 2 h. Saturated aqueous sodium bicarbonate (12 ml) was then added in portions with stirring and the mixture left in a fridge over weekend. The mixture was extracted into chloroform three times. The combined chloroform extracts were filtered through a hydrophobic frit and the solvent was evaporated in vacuo to give 1-bromo-2-(bromomethyl)-3-[(trifluoromethyl)oxy]benzene as a colourless oil (0.6 g).

2,6-difluoro-N-1H-pyrazol-3-ylbenzamide (for a preparation see Intermediate 9)(45 mg, 0.202 mmol) in dry THF (3.0 ml) was stirred under nitrogen at ambient temperature, 1.0 M lithium bis(trimethylsilyl)amide (0.20 ml, 0.20 mmol) was added dropwise and the solution stirred for approximately 90 min then 1-bromo-2-(bromomethyl)-3-[(trifluoromethyl)oxy]benzene (67.3 mg, 1 equiv) in THF (2 ml) was added. The solution was stirred for 5 h then left to stand overnight. The solvent was removed using a stream of nitrogen. To the residue was added aqueous sodium bicarbonate and the mixture was extracted with chloroform three times. The combined organic extracts were filtered through a hydrophobic frit and the filtrate was concentrated in vacuo. The residue was purified by MDAP (Method B). The appropriate fractions were combined and evaporated in vacuo to give the title compound as a white solid (80.6 mg) after drying at high vacuum at 45° C.; LCMS: (System 4) MH$^+$=476, $t_{RET}$=3.01 min.

Similarly prepared was: (starting from 2-chloro-6-difluoromethoxybenzoic acid synthesised according to WO 2007144327A2)

| Example | Structure | Name | LCMS $t_{RET}$/min | MH$^+$ |
|---|---|---|---|---|
| 107 | 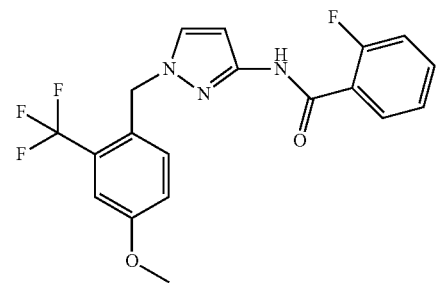 [SMILES: COc1ccc(Cn2ccc(NC(=O)c3ccccc3F)n2)c(C(F)(F)F)c1] | N-[1-({2-chloro-6-[(difluoromethyl)oxy]phenyl}methyl)-1H-pyrazol-3-yl]-2,6-difluorobenzamide | 2.86 (System 4) | 414 |

Example 108

2-Fluoro-N-(1-{[4-(methyloxy)-2-(trifluoromethyl)phenyl]methyl}-1H-pyrazol-3-yl)benzamide 1.0 M lithium bis(trimethylsilyl)amide (100 μl, 0.1 mmol, Aldrich) was slowly added to a solution of 2-fluoro-N-1H-pyrazol-3-ylbenzamide (for a preparation see Intermediate 43) (20.5 mg, 0.1 mmol) in THF (400 μl). The resulting solution was then transferred to a solution of 1-(bromomethyl)-4-(methyloxy)-2-(trifluoromethyl)benzene 24.7 mg, 0.1 mmol, JRD Fluorochemicals Ltd) in THF (200 μl) and stirred for 2 h under nitrogen at ambient temperature. The mixture was diluted with DMSO (0.6 ml) and purified by MDAP using the Sunfire C18 column (Method D) using Acetonitrile-Water with a TFA modifier. The solvent was removed under a stream of nitrogen to give the title compound (27 mg). LCMS (System 4)

MH$^+$=394, $t_{RET}$=3.11 min.

Similarly prepared were

| Example | Structure | Name | LCMS $t_{RET}$/min | MH$^+$ |
|---|---|---|---|---|
| 109 | 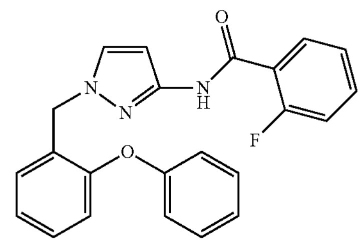 [SMILES: O=C(Nc1ccn(Cc2ccccc2Oc2ccccc2)n1)c1ccccc1F] | 2-Fluoro-N-(1-{[2-(phenyloxy)phenyl]methyl}-1H-pyrazol-3-yl)benzamide | 3.29 (System 4) | 388 |
| 110 | 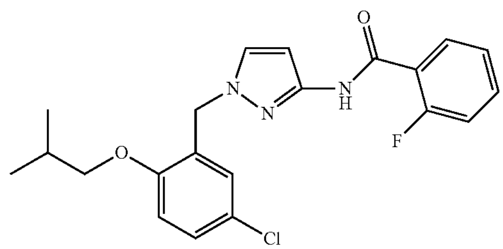 [SMILES: CC(C)COc1ccc(Cl)cc1Cn1ccc(NC(=O)c2ccccc2F)n1] | N-[1-({5-chloro-2-[(2-methylpropyl)oxy]phenyl}methyl)-1H-pyrazol-3-yl]-2-fluorobenzamide | 1.34 (System 3) | 402 |
| 111 | 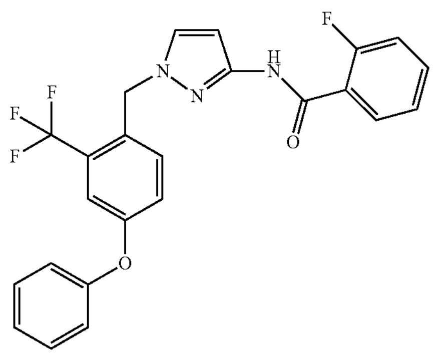 [SMILES: O=C(Nc1ccn(Cc2ccc(Oc3ccccc3)cc2C(F)(F)F)n1)c1ccccc1F] | 2-Fluoro-N-(1-{[4-(phenyloxy)-2-(trifluoromethyl)phenyl]methyl}-1H-pyrazol-3-yl)benzamide | 1.34 (System 3) | 456 |
| 112 | 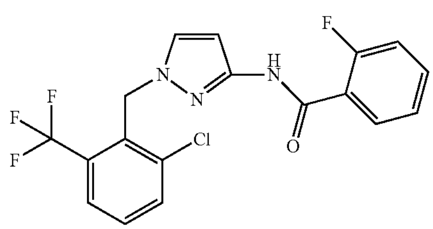 [SMILES: O=C(Nc1ccn(Cc2c(Cl)cccc2C(F)(F)F)n1)c1ccccc1F] | N-(1-{[2-chloro-6-(trifluoromethyl)phenyl]methyl}-1H-pyrazol-3-yl)-2-fluorobenzamide | 1.17 (System 3) | 398 |
| 152 | 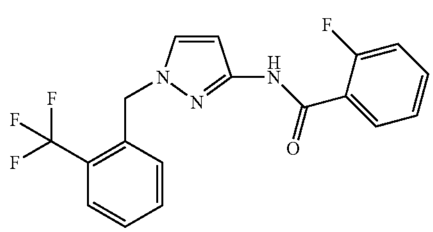 [SMILES: O=C(Nc1ccn(Cc2ccccc2C(F)(F)F)n1)c1ccccc1F] | 2-Fluoro-N-(1-{[2-(trifluoromethyl)phenyl]methyl}-1H-pyrazol-3-yl)benzamide | 3.07 (System 4) | 364 |

-continued

| Example | Structure | Name | LCMS t_{RET}/min | MH+ |
|---|---|---|---|---|
| 153 | 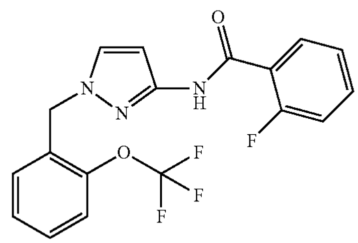 [SMILES: O=C(Nc1ccn(Cc2ccccc2OC(F)(F)F)n1)c1ccccc1F] | 2-Fluoro-N-[1-({2-[(trifluoromethyl)oxy]phenyl}methyl)-1H-pyrazol-3-yl]benzamide | 3.10 (System 4) | 380 |
| 154 | 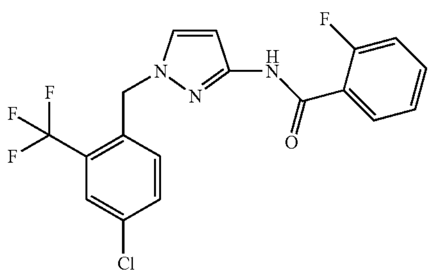 [SMILES: O=C(Nc1ccn(Cc2ccc(Cl)cc2C(F)(F)F)n1)c1ccccc1F] | N-(1-{[4-chloro-2-(trifluoromethyl)phenyl]methyl}-1H-pyrazol-3-yl)-2-fluorobenzamide | 1.24 (System 3) | 398 |
| 155 | 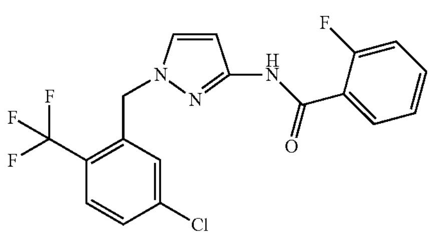 [SMILES: O=C(Nc1ccn(Cc2cc(Cl)ccc2C(F)(F)F)n1)c1ccccc1F] | N-(1-{[5-chloro-2-(trifluoromethyl)phenyl]methyl}-1H-pyrazol-3-yl)-2-fluorobenzamide | 1.21 (System 3) | 398/400 |
| 156 | 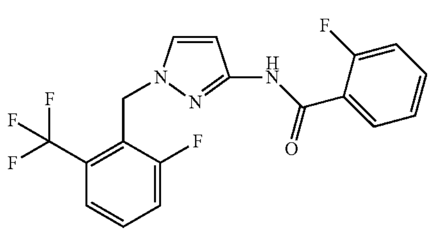 [SMILES: O=C(Nc1ccn(Cc2c(F)cccc2C(F)(F)F)n1)c1ccccc1F] | 2-Fluoro-N-(1-{[2-fluoro-6-(trifluoromethyl)phenyl]methyl}-1H-pyrazol-3-yl)benzamide | 2.99 (System 4) | 382/384 |
| 157 | 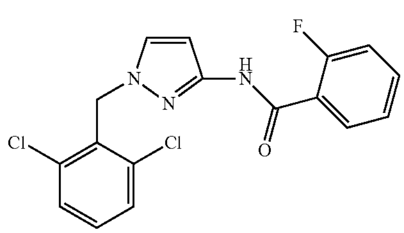 [SMILES: O=C(Nc1ccn(Cc2c(Cl)cccc2Cl)n1)c1ccccc1F] | N-{1-[(2,6-dichlorophenyl)methyl]-1H-pyrazol-3-yl}-2-fluorobenzamide | 1.14 (System 3) | 364/366 |

Example 113

2,6-Dichloro-N-(1-{[2-(trifluoromethyl)phenyl]methyl}-1H-pyrazol-3-yl)benzamide

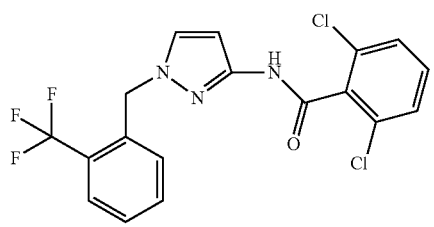 [SMILES: O=C(Nc1ccn(Cc2ccccc2C(F)(F)F)n1)c1c(Cl)cccc1Cl]

1.0 M lithium bis(trimethylsilyl)amide (100 µl, 0.1 mmol, Aldrich) was slowly added to a solution of 2,6-dichloro-N-1H-pyrazol-3-ylbenzamide (for a preparation see Intermediate 44)(26 mg, 0.1 mmol) in THF (400 µl). The resulting solution was then transferred to a solution of 1-(bromomethyl)-2-(trifluoromethyl)benzyl bromide (24.7 mg, 0.1 mmol, Apollo Scientific Limited) in THF (200 µl) and stirred for 2 h under nitrogen at ambient temperature. The mixture was diluted with DMSO (0.6 ml) and purified by MDAP using the Sunfire C18 column (Method D) using Acetonitrile-Water with a TFA modifier. The solvent was removed under a stream of nitrogen to give the title compound (27 mg); LCMS (System 4) MH$^+$=415, $t_{RET}$=3.11 min.

Similarly prepared were

| Example | Structure | Name | LCMS $t_{RET}$/min | MH$^+$ |
|---|---|---|---|---|
| 114 | 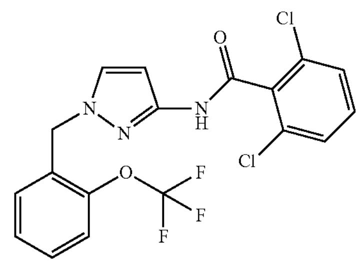 [SMILES: O=C(Nc1ccn(Cc2ccccc2OC(F)(F)F)n1)c1c(Cl)cccc1Cl] | 2,6-Dichloro-N-[1-({2-[(trifluoromethyl)oxy]phenyl}methyl)-1H-pyrazol-3-yl]benzamide | 3.07 (System 4) | 431 |
| 115 | 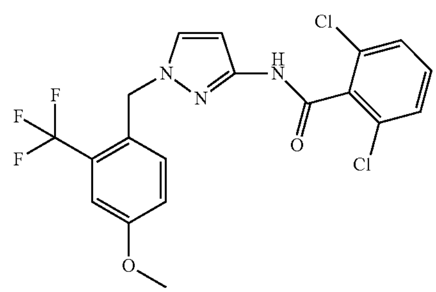 [SMILES: COc1ccc(Cn2ccc(NC(=O)c3c(Cl)cccc3Cl)n2)c(C(F)(F)F)c1] | 2,6-Dichloro-N-(1-{[4-(methyloxy)-2-(trifluoromethyl)phenyl]methyl}-1H-pyrazol-3-yl)benzamide | 3.16 (System 4) | 445 |
| 116 | 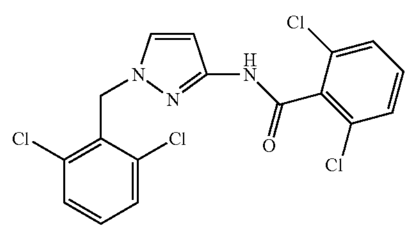 [SMILES: O=C(Nc1ccn(Cc2c(Cl)cccc2Cl)n1)c1c(Cl)cccc1Cl] | 2,6-Dichloro-N-{1-[(2,6-dichlorophenyl)methyl]-1H-pyrazol-3-yl}benzamide | 1.17 (System 3) | 416 |
| 117 | 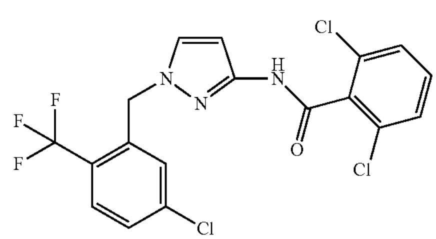 [SMILES: O=C(Nc1ccn(Cc2cc(Cl)ccc2C(F)(F)F)n1)c1c(Cl)cccc1Cl] | 2,6-Dichloro-N-(1-{[5-chloro-2-(trifluoromethyl)phenyl]methyl}-1H-pyrazol-3-yl)benzamide | 1.22 (System 3) | 449 |

-continued

| Example | Structure | Name | LCMS $t_{RET}$/min | MH⁺ |
|---|---|---|---|---|
| 118 | 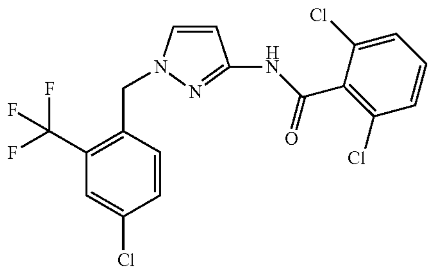 [SMILES: O=C(Nc1ccn(Cc2ccc(Cl)cc2C(F)(F)F)n1)c1c(Cl)cccc1Cl] | 2,6-Dichloro-N-(1-{[4-chloro-2-(trifluoromethyl)phenyl]methyl}-1H-pyrazol-3-yl)benzamide | 1.25 (System 3) | 449 |
| 119 | 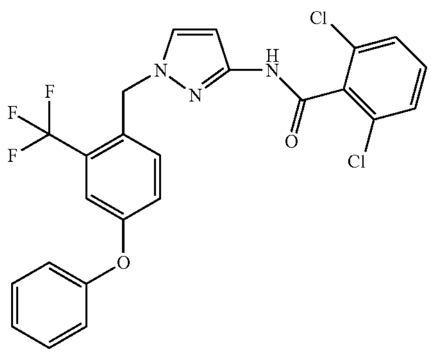 [SMILES: O=C(Nc1ccn(Cc2ccc(Oc3ccccc3)cc2C(F)(F)F)n1)c1c(Cl)cccc1Cl] | 2,6-Dichloro-N-(1-{[4-(phenyloxy)-2-(trifluoromethyl)phenyl]methyl}-1H-pyrazol-3-yl)benzamide | 1.34 (System 3) | 507 |
| 158 | 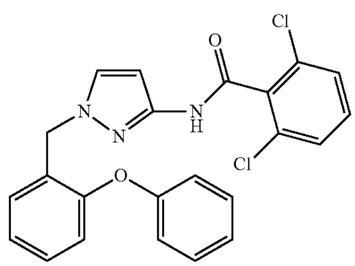 [SMILES: O=C(Nc1ccn(Cc2ccccc2Oc2ccccc2)n1)c1c(Cl)cccc1Cl] | 2,6-Dichloro-N-(1-{[2-(phenyloxy)phenyl]methyl}-1H-pyrazol-3-yl)benzamide | 3.32 (System 4) | 438/440 |
| 159 | 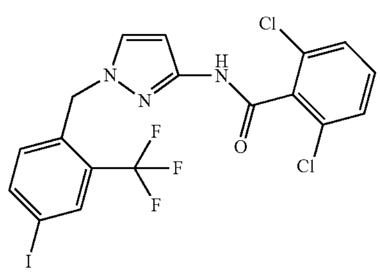 [SMILES: O=C(Nc1ccn(Cc2ccc(I)cc2C(F)(F)F)n1)c1c(Cl)cccc1Cl] | 2,6-Dichloro-N-(1-{[4-iodo-2-(trifluoromethyl)phenyl]methyl}-1H-pyrazol-3-yl)benzamide | 3.40 (System 4) | 540/542 |
| 160 | 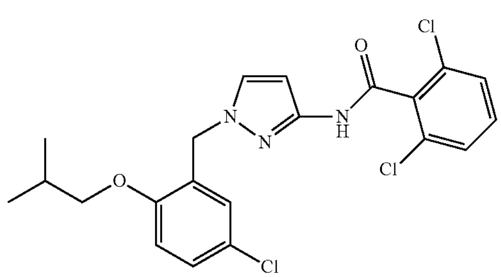 [SMILES: CC(C)COc1ccc(Cl)cc1Cn1ccc(NC(=O)c2c(Cl)cccc2Cl)n1] | 2,6-Dichloro-N-[1-({5-chloro-2-[(2-methylpropyl)oxy]phenyl}methyl)-1H-pyrazol-3-yl]benzamide | 1.30 (System 3) | 452/454 |

| Example | Structure | Name | LCMS $t_{RET}$/min | MH+ |
|---|---|---|---|---|
| 161 | 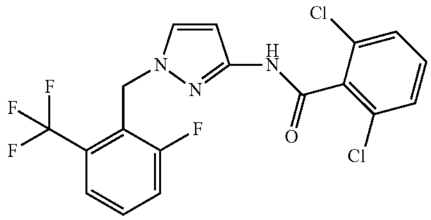 [SMILES: O=C(Nc1ccn(Cc2c(F)cccc2C(F)(F)F)n1)c1c(Cl)cccc1Cl] | 2,6-Dichloro-N-(1-{[2-fluoro-6-(trifluoromethyl)phenyl]methyl}-1H-pyrazol-3-yl)benzamide | 3.06 (System 4) | 432/434 |
| 162 | 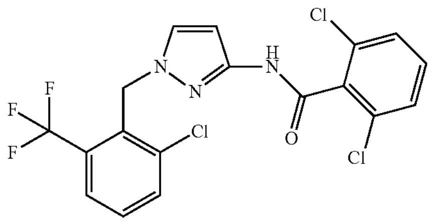 [SMILES: O=C(Nc1ccn(Cc2c(Cl)cccc2C(F)(F)F)n1)c1c(Cl)cccc1Cl] | 2,6-Dichloro-N-(1-{[2-chloro-6-(trifluoromethyl)phenyl]methyl}-1H-pyrazol-3-yl)benzamide | 1.18 (System 3) | 448/450 |

Example 120

2-Chloro-N-(1-{[2-fluoro-6-(trifluoromethyl)phenyl]methyl}-1H-pyrazol-3-yl)benzamide

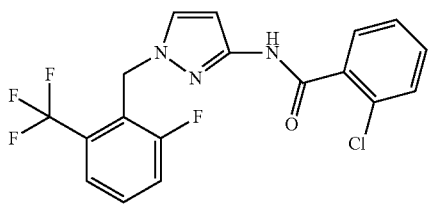 [SMILES: O=C(Nc1ccn(Cc2c(F)cccc2C(F)(F)F)n1)c1ccccc1Cl]

1.0 M lithium bis(trimethylsilyl)amide (100 µl, 0.1 mmol, Aldrich) was slowly added to a solution of 2-chloro-N-1H-pyrazol-3-ylbenzamide (for a preparation see Intermediate 45) (22 mg, 0.1 mmol) in THF (400 µl). The resulting solution was then transferred to a solution of 2-fluoro-6-(trifluoromethyl)benzyl bromide (26 mg, 0.1 mmol, Aldrich) in THF (200 µl) and stirred for 2 h under nitrogen at ambient temperature. The mixture was diluted with DMSO (0.6 ml) and purified by MDAP using a Sunfire C18 column (Method D) using Acetonitrile-Water with a TFA modifier. The solvent was removed under a stream of nitrogen to give the title compound (27 mg); LCMS (System 4) MH+=398, $t_{RET}$=2.96 min.

Similarly prepared were

| Example | Structure | Name | LCMS $t_{RET}$/min | MH+ |
|---|---|---|---|---|
| 121 | 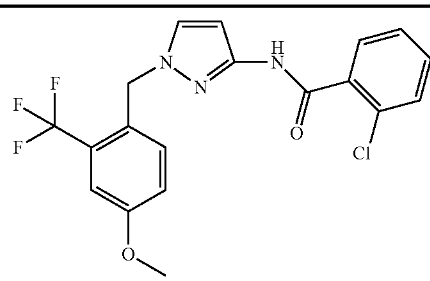 | 2-Chloro-N-(1-{[4-(methyloxy)-2-(trifluoromethyl)phenyl]methyl}-1H-pyrazol-3-yl)benzamide | 3.07 (System 4) | 410 |
| 122 | 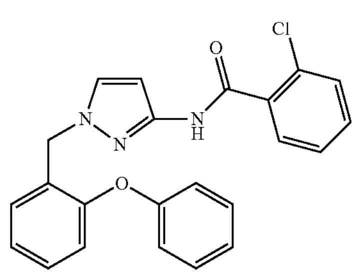 [SMILES: O=C(Nc1ccn(Cc2ccccc2Oc2ccccc2)n1)c1ccccc1Cl] | 2-Chloro-N-(1-{[2-(phenyloxy)phenyl]methyl}-1H-pyrazol-3-yl)benzamide | 3.24 (System 4) | 404 |

| Example | Structure | Name | LCMS $t_{RET}$/min | MH+ |
|---|---|---|---|---|
| 123 | 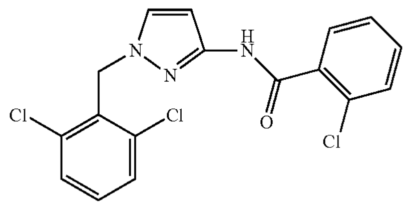 [SMILES: O=C(Nc1ccn(Cc2c(Cl)cccc2Cl)n1)c1ccccc1Cl] | 2-Chloro-N-{1-{(2,6-dichlorophenyl)methyl]-1H-pyrazol-3-yl)benzamide | 1.13 (System 3) | 381 |
| 124 | 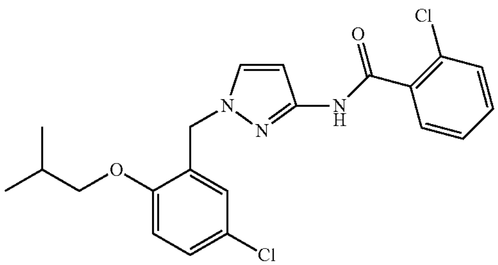 [SMILES: CC(C)COc1ccc(Cl)cc1Cn1ccc(NC(=O)c2ccccc2Cl)n1] | 2-Chloro-N-[1-({5-chloro-2-[(2-methylpropyl)oxy]phenyl}methyl)-1H-pyrazol-3-yl]benzamide | 1.32 (System 3) | 419 |
| 125 | 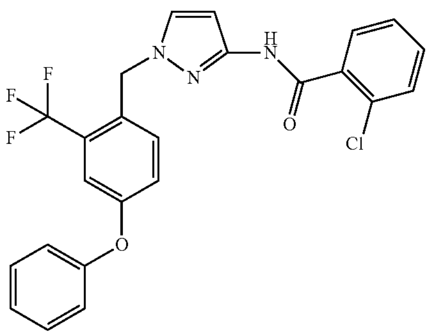 [SMILES: O=C(Nc1ccn(Cc2ccc(Oc3ccccc3)cc2C(F)(F)F)n1)c1ccccc1Cl] | 2-Chloro-N-(1-{[4-(phenyloxy)-2-(trifluoromethyl)phenyl]methyl}-1H-pyrazol-3-yl)benzamide | 1.32 (System 3) | 472 |
| 126 | 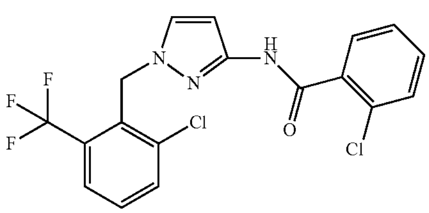 [SMILES: O=C(Nc1ccn(Cc2c(Cl)cccc2C(F)(F)F)n1)c1ccccc1Cl] | 2-Chloro-N-(1-{[2-chloro-6-(trifluoromethyl)phenyl]methyl}-1H-pyrazol-3-yl)benzamide | 1.15 (System 3) | 415 |
| 127 | 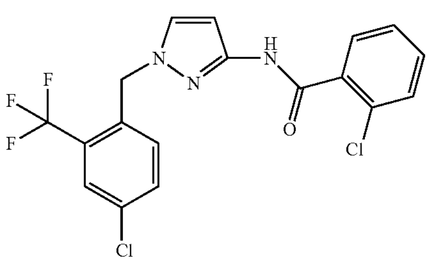 [SMILES: O=C(Nc1ccn(Cc2ccc(Cl)cc2C(F)(F)F)n1)c1ccccc1Cl] | 2-Chloro-N-(1-{[4-chloro-2-(trifluoromethyl)phenyl]methyl}-1H-pyrazol-3-yl)benzamide | 1.22 (System 3) | 415 |
| 163 | 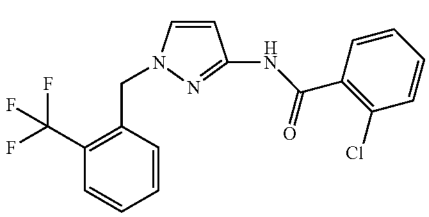 [SMILES: O=C(Nc1ccn(Cc2ccccc2C(F)(F)F)n1)c1ccccc1Cl] | 2-Chloro-N-(1-{[2-(trifluoromethyl)phenyl]methyl}-1H-pyrazol-3-yl)benzamide | 3.02 (System 4) | 380/382 |

| Example | Structure | Name | LCMS $t_{RET}$/min | MH+ |
|---|---|---|---|---|
| 164 | 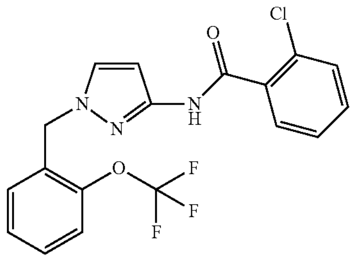 [SMILES: O=C(Nc1ccn(Cc2ccccc2OC(F)(F)F)n1)c1ccccc1Cl] | 2-Chloro-N-[1-({2-[(trifluoromethyl)oxy]phenyl}methyl)-1H-pyrazol-3-yl]benzamide | 3.07 (System 4) | 396/398 |
| 165 | 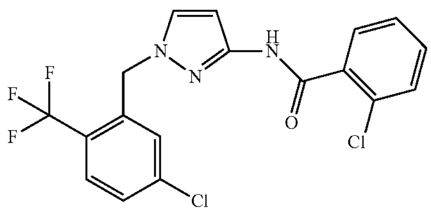 [SMILES: O=C(Nc1ccn(Cc2cc(Cl)ccc2C(F)(F)F)n1)c1ccccc1Cl] | 2-Chloro-N-(1-{[5-chloro-2-(trifluoromethyl)phenyl]methyl}-1H-pyrazol-3-yl)benzamide | 1.19 (System 3) | 414/416 |

Example 128

N-(1-{[2-fluoro-6-(trifluoromethyl)phenyl]methyl}-1H-pyrazol-3-yl)-2-methylbenzamide

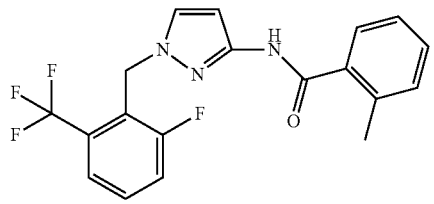 [SMILES: Cc1ccccc1C(=O)Nc1ccn(Cc2c(F)cccc2C(F)(F)F)n1]

1.0 M lithium bis(trimethylsilyl)amide (100 µl, 0.1 mmol, Aldrich) was slowly added to a solution of 2-methyl-N-1H-pyrazol-3-ylbenzamide (for a preparation see Intermediate 46)(22 mg, 0.1 mmol) in THF (400 µl). The resulting solution was then transferred to a solution of 2-fluoro-6-(trifluoromethyl)benzyl bromide (26 mg, 0.1 mmol, Aldrich) in THF (200 µl) and stirred for 1 h under nitrogen at ambient temperature. The mixture was diluted with DMSO (0.6 ml) and purified by MDAP using a Sunfire C18 (Method D) column using Acetonitrile-Water with a TFA modifier. The solvent was removed under a stream of nitrogen to give the title compound (27 mg); LCMS (System 3) MH+=378, $t_{RET}$=1.13 min.

Similarly prepared were

| Example | Structure | Name | LCMS $t_{RET}$/min | MH+ |
|---|---|---|---|---|
| 129 | 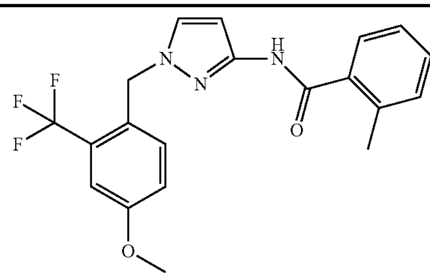 | 2-Methyl-N-(1-{[4-(methyloxy)-2-(trifluoromethyl)phenyl]methyl}-1H-pyrazol-3-yl)benzamide | 1.16 (System 3) | 390 |
| 130 | 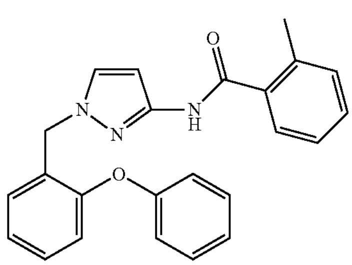 [SMILES: Cc1ccccc1C(=O)Nc1ccn(Cc2ccccc2Oc2ccccc2)n1] | 2-Methyl-N-(1-{[2-(phenyloxy)phenyl]methyl}-1H-pyrazol-3-yl)benzamide | 1.23 (System 3) | 384 |

| Example | Structure | Name | LCMS $t_{RET}$/min | MH+ |
|---|---|---|---|---|
| 131 | 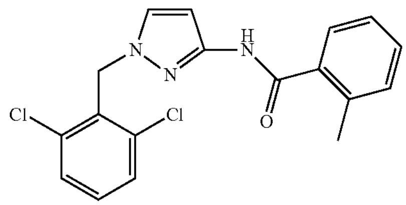 [SMILES: Cc1ccccc1C(=O)Nc1ccn(Cc2c(Cl)cccc2Cl)n1] | N-{1-[(2,6-dichlorophenyl)methyl]-1H-pyrazol-3-yl}-2-methylbenzamide | 1.14 (System 3) | 361 |
| 132 | 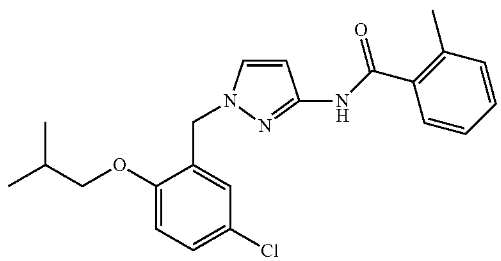 [SMILES: Cc1ccccc1C(=O)Nc1ccn(Cc2cc(Cl)ccc2OCC(C)C)n1] | N-[1-({5-chloro-2-[(2-methylpropyl)oxy]phenyl}methyl)-1H-pyrazol-3-yl]-2-methylbenzamide | 1.33 (System 3) | 398 |
| 133 | 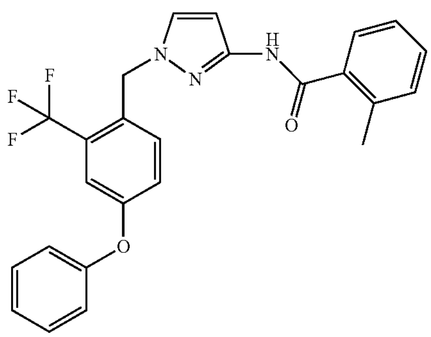 [SMILES: Cc1ccccc1C(=O)Nc1ccn(Cc2ccc(Oc3ccccc3)cc2C(F)(F)F)n1] | 2-Methyl-N-(1-{[4-(phenyloxy)-2-(trifluoromethyl)phenyl]methyl}-1H-pyrazol-3-yl)benzamide | 1.33 (System 3) | 452 |
| 134 | 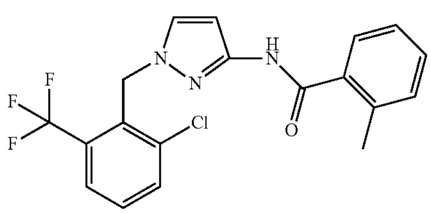 | N-(1-{[2-chloro-6-(trifluoromethyl)phenyl]methyl}-1H-pyrazol-3-yl)-2-methylbenzamide | 1.16 (System 3) | 394 |
| 135 | 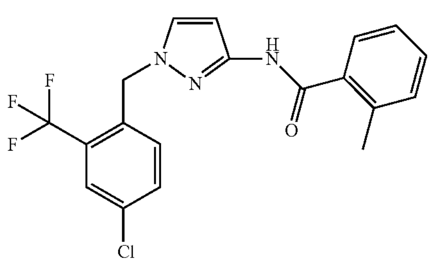 [SMILES: Cc1ccccc1C(=O)Nc1ccn(Cc2ccc(Cl)cc2C(F)(F)F)n1] | N-(1-{[4-chloro-2-(trifluoromethyl)phenyl]methyl}-1H-pyrazol-3-yl)-2-methylbenzamide | 1.23 (System 3) | 394 |
| 166 | 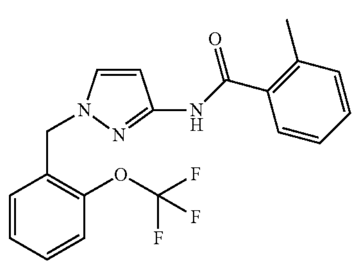 [SMILES: Cc1ccccc1C(=O)Nc1ccn(Cc2ccccc2OC(F)(F)F)n1] | 2-Methyl-N-[1-({2-[(trifluoromethyl)oxy]phenyl}methyl)-1H-pyrazol-3-yl]benzamide | 1.16 (System 3) | 376 |

-continued

| Example | Structure | Name | LCMS $t_{RET}$/min | MH⁺ |
|---|---|---|---|---|
| 167 | 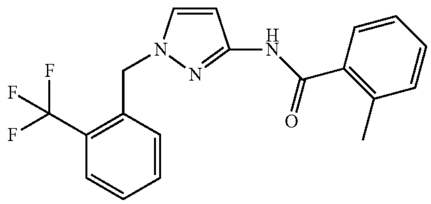 [SMILES: Cc1ccccc1C(=O)Nc1ccn(Cc2ccccc2C(F)(F)F)n1] | 2-Methyl-N-(1-{[2-(trifluoromethyl)phenyl]methyl}-1H-pyrazol-3-yl)benzamide | 1.15 (System 3) | 360 |
| 168 | 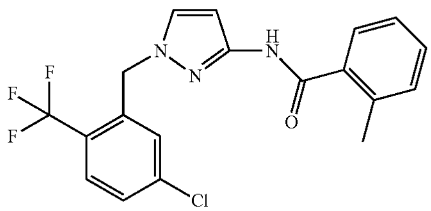 [SMILES: Cc1ccccc1C(=O)Nc1ccn(Cc2cc(Cl)ccc2C(F)(F)F)n1] | N-(1-{[5-chloro-2-(trifluoromethyl)phenyl]methyl}-1H-pyrazol-3-yl)-2-methylbenzamide | 1.20 (System 3) | 394/396 |

Example 136

2,6-Difluoro-N-{1-[(2-methyl-5-{[3-(methyloxy)propyl]oxy}phenyl)methyl]-1H-pyrazol-3-yl}benzamide

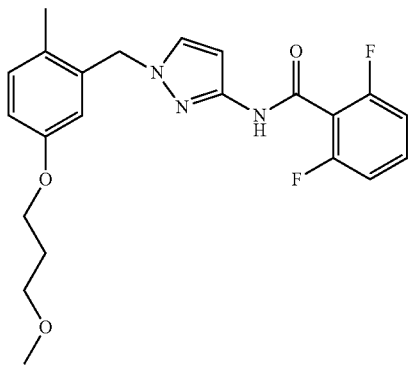 [SMILES: COCCCOc1ccc(C)c(Cn2ccc(NC(=O)c3c(F)cccc3F)n2)c1]

To a solution of 2,6-difluoro-N-{1-[(5-hydroxy-2-methylphenyl)methyl]-1H-pyrazol-3-yl}benzamide (for a preparation see Intermediate 49)(82 mg, 0.239 mmol) in DMSO (1 ml) was added cesium carbonate (155 mg, 0.476 mmol) and then a solution of 1-bromo-3-(methyloxy)propane (45 mg, 0.294 mmol, Matrix Scientific) in DMSO (0.1 ml). The resulting red solution was stirred at ambient temperature under nitrogen overnight. The solution was filtered using a hydrophobic frit and diluted with methanol (0.9 ml). The mixture was purified by MDAP on a Sunfire C18 column (Method B) using Acetonitrile-Water with a Formic acid modifier. The solvent was evaporated in vacuo to give the title compound as a luminous yellow gum (19.4 mg); LCMS (System 4) MH⁺=416, $t_{RET}$=2.79 min.

Similarly prepared was

| Example | Structure | Name | LCMS $t_{RET}$/min | MH⁺ |
|---|---|---|---|---|
| 169 | 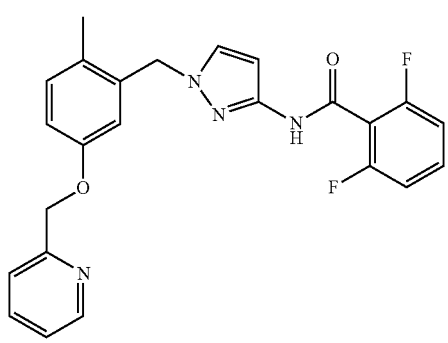 [SMILES: Cc1ccc(OCc2ccccn2)cc1Cn1ccc(NC(=O)c2c(F)cccc2F)n1] | 2,6-Difluoro-N-{1-({2-methyl-5-[(2-pyridinylmethyl)oxy]phenyl}methyl)-1H-pyrazol-3-yl]benzamide | 2.27 (System 4) | 435 |

Example 170

N-(1-{[2-(ethyloxy)phenyl]methyl}-1H-pyrazol-3-yl)-2,6-difluorobenzamide

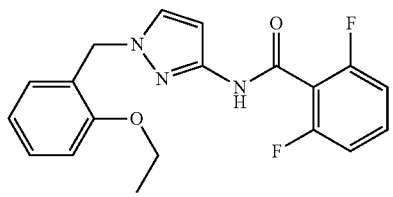 [SMILES: CCOc1ccccc1Cn1ccc(NC(=O)c2c(F)cccc2F)n1]

To 2,6-difluoro-N-1H-pyrazol-3-ylbenzamide (for a preparation see Intermediate 9)(23 mg, 0.10 mmol) in a microwave vial was added a solution of 1-(bromomethyl)-2-(ethyloxy)benzene (26 mg, 0.12 mmol) in acetonitrile (0.5 ml). To the mixture was added 2,6-lutidine (15 μl, 0.13 mmol, Aldrich). The mixture was heated in a microwave at 160° C. for 30 min. The colourless mixture was concentrated using a stream of nitrogen. The residue was dissolved in methanol (1 ml) and purified by MDAP on a Sunfire C18 column (Method B) to give the title compound as a colourless gum (19 mg); LCMS (System 4) MH+=358, $t_{RET}$=2.89 min.

Example 171

2,6-Difluoro-N-(1-{[4-(2-pyrimidinyloxy)-2-trifluoromethyl)phenyl]methyl}-1H-pyrazol-3-yl)benzamide

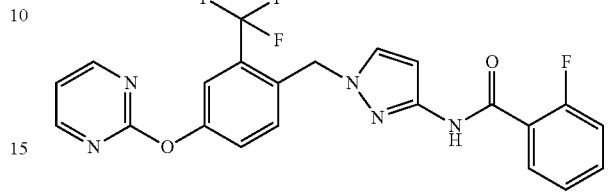

To a solution of 2,6-difluoro-N-(1-{[4-hydroxy-2-(trifluoromethyl)phenyl]methyl}-1H-pyrazol-3-yl)benzamide (for a preparation see Example 36)(100 mg, 0.25 mmol) in dimethyl sulfoxide (1 ml) was added potassium t-butoxide (36 mg, 0.32 mmol). The slight suspension was stirred for 5 min. To the mixture was added 2-chloropyrimidine (50 mg, 0.44 mmol, Aldrich) and the reaction vessel was sealed and heated in Biotage Initiator microwave to 150° C. for 15 min. The mixture was diluted with methanol (1 ml) and filtered through a hydrophobic frit. The filtrate was purified by MDAP on Sunfire C18 column using Acetonitrile-Water with a Formic acid modifier (Method B). The solvent was evaporated in vacuo to give the title compound as a white foam (75 mg);

LCMS (System 4) MH+=476, $t_{RET}$=2.67 min.

Similarly prepared were

| Example | Structure | Name | LCMS $t_{RET}$/min | MH+ |
|---|---|---|---|---|
| 172 | 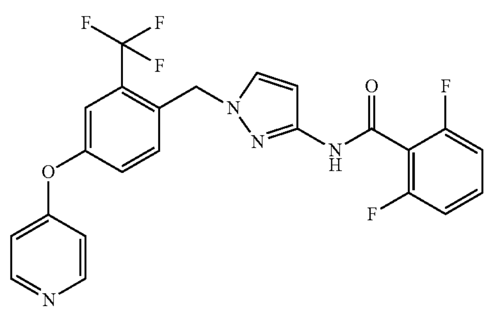 [SMILES: O=C(Nc1ccn(Cc2ccc(Oc3ccncc3)cc2C(F)(F)F)n1)c1c(F)cccc1F] | 2,6-Difluoro-N-(1-{[4-(4-pyridinyloxy)-2-(trifluoromethyl)phenyl]methyl}-1H-pyrazol-3-yl)benzamide | 1.94 (System 4) | 475 |
| 173 | 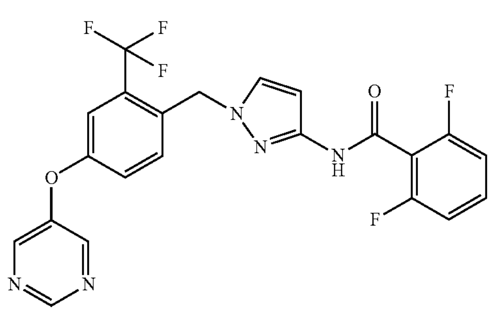 [SMILES: O=C(Nc1ccn(Cc2ccc(Oc3cncnc3)cc2C(F)(F)F)n1)c1c(F)cccc1F] | 2,6-Difluoro-N-(1-{[4-(5-pyrimidinyloxy)-2-(trifluoromethyl)phenyl]methyl}-1H-pyrazol-3-yl)benzamide | 2.63 (System 4) | 476 |

Example 174

3-Chloro-N-(1-{[4-(methyloxy)-2-(trifluoromethyl)phenyl]methyl}-1H-pyrazol-3-yl)-4-pyridinecarboxamide

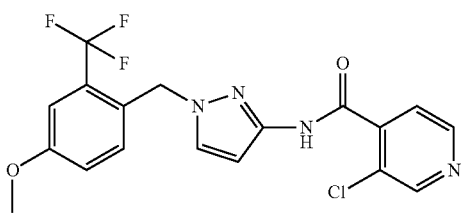 [SMILES: COc1ccc(Cn2ccc(NC(=O)c3ccncc3Cl)n2)c(C(F)(F)F)c1]

To a solution of 3-chloro-4-pyridinecarboxylic acid (103 mg, 0.654 mmol, Aldrich) in N,N-dimethylformamide (0.5 ml) was added HATU (250 mg, 0.657 mmol), DIPEA (0.27 ml, 1.55 mmol) and then 1-{[4-(methyloxy)-2-(trifluoromethyl)phenyl]methyl}-1H-pyrazol-3-amine (for a preparation see Intermediate 52)(135 mg, 0.498 mmol). The resulting brown solution was stirred at ambient temperature for 30 min. The reaction mixture was diluted with methanol (1 ml) and purified by MDAP on an Xbridge column using Acetonitrile-Water with an ammonium carbonate modifier (Method E). The solvent was evaporated in vacuo to give the title compound as an orange foam (160 mg); LCMS (System 4) $MH^+=411$, $t_{RET}=2.69$ min.

Similarly prepared were

| Example | Structure | Name | LCMS $t_{RET}$/min | $MH^+$ |
|---|---|---|---|---|
| 175 | 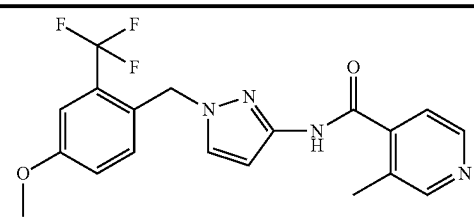 | 3-Methyl-N-(1-{[4-(methyloxy)-2-(trifluoromethyl)phenyl]methyl}-1H-pyrazol-3-yl)-4-pyridinecarboxamide | 2.18 (System 4) | 391 |
| 176 | 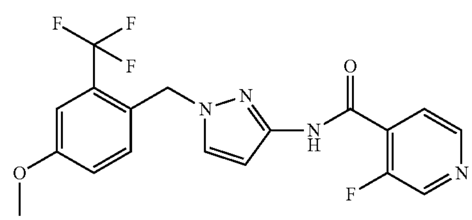 [SMILES: COc1ccc(Cn2ccc(NC(=O)c3ccncc3F)n2)c(C(F)(F)F)c1] | 3-Fluoro-N-(1-{[4-(methyloxy)-2-(trifluoromethyl)phenyl]methyl}-1H-pyrazol-3-yl)-4-pyridinecarboxamide | 2.63 (System 4) | 395 |

Example 177

N-(1-{[4-hydroxy-2-(trifluoromethyl)phenyl]methyl}-1H-pyrazol-3-yl)-3-methyl-4-pyridinecarboxamide

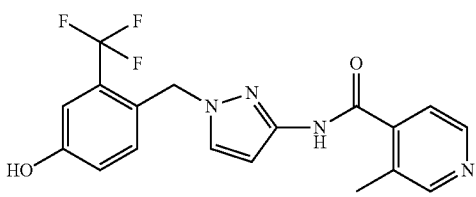 [SMILES: Cc1cnccc1C(=O)Nc1ccn(Cc2ccc(O)cc2C(F)(F)F)n1]

To a solution of 3-methyl-N-(1-{[4-(methyloxy)-2-(trifluoromethyl)phenyl]methyl}-1H-pyrazol-3-yl)-4-pyridinecarboxamide (for a preparation see Example 175)(50 mg, 0.128 mmol) in dichloromethane (1 mL) was added slowly 1.0 M boron tribromide in DCM (0.26 mL, 0.260 mmol). The resulting colourless solution was stirred under nitrogen for 2 days. The reaction mixture ran dry, so further amounts of dichloromethane (1 ml) and 1.0 M boron tribromide in DCM (0.26 mL, 0.260 mmol) were added. The resulting white suspension was stirred at ambient temperature under nitrogen overnight. A further amount of 1.0 M boron tribromide in DCM (0.26 ml, 0.26 mmol) was added and stirred for a further 4 h. The solvent was removed in vacuo and the residue dissolved in 1:1 MeOH:DMSO (1 ml) and purified by MDAP on an Xbridge column using Acetonitrile-Water with an ammonium carbonate modifier (Method E). The solvent was evaporated in vacuo to give the title compound as a white solid (11 mg); LCMS (System 8) $MH^+=376$, $t_{RET}=2.13$ min.

Similarly prepared were

| Example | Structure | Name | LCMS $t_{RE}$/min | MH⁺ |
|---|---|---|---|---|
| 178 | 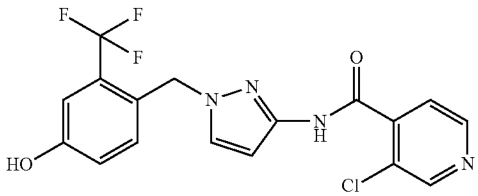 [SMILES: O=C(Nc1ccn(Cc2ccc(O)cc2C(F)(F)F)n1)c1ccncc1Cl] | 3-Chloro-N-(1-{[4-hydroxy-2-(trifluoromethyl)phenyl]methyl}-1H-pyrazol-3-yl)-4-pyridinecarboxamide | 2.26 | 397 |
| 179 | 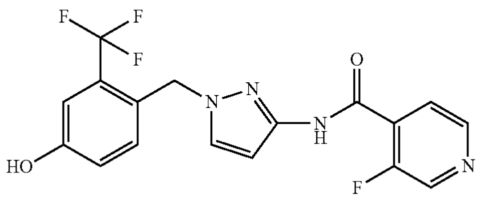 [SMILES: O=C(Nc1ccn(Cc2ccc(O)cc2C(F)(F)F)n1)c1ccncc1F] | 3-Fluoro-N-(1-{[4-hydroxy-2-(trifluoromethyl)phenyl]methyl}-1H-pyrazol-3-yl)-4-pyridinecarboxamide | 0.85 | 380.9 |

Example 180

2-Chloro-N-[1-({5-chloro-2-[(phenylmethyl)oxy]phenyl}methyl)-1H-pyrazol-3-yl]-6-fluorobenzamide

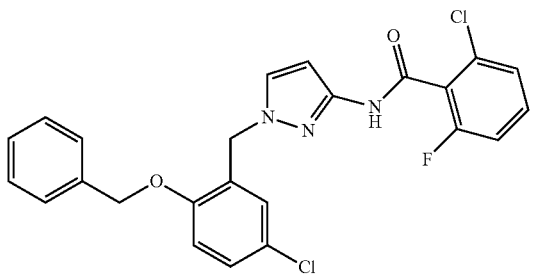 [SMILES: O=C(Nc1ccn(Cc2cc(Cl)ccc2OCc2ccccc2)n1)c1c(F)cccc1Cl]

To a solution of 2-chloro-6-fluorobenzoic acid (18 mg, 0.1 mmol, Aldrich) in DMF (0.1 ml) was added a solution of HATU (38 mg, 0.1 mmol) in DMF (0.2 ml). After 5 min, DIPEA (0.050 ml, 0.27 mmol) was added to the mixture. To the mixture was added a solution of 1-({5-chloro-2-[(phenylmethyl)oxy]phenyl}methyl)-1H-pyrazol-3-amine (for a preparation see Intermediate 55)(0.1 mmol) in DMF (0.1 ml). After shaking for 10 min, the resulting solution was allowed to stand for 16 h at ambient temperature. The solvent was removed using a genevac. The sample was dissolved in 1:1 MeOH:DMSO (0.6 ml) and purified by MDAP on a C18 column using Acetonitrile-Water with a TFA modifier (Method D). The solvent was evaporated in vacuo using the Genevac to give the title compound; LCMS (System 3) MH⁺=470/472, $t_{RET}$=1.32 min.

Example 181

N-(1-{[2-chloro-5-(5-methyl-1,3,4-oxadiazol-2-yl)phenyl]methyl}-1H-pyrazol-3-yl)-2,6-difluorobenzamide

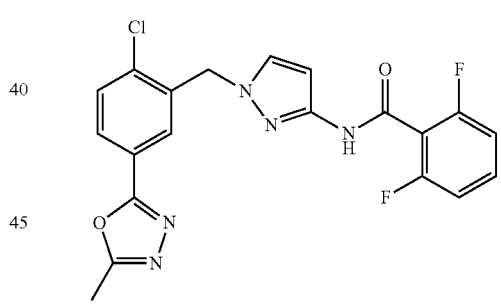

To a solution of N-[1-({5-[(2-acetylhydrazino)carbonyl]-2-chlorophenyl}methyl)-1H-pyrazol-3-yl]-2,6-difluorobenzamide (for a preparation see Intermediate 51)(130 mg, 0.290 mmol) in THF (4 ml) was added 4A molecular sieves (513 mg) (pre-dried in an oven) and then (methoxycarbonylsulfamoyl)triethylammonium hydroxide, inner salt (21 mg, 0.088 mmol, Fluka). The reaction vessel was sealed and heated in a Biotage Initiator microwave to 150° C. for 25 min. The solvent was evaporated in vacuo, the residue was dissolved in methanol (1 ml) and then filtered through a hydrophobic frit. The filtrate was dissolved in DMSO (1 ml) and the sample was purified by MDAP on Sunfire C18 column using Acetonitrile-Water with a Formic acid modifier (Method B). The solvent was evaporated in vacuo to give the title compound as a white solid (13 mg); LCMS (System 3) MH⁺=430/432, $t_{RET}$=2.54 min.

Example 182

2,6-Difluoro-N-(1-{[2-methyl-6-(methyloxy)phenyl]methyl}-1H-pyrazol-3-yl)benzamide

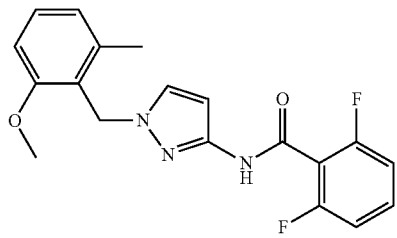 [SMILES: COc1cccc(C)c1Cn1ccc(NC(=O)c2c(F)cccc2F)n1]

To a stirred solution of 2,6-difluoro-N-1H-pyrazol-3-yl-benzamide (for a preparation see Intermediate 9)(50 mg, 0.224 mmol) in dry THF (1.75 ml) under nitrogen was added 1.0 lithium bis(trimethylsilyl)amide in THF (0.2 ml, 0.2 mmol) dropwise and the solution stirred for 30 min. To the solution was added a solution of 2-(bromomethyl)-1-methyl-3-(methyloxy)benzene (for a preparation see intermediate 57)(48 mg, 0.224 mmol) in THF (1.75 ml). The solution was stirred for 1.5 h and then allowed to stand overnight. The solvent was blown down using a stream of nitrogen and aqueous sodium bicarbonate added to the residue. The aqueous phase was then extracted with chloroform. The organic extract was removed in vacuo to give a gum (84 mg). The residue was purified on MDAP (Method B). The solvent was removed and the residue dried at −45° C. under high vacuum to give the title compound as a white solid; LCMS (System 4) $MH^+=358$, $t_{RET}=2.77$ min.

Similarly prepared were

Example 185

2,6-dichloro-N-{1-[(2-methylphenyl)methyl]-1H-pyrazol-3-yl}benzamide

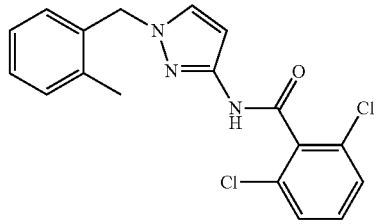 [SMILES: Cc1ccccc1Cn1ccc(NC(=O)c2c(Cl)cccc2Cl)n1]

LCMS (System 1) $MH^+=360/362$, $t_{RET}=2.74$ min.

Example 186

Prodrug of Example 36

4-[(3-{[(2,6-Difluorophenyl)carbonyl]amino}-1H-pyrazol-1-yl)methyl]-3-(trifluoromethyl)phenyl dihydrogen phosphate disodium salt

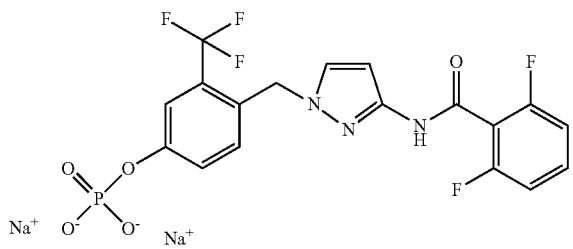 [SMILES: [Na+] ; O=C(Nc1ccn(Cc2ccc(OP(=O)([O-])[O-])cc2C(F)(F)F)n1)c1c(F)cccc1F ; [Na+]]

| Example | Structure | Name | LCMS $t_{RET}$/min | $MH^+$ |
|---|---|---|---|---|
| 183 | 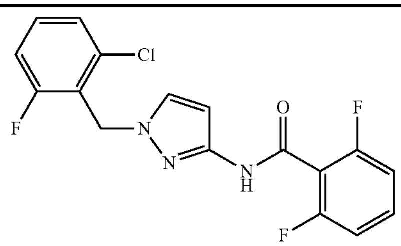 | N-{1-[(2-chloro-6-fluorophenyl)methyl]-1H-pyrazol-3-yl}-2,6-difluorobenzamide | 2.78 | 366/368 |
| 184 | 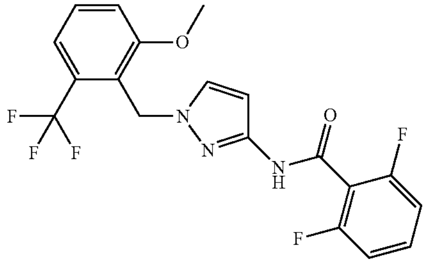 | 2,6-Difluoro-N-(1-{[2-(methyloxy)-6-(trifluoromethyl)phenyl]methyl}-1H-pyrazol-3-yl)benzamide | 2.86 | 412 |

A solution of 4-[(3-{[(2,6-difluorophenyl)carbonyl]amino}-1H-pyrazol-1-yl)methyl]-3-(trifluoromethyl)phenyl bis(phenylmethyl) phosphate (for a preparation see Intermediate 58)(15.85 g, 24.1 mmol) in ethanol (200 ml) was hydrogenated using the H-cube midi (settings: 25° C., 15 bar, 10 ml/min flow rate) and 10% Pd/C CatCart as the catalyst. The solvent was evaporated in vacuo to give a white foam. The sample was loaded in methanol/DMSO and purified on reverse phase (C18) 1900 g using a 0-50% acetonitrile (+0.1% TFA)-water(+0.1% TFA) over 7 column volumes. The appropriate fractions were combined and the acetonitrile was removed in vacuo. The resulting suspension was filtered to give 4-[(3-{[(2,6-difluorophenyl)carbonyl]amino}-1H-pyrazol-1-yl)methyl]-3-(trifluoromethyl)phenyl dihydrogen phosphate (5.02 g). The filtrate was extracted using ethyl acetate (600 ml). The organic phase was dried over magnesium sulphate and evaporated in vacuo to give a further amount of 4-[(3-{[(2,6-difluorophenyl)carbonyl]amino}-1H-pyrazol-1-yl)methyl]-3-(trifluoromethyl)phenyl dihydrogen phosphate as a white solid (2.39 g).

To a solution of 4-[(3-{[(2,6-difluorophenyl)carbonyl]amino}-1H-pyrazol-1-yl)methyl]-3-(trifluoromethyl)phenyl dihydrogen phosphate (3.58 g, 7.50 mmol) in methanol (100 ml) was added 2 M aqueous sodium hydroxide solution (7.50 ml, 15.0 mmol). The solvent was removed in vacuo. The residue was dissolved in methanol (50 ml) and the solution evaporated in vacuo (×2). The residue was dissolved in methanol (50 ml) and then concentrated to approximately 5 ml. To the residue was added diethyl ether (150 ml). The solid was collected by filtration and washed with diethyl ether (50 ml). The solid was dried in vacuo at 40° C. to give the title compound as a white solid (3.63 g); LCMS (System 3) MH$^+$=478, $t_{RET}$=0.68 min.

Example 187

Prodrug of Example 29

[[(2,6-Difluorophenyl)carbonyl](1-{[2-fluoro-6-(trifluoromethyl)phenyl]methyl}-1H-pyrazol-3-yl)amino]methyl dihydrogen phosphate disodium salt

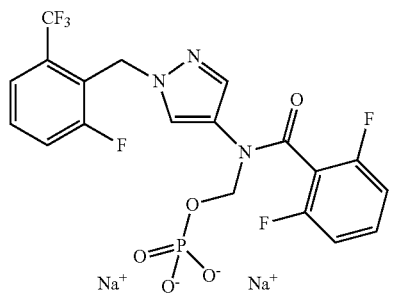 [SMILES: O=C(c1c(F)cccc1F)N(COP(=O)([O-])[O-])c1cnn(Cc2c(F)cccc2C(F)(F)F)c1 ; [Na+] ; [Na+]]

To a solution of [[(2,6-difluorophenyl)carbonyl](1-{[2-fluoro-6-(trifluoromethyl)phenyl]methyl}-1H-pyrazol-3-yl)amino]methyl bis(1,1-dimethylethyl) phosphate (for a preparation see Intermediate 61)(35 g, 56.3 mmol) in methanol (300 ml) was added sodium acetate/acetic acid pH 4 buffer (300 ml, 300 mmol) and the reaction mixture was heated at 75° C. for 4 h. The pH was adjusted to pH 5 using acetic acid. The reaction mixture was heated at 75° C. for 24 h. The reaction mixture was concentrated using a rotary evaporator to 300 ml. To this was added 10 N sodium hydroxide solution to approximately pH 10. The resultant solid was removed by filtration and washed with water. The combined filtrate and washings (500 ml) were applied to a 1900 g C18 silica cartridge. This was eluted with 3 column volumes of 5% acetonitrile (+NH$_3$) in water (10 mM ammonium bicarbonate), followed by a gradient of 0-40% acetonitrile (+NH$_3$) in water (10 mM ammonium bicarbonate).

The required fractions were combined and concentrated on a rotary evaporator. The sample was freeze-dried to give a white solid (16.9 g, batch 1). The residue from the flasks from the freeze drying was re-dissolved in water and freeze-dried to give a white solid (0.5 g). This was suspended in isopropanol (40 ml) and warmed. The solid was removed by filtration and the filtrate was evaporated in vacuo to give a white solid (0.4 g, batch 2). A portion (150 mg) of the 16.9 g was suspended in ethanol (10 ml) and heated to 60° C. The mixture was filtered and the filtrate was evaporated in vacuo to give a white solid (119 mg, batch 3). The combined three batches of material obtained at this stage contains 1 mole equivalent of sodium bicarbonate. This was suspended in ethanol (250 ml). The mixture was heated at 60° C. for 30 min. The mixture was filtered whilst warm. The filtrate was evaporated in vacuo to give the title compound as a white solid (13.38 g); LCMS: (System 8) MH$^+$=510, $t_{RET}$=1.72 min. $^1$H NMR (400 MHz, D$_2$O) δ=7.68-7.58 (3H, m), 7.49-7.42 (1H, m), 7.15 (1H, tt, J=7.0, 8.5 Hz), 6.63 (2H, t, J=8.5 Hz), 6.45 (1H, d, J=2.0 Hz), 5.42 (2H, d, J=4.0 Hz), 5.36 (2H, s) (referenced to H$_2$O at 4.80 ppm).

Biological Experimental

The compounds can be tested according to the following or similar procedures.

This ICRAC assay uses the SERCA inhibitor thapsigargin to produce calcium depletion and activate an ICRAC current. The cells are incubated in a calcium-free environment, thus ionic movement does not occur until the calcium is added back and subsequently enters the cell via the open channels. Changes in intracellular calcium levels are determined by the inclusion of the calcium sensitive fluorescent dye Fluo-4 and the use of the FLIPR detection system. Inhibitors of ICRAC would be expected to decrease the calcium influx upon calcium add-back, thus reducing fluorescent signal.

Jurkat E6-1 is an established immortalised T lymphocyte cell line previously shown to express a functional ICRAC current. Jurkat cells grow in suspension, are cultured in DMEM+10% FBS, maintained in T175 flasks at 37° C./5% CO$_2$, and are subcultured twice a week with either 1:10-1:20 splits. 1 confluent T175 yields 100 ml of approximately 2×10$^6$ cells/ml.

Loading buffer contains; NaCl 145 mM, KCl 2.5 mM, HEPES 10 mM, Glucose 10 mM, MgCl$_2$ 1.2 mM, made up with water, then pH adjusted to 7.4 using NaOH 1 M. Finally Fluo-4AM & brilliant black are added to give a final assay concentration of 2 μM and 250 μM respectively.

Test buffer contains thapsigargin to give a final assay concentration of 5 μM, and test ICRAC inhibitor to give a final assay concentration of 15 μM to 14 μM. In instances of pIC$_{50}$<4.8, compounds of the invention could be screened at a maximum concentration of either 50 μM or 150 μM.

The required seeding density for a 384 plate is 20,000 cells per well. Cells are plated onto a 384 well plate, and loading buffer is added before being incubated at room temperature for 2.5 hours. Subsequently, test buffer is added to the cell plate and incubated at room temperature for a further 10 minutes. Plates are then transferred to the FLIPR which initially measures baseline fluorescence, followed by any increase in fluorescence evoked by the online addition of a 6 mM (1.2 mM FAC) calcium solution.

Fluorescence in the absence of ICRAC inhibitor gives a 100% maximal signal, and increasing concentrations of an ICRAC inhibitor result in a decreased fluorescence signal which is expressed as a percentage inhibition of maximal signal. From the concentration-response relationship, the concentration producing a 50% inhibition of the maximal signal ($pIC_{50}$) can then be determined.

In the above assay the compounds of the following examples were found to have a $pIC_{50} \geq 6.0$:
7, 10, 15-18, 19, 21-24, 26-28, 35, 55, 59, 63, 68, 73, 75-77, 80, 94, 97, 98 and 102

In the above assay the compounds of the following examples were found to have a $pIC_{50} \geq 5.3$ and $<6.0$.
1-6, 8, 9, 11, 12, 20, 25, 29-34, 36-54, 56-58, 60-62, 64-67; 69-72, 74, 78, 79, 81-93, 95, 96, 99-101, 103-118, 120-136, 139, 144-150, 174 and 176.

Examples 186 and 187 were found to have a $pIC_{50}$ of 4.9 and <4.8 respectively (at a final assay concentration of 15 μM).

All other examples were found to have a $pIC_{50} \geq 4.4$ with the exception of examples 13, 14, 119 and 160 which were found to have a $pIC_{50} \leq 4.3$.

All publications, including but not limited to patents and patent applications, cited in this specification are herein incorporated by reference as if each individual publication were specifically and individually indicated to be incorporated by reference herein as though fully set forth.

The invention claimed is:
1. A compound of formula (I) or a prodrug thereof

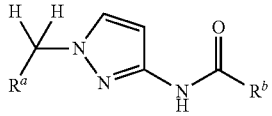

(I)

in which
$R^a$ is a group of formula (a1)

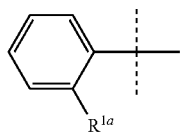

(a1)

in which
$R^{1a}$ is $C_{1-6}$alkyl, $CF_3$, $OCF_3$, $C_{1-6}$alkoxy or $R^{1a}$ is a group $L^1$-$Z^1$ in which $L^1$ is O, $CH_2$, $OCH_2$ or $CH_2O$ and $Z^1$ is $C_{3-7}$cycloalkyl or aryl;
or $R^a$ is a group of formula (a2)

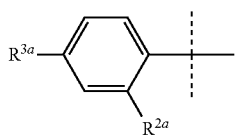

(a2)

in which
$R^{2a}$ is halogen, $C_{1-6}$alkyl, $CF_3$ or $OCH_2Ph$; and
$R^{3a}$ is halogen, $C_{1-6}$alkyl, $C_{1-6}$alkoxy, hydroxy, $C_{3-7}$cycloalkyl, $CO_2C_{1-4}$alkyl or $R^{3a}$ is a group $L^2$-$Z^2$ in which $L^2$ is O, $CH_2$ or $O(CH_2)_n$ wherein n is an integer from 1-7; and $Z^2$ is hydroxy, methoxy, $CO_2C_{1-4}$ alkyl, $C_{3-7}$cycloalkyl, aryl or heteroaryl;
or $R^a$ is a group of formula (a3)

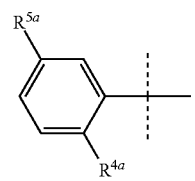

(a3)

in which
$R^{4a}$ is halogen, $C_{1-6}$alkyl, $C_{1-6}$alkoxy, $CF_3$ or $OCH_2Ph$; and
$R^{5a}$ is halogen, $C_{1-6}$alkyl, hydroxy, $C_{1-6}$alkoxy optionally substituted by methoxy, or $R^{5a}$ is a group $L^3$-$Z^3$ in which $L^3$ is a single bond, O, $CH_2$, $OCH_2$ or $CH_2O$ and $Z^3$ is $C_{3-7}$cycloalkyl, aryl or heteroaryl;
or $R^a$ is a group of formula (a4)

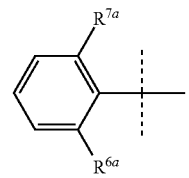

(a4)

in which
$R^{6a}$ is Cl, Br, $C_{1-6}$alkyl or $CF_3$; and
$R^{7a}$ halogen, $C_{1-6}$alkyl, $CF_3$, $OCF_3$, $OCHF_2$, $C_{1-6}$alkoxy or $R^{7a}$ is group $L^4$-$Z^4$ in which $L^4$ is $OCH_2$ and $Z^4$ is $C_{3-7}$cycloalkyl
$R^b$ is a group of formula (b)

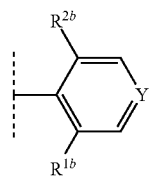

(b)

wherein
Y is CH or N,
$R^{1b}$ is halogen, $C_{1-6}$alkyl or $CF_3$;
$R^{2b}$ is H, halogen, $C_{1-6}$alkyl or $C_{1-6}$alkoxy
or a salt thereof
subject to the proviso that it is not a compound selected from
2,6-Difluoro-N-{1-[(2-methylphenyl)methyl]-1H-pyrazol-3-yl}benzamide;
2-Fluoro-N-{1-[(2-methylphenyl)methyl]-1H-pyrazol-3-yl}benzamide;
2,6-Dichloro-N-{1-[(2-methylphenyl)methyl]-1H-pyrazol-3-yl}benzamide;

2-Methyl-N-{1-[(2-methylphenyl]-1H-pyrazol-3-yl}benzamide; and
2-Bromo-N-[1-{(2,5-dichlorophenyl)methyl]-1H-pyrazol-3-yl}benzamide.

2. A compound or prodrug thereof according to claim 1, or a salt thereof, wherein $R^a$ is a group of formula (a1) in which $R^{1a}$ is a group $L^1$-$Z^1$ wherein $L^1$ is as defined in claim 1 and $Z^1$ is phenyl or wherein $L^1$ is $OCH_2$ and $Z^1$ is $C_{3-7}$cycloalkyl.

3. A compound or prodrug thereof according to claim 1, or a salt thereof, wherein $R^a$ is a group of formula (a2) in which $R^{3a}$ is a group $L^2$-$Z^2$ wherein $L^2$ is O and $Z^2$ is aryl or in which $L^2$ is $O(CH_2)_n$ wherein n is 1 and $Z^2$ is $C_{3-7}$cycloalkyl, aryl or heteroaryl.

4. A compound or prodrug thereof according to claim 1, or a salt thereof, wherein $R^a$ is a group of formula (a3) in which $R^{4a}$ is halogen, $C_{1-6}$alkyl, or $CF_3$ and $R^{5a}$ is a group $L^3$-$Z^3$ wherein $L^3$ is $OCH_2$ and $Z^3$ is $C_{3-7}$cycloalkyl, aryl or heteroaryl.

5. A compound or prodrug thereof according to claim 1, or a salt thereof, wherein $R^a$ is a group of formula (a4) in which $R^{6a}$ is Cl or $CF_3$ and $C^{7a}$ is halogen, $C_{1-6}$alkoxy or $C^{7a}$ is a group $L^4$-$Z^4$ wherein $L^4$ is $OCH_2$ and $Z^4$ is $C_{3-7}$cycloalkyl.

6. A compound or prodrug thereof according to claim 1, or a salt thereof, wherein $R^{1b}$ and $R^{2b}$ are both fluoro.

7. A compound selected from the group consisting of
N-[1-({2-Chloro-5-[(cyclopropylmethyl)oxy]phenyl}methyl)-1H-pyrazol-3-yl]-2,6-difluorobenzamide;
N-{1-[(2,4-Dichlorophenyl)methyl]-1H-pyrazol-3-yl}-2,6-difluorobenzamide;
2-Bromo-N-{1-[(2,4-dichlorophenyl)methyl]-1H-pyrazol-3-yl}-6-fluorobenzamide;
2-Chloro-N-{1-[(2,4-dichlorophenyl)methyl]-1H-pyrazol-3-yl}-6-fluorobenzamide;
2,6-Dichloro-N-{1-[(2,4-dichlorophenyl)methyl]-1H-pyrazol-3-yl}benzamide;
N-{1-[(2,4-dichlorophenyl)methyl]-1H-pyrazol-3-yl}-3,5-difluoro-4-pyridinecarboxamide;
N-[1-({5-chloro-2-[(phenylmethyl)oxy]phenyl}methyl)-1H-pyrazol-3-yl]-2,6-difluorobenzamide;
N-{1-[(2,6-dichlorophenyl)methyl]-1H-pyrazol-3-yl}-2,6-difluorobenzamide;
N-[1-({5-chloro-2-[(2-methylpropyl)oxy]phenyl}methyl)-1H-pyrazol-3-yl]-2,6-difluorobenzamide;
N-(1-{[2-bromo-5-(methyloxy)phenyl]methyl}-1H-pyrazol-3-yl)-2,6-difluorobenzamide;
N-(1-{[5-chloro-2-(methyloxy)phenyl]methyl}-1H-pyrazol-3-yl)-2,6-difluorobenzamide;
2,6-Difluoro-N-(1-{[2-(phenyloxy)phenyl]methyl}-1H-pyrazol-3-yl)benzamide;
N-[1-({5-bromo-2-[(phenylmethyl)oxy]phenyl}methyl)-1H-pyrazol-3-yl]-2,6-difluorobenzamide;
2,6-Difluoro-N-[1-({2-[(trifluoromethyl)oxy]phenyl}methyl)-1H-pyrazol-3-yl]benzamide;
2,6-Difluoro-N-(1-{[4-[(phenylmethyl)oxy]-2-(trifluoromethyl)phenyl]methyl}-1H-pyrazol-3-yl)benzamide ;
N-{1-[(2-Bromo-6-chlorophenyl)methyl]-1H-pyrazol-3-yl}-2,6-difluorobenzamide;
2,6-Difluoro-N-[1-({2-[(phenylmethyl)oxy]phenyl}methyl)-1H-pyrazol-3-yl]benzamide;
N-[1-({2-chloro-5-[(2-methylpropyl)oxy]phenyl}methyl)-1H-pyrazol-3-yl]-2,6-difluorobenzamide;
N-(1-{[4-[(cyclopropylmethyl)oxy]-2-(trifluoromethyl)phenyl]methyl}-1H-pyrazol-3-yl)-2,6-difluorobenzamide;
2,6-Difluoro-N-(1-{[4-iodo-2-(trifluoromethyl)phenyl]methyl}-1H-pyrazol-3-yl)benzamide;
2,6-Difluoro-N-(1-{[4-methyl-2-(trifluoromethyl)phenyl]methyl}-1H-pyrazol-3-yl)benzamide;
N-(1-{[4-cyclopropyl-2-(trifluoromethyl)phenyl]methyl}-1H-pyrazol-3-yl)-2,6-difluorobenzamide;
2,6-Difluoro-N-{1-[(4-iodo-2-methylphenyl)methyl]-1H-pyrazol-3-yl}benzamide;
N-(1-{[4-chloro-2-(trifluoromethyl)phenyl]methyl}-1H-pyrazol-3-yl)-2,6-difluorobenzamide;
2-Fluoro-N-(1-{[4-iodo-2-(trifluoromethyl)phenyl]methyl}-1H-pyrazol-3-yl)benzamide;
2-Chloro-N-(1-{[4-cyclopropyl-2-(trifluoromethyl)phenyl]methyl}-1H-pyrazol-3-yl)benzamide;
N-(1-{[4-cyclopropyl-2-(trifluoromethyl)phenyl]methyl}-1H-pyrazol-3-yl)-2-fluorobenzamide; and
2,6-Difluoro-N-(1-{[5-iodo-2-(trifluoromethyl)phenyl]methyl}-1H-pyrazol-3-yl)benzamide or a salt thereof.

8. A compound which is or a pharmaceutically acceptable salt thereof.

9. A compound which is 4-[(3-{[(2,6-Difluorophenyl)carbonyl]amino}-1H-pyrazol-1-yl)methyl]-3-(trifluoromethyl)phenyl dihydrogen phosphate disodium salt.

10. A pharmaceutical composition comprising a compound or prodrug thereof as defined in claim 1, or a pharmaceutically acceptable salt, thereof and one or more pharmaceutically acceptable carriers, diluents or excipients.

11. A method of treating asthma or rhinitis in a subject in need thereof which comprises administering a therapeutically effective amount of compound of formula (I) or a prodrug thereof as defined in claim 1 or a pharmaceutically acceptable salt thereof.

* * * * *